US006869777B2

(12) United States Patent
Chamberlain et al.

(10) Patent No.: US 6,869,777 B2
(45) Date of Patent: Mar. 22, 2005

(54) MINI-DYSTROPHIN NUCLEIC ACID SEQUENCES

(75) Inventors: Jeffrey S. Chamberlain, Seattle, WA (US); Scott Q. Harper, Iowa City, IA (US)

(73) Assignee: Regents of the University of Michigan, Ann Arbor, MI (US)

( * ) Notice: Subject to any disclaimer, the term of this patent is extended or adjusted under 35 U.S.C. 154(b) by 102 days.

(21) Appl. No.: 10/149,736

(22) PCT Filed: Oct. 4, 2001

(86) PCT No.: PCT/US01/31126

§ 371 (c)(1),
(2), (4) Date: Nov. 25, 2002

(87) PCT Pub. No.: WO02/29056

PCT Pub. Date: Apr. 11, 2002

(65) Prior Publication Data

US 2003/0216332 A1 Nov. 20, 2003

Related U.S. Application Data

(60) Provisional application No. 60/238,848, filed on Oct. 6, 2000.

(51) Int. Cl.[7] ............................................... C12P 21/06

(52) U.S. Cl. ................................................... 435/69.1

(58) Field of Search ......................... 435/69.1; 514/12; 530/350

(56) References Cited

U.S. PATENT DOCUMENTS

| | | | |
|---|---|---|---|
| 5,096,815 A | 3/1992 | Ladner et al. | 435/69.1 |
| 5,198,346 A | 3/1993 | Ladner et al. | 435/69.1 |
| 5,223,409 A | 6/1993 | Ladner et al. | 435/69.7 |
| 5,239,060 A | 8/1993 | Kunkel et al. | 530/350 |
| 5,260,209 A | 11/1993 | Campbell et al. | 435/240.2 |
| 5,308,752 A | 5/1994 | Campbell et al. | 435/7.21 |
| 5,430,129 A | 7/1995 | Campbell et al. | 530/395 |
| 5,449,616 A | 9/1995 | Campbell et al. | 435/240.2 |
| 5,541,074 A | 7/1996 | Kunkel et al. | 435/7.21 |
| 5,621,091 A | 4/1997 | Kunkel et al. | 536/23.5 |
| 5,686,073 A | 11/1997 | Campbell et al. | 424/185.1 |
| 5,863,743 A | 1/1999 | Campbell et al. | 435/7.21 |

FOREIGN PATENT DOCUMENTS

| | | |
|---|---|---|
| EP | 1059354 | 6/2000 |
| WO | WO 88/06630 | 7/1988 |
| WO | WO 90/02909 | 2/1992 |
| WO | WO 97/22696 | 6/1997 |
| WO | WO/0183695 | 8/2001 |

OTHER PUBLICATIONS

Davison MD, Baron MD, Critchley DR, Wootton JC. Structural analysis of homologous repeated domains in alpha–actinin and spectrin.Int J Biol Macromol. 1989 Apr.;11(2):81–90.*

Yausa et al. (including Shinichi Takeda), FEBS Letters 425:329–336, 1998.
Wang et al. (including Xiao Xiao) PNAS, 97(25):13714–13719, Dec. 5, 2000.
Phelps et al., Hum. Mol. Gen.; 4(8):1251–1258 (1995).
Hauser and Chamberlain, J. of Endocrinology, 149:373–378 (1996).
Rafael et al., Hum. Mol. Gen., 3(10):1725–1733 (1994).
Cox et al., Nature, 364:725–729 (1993).
Hartigan–O'Conner and Chamberlain, Microscopy Research and Technique, 48:223–238 (Feb., 2000).
Wells et al., Hum. Mol. Genet, 4(8):1245–50 (1995).
Corrado et al., FEBS Letters, 344:255–260 [1994].
Jung et al., JBC, 270 (45):27305 [1995].
Blake et al., Brain Pathology, 6:37 [1996].
Winder, J. Muscle Res. Cell. Motil., 18:617 [1997].
Tinsley et al., PNAS, 91:8307 [1994].
Winder et al., Febs Letters, 369:27–33 (1995).
Dhermy, 1991. Biol. Cell, 71:249–254.
Speicher and Ursitti, Current Biology, 4:154 [1994].
Yan et al., Science, 262–2027 [1993].
Matsudaira, Trends Biochem Scri, 16:87 [1991].
Speicher and Marchesi, Nature, 311:177 [1984].
Love et al., Nature 339–55 [1989].
Winkler et al., Eur. J. Biochem., 248:193 [1997].
Stryer (ed.), Biochemistry, 2nd ed, WH Freeman and Co. [1981].
Narang, Tetrahedron Lett, 39:3 9 [1983].
Itakura et al., Recombinant DNA, in Walton (ed.), Proceedings of the 3rd Cleveland Symposium on Macromolecules, Elsevier, Amsterdam, pp 273–289 [1981].
Itakura et al., Annu. Rev. Biochem., 53:323 [1984].
Itakura et al., Science 198:1056 [1984].
Ike et al., Nucl. Acid Res., 11:477 [1983].
Scott et al., Science, 249:386–390 [1980].
Roberts et al., Proc. Natl. Acad. Sci. USA, 89:2429–2433 [1992].
Devlin et al., Science, 249: 404–406 [1990].
Cwirla et al., Proc. Natl. Acad. Sci. USA, 87: 6378–6382 [1990].
Fuchs et al., BioTechnol., 9:1370 [1991].
Goward et al., TIBS 18:136 [1992].
Marks et al., J. Biol. Chem., 267:16007 [1992].
Griffths et al., EMBO J., 12:725 [1993].
Clackson et al., Nature, 352:624 [1991].

(List continued on next page.)

Primary Examiner—Karen Cochrane Carlson
Assistant Examiner—Sheridan Snedden
(74) Attorney, Agent, or Firm—Hedlen & Carroll, LLP

(57) ABSTRACT

The present invention relates to compositions and methods for expressing mini-dystrophin peptides. In particular, the present invention provides compositions comprising nucleic acid sequences that are shorter than wild-type dystrophin cDNA and that express mini-dystrophin peptides that function in a similar manner as wild-type dystrophin proteins. The present invention also provides compositions comprising mini-dystrophin peptides, and methods for expressing mini-dystrophin peptides in target cells.

34 Claims, 66 Drawing Sheets

OTHER PUBLICATIONS

Barbas et al., Proc. Natl. Acad. Sci., 89:4457 [1992].
Ruf et al., Biochem., 33:1565 [1994].
Wang et al., J. Biol. Chem., 269:3095 [1994].
Balint et al. Gene 137:109 [1993].
Grodberg et al., Eur. J. Biochem., 218:597 [1993].
Nagashima et al., J. Biol. Chem., 268:2888 [1993].
Lowman et al., Biochem., 30:10832 [1991].
Cunningham et al., Science, 244:1081 [1989].
Gustin et al., Virol., 193:653 [1993].
Brown et al., Mol. Cell. Biol., 12:2644 [1992].
McKnight et al., Science, 21732:316 (1982).
Meyers et al., Biochemistry 30:7666–7672 [1991].
Blake et al., *Trends Biochem. Sci.*, 20:133, 1995).
Sadoulet–Puccio et al., *PNAS*, 94:12413, 1997).
Grady et al., *Nat. Cell. Biol*, 1:215, 1999).
Rafael et al., *Hum. Mol. Genet.*, 3:1725, 1994.
Rafael et al., *J. Cell Biol.*, 134:93 1996).
Shield, et al., *Mol. Cell. Biol.*, 16:5058 (1996).
Trask, et al., *Nucleic Acids Res.*, 20:2313 (1992).
Amalfitano et al., "Production and Characterization of Improved Adenovirus Vectors With the E1, E2b, and E3 Genes Deleted," J. Virol. 72:926–933 (1998).
Kumar–Singh et al, *Hum. Mol. Genet.*, 5:913 (1996).
Fisher et al. "Recombinant Adenovirus Deleted of All Viral Genes for Gene Therapy of Cystic Fibrosis," *Virology* 217:11–22 (1996).
Kochanek et al, "A New Adenoviral Vector: Replacement of All Viral Coding Sequences With 28 kb of DNA Independently Expressing Both Full–length Dystrophin and Beta–galactosidase" *Proc. Nat. Acad. Sci. USA* 93:5731–5736 (1996).
Hardy et al., "Construction of Adenovirus Vectors Through Cre–lox Recombination," J. Virol. 71:1842–1849 (1997).
Hartigan–O'Conner et al., "Improved Production of Gutted Adenovirus in Cells Expressing Adenovirus Preterminal Protein and DNA Polymerase," *J. Virol.* 73:7835–7841 (1999).
Yan et al., *PNAS*, 97:6716–6721, 2000).
Fisher, et al., *J. Virol.* 70:520–532, 1996).
Duan, et al., *Virus Res.* 48:41–56, 1997).
Brennan, et al., *J. Biol. Chem.* 268:719, 1993).
MacGregor and Caskey, Nuc. Acid. Res., 17:2365, 1989).
Cox et al., *Nat. Genet.*, 8:333–339, 1994).
Straub et al., *J. Cell. Biol.*, 139:375–385, 1997).
Duclos et al., *J. Cell. Biol.*, 142:1461, 1998.
Lynch et al., *Am. J. Physiol.*, 272:C2063, 1997).
Ohlendieck et al., *J. Cell. Biol.*, 112:135, 1991).
Matsuda et al., *J. Biochem.* (Tokyo), 118:959, 1995).
Torres and Duchen, *Brain*, 110:269, 1987.
Ohlendieck et al., *Neuron*, 7:499–508, 1991).
Hauser et al., *Mol Ther.*, 2:16–25, 2000.
Crawford et al., *J. Cell. Biol.*, 150:1399, 2000.
Niwa et al., *Genes Dev.* 4:1552, 1990).
Petrof, et al., *Proc. Natl. Acad. Sci. USA*. 90:3710–3714, 1993.
England et al., Nature (London), 343(6254):180–182 (1990).
Clemens et al., Human Gene Therapy, 6:1477–1485 (1995).
Ascadi et al., Nature (London) 352(6338)85–818 (1991).
Amalfitano et al., Gene, Protein and Cell Biology, 1997, pp. 1–26, Cambridge University Press, ISBN, 0–521–55033–5.
U.S. Appl. No. 60/200,777, filed Apr. 28, 2000, Xiaoel et al.

* cited by examiner

FIGURE 1 (Human Dystrophin cDNA, Acc. No. M18533, SEQ ID NO:1)

```
   1 gggattccct cactttcccc ctacaggact cagatctggg aggcaattac cttcggagaa
  61 aaacgaatag gaaaaactga agtgttactt tttttaaagc tgctgaagtt tgttggtttc
 121 tcattgtttt taagcctact ggagcaataa agtttgaaga actttttacca ggttttttttt
 181 atcgctgcct tgatatacac ttttcaaaat gctttggtgg gaagaagtag aggactgtta
 241 tgaaagagaa gatgttcaaa agaaaacatt cacaaaatgg gtaaatgcac aattttctaa
 301 gtttgggaag cagcatattg agaacctctt cagtgaccta caggatggga ggcgcctcct
 361 agacctcctc gaaggcctga cagggcaaaa actgccaaaa gaaaaaggat ccacaagagt
 421 tcatgccctg aacaatgtca acaaggcact gcgggttttg cagaacaata atgttgattt
 481 agtgaatatt ggaagtactg acatcgtaga tggaaatcat aaactgactc ttggtttgat
 541 ttggaatata atcctccact ggcaggtcaa aaatgtaatg aaaaatatca tggctggatt
 601 gcaacaaacc aacagtgaaa agattctcct gagctgggtc cgacaatcaa ctcgtaatta
 661 tccacaggtt aatgtaatca acttcaccac cagctggtct gatggcctgg ctttgaatgc
 721 tctcatccat agtcataggc cagacctatt tgactggaat agtgtggttt gccagcagtc
 781 agccacacaa cgactggaac atgcattcaa catcgccaga tatcaattag catagagaa
 841 actactcgat cctgaagatg ttgataccac ctatccagat aagaagtcca tcttaatgta
 901 catcacatca ctcttccaag ttttgcctca acaagtgagc attgaagcca tccaggaagt
 961 ggaaatgttg ccaaggccac ctaaagtgac taaagaagaa catttttcagt tacatcatca
1021 aatgcactat tctcaacaga tcacggtcag tctagcacag ggatatgaga gaacttcttc
1081 ccctaagcct cgattcaaga gctatgccta cacacaggct gcttatgtca ccacctctga
1141 ccctacacgg agcccatttc cttcacagca tttggaagct cctgaagaca agtcatttgg
1201 cagttcattg atggagagtg aagtaaacct ggaccgttat caaacagctt tagaagaagt
1261 attatcgtgg cttctttctg ctgaggacac attgcaagca caggagaga tttctaatga
1321 tgtggaagtg gtgaaagacc agtttcatac tcatgagggg tacatgatgg atttgacagc
1381 ccatcagggc cgggttggta atattctaca attgggaagt aagctgattg gaacaggaaa
1441 attatcagaa gatgaagaaa ctgaagtaca agagcagatg aatctcctaa attcaagatg
1501 ggaatgcctc agggtagcta gcatggaaaa acaaagcaat ttacatagag ttttaatgga
1561 tctccagaat cagaaactga aagttgaa tgactggcta acaaaaacag aagaaagaac
1621 aaggaaaatg gaggaagagc ctcttggacc tgatcttgaa gacctaaaac gccaagtaca
1681 acaacataag gtgcttcaag aagatctaga acaagaacaa gtcagggtca attctctcac
1741 tcacatggtg gtggtagttg atgaatctag tggagatcac gcaactgctg ctttggaaga
1801 acaacttaag gtattgggag atcgatgggc aaacatctgt agatggacag aagaccgctg
1861 ggttctttta caagacatcc ttctcaaatg gcaacgtctt actgaagaac agtgcctttt
1921 tagtgcatgg ctttcagaaa aagaagatgc agtgaacaag attcacacaa ctggctttaa
1981 agatcaaaat gaaatgttat caagtcttca aaaactggcc gttttaaaag cggatctaga
2041 aaaagaaaag caatccatgg gcaaactgta ttcactcaaa caagatcttc tttcaacact
2101 gaagaataag tcagtgaccc agaagacgga agcatggctg gataactttg cccggtgttg
2161 ggataattta gtccaaaaac ttgaaaagag tacagcacag atttcacagg ctgtcaccac
2221 cactcagcca tcactaacac agacaactgt aatggaaaca gtaactacgg tgaccacaag
2281 ggaacagatc ctggtaaagc atgctcaaga ggaacttcca ccaccctc cccaaaagaa
2341 gaggcagatt actgtggatt ctgaaattag gaaaaggttg gatgttgata taactgaact
2401 tcacagctgg attactcgct cagaagctgt gttgcagagt cctgaatttg caatctttcg
2461 gaaggaaggc aacttctcag acttaaaga aaaagtcaat gccatagagc gagaaaagc
2521 tgagaagttc agaaaactgc aagatgccag cagatcagct caggcctgg tggacagat
2581 ggtgaatgag ggtgttaatg cagatagcat caaacaagcc tcagaacaac tagaacagcg
2641 gtggatcgaa ttctgccagt tgctaagtga gagacttaac tggctggagt atcagaacaa
2701 catcatcgct ttctataatc agctacaaca attggagcag atgacaacta ctgctgaaaa
2761 ctggttgaaa atccaaccca ccaccccatc agagccaaca gcaattaaaa gtcagttaaa
2821 aatttgtaag gatgaagtca ccgcctatc aggtcttcaa cctcaaatt aacgattaaa
2881 aattcaaagc atagccctga aagagaaagg acaaggaccc atgttcctgg atgcagactt
2941 tgtggccttt acaaatcatt ttaagcaagt cttttctgat gtgcaggcca gagagaaga
3001 gctacagaca attttgaca ctttgccacc aatgcgctat cagggagacca tgagtgccat
3061 caggacatgg tccagcagt cagaaccaat actctccata cctcaactta gtgtcaccga
3121 ctatgaaatc atgagcagca gactcggga attgcaggtc ttacaaagtt ctctccaaga
3181 gcaacaaagt ggcctatact atctcagcac cactgtgaaa gagatgtcga gaaagcgcc
3241 ctctgaaatt agccggaaat atcaatcaga atttgaagaa attgagggac gctggaagaa
3301 gctctcctcc cagctggttg agcattgtca aaagctagag gagcaaatga ataaactccg
3361 aaaaattcag aatcacatac aaacctgaa gaatggatg gctgaagttg atgttttcct
3421 gaaggaggaa tggcctgccc ttgggagtc agaaattcta aaaagcagc tgaaacagtg
3481 cagactttta gtcagtgata ttcagacaat tcagcccagt ctaaacagtg tcaatgaagg
3541 tgggcagaag ataaagaatg aagcagagcc agagtttgct tcagacttg agacagaact
3601 caaagaactt aacactcagt gggatcacat gtgccaacag gtctatgcca gaaaggagc
```

FIGURE 1 (cont.)

```
3661 cttgaaggga ggtttggaga aaactgtaag cctccagaaa gatctatcag agatgcacga
3721 atggatgaca caagctgaag aagagtatct tgagagagat tttgaatata aaactccaga
3781 tgaattacag aaagcagttg aagagatgaa gagagctaaa gaagaggccc aacaaaaaga
3841 agcgaaagtg aaactcctta ctgagtctgt aaatagtgtc atagctcaag ctccacctgt
3901 agcacaagag gccttaaaaa aggaacttga aactctaacc accaactacc agtggctctg
3961 cactaggctg aatgggaaat gcaagacttt ggaagaagtt tgggcatgtt ggcatgagtt
4021 attgtcatac ttggagaaag caaacaagtg gctaaatgaa gtagaattta aacttaaaac
4081 cactgaaaac attcctggcg gagctgagga aatctctgag gtgctagatt cacttgaaaa
4141 tttgatgcga cattcagagg ataacccaaa tcagattcgc atattggcac agaccctaac
4201 agatggcgga gtcatgaatg agctaatcaa tgaggaactt gagacattta attctcgttg
4261 gagggaacta catgaagagg ctgtaaggag gcaaaagttg cttgaacaga gcatccagtc
4321 tgcccaggag actgaaaaat ccttacactt aatccaggag tccctcacat tcattgacaa
4381 gcagttggca gcttatattg cagacaaggt ggacgcagct caaatgcctc aggaagccca
4441 gaaaatccaa tctgatttga caagtcatga gatcagttta gaagaaatga agaaacataa
4501 tcaggggaag gaggctgccc aaagagtcct gtctcagatt gatgttgcac agaaaaaatt
4561 acaagatgtc tccatgaagt ttcgattatt ccagaaacca gccaattttg agctgcgtct
4621 acaagaaagt aagatgattt tagatgaagt gaagatgcac ttgcctgcat tggaaacaaa
4681 gagtgtggaa caggaagtag tacagtcaca gctaaatcat tgtgtgaact tgtataaaag
4741 tctgagtgaa gtgaagtctg aagtggaaat ggtgataaag actggacgtc agattgtaca
4801 gaaaaagcag acggaaaatc ccaaagaact tgatgaaaag gtaacagctt tgaaattgca
4861 ttataatgag ctgggagcaa aggtaacaga aagaaagcaa cagttggaga aatgcttgaa
4921 attgtcccgt aagatgcgaa aggaaatgaa tgtcttgaca gaatggctgg cagctacaga
4981 tatggaattg acaaagagat cagcagttga aggaatgcct agtaatttgg attctgaagt
5041 tgcctgggga aaggctactc aaaaagagat tgagaaacag aaggtgcacc tgaagagtat
5101 cacagaggta ggagaggcct tgaaaacagt tttgggcaag aaggagacgt tggtggaaga
5161 taaactcagt cttctgaata gtaactggat agctgtcacc tcccgagcag aagagtggtt
5221 aaatcttttg ttggaatacc agaaacacat ggaacttttt gaccagaatg tggaccacat
5281 cacaaagtgg atcattcagg ctgacacact tttggatgaa tcagagaaaa agaaacccca
5341 gcaaaaagaa gacgtgctta agcgtttaaa ggcagaactg aatgacatac gcccaaaggt
5401 ggactctaca cgtgaccaag cagcaaactt gatggcaaac cgcggtgacc actgcaggaa
5461 attagtagag ccccaaatct cagagctcaa ccatcgattt gcagccattt cacacagaat
5521 taagactgga aaggcctcca ttcctttgaa ggaattggag cagtttaact cagatataca
5581 aaaattgctt gaaccactgg aggctgaaat tcagcagggg gtgaatctga aagaggaaga
5641 cttcaataaa gatatgaatg aagacaatga gggtactgta aaagaattgt tgcaagaggg
5701 agacaactta caacaaagaa tcacagatga gagaaagaga gaggaaataa agataaaaca
5761 gcagctgtta cagacaaaac ataatgctct caaggatttg aggtctcaaa gaagaaaaaa
5821 ggctctagaa atttctcatc agtggtatca gtacaagagg caggctgatg atctcctgaa
5881 atgcttggat gacattgaaa aaaattagc cagcctacct gagcccagag atgaaaggaa
5941 aataaaggaa attgcagggg aattgcagaa gaagaaagag gagctgaatg cagtgcgtag
6001 gcaagctgag ggcttgctga aggatgggc cgcaatgca gtggagcaa ctcagatcca
6061 gctcagcaag cgctggcggg aaattgagag caaatttgct cagtttcgaa gactcaactt
6121 tgcacaaatt cacactgtcc gtgaagaaac gatgatggtg atgactgaag acatgccttt
6181 ggaaatttct tatgtgcctt ctacttattt gactgaaatc actcatgtct cacaagccct
6241 attagaagtg gaacaactct caatgctcc tgacctctgt gctaaggact ttgaagatct
6301 ctttaagcaa gaggagtctc tgaagaatat aaaagatagt ctacaacaaa gctcaggtcg
6361 gattgacatt attcatagca agaagacagc agcattgcaa agtgcaacgc ctgtggaaag
6421 ggtgaagcta caggaagctc tctcccagct tgatttccaa tgggaaaaag ttaacaaaat
6481 gtacaaggac cgacaggacc gatttgacag atctgttgag aaatggcggc gtttttcatta
6541 tgatataaag atatttaatc agtggctaac agaagctgaa cagtttctca gaaagacaca
6601 aattcctgag aattgggaac atgctaaata caatggtat cttaaggaac tccaggatgg
6661 cattgggcag cggcaaactg ttgtcagaac attgaatgca actggggaag aaataattca
6721 gcaatcctca aaaacagatg ccagtattct acaggaaaaa tgggaagcc tgaatctgcg
6781 gtggcaggag gtctgcaaac agctgtcaga cagaaaaaag aggctagaag aacaaaagaa
6841 tatcttgtca gaatttcaaa gagatttaaa tgaattgtt ttatggttgg aggaagcaga
6901 taacattgct agtatcccac ttgaacctgg aaaagagcag caactaaaag aaaagcttga
6961 gcaagtcaag ttactggtgg aagagttgcc cctgcgccag gaattctca aacaattaaa
7021 tgaaactgga ggaccgtgc ttgtaagtgc tcccataagc ccagaagagc aagataaact
7081 tgaaaataag ctcaagcaga caaatctcca gtggataaag gtttccagag ctttacctga
7141 gaaacaagga gaaattgaag ctcaaataaa agaccttggg cagcttgaaa aaaagcttga
7201 agaccttgaa gagcagttaa atcatctgct gctgtggtta tctcctatta ggaatcagtt
7261 ggaaatttat aaccaaccaa accaagaagg accatttgac gttcaggaaa ctgaaatagc
7321 agttcaagct aaacaaccgg atgtggaaga gatttgtctc aaagggcagc atttgtacaa
7381 ggaaaaacca gccactcagc cagtgaagag gaagttagaa gatctgagct ctgagtggaa
7441 ggcggtaaac cgtttacttc aagagctgag ggcaaagcag cctgacctag ctcctggact
```

FIGURE 1 (cont.)

```
7501 gaccactatt ggagcctctc ctactcagac tgttactctg gtgacacaac ctgtggttac
7561 taaggaaact gccatctcca aactagaaat gccatcttcc ttgatgttgg aggtacctgc
7621 tctggcagat ttcaaccggg cttggacaga acttaccgac tggctttctc tgcttgatca
7681 agttataaaa tcacagaggg tgatggtggg tgaccttgag gatatcaacg agatgatcat
7741 caagcagaag gcaacaatgc aggatttgga acagaggcgt ccccagttgg aagaactcat
7801 taccgctgcc caaaatttga aaacaagac cagcaatcaa gaggctagaa caatcattac
7861 ggatcgaatt gaaagaattc agaatcagtg ggatgaagta caagaacacc ttcagaaccg
7921 gaggcaacag ttgaatgaaa tgttaaagga ttcaacacaa tggctggaag ctaaggaaga
7981 agctgagcag gtcttaggac aggccagagc caagcttgag tcatggaagg agggtcccta
8041 tacagtagat gcaatccaaa agaaaatcac agaaaccaag cagttggcca aagacctccg
8101 ccagtggcag acaaatgtag atgtggcaaa tgacttggcc ctgaaacttc tccgggatta
8161 ttctgcagat gataccagaa aagtccacat gataacagag aatatcaatg cctcttggag
8221 aagcattcat aaaagggtga gtgagcgaga ggctgctttg gaagaaactc atagattact
8281 gcaacagttc cccctggacc tggaaaagtt tcttgcctgg cttacagaag ctgaaacaac
8341 tgccaatgtc ctacaggatg ctaccgtaa ggaaaggctc ctagaagact ccaagggagt
8401 aaaagagctg atgaaacaat ggcaagacct ccaaggtgaa attgaagctc acacagatgt
8461 ttatcacaac ctggatgaaa acagccaaaa aatcctgaga tccctggaag gttccgatga
8521 tgcagtcctg ttacaaagac gtttggataa catgaacttc aagtggagtg aacttcggaa
8581 aaagtctctc aacattaggt cccatttgga agccagttct gaccagtgga agcgtctgca
8641 ccttttctctg caggaacttc tggtgtggct acagctgaaa gatgatgaat taagccggca
8701 ggcacctatt ggaggcgact ttccagcagt tcagaagcag aacgatgtac atagggcctt
8761 caagagggaa ttgaaaacta agaacctgt aatcatgagt actcttgaga ctgtacgaat
8821 atttctgaca gagcagcctt tggaaggact agagaaactc taccaggagc ccagagagct
8881 gcctcctgag gagagagccc agaatgtcac tcggcttcta cgaaagcagg ctgaggaggt
8941 caatactgag tgggaaaaat tgaacctgca ctccgctgac tggcagagaa aaatagatga
9001 gaccctgaa agactccagg aacttcaaga ggccacggat gagctggacc tcaagctgcg
9061 ccaagctgag gtgatcaagg atcctggca gcccgtgggc gatctcctca ttgactctct
9121 ccaagatcac ctcgagaaag tcaaggcact tcgaggagaa attgcgcctc tgaaagagaa
9181 cgtgagccac gtcaatgacc ttgctcgcca gcttaccact ttgggcattc agctctcacc
9241 gtataacctc agcactctgg aagacctgaa caccagatgg aagcttctgc aggtggccgt
9301 cgaggaccga gtcaggcagc tgcatgaagc ccacagggac tttggtccag catctcagca
9361 ctttctttcc acgtctgtcc agggtccctg ggagagagcc atctcgccaa acaaagtgcc
9421 ctactatatc aaccacgaga ctcaaacaac ttgctgggac catcccaaaa tgacagagct
9481 ctaccagtct ttagctgacc tgaataatgt cagattctca gcttatagga ctgccatgaa
9541 actccgaaga ctgcagaagg ccctttgctt ggatctcttg agcctgtcag ctgcatgtga
9601 tgccttggac cagcacaacc tcaagcaaaa tgaccagccc atggatatcc tgcagattat
9661 taattgtttg accactattt atgaccgcct ggagcaagag cacaacaatt tggtcaacgt
9721 ccctctctgc gtggatatgt gtctgaactg gctgctgaat gtttatgata cggggacgaac
9781 agggaggatc cgtgtcctgt cttttaaaac tgcatcatt tccctgtgta agcacattt
9841 ggaagacaag tacagatacc ttttcaagca agtggcaagt tcaacaggat tttgtgacca
9901 gcgcaggctg ggcctccttc tgcatgattc tatccaaatt ccaagacagt tgggtgaagt
9961 tgcatccttt gggggcagta acattgagcc aagtgtccgg agctgcttcc aatttgctaa
10021 taataagcca gagatcgaag cggccctctt cctagactgg atgagactgg aaccccagtc
10081 catggtgtgg ctgccgtcc tgcacagagt ggctgctgca gaaactgcca agcatcaggc
10141 caaatgtaac atctgcaaag agtgccaat cattggattc aggtacagga gtctaaagca
10201 ctttaattat gacatctgcc aaagctgctt ttttctggt cgagttgcaa aaggccataa
10261 aatgcactat cccatggtgg aatattgcac tccgactaca tcaggagaag atgttcgaga
10321 ctttgccaag gtactaaaaa acaaatttcg aaccaaaagg tattttgcga agcatccccg
10381 aatgggctac ctgccagtgc agactgtctt agaggggga acatggaaa ctcccgttac
10441 tctgatcaac ttctggccaa tagattctgc gcctgcctcg tcccctcagc tttcacacga
10501 tgatactcat tcacgcattg aacattgta tagcaggcta gcagaaatgg aaaacagcaa
10561 tggatcttat ctaaatgata gcatctctcc taatgagagc atagatgatg aacatttgtt
10621 aatccagcat tactgccaaa gtttgaacca ggactccccc ctgagccagc ctcgtagtcc
10681 tgcccagatc ttgatttcct tagagagtga ggaaagaggg gagctagaga gaatcctagc
10741 agatcttgag gaagaaaaca ggaatctgca agcagaatat gaccgtctaa agcagcagca
10801 cgaacataaa ggcctgtccc cactgccgtc ccctcctgaa atgatgccca cctctcccca
10861 gagtccccgg gatgctgagc tcattgctga ggccaagcta ctgcgtcaac acaaaggccg
10921 cctggaagcc aggatgcaaa tcctggaaga ccacaataaa cagctggagt cacagttaca
10981 caggctaagg cagctgctgg agcaacccca ggcagaggcc aaagtgaatg cacaacggt
11041 gtcctctcct tctacctctc tacagaggtc cgacagcagt cagcctatgc tgctccgagt
11101 ggttggcagt caaacttcgg actccatggg tgaggaagat cttctcagtc ctcccaggga
11161 cacaagcaca gggttagagg aggtgatgga gcaactcaac aactccttcc ctagttcaag
11221 aggaagaaat accctggaa agccaatgag agaggacaca atgtaggaag tctttccac
11281 atggcagatg atttgggcag agcgatggag tccttagtat cagtcatgac agatgaagaa
```

FIGURE 1 (cont.)

```
11341 ggagcagaat aaatgtttta caactcctga ttcccgcatg gtttttataa tattcataca
11401 acaaagagga ttagacagta agagtttaca agaaataaat ctatatttt gtgaagggta
11461 gtggtattat actgtagatt tcagtagttt ctaagtctgt tattgttttg ttaacaatgg
11521 caggttttac acgtctatgc aattgtacaa aaaagttata agaaaactac atgtaaaatc
11581 ttgatagcta aataacttgc catttcttta tatggaacgc attttgggtt gtttaaaaat
11641 ttataacagt tataaagaaa gattgtaaac taaagtgtgc tttataaaaa aaagttgttt
11701 ataaaaaccc ctaaaaacaa aacaaacaca cacacacaca catacacaca cacacacaaa
11761 actttgaggc agcgcattgt tttgcatcct tttggcgtga tatccatatg aaattcatgg
11821 cttttttcttt ttttgcatat taaagataag acttcctcta ccaccacacc aaatgactac
11881 tacacactgc tcatttgaga actgtcagct gagtggggca ggcttgagtt ttcatttcat
11941 atatctatat gtctataagt atataaatac tatagttata tagataaaga gatacgaatt
12001 tctatagact gactttttcc attttttaaa tgttcatgtc acatcctaat agaaagaaat
12061 tacttctagt cagtcatcca ggcttacctg cttggtctag aatggatttt tcccggagcc
12121 ggaagccagg aggaaactac accacactaa aacattgtct acagctccag atgtttctca
12181 ttttaaacaa ctttccactg acaacgaaag taaagtaaag tattggatt tttaaaggg
12241 aacatgtgaa tgaatacaca ggacttatta tatcagagtg agtaatcggt tggttggttg
12301 attgattgat tgattgatac attcagcttc ctgctgctag caatgccacg atttagattt
12361 aatgatgctt cagtggaaat caatcagaag gtattctgac cttgtgaaca tcagaaggta
12421 ttttttaact cccaagcagt agcaggacga tgatagggct ggagggctat ggattcccag
12481 cccatccctg tgaaggagta ggccactctt taagtgaagg attggatgat tgttcataat
12541 acataaagtt ctctgtaatt acaactaaat tattatgccc tcttctcaca gtcaaaagga
12601 actgggtggt ttggtttttca ttgcttttt agatttattg tcccatgtgg gatgagtttt
12661 taaatgccac aagacataat ttaaaataaa taaactttgg gaaaaggtgt aagacagtag
12721 ccccatcaca tttgtgatac tgacaggtat caacccagaa gcccatgaac tgtgtttcca
12781 tcctttgcat ttctctgcga gtagttccac acaggtttgt aagtaagtaa gaaagaaggc
12841 aaattgattc aaatgttaca aaaaaccct tcttggtgga ttagacaggt taaatatata
12901 aacaaacaaa caaaaattgc tcaaaaaaga ggagaaaagc tcaagaggaa aagctaagga
12961 ctggtaggaa aaagctttac tctttcatgc cattttattt cttttttgatt tttaaatcat
13021 tcattcaata gataccaccg tgtgacctat aatttttgcaa atctgttacc tctgacatca
13081 agtgtaatta gcttttggag agtgggctga catcaagtgt aattagcttt tggagagtgg
13141 gttttgtcca ttattaataa ttaattaatt aacatcaaac acggcttctc atgctatttc
13201 tacctcactt tggttttggg gtgttcctga taattgtgca cacctgagtt cacagcttca
13261 ccacttgtcc attgcgttat tttcttttc ccttataatt ctttctttt ccttcataat
13321 tttcaaaaga aaacccaaag ctctaaggta acaaattacc aaattacatg aagatttggt
13381 ttttgtcttg cattttttc ctttatgtga cgctggacct tttctttacc caaggatttt
13441 taaaactcag atttaaaaca aggggttact ttacatccta ctaagaagtt taagtaagta
13501 agtttcattc taaaatcaga ggtaaataga gtgcataaat aattttgttt taatcttttt
13561 gttttttcttt tagacacatt agctctggag tgagtctgtc ataatatttg aacaaaaatt
13621 gagagcttta ttgctgcatt ttaagcataa ttaatttgga cattatttcg tgttgtgttc
13681 tttataacca ccgagtatta aactgtaaat cataatgtaa ctgaagcata aacatcacat
13741 ggcatgtttt gtcattgttt tcaggtactg agttcttact tgagtatcat aatatattgt
13801 gttttaacac caacactgta acatttacga attattttt taaacttcag ttttactgca
13861 ttttcacaac atatcagact tcaccaaata tatgccttac tattgtatta tagtactgct
13921 ttactgtgta tctcaataaa gcacgcagtt atgttac
```

FIGURE 2 (Mouse Dystrophin cDNA, Acc. No. M68859, SEQ ID NO:2)

```
   1 cctcactcac ttgcccctta caggactcag ctcttgaagg caatagcttt atagaaaaaa
  61 cgaataggaa gacttgaagt gctatttttt tttttttttt tgtcaaggct gctgaagttt
 121 attggcttct catcgtacct aagcctcctg gagcaataaa actgggagaa acttttacca
 181 agatttttat ccctgccttg atatatactt tttcttccaa atgctttggt gggaagaagt
 241 agaggactgt tatgaaagag aagatgttca aaagaaaaca ttcacaaaat ggataaatgc
 301 acaattttct aagtttggaa agcaacacat agacaacctc ttcagtgacc tgcaggatgg
 361 aaaacgcctc ctagacctct tggaaggcct tacagggcaa aaactgccaa aagaaaaggg
 421 atctacaaga gttcatgccc tgaacaatgt caacaaggca ctgcgggtct tacagaaaaa
 481 taatgttgat ttagtgaata taggaagcac tgacatagtg gatggaaatc ataaactcac
 541 tcttggtttg atttggaata taatcctcca ctggcaggtc aaaaatgtga tgaaaactat
 601 catggctgga ttgcagcaaa ccaacagtga aaagattctt ctgagctggg ttcgacagtc
 661 aacacgtaat tatccacagg ttaacgtcat caacttcacc tctagctggt ccgacgggtt
 721 ggctttgaat gctcttatcc atagtcacag gcccgacctg tttgattgga atagtgtggt
 781 ttcacagcac tcagccaccc aaagactgga acatgccttc aacattgcaa aatgccagtt
 841 aggcatagaa aaacttcttg atcctgaaga tgttgctacc acttatccag acaagaagtc
 901 catcttaatg tacatcacat cactctttca agtttgcca caacaagtga gcattgaagc
 961 cattcaagaa gtggaaatgt tgcccaggac atcttcaaaa gtaactagag aagaacattt
1021 tcaattacat caccagatgc attactctca acagatcaca gtcagtctag cacagggcta
1081 tgaacaaact tcttcatctc ctaagcctcg attcaagagt tatgccttca cacaggctgc
1141 ttatgttgcc acctctgatt ccacacagag cccctatcct tcacagcatt tggaagctcc
1201 cagagacaag tcacttgaca gttcattgat ggagacggaa gtaaatctgg atagttacca
1261 aactgcttta gaagaagtac tttcatggct tctttctgcc gaggatacat tgcgagcaca
1321 aggagagatt tcaaatgatg ttgaagaagt gaaagaacag tttcatgctc atgagggatt
1381 catgatggat ctgacatctc atcaaggact tgttggtaat gttctacagt taggaagtca
1441 actagttgga aaagggaaat tatcagaaga tgaagaagct gaagtgcaag aacaaatgaa
1501 tctcctaaat tcaagatggg aatgtctcag ggtagctagc atggaaaaac aaagcaaatt
1561 acacaaagtt ctaatggatc tccagaatca gaaattaaaa gaactagatg actggttaac
1621 aaaaactgaa gagagaacta agaaaatgga ggaagagccc tttggacctg atcttgaaga
1681 tctaaaatgc caagtacaac aacataaggt gcttcaagaa gatctagaac aggagcaggt
1741 cagggtcaac tcgctcactc acatggtagt agtggttgat gaatccagcg gtgatcatgc
1801 aacagctgct tggaagaac aacttaaggt actgggagat cgatgggcaa atatctgcag
1861 atggactgaa gaccgctgga ttgttttaca agatattctt ctaaaatgca gcatttttac
1921 tgaagaacag tgccttttta gtacatggct ttcagaaaaa gaagatgcaa tgaagaacat
1981 tcagacaagt ggctttaaag atcaaaatga aatgatgtca agtcttcaca aatatctac
2041 tttaaaaata gatctagaaa agaaaaagcc aaccatggaa aaactaagtt cactcaatca
2101 agatctactt cggcactga aaaatagtc agtgactcaa aagtggaaa tctggatgga
2161 aaactttgca caacgttggg acaatttaac ccaaaaactt gaaaagagtt cagcacaaat
2221 ttcacaggct gtcaccacca ctcaaccatc cctaacacag acaactgtaa tggaaacggt
2281 aactatggtg accacaaggg aacaaatcat ggtaaaacat gcccaagagg aacttccacc
2341 accacctcct caaagaagga ggcagataac tgtggattct gaactcagga aaggttgga
2401 tgtcgatata actgaacttc acagttggat tactcgttca gaagctgtat tacagagttc
2461 tgaatttgca gtctatcgaa aagaaggcaa catctcagac ttgcaagaaa aagtcaatgc
2521 catagcacga gaaaaagcag agaagttcag aaaactgcaa gatgccagca gatcagctca
2581 ggccctggtg aacagatgg caaatgaggg tgttaatgct gaaagtatca gacaagcttc
2641 agaacaactg aacagccggt ggacagaatt ctgccaattg ctgagtgaga gagttaactg
2701 gctagagtat caaaccaaca tcattacctt ttataatcag ctacaacaat ggaacagat
2761 gacaactact gccgaaaact gttgaaaac ccagtctacc acctatcag agccaacagc
2821 aattaaaagc cagttaaaaa tttgtaagga tgaagtcaac agattgtcag ctcttcagcc
2881 tcaaattgag caattaaaaa ttcagagtct acaactgaaa gaaaagggac aggggccaat
2941 gtttctggat gcagactttg tggcctttac taatcatttt aaccacatct ttgatggtgt
3001 gaggcccaaa gagaaagagc tacagacaat ttttgacact taccaccaa tgcgctatca
3061 ggagacaatg agtagcatca ggacgtggat ccagcagtca gaaagcaaac tctctgtacc
3121 ttatcttagt gttactgaat atgaataat ggaggagaga ctcgggaaat tacaggctct
3181 gcaaagttct ttgaaggaca aacaaatgg cttcaactat ctgagtgaca ctgtgaagga
3241 gatggccaag aaagcaccct cagaaaatat ctgcagaat ttgaagagat
3301 tgaggggcac tggaagaaac ttcctccca gttggtggaa agctgccaaa agctagaaga
3361 acatatgaat aaacttcgaa aatttcagaa tcacataaaa accttacaga atggatggtgc
3421 tgaagttgat gtttttctga aagaggaatg gcctgccctg ggggatgctg aaatcctgaa
3481 aaaacagctc aaacaatgca gacttttagt tggtgatatt caaacaattc agcccagttt
3541 aaatagtgtt aatgaaggtg ggcagaagat aaagagtgaa gctgaacttg agtttgcatc
3601 cagactggag acagaactta gagagcttaa cactcagtgg gatcacatat gccgccaggt
```

FIGURE 2 (cont.)

```
3661 ctacaccaga aaggaagcct taaaggcagg tttggataaa accgtaagcc tccaaaaaga
3721 tctatcagag atgcatgagt ggatgacaca agctgaagaa gaatatctag agagagattt
3781 tgaatataaa actccagatg aattacagac tgctgttgaa gaaatgaaga gagctaaaga
3841 agaggcacta caaaaagaaa ctaaagtgaa actccttact gagactgtaa atagtgtaat
3901 agctcacgct ccaccctcag cacaagaggc cttaaaaaag gaacttgaaa ctctgaccac
3961 caactaccaa tggctgtgca ccaggctgaa tggaaaatgc aaaactttgg aagaagtttg
4021 ggcatgttgg catgagttat tgtcatattt agagaaagca aacaagtggc tcaatgaagt
4081 agaattgaaa cttaaaacca tggaaaatgt tcctgcagga cctgaggaaa tcactgaagt
4141 gctagaatct cttgaaaatc tgatgcatca ttcagaggag aacccaaatc agattcgtct
4201 attggcacag actcttacag atggaggagt catggatgaa ctgatcaatg aggagcttga
4261 gacgtttaat tctcgttgga gggaactaca tgaagaggct gtgaggaaac aaaagttgct
4321 tgaacagagt atccagtctg cccaggaaat tgaaaagtcc ttgcacttaa ttcaggagtc
4381 gcttgaattc attgacaagc agttggcagc ttatatcact gacaaggtgg atgcagctca
4441 aatgcctcag gaagcccaga aaatccaatc agatttgaca agtcatgaga taagtttaga
4501 agaaatgaag aaacataacc aggggaagga tgccaaccaa agggttcttt cacaaattga
4561 tgttgcacag aaaaaattac aagatgtctc catgaaattt cgattattcc aaaaaccagc
4621 caatttgaa caacgtctag aggaaagtaa gatgatttta gatgaagtca agatgcattt
4681 gcctgcattg gaaccaaga gtgttgaaca ggaagtaatt cagtcacaac taagtcattg
4741 tgtgaacttg tataaaagcc tgagtgaagt caagtctgaa gtggaaatgg tgattaaaac
4801 cggacgtcaa attgtacaga aaagcagac agaaaatccc aaagagcttg atgaacgagt
4861 aacagctttg aaattgcatt acaatgagtt gggtgcgaag gtaacagaga gaaagcaaca
4921 gttggagaaa tgcttgaagt tgtcccgtaa gatgagaaag gaaatgaatg tcttaacaga
4981 atggctggca gcaacagata cagaattgac gaagagatca gcagttgaag gaatgccaag
5041 taatttggat tctgaagttg cctggggaaa ggctactcaa aaagagattg agaaacagaa
5101 ggctcacttg aagagtgtta cagaattagg agagtctttg aaaatggtgt tgggcaagaa
5161 agaaaccttg gtagaagata aactgagtct tctgaacagt aactggatag ctgtcacctc
5221 cagagtagaa gaatggctaa atcttttgtt ggaataccag aaacacatgg aaacctttga
5281 tcagaacata gaacaaatca caaagtggat cattcatgca gatgaacttt tagatgagtc
5341 tgaaaagaag aaaccacaac aaaaggaaga cattcttaag cgtttaaagg ctgaaatgaa
5401 tgacatgcgc ccaaagtgg actccacacg tgaccaagca gcaaaattga tggcaaaccg
5461 cggtgaccac tgcaggaaag tagtagagcc ccaaatctct gagctcaacc gtcgatttgc
5521 agctatttct cacagaatta agactggaaa ggcctccatt cctttgaagg aattggagca
5581 gtttaactca gatatacaaa aattgcttga accactggag gctgaaattc agcaggggt
5641 gaatctgaaa gaggaagact tcaataaaga tatgagtgaa gacaatgagg gtactgtaaa
5701 tgaattgttg caaagaggag acaacttaca acaaagaatc acagatgaga gaaagcgaga
5761 ggaaataaag ataaacagc agctgttaca gacaaaacat aatgctctca aggatttgag
5821 gtctcaaaga agaaaaaagg ccctagaaat ttctcaccag tggtatcagt acaagaggca
5881 ggctgatgat ctcctgaaat gcttggatga aattgaaaaa aaattagcca gcctacctga
5941 acccagagat gaaagaaaat taaaggaaat tgatcgtgaa ttgcagaaga gaaagagga
6001 gctgaatgca gtgcgcaggc aagctgaggg cttgtctgag aatggggccg caatggcagt
6061 ggagccaact cagatccagc tcagcaagcg ctggcggcaa attgagagca attttgctca
6121 gtttcgaaga ctcaactttg cacaaattca cactctccat gaagaaacta tggtagtgac
6181 gactgaagat atgcctttgg atgtttctta tgtgccttct acttatttga ccgagatcag
6241 tcatatctta caagctcttt cagaagttga tcatcttcta aatactcctg aactctgtgc
6301 taaagatttt gaagatcttt ttaagcaaga ggagtctctt aagaatataa aagacaattt
6361 gcaacaaatc tcaggtcgga ttgatattat tcacaagaag aagacagcag ccttgcaaag
6421 tgccacctcc atggaaaagg tgaaagtaca ggaagccgtg gcacagatgg atttccaggg
6481 ggaaaaactt catagaatgt acaaggaacg acaagggcga ttcgacagat cagttgaaaa
6541 atggcgacac tttcattatg atatgaaggt atttaatcaa tggctgaatg aagttgaaca
6601 gtttttcaaa aagacacaaa atcctgaaaa ctgggaacat gctaaataca aatggtatct
6661 taaggaactc caggatggca ttgggcagcg tcaagctgtt gtcagaacac tgaatgcaac
6721 tggggaagaa ataattcaac agtcttcaaa aacagatgtc aatattctac aagaaaaatt
6781 aggaagcttg agtctgcggt ggcacgacat ctgcaaagag ctggcagaaa ggagaagag
6841 gattgaagaa caaagaatg tcttgtcaga atttcaaaga gatttaaatg aatttgtttt
6901 gtggctggaa gaagcagata cattgctat tactccactt ggagatgagc agcagctaaa
6961 agaacaactt gaacaagtca agttactggc agaagagttg ccctgcgcc agggaattct
7021 aaaacaatta aatgaaacag gaggagcagt acttgtaagt gctcccataa ggccagaaga
7081 gcaagataaa cttgaaaaga agctcaaaca gacaaatctc cagtggataa aggtctccag
7141 agctttacct gagaaacaag gagagcttga ggttcactta aaagattta ggcagcttga
7201 agagcagctg gatcacctgc ttctgtggct ctctcctatt agaaaccagt tggaaattta
7261 taaccaacca agtcaggcag gaccgtttga cataaaggag attgaagtaa cagttcacgg
7321 taaacaagcg gatgtggaaa ggcttttgtc gaaagggcag catttgtata aggaaaaacc
7381 aagcactcag ccagtgaaga ggaagttaga agatctgagg tctgagtggg aggctgtaaa
7441 ccatttactt cgggagctga ggacaaagca gcctgaccgt gcccctggac tgagcactac
```

FIGURE 2 (cont.)

```
 7501 tggagcctct gccagtcaga ctgttactct agtgacacaa tctgtggtta ctaaggaaac
 7561 tgtcatctcc aaactagaaa tgccatcttc tttgctgttg gaggtacctg cactggcaga
 7621 cttcaaccga gcttggacag aacttacaga ctggctgtct ctgcttgatc gagttataaa
 7681 atcacagaga gtgatggtgg gtgatctgga agacatcaat gaaatgatca tcaaacagaa
 7741 ggcaacactg caagatttgg aacagagacg cccccaattg gaagaactca ttactgctgc
 7801 ccagaatttg aaaaacaaaa ccagcaatca agaagctaga acaatcatta ctgatcgaat
 7861 tgaaagaatt cagattcagt gggatgaggt tcaagaacag ctgcagaaca ggagacaaca
 7921 gttgaatgaa atgttaaagg attcaacaca atggctggaa gctaaggaag aagccgaaca
 7981 ggtcatagga caggtcagag gcaagcttga ctcatggaaa gaaggtcctc acacagtaga
 8041 tgcaatccaa aagaagatca cagaaaccaa gcagttggcc aaagacctcc gtcaacggca
 8101 gataagtgta gacgtggcaa atgatttggc actgaaactt cttcgggact attctgctga
 8161 tgataccaga aaagtacaca tgataacaga gaatatcaat acttcttggg gaaacattca
 8221 taaaagagta agtgagcaag aggctgcttt ggaagaaact catagattac tgcagcagtt
 8281 ccctctggac ctggagaagt ttctttcctg gattacggaa gcagaaacaa ctgccaatgt
 8341 cctacaggac gcttcccgta aggagaagct cctagaagac tccaggggag tcagagagct
 8401 gatgaaacca tgcaagatc tccaaggaga aattgaaact cacacagata tctatcacaa
 8461 tcttgatgaa aatggccaaa aaatcctgag atccctggaa ggttcggatg aagcacccct
 8521 gttacaaaga cgtttggata acatgaattc caagtggagt gaacttcaga aaaagtctct
 8581 caacattagg tcccatttgg aagcaagttc tgaccagtgg aagcgtttgc atcttttctct
 8641 tcaggaactt cttgtttggc tacagctgaa agatgatgaa ctgagccgtc aggcacccat
 8701 cggtggtgat ttcccagcag ttcagaagca gaatgatata catagggcct tcaagaggga
 8761 attgaaaact aaagaacctg taatcatgag tactctgagg actgtgagaa tatttctgac
 8821 agagcagcct ttggaaggac tagagaaact ctaccaggag cccagagaac tgcctcctga
 8881 agaaagagct cagaatgtca ctcggctcct acgaaagcag gctgaagagg tcaacgctga
 8941 atgggacaaa ttgaacctgc gctcagctga ttggcagaga aaaatagatg aagctcttga
 9001 aagactccag gaacttcagg aagctgccga tgaactggac ctcaagttgc gccaagctga
 9061 ggtgatcaag ggatcctggc agccagtggg ggatctcctc attgactctc tgcaagatca
 9121 ccttgaaaaa gtcaaggcac ttcggggaga aattgcacct cttaaagaga atgtcaatcg
 9181 tgtcaatgac cttgcacatc agctgaccac actgggcatt cagctctcac cttataacct
 9241 cagcactttg gaagatctga ataccagatg gaggcttcta caggtggctg tggaggaccg
 9301 tgtcagacag ctgcatgaag cccacaggga ctttggtcct gcatcccagc acttcctttc
 9361 cacttcagtt cagggtccct gggagagagc catctcacca aacaaagtgc cctactatat
 9421 caaccacgag acccaaacca cttgttggga ccacccccaaa atgacagagc tctaccagtc
 9481 tttagctgac ctgaataatg tcaggttctc cgcgtatagg actgccatga agctcagaag
 9541 gctccagaag gccctttgct tggatctctt gagcctgtca gctgcatgtg atgccctgga
 9601 ccagcacaac ctcaagcaaa atgaccagcc catggatatc ctgcagataa ttaactgttt
 9661 gactacaatt tatgatcgtc tggagcaaga gcacaacaat ctggtcaatg tccctctctg
 9721 tgtggatatg tgtctcaact ggcttctcaa tgtttatgat acgggacgaa cagggaggat
 9781 ccgtgtcctg tcttttaaaa ctggcatcat ttctctgtgt aaagcacact tggaagacaa
 9841 gtacagatac cttttcaagc aagtggcaag ttcaactggc ttttgtgacc agcgtaggct
 9901 gggtcttctt ctgcatgatt ctattcaaat cccaagacag ttgggtgaag ttgcttcctt
 9961 tgggggcagt aacattgagc cgagtgtcag gagctgcttc caatttgcca ataataaacc
10021 tgagattgaa gctgctctct tccttgactg gatgcgcctg gaaccccagt ctatggtgtg
10081 gctgcccgtc ttgcacagag tggctgctgc tgaaactgcc aagcatcaag ccaagtgtaa
10141 catctgtaag gagtgtccaa tcattggatt caggtacaga agcctaaagc attttaatta
10201 tgacatctgc caaagttgct tttttctgg ccgagttgca aagggccata aaatgcacta
10261 ccccatggta gagtattgca ctccgactac atccggagaa gatgttcgcg acttcgccaa
10321 ggtactaaaa aacaaatttc gaaccaaaag gtattttgcg aagcatcccc gaatgggcta
10381 cctgccagtg cagactgtgt tagaggggga aacatggaa actcccgtta ctctgatcaa
10441 cttctggcca gtagattctg cgcctgcctc gtcccccag ctttcacacg atgatactca
10501 ttcacgcatt gaacattatg ctagcaggct agcagaaatg gaaaacagca atggatctta
10561 tctaaatgat agcatctctc ctaatgagag catagatgat gaacatttgt taatccagca
10621 ttactgccaa agtttgaacc aggactcccc cctgagccag cctcgtagtc ctgcccagat
10681 cttgatttcc ttagagagtg aggaaagagg ggagctagag agaatcctag cagatcttga
10741 ggaagaaaac aggaatctgc aagcagaata tgatcgcctg aagcagcagc atgagcataa
10801 aggcctgtct ccactgccat ctcctcctga gatgatgccc acctctcctc agagtcccag
10861 ggatgctgag ctcattgctg aggctaagct actgcgccaa cacaaggac gcctggaagc
10921 caggatgcaa atcctggaag accacaataa acagctggag tctcagttac atagactgag
10981 acagctcctg gagcagcccc aggctgaagc taaggtgaat ggcaccacgg tgtcctctcc
11041 ttccacctct ctgcagaggt cagatagcag tcagcctatg ctgctccgag tggttggcag
11101 tcaaacttca gaatctatgg gtgaggaaga tcttctgagt cctcccagg acaagagcac
11161 agggttagaa gaagtgatgg agcaactcaa caactccttc cctagttcaa gaggaagaaa
11221 tgccccgga aagccaatga gagggacac aatgtaggaa gccttttcca catggcagat
11281 gatttgggca gagcgatgga gtccttagtt tcagtcatga cagatgaaga aggagcagaa
```

FIGURE 2 (cont.)

```
11341 taaatgtttt acaactcctg attcccgcat ggtttttata atattcgtac aacaaagagg
11401 attagacagt aagagtttac aagaaataaa atctatattt ttgtgaaggg tagtggtact
11461 atactgtaga tttcagtagt ttctaagtct gttattgttt tgttaacaat ggcaggtttt
11521 acacgtctat gcaattgtac aaaaaagtta aaagaaaaca tgtaaaatct tgatagctaa
11581 ataacttgcc atttctttat atggaacgca ttttgggttg tttaaaaatt tataacagtt
11641 ataagagag attgtaaact aaagtgtgct ttataaaaaa agttgtttat aaaaacccct
11701 aaacaaatac acacgcacac acacacacac acacacacac acacacacac gcacacatac
11761 atgcacgaac ccaccacaca cacacacaca cacacacaca ctgaggcagc acattgtttt
11821 gcattacttt agcgtggtat tcatatggaa ttcatgacgt ttttttattt tcttgcatac
11881 gaacccacc aaatgactgc ttcatattgc tcttttgaga attgttgact gagtggggct
11941 ggctatgggc tttcatttta tacatctata tgtctacaag tatataaata ctataggtat
12001 atagataaat agatatgaag ttacttcttc aaatgttctt gccacttcct aatggaaatt
12061 gcttctagtc atctgggctt atctgcttgg gcaagagtga attttccctg gagcccaaag
12121 ccaggagact accgccacac taaaatattg tctagggctc cagatgtttc tagttttaaa
12181 ctttccactg agagctagag gattcatttt tttcaaggaa catgcgaatg aatacacagg
12241 acttactatc atagtaattt gttggctgat atattcaact tcctactgtt gggttatatt
12301 taatgatgtt tctgcaatag aacatcagat gacatttta actcccagac agtaggagga
12361 agatggtagg agctaaaggt tgcggctcct cagtcaattt atatgagggg agcaacaact
12421 ctgtaaaaga atggatgaat atttacaact atacatataa acatctctat aattacaact
12481 aaattgttct gccctcttca taaactcaac ctgaagtggg tggtttgtt gttgttgttg
12541 ttgttgttgt tgatgatgat gatgaatttt agattttaga ttttttgggt ttttttttct
12601 tcattgtgat gattttttt tttaatgctg caagacttag gattactgtt aagaaagtaa
12661 cccaatcaca ttgtgaccct ggtgaatatc agtccagaag cccatgaact gcatttgtct
12721 cctttgcatt ggtttccctg caagtaactc cacacaggat tgtgggtgag aaggcacagt
12781 ggttggaaag ttttgagagc aaaagcgtct ccaaactctc tggtctagtt gacgggctga
12841 aatgtctaaa caaatgcaag tcattgaacc aggagaaaaa gtgcaacaga aagctaagga
12901 ctgctaggaa gagctttact cctctcatgc cagtttcttc ttcttagcat ttaaagagca
12961 ttctctcaat agaaatcact gtcctatcat tttgcaaatc tgttacctct aacgtcaagt
13021 gtaattaact tctagcgagt gggttttgtc cattattaat tgtaattaac atcaaacaca
13081 gcttctcatg ctatttctac ctcactttgg ttttggggtg tttctagtaa ttgtgcacac
13141 ctaatttcac aacttcacca cttgtctgtt gtgtggacac cagtttcctt ttttcattta
13201 taatttccaa aagaaaaccc aaagctctaa gataacaaat tgaaatttgg ttctggtctt
13261 gcttttctct ctctctctcc tttatgtggc actgggcatt ttctttatcc aaggatttgt
13321 tttcaccaag atttaaaaca aggggttcct ttcctactaa gaagttttaa gtttcattct
13381 aaaatccaag gtagatagag tgcatagttt tgttttaatc ttttcgtttt atctttttaga
13441 tattagttct ggagtgaatc tatcaaaata tttgaataaa aactgagagc tttattgctg
13501 attttaagca taatttggac atcatttcat gttctttata accatcaagt attaaagtgt
13561 aaatcataat cagtgtaact gaagcataat catcacatgg catgtatcat cattgtctcc
13621 aggtactgga ctcttacttg agtatcataa tagattgtgt tttaacacca acactgtaac
13681 atttactaat tattttttta aacttcagtt ttactgcatt ttcacaacat atcagatttc
13741 accaaatata tgccttacta ttgtattata ttactgcttt actgtgtatc tcaataaagc
13801 acgcagttat gttac
```

FIGURE 3  (Human Utrophin cDNA, Acc. No. X69086, SEQ ID NO:3)

```
   1 atggccaagt atggagaaca tgaagccagt cctgacaatg ggcagaacga attcagtgat
  61 atcattaagt ccagatctga tgaacacaat gacgtacaga agaaaaccTt taccaaatgg
 121 ataaatgctc gattttcaaa gagtgggaaa ccacccatca atgatatgtt cacagacctc
 181 aaagatggaa ggaagctatt ggatcttcta gaaggcctca caggaacatc actgccaaag
 241 gaacgtggtt ccacaagggt acatgcctta ataacgtca acagagtgct gcaggtttta
 301 catcagaaca atgtggaatt agtgaatata gggggaactg acattgtgga tggaaatcac
 361 aaactgactt tggggttact ttggagcatc attttgcact ggcaggtgaa agatgtcatg
 421 aaggatgtca tgtcggacct gcagcagacg aacagtgaga agatcctgct cagctgggtg
 481 cgtcagacca ccaggcccta cagccaagtc aacgtcctca acttcaccac cagctggaca
 541 gatggactcg cctttaatgc tgtcctccac cgacataaac ctgatctctt cagctgggat
 601 aaagttgtca aatgtcacc aattgagaga ctgaacatg ccttcagcaa ggctcaaact
 661 tatttgggaa ttgaaaagct gttagatcct gaagatgttg ccgttcggct tcctgacaag
 721 aaatccataa ttatgtattt aacatctttg tttgaggtgc tacctcagca agtcaccata
 781 gacgccatcc gtgaggtaga gacactccca aggaaatata aaaagaatg tgaagaagag
 841 gcaattaata tacagagtac agcgcctgag gaggagcatg agagtcccg agctgaaact
 901 cccagcactg tcactgaggt cgacatggat ctggacagct atcagattgc gttggaggaa
 961 gtgctgacct ggttgctttc tgctgaggac acttccagg agcaggatga tatttctgat
1021 gatgttgaag aagtcaaaga ccagtttgca acccatgaag cttttatgat ggaactgact
1081 gcacaccaga gcagtgtggg cagcgtcctg caggcaggca accaactgat aacacaagga
1141 actctgtcag acgaagaaga atttgagatt caggaacaga tgaccctgct gaatgctaga
1201 tgggaggctc ttagggtgga gagtatggac agacagtccc ggctgcacga tgtgctgatg
1261 gaactgcaga agaagcaact gcagcagctc tccgcctggt taacactcac agaggagcgc
1321 attcagaaga tggaaacttg cccctggat gatgatgtaa aatctctaca aaagctgcta
1381 gaagaacata aaagtttgca aagtgatctt gaggctgaac aggtgaaagt aaattcacta
1441 actcacatgg tggtcattgt tgatgaaaac agtggtgaga gcgctacagc tatcctagaa
1501 gaccagttac agaaacttgg tgagcgctgg acagcagtat gccgttggac tgaagaacgc
1561 tggaataggt tacaagaaat caatatattg tggcaggaat tattggaaga acagtgcttg
1621 ttgaaagctt ggttaaccga aaaagaagag gctttaaata agtccagac aagcaacttc
1681 aaagaccaaa aggaactaag tgtcagtgtt cgacgtctgg ctattttgaa ggaagacatg
1741 gaaatgaagc gtcaaacatt ggatcagctg agtgagattg ccaggatgt gggacaatta
1801 cttgataatt ccaaggcatc taagaagatc aacagtgact cagaggaact gactcaaaga
1861 tgggattctt tggtcagag actagaagat tcctccaacc aggtgactca ggctgtagca
1921 aagctgggga tgtctcagat tcctcagaag gacctttgg agactgttcg tgtaagagaa
1981 caagcaatta caaaaaatc taagcaggaa ctgcctcctc ctcctccccc aaagaagaga
2041 cagatccatg tggatattga agctaagaaa aagtttgatg ctataagtgc agagctgttg
2101 aactggattt tgaaatggaa aactgccatt cagaccacag agataaaaga gtatatgaag
2161 atgcaagaca cttccgaaat gaaaagaag ttgaaggcat tagaaaaaga acagagagaa
2221 agaatcccca gagcagatga attaaaccaa actggacaaa tccttgtgga gcaaatggga
2281 aaagaaggcc ttcctactga gaaaataaaa aatgttctgg agaaggtttc atcagaatgg
2341 aagaatgtat ctcaacattt ggaagatcta gaaagaaga ttcagctaca ggaagatata
2401 aatgcttatt tcaagcagct tgatgagctt gaaaaggtca tcaagacaaa ggaggagtgg
2461 gtaaaacaca cttccatttc tgaatcttcc ggcagtcct tgccaagctt gaaggattcc
2521 tgtcagcggg aattgacaaa tcttcttggc cttcacccca aaattgaaat ggctcgtgca
2581 agctgctcgg ccctgatgtc tcagccttct gccccagatt ttgtccagcg ggcttcgat
2641 agctttctgg ccgctacca agctgtacaa gaggctgtag aggatcgtca acaacatcta
2701 gagaatgaac tgaagggcca acctggacat gcatatctgg aaacattgaa aacactgaaa
2761 gatgtgctaa atgattcaga aaataaggcc aggtgtctc tgaatgtcct taatgatctt
2821 gccaaggtgg agaaggcccT gcaagaaaaa aagaccttg atgaaatcct tgagaatcag
2881 aaacctgcat tacataaact tgcagaagaa acaaaggctc tggagaaaaa tgttcatcct
2941 gatgtagaaa aattatataa gcaagaattt gatgatgtgc aaggaaagtg aacaagcta
3001 aaggtcttgg tttccaaaga tctacatttg ctTgaggaaa ttgctctcac actcagagct
3061 tttgaggccg attcaacagt cattgagaag tggatggatg cgtgaaaga cttcttaatg
3121 aaacagcagg ctgcccaagg agacgacgca ggtcatcaga ggcagttaga ccagtgctct
3181 gcatttgtta atgaaataga aacaattgaa tcatctctga aaaacatgaa ggaaatagag
3241 actaatcttc gaagtggtcc agttgctgga ataaaaactt gggtgcagac aagactaggt
3301 gactaccaaa ctcaactgga gaaacttagc aaggagatcg ctactcaaaa aagtaggttg
3361 tctgaaagtc aagaaaaagc tgcgaacctg aagaaagact ggcagagat gcaggaatgg
3421 atgaaccagg ccgaggaaga atttggag cgggattttg agtacaagtc accagaagag
3481 cttgagagtg ctgtggaaga gatgaagagg gcaaaagagg atgtgttgca gaaggaggtg
3541 agagtgaaga tttcaaggga caacatcaag ttattagctg ccaaggtgcc ctctggtggc
3601 caggagttga cgtctgagct gaatgttgtg ctggagaatt accaacttct ttgtaataga
```

FIGURE 3 (cont.)

```
3661 attcgaggaa agtgccacac gctagaggag gtctggtctt gttggattga actgcttcac
3721 tatttggatc ttgaaactac ctggttaaac actttggaag agcggatgaa gagcacagag
3781 gtcctgcctg agaagacgga tgctgtcaac gaagccctgg agtctctgga atctgttctg
3841 cgccacccgg cagataatcg cacccagatt cgagagcttg gccagactct gattgatggg
3901 gggatcctgg atgatataat cagtgagaaa ctggaggctt tcaacagccg atatgaagat
3961 ctaagtcacc tggcagagag caagcagatt tctttggaaa agcaactcca ggtgctgcgg
4021 gaaactgacc agatgcttca agtcttgcaa gagagcttgg gggagctgga caaacagctc
4081 accacatacc tgactgacag gatagatgct ttccaagttc cacaggaagc tcagaaaatc
4141 caagcagaga tctcagccca tgagctaacc ctagaggagt tgagaagaaa tatgcgttct
4201 cagcccctga cctcccaga gagtaggact gccagaggag gaagtcagat ggatgtgcta
4261 cagaggaaac tccgagaggt gtccacaaag ttccagcttt tccagaagcc agctaacttc
4321 gagcagcgca tgctggactg caagcgtgtg ctggatggcg tgaaagcaga acttcacgtt
4381 ctggatgtga aggacgtaga ccctgacgtc atacagacgc acctggacaa gtgtatgaaa
4441 ctgtataaaa ctttgagtga agtcaaactt gaagtggaaa ctgtgattaa aacaggaaga
4501 catattgtcc agaaacagca aacggacaac ccaaaaggga tggatgagca gctgacttcc
4561 ctgaaggttc tttacaatga cctggcgca caggtgacag aaggaaaaca ggatctggaa
4621 agagcatcac agttggcccg gaaaatgaag aaagaggctg ctctctctc tgaatggctt
4681 tctgctactg aaactgaatt ggtacagaag tccacttcag aaggtctgct tggtgacttg
4741 gatacagaaa tttcctgggc taaaaatgtt ctgaaggatc tggaaaagag aaaagctgat
4801 ttaaatacca tcacagagag tagtgctgcc ctgcaaaact tgattgaggg cagtgagcct
4861 attttagaag agaggctctg cgtccttaac gctgggtgga gccgagttcg tacctggact
4921 gaagattggt gcaataccct gatgaaccat cagaaccagc tagaaatatt tgatgggaac
4981 gtggctcaca taagtacctg gctttatcaa gctgaagctc tattggatga aattgaaaag
5041 aaaccaacaa gtaaacagga agaaattgtg aagcgtttag tatctgagct ggatgatgcc
5101 aacctccagg ttgaaaatgt ccgcgatcaa gcccttattt tgatgaatgc ccgtggaagc
5161 tcaagcaggg agcttgtgga accaaagtta gctgagctga ataggaactt tgaaaaggtg
5221 tctcaacata tcaaaagtgc caaattgcta attgctcagg aaccattata ccaatgtttg
5281 gtcaccactg aaacatttga aactggtgtg cctttctctg acttggaaaa attagaaaat
5341 gacatagaaa atatgttaaa atttgtggaa aaacacttgg aatccagtga tgaagatgaa
5401 aagatggatg aggagagtgc ccagattgag gaagttctac aagaggaga agaaatgtta
5461 catcaaccta tggaagataa taaaaaagaa aagatccgtt tgcaattatt acttttgcat
5521 actagataca acaaaattaa ggcaatccct attaacaga ggaaaatggg tcaacttgct
5581 tctggaatta gatcatcact tcttcctaca gattatctgg ttgaaattaa caaaattta
5641 ctttgcatgg atgatgttga attatcgctt aatgttccag agctcaacac tgctatttac
5701 gaagacttct cttttcagga agactctctg aagaatatca aagaccaact ggacaaactt
5761 ggagagcaga ttgcagtcat tcatgaaaaa cagccagatg tcatccttga agcctctgga
5821 cctgaagcca ttcagatcag agatacactt actcagctga atgcaaaatg ggacagaatt
5881 aatagaatgt acagtgatcg gaaaggttgt tttgacaggg caatgaaaga atggagacag
5941 ttccattgtg accttaatga cctcacacag tggataacag aggctgaaga attactggtt
6001 gatacctgtg ctccaggtgg cagcctggac ttagagaaag ccaggataca tcagcaggaa
6061 cttgaggtgg gcatcagcag ccaccagccc agttttgcag cactaaaccg aactggggat
6121 gggattgtgc agaaactctc ccaggcagat ggaagcttct tgaaagaaaa actggcaggt
6181 ttaaaccaac gctgggatgc aattgttgca gaagtgaagg ataggcagcc aaggctaaaa
6241 ggagaaagta agcaggtgat gaagtacagg catcagctag atgagattat ctgttggtta
6301 acaaaggctg agcatgctat gcaaagaga tcaaccaccg aattgggaga aaacctgcaa
6361 gaattaagag acttaactca agaaatggaa gtacatgctg aaaaactcaa atggctgaat
6421 agaactgaat tggagatgct ttcagataaa agtctgagtt tacctgaaag ggataaaatt
6481 tcagaaagct taaggactgt aaatatgaca tggaataaga tttgcagga ggtgcctacc
6541 accctgaagg aatgcatcca ggagcccagt tctgtttcac agacaaggat tgctgctcat
6601 cctaatgtcc aaaaggtggt gctagtatca tctgcgtcag atattcctgt tcagtctcat
6661 cgtacttcgg aaatttcaat tcctgctgat cttgataaaa ctataacaga actagccgac
6721 tggctggtat taatcgacca gatgctgaag tccaacattg tcactgttgg ggatgtagaa
6781 gagatcaata gaccgtttc ccgaatgaaa attacaaagg ctgacttaga acagcgccat
6841 cctcagctgg attatgtttt tacattggca cagaatttga aaataaagc ttccagttca
6901 gatatgagaa cagcaattac agaaaaattg gaaagggtca agaaccagtg ggatggcacc
6961 cagcatggcg ttgagctaag acagcagcag cttgaggaca tgattattga cagtcttcag
7021 tgggatgacc ataggagga gactgaagaa ctgatgagaa atatgaggc tcgactctat
7081 attcttcagc aagcccgacg ggatccactc accaaaacaaa tttctgataa ccaaatactg
7141 cttcaagaac tgggtcctgg agatggtatc gtcatggcgt tcgataacgt cctgcagaaa
7201 ctcctggagg aatatgggag tgatgacaca aggaatgtga aagaaaccac agagtactta
7261 aaaacatcat ggatcaatct caaacaaagt attgctgaca gacagaacgc cttgagggct
7321 gagtggagga cggtgcaggc ctctcgcaga gatctggaaa acttcctgaa gtggatccaa
7381 gaagcagaga ccacagtgaa tgtgcttgtg gatgcctctc atcgggagaa tgctcttcag
7441 gatagtatct tggccaggga actcaaacag cagatgcagg acatccaggc agaaattgat
```

FIGURE 3 (cont.)

```
 7501 gcccacaatg acatatttaa aagcattgac ggaaacaggc agaagatggt aaaagctttg
 7561 ggaaattctg aagaggctac tatgcttcaa catcgactgg atgatatgaa ccaaagatgg
 7621 aatgacttaa aagcaaaatc tgctagcatc agggcccatt tggaggccag cgctgagaag
 7681 tggaacaggt tgctgatgtc cttagaagaa ctgatcaaat ggctgaatat gaaagatgaa
 7741 gagcttaaga aacaaatgcc tattggagga gatgttccag ccttacagct ccagtatgac
 7801 cattgtaagg ccctgagacg ggagttaaag gagaaagaat attctgtcct gaatgctgtc
 7861 gaccaggccc gagtttttctt ggctgatcag ccaattgagg ccctgaaga gccaagaaga
 7921 aacctacaat caaaaacaga attaactcct gaggagagag cccaaaagat tgccaaagcc
 7981 atgcgcaaac agtcttctga agtcaaagaa aaatgggaaa gtctaaatgc tgtaactagc
 8041 aattggcaaa agcaagtgga caaggcattg gagaaactca gagacctgca gggagctatg
 8101 gatgacctgg acgctgacat gaaggaggca gagtccgtgc ggaatggctg gaagcccgtg
 8161 ggagacttac tcattgactc gctgcaggat cacattgaaa aaatcatggc atttagagaa
 8221 gaaattgcac caatcaactt taagttaaa acggtgaatg atttatccag tcagctgtct
 8281 ccacttgacc tgcatccctc tctaaagatg tctcgccagc tagatgacct taatatgcga
 8341 tggaaacttt tacaggtttc tgtggatgat cgccttaaac agcttcagga agcccacaga
 8401 gatttggac catcctctca gcatttctc tctacgtcag tccagctgcc gtggcaaaga
 8461 tccatttcac ataataaagt gccctattac atcaaccatc aaacacagac cacctgttgg
 8521 gaccatccta aaatgaccga actctttcaa tcccttgctg acctgaataa tgtacgtttt
 8581 tctgcctacc gtacagcaat caaatccga agactacaaa aagcactatg tttggatctc
 8641 ttagagttga gtacaacaaa tgaattttc aaacagcaca agttgaacca aaatgaccag
 8701 ctcctcagtg ttccagatgt catcaactgt ctgacaacaa cttatgatgg acttgagcaa
 8761 atgcataagg acctggtcaa cgttccactc tgtgttgata tgtgtctcaa ttggttgctc
 8821 aatgtctatg acacgggtcg aactggaaaa attagagtgc agagtctgaa gattggatta
 8881 atgtctctct ccaaaggtct cttggaagaa aaatacagat atctctttaa ggaagttgcg
 8941 gggccgacag aaatgtgtga ccagaggcag ctgggcctgt tacttcatga tgccatccag
 9001 atcccccggc agctaggtga agtagcagct tttggaggca gtaatattga gcctagtgtt
 9061 cgcagctgct tccaacagaa taacaataaa ccagaaataa gtgtgaaaga gtttatagat
 9121 tggatgcatt tggaaccaca gtccatggtt tggctcccag ttttacatcg agtggcagca
 9181 gcggagactg caaaacatca ggccaaatgc aacatctgta aagaatgtcc aattgtcggg
 9241 ttcaggtata gaagccttaa gcattttaac tatgatgtct gccagagttg tttcttttcg
 9301 ggtcgaacag caaaaggtca caaattacat tacccaatgg tggaatattg tatacctaca
 9361 acatctgggg aagatgtacg agacttcaca aaggtactta gaacaagtt caggtcgaag
 9421 aagtactttg ccaaacaccc tcgacttggt tacctgcctg tccagacagt tcttgaaggt
 9481 gacaacttag agactcctat cacactcatc agtatgtggc cagcacta tgaccctca
 9541 caatctcctc aactgtttca tgatgacacc cattcaagaa tagaacaata tgccacacga
 9601 ctggcccaga tggaaggac taatgggtct tttctcactg atagcagctc caccacagga
 9661 agtgtggaag acgagcacgc cctcatccag cagtattgcc aaacactcgg aggagagtcc
 9721 ccagtgagcc agccgcagag cccagctcag atcctgaagt cagtagagag ggaagaacgt
 9781 ggagaactgg agaggatcat tgctgacctg gaggaagaac aaagaaatct acaggtggag
 9841 tatgagcagc tgaaggacca gcacctccga aggggggcaac ctgtcggttc accgccagag
 9901 tcgattatat ctccccatca cacgtctgag gattcagaac ttatagcaga agcaaaactc
 9961 ctcaggcagc acaaaggtcg gctggaggct aggatgcaga ttttagaaga tcacaataaa
10021 cagctggagt ctcagctcca ccgcctccga cagctgctgg agcagcctga atctgattcc
10081 cgaatcaatg gtgtttcccc atgggcttct cctcagcatt ctgcactgag ctactcgctt
10141 gatccagatg cctccggccc acagttccac caggcagcgg gagaggacct gctggcccca
10201 ccgcacgaca ccagcacgga tctcacggag gtcatggagc agattcacag cacgtttcca
10261 tcttgctgcc caaatgttcc cagcaggcca caggcaatgt ga
```

FIGURE 4  (Mouse Utrophin cDNA, Acc. No. Y12229, SEQ ID NO:4)

```
   1 atggccaagt atggggacct tgaagccagg cctgatgatg ggcagaacga attcagtgac
  61 atcattaagt ccagatctga tgaacacaat gatgtacaga agaaaacctt taccaaatgg
 121 ataaacgctc gatttccaa gagtgggaaa ccacccatca gtgatatgtt ctcagacctc
 181 aaagatggga gaaagctctt ggatcttctc gaaggcctca caggaacatc attgccaaag
 241 gaacgtggtt ccacaagggt gcatgcctta acaatgtca accgagtgct acaggtttta
 301 catcagaaca atgtggactt ggtgaatatt ggaggcacgg acattgtggc tggaaatccc
 361 aagctgactt tagggttact ctggagcatc attctgcact ggcaggtgaa ggatgtcatg
 421 aaagatatca tgtcagacct gcagcagaca aacagcgaga agatcctgct gagctgggtg
 481 cggcagacca ccaggcccta cagtcaagtc aacgtcctca acttcaccac cagctggacc
 541 gatggactcg cgttcaacgc cgtgctccac cggcacaaac cagatctctt cgactgggac
 601 gagatggtca aaatgtcccc aattgagaga cttgaccatg cttttgacaa ggcccacact
 661 tctttgggaa ttgaaaagct cctaagtcct gaaactgttg ctgtgcatct ccctgacaag
 721 aaatccataa ttatgtattt aacgtctctg tttgaggtgc ttcctcagca agtcacgata
 781 gatgccatcc gagaggtgga gactctccca aggaagtata agaagaatg tgaagaggaa
 841 gaaattcata tccagagtgc agtgctggca gaggaaggcc agagtccccg agctgagacc
 901 cctagcaccg tcactgaagt ggacatggat ttggacagct accagatagc gctagaggaa
 961 gtgctgacgt ggctgctgtc cgcggaggac acgttccagg agcaacatga catttctgat
1021 gatgtcgaag aagtcaaaga gcagtttgct acccatgaaa ctttatgat ggagctgaca
1081 gcacaccaga gcagcgtggg gagcgtcctg caggctggca accagctgat gacacaaggg
1141 actctgtcca gagaggagga gtttgagatc caggaacaga tgaccttgct gaatgcaagg
1201 tgggaggcgc tccgggtgga gagcatggag aggcagtccc ggctgcacga cgctctgatg
1261 gagctgcaga gaaacagct gcagcagctc tcaagctggc tggccctcac agaagagcgc
1321 attcagaaga tggagagcct cccgctgggt gatgacctgc cctccctgca gaagctgctt
1381 caagaacata aagtttgca aaatgacctt gaagctgaac aggtgaaggt aaattcctta
1441 actcacatgg tggtgattgt ggatgaaaac agtgggggaga gtgccacagc tcttctggaa
1501 gatcagttac agaaactggg tgagcgctgg acagctgtat gccgctggac tgaagaacgt
1561 tggaacaggt tgcaagaaat cagtattctg tggcaggaat tattggaaga gcagtgtctg
1621 ttggaggctt ggctcaccga aaaggaagag gctttggata aagttcaaac cagcaacttt
1681 aaagaccaga aggaactaag tgtcagtgtc cggcgtctgg ctatattgaa ggaagacatg
1741 gaaatgaaga ggcagactct ggatcaactg agtgagattg gccaggatgt gggccaatta
1801 ctcagtaatc ccaaggcatc taagaagatg aacagtgact ctgaggagct aacacagaga
1861 tgggattctc tggttcagag actcgaagac tcttctaacc aggtgactca ggcggtagcg
1921 aagctcggca tgtccagat tccacagaag gacctattgg agaccgttca tgtgagagaa
1981 caagggatgg tgaagaagcc caagcaggaa ctgcctcctc ctcccccacc aaagaagaga
2041 cagattcacg tggacgtgga ggccaagaaa aagtttgatg ctataagtac agagctgctg
2101 aactggattt tgaaatcaaa gactgccatt cagaacacag agatgaaaga atataagaag
2161 tcgcaggaga cctcaggaat gaaaaagaaa ttgaagggat tagagaaaga acagaaggaa
2221 aatctgcccc gactggacga actgaatcaa accggacaaa ccctccggga gcaaatggga
2281 aaagaaggcc ttccactgaa agaagtaaac gatgttctgg aaagggtttc gttggagtgg
2341 aagatgatat ctcagcagct agaagatctg ggaaggaaga tccagctgca ggaagatata
2401 aatgcttatt ttaagcagct tgatgccatt gaggagacca tcaaggagaa ggaagagtgg
2461 ctgaggggca cacccatttc tgaatcgccc cggcagccct tgccaggctt aaaggattct
2521 tgccagaggg aactgacaga tctccttggc cttcacccca gaattgagac gctgtgtgca
2581 agctgttcag ccctgaagtc tcagccctgt gtccaggtt ttgtccagca gggtttttgac
2641 gaccttcgac atcattacca ggctgttgcg aaggctttag aggaatacca acaacaacta
2701 gaaaatgagc tgaagagcca gcctggaccc gagtatttgg acacactgaa taccctgaaa
2761 aaaatgctaa gcgagtcaga aaaggcggcc caggcctctc tgaatgccct gaacgatccc
2821 atagcggtgg agcaggccct gcaggagaaa aaggcccttg atgaaccct tgagaatcag
2881 aaacatacgt tacataagct ttcagaagaa acgaagactt tggagaaaaa tatgcttcct
2941 gatgtgggga aaatgtataa acaagaattt gatgatgtcc aaggcagatg gaataaagta
3001 aagaccaagg tttccagaga cttacacttg ctcgaggaaa tcaccccag actccgagat
3061 tttgaggctg attcagaagt cattgagaag tgggtgagtg gcatcaaaga cttcctcatg
3121 aaagaacagg ctgcccaagg agacgctgct gcgcagagcc agcttgacca atgtgctacg
3181 tttgctaatg aaatcgaaac catcgagtca tctctgaaga acattgaggga agtagagact
3241 agccttcaga ggtgtccagt cactggagtc aagacatggg tacaggcaag actagtggat
3301 taccaatccc aactggagaa attcagcaaa gagattgcta ttcaaaaaag caggctgtta
3361 gatagtcaag aaaaagccct gaacttgaaa aaggatttgg ctgagatgca ggagtggatg
3421 gcacaggctg aagaggacta cctggagagg gacttcgagt acaaatctcc agaagaactc
3481 gagagtgcgg tggaggaaat gaagagggca aaaagggatg tgctgcagaa ggaggtgagg
3541 gtgaaaattc tgaaggacag catcaagctg gtggctgcca aggtgccctc tggtggccag
3601 gagttgacgt cggaattcaa cgaggtgctg gagagctacc agcttctgtg caatagaatt
```

FIGURE 4 (cont.)

```
3661 cgagggaagt gccacacact ggaggaggtc tggtcttgct gggtggagct gcttcactat
3721 ctggacctgg agaccacgtg gttgaacacc ttggaggagc gcgtgaggag cacggaggcc
3781 ctgcctgaga gggcagaagc tgttcatgaa gctctggagt ctcttgagtc tgttttgcgc
3841 catccagcgg ataatcgcac ccagattcgg gaacttgggc agactctgat tgatggtgga
3901 atcctggatg acataatcag cgagaagctg gaggctttta acagccgcta cgaagagctg
3961 agtcacttgg cggagagcaa acagatttct ttggagaagc aactccaggt cctccgcgaa
4021 actgaccaca tgcttcaggt gctgaaggag agcctggggg agctggacaa acagcttacc
4081 acatacctga cggacaggat cgatgccttc caactgccac aggaagctca gaagatccaa
4141 gccgaaatct cagcccatga gctcaccctg gaggagctga ggaagaatgt gcgctcccag
4201 cccccgacgt ccctgaggg cagggccacc agaggaggaa gtcagatgga catgctacag
4261 aggaaacttc gagaggtctc caccaaattc cagcttttcc agaagcccgc aaatttcgag
4321 cagcggatgc tggactgcaa gcgtgtgttg gagggagtga aggccgagct tcatgtcctc
4381 gatgtgaggg atgtgaccc tgatgtcatt caggcccact tggacaagtg catgaaacta
4441 tataaaacgt tgagtgaagt caaacttgaa gttgagactg tcatcaaaac agggaggcac
4501 attgtccaga agcagcagac ggacaacccg aaaagcatgg acgaacagct tacatctctg
4561 aaagtcctct acaatgacct gggcgcacag gtgacagaag ggaagcaaga cctggaaaga
4621 gcctcacagc tgtccaggaa gatgaagaag gaggctgccg tcctctctga atggctctct
4681 gccacagagg cagaactagt gcagaaatcc acatcagaag gcgtgattgg tgacctggac
4741 acagaaatct cctgggctaa aagtattctc aaggatctgg aaaagaggaa agttgactta
4801 aatggcatta cagagagcag tgctgccctt cagcacttgg tcttgggcag tgagtctgtt
4861 ctggaagaga acctctgtgt gctcaatgct ggatggagcc gagtgcggac gtggaccgaa
4921 gactggtgca acaccttgct gaaccatcaa aaccagctgg agctatttga tggacacgtc
4981 gctcacatca gtacctggct ctatcaagca gaagctctgc tggatgagat cgaaaagaaa
5041 ccagcgagta aacaggaaga aattgtgaag cgtttactgt ctgaattgga tgatgccagc
5101 ctccaggttg agaatgttcg ggaacaagcc atcatcttgt tgaatgctcg tggaagcgcc
5161 agcagggaac tcgtggaacc aaaattagcc gagctgagca ggaacttgca aaggtgtcc
5221 cagcacataa agagcgcccg aatgctgatt ggtcaggacc cttcatccta ccaaggcttg
5281 gaccctgctg gaactgttca agctgctgag tctttctctg acttggaaaa cttagaacaa
5341 gacatagaaa acatgttgaa agttgtggaa aagcacttgg accccaataa cgatgagaag
5401 atggatgagg agcaagccca gattgaggaa gttctacaaa gaggggagca tttgttacat
5461 gaacctatgg aggacagtaa gaaagaaaag atccgcttgc agttgttact tttgcatact
5521 cgttacaaca aaattaagac aatccctatc cagcagagaa aaacaattcc agtttcttct
5581 ggaattacat catcagccct ccctgcagat tatttggttg aaattaataa aattttactc
5641 actctggatg acattgaatt atcacttaat atgccggagc taaacaccac tgtctacaaa
5701 gacttctctt tccaggaaga ctctctgaag agtatcaaag gtcaactgga cagacttgga
5761 gagcagattg cagttgttca cgagaagcag ccggatgtca tcgtggaagc ctctggccct
5821 gaggccattc agatcaggga catgctcgct cagctgaacg caaaatggga ccgagtgaat
5881 agagtgtaca gtgatcggag agggtccttt gccagggctg tggaggaatg gaggcagttc
5941 caccatgacc ttgatgacct tacacagtgg ctatctgaag ctgaagacct gctggtagac
6001 acttgtgctc cagatggtag cctggacctg gagaaagcca gggcacagca gctggaactg
6061 gaagagggcc tcagcagcca ccagcccagc ctgatcaagg ttaaccgaaa gggggaggac
6121 cttgttcaga gactccgccc ctcggaggca agcttcctga aggagaagct ggcaggtttc
6181 aaccagcgct ggagcactct tgtagctgag gtggaggctt tgcagcccag gctaaaagga
6241 gaaagtcagc aggtgttggg gtataagaga cggctagatg aggtcacctg ctggttaacg
6301 aaagtggaga gtgctgtgca gaagagatca acccctgacc cggaagaaag cccacaggaa
6361 ttaacagatt tagcccaaga gacggaagtt caagctgaaa acattaagtg gctgaacaga
6421 gcagaactgg aaatgctttc agacaaaaat ctgagtttgc gtgaaagaga gaaactttcg
6481 gaaagtttaa agaatgtaaa cacaacatgg accaaggtat gcagagaagt gcctagcctc
6541 ctgaagacac gcaccaaga cccctgcta gccccacaga cagaggatgg tgctcatccc
6601 aacgtccaaa aggtggtgct agtatcatct gcatcagatg ctcctctgcg tggcggcctg
6661 gaaatctcgg ttcctgctga tttggataaa accatcacag aactggctga ctggctggta
6721 ttgatcgacc aaatgctgaa gtccaacatt gtcactgtgg gggacgtgaa agagatcaat
6781 aagacagttt cccggatgaa aatcacaaag gctgatttag aacaacgcca tcctcagctt
6841 gattgtgtat ttacgttggc ccaaaatttg aaaaacaaag cttccagttc agatgtgaga
6901 acagcaatca cagaaaaatt ggaaagctg aagacccagt gggagagtac tcagcatggt
6961 gtggagctgc ggcggcagca gctggaggac atggttgtgg acagcctgca gtgggacgac
7021 cacagggaag agactgaaga gctcatgaga aaatacgagg ctcgcttcta catgctgcag
7081 caggcccgcc gggacccact tagcaaacaa gtttctgata tcaactatt gcttcaagag
7141 ctggggtctg gcgatggtgt catcatggcg ttgataatg tcctgcagaa acttctggaa
7201 gaatacagtg gcgatgacac aaggaatgtg gaagaaacca cggagtactg gaaaacatca
7261 tggtcaatc tcaaacaaag catcgctgat agacagagtg ccttggaggc tgagctacag
7321 acagtgcaga cttctcgtag agacctggat aactttgtca gtggcttca ggaagcagaa
7381 accacagcaa atgtgctggc cgatgcctct cagcgggaga atgctcttca ggacagtgtc
7441 ctggcccggc agctccgaca gcagatgctg gacatccagg cagaaattga tgcccacaat
```

FIGURE 4 (cont.)

```
7501 gacatattta aaagcatcga tggaaaccgg cagaagatgg tgaaagctct ggggaattct
7561 gaggaagcaa caatgcttca acatcgactg gatgacatga accaaagatg gaatgatttg
7621 aaggcaaaat ctgctagcat cagggcccat ttggaggcca gtgctgagaa atggaaccgg
7681 ttgctggcat cgctggaaga gctgatcaaa tggctcaata tgaaagatga ggagcttaag
7741 aagcagatgc ccattggagg ggacgtccct gccttacagc tccagtatga ccactgcaag
7801 gtgctgagac gtgagctaaa ggagaaagag tattctgtgc tgaacgccgt agatcaagct
7861 cgagtttttc tggctgatca gccaatagag gcccccgaag aaccaagaag aaacccacaa
7921 tcaaagacag agttgactcc tgaggagaga gcccagaaga tcgccaaagc catgcgcaag
7981 cagtcttctg aagtccgaga gaagtgggaa aatctaaatg ctgtcactag caactggcaa
8041 aagcaagtag ggaaggcgtt agagaaactc cgagacctgc agggagctat ggacgacctg
8101 gacgcagaca tgaggaggt ggaggctgtg cggaatggct ggaagcccgt gggagacctg
8161 cttatagact ccctgcagga tcacatcgag aaaaccctgg cgtttagaga agaaattgca
8221 ccaatcaact aaaagtaaa aacaatgaat gacctgtcca gtcagctgtc tccacttgac
8281 ttgcatccat ctctaaagat gtctcgccag ctggatgacc ttaatatgcg atggaaactt
8341 ctacaggttt ccgtggacga tcgccttaag cagctccagg aagcccacag agattttggg
8401 ccatcttctc aacactttct gtccacttca gtccagctgc cgtggcagag atccatttca
8461 cataataaag tgccctatta catcaaccat caaacacaga caacctgttg ggatcatcct
8521 aaaatgactg agctcttcca atcccttgct gatctgaata atgtacgttt ctctgcctac
8581 cgcacagcaa tcaaaattcg aaggctgcaa aaagcattat gtctggatct cttagagctg
8641 aatacgacga atgaagtttt caagcagcac aaactgaacc aaaatgatca gctcctgagt
8701 gtcccagacg tcatcaactg tctgaccacc acttacgatg ggcttgagca gctgcacaag
8761 gacttggtca atgttccact ctgcgtcgat atgtgtctca actggctgct caacgtatac
8821 gacacgggcc ggactggaaa aattcgggta cagagtctga agattggatt gatgtctctc
8881 tccaaaggcc tcttagaaga gaaatacaga tgtctcttta aggaggtggc agggccaact
8941 gagatgtgtg accagcggca gcttggcctg ctacttcacg atgccatcca gatccctagg
9001 cagctggggg aagtagcagc cttttggggc agtaacattg agcccagtgt ccgcagctgc
9061 ttccagcaga ataacaacaa gccagaaatc agtgtgaagg agtttataga ctggatgcat
9121 ttggaaccc agtccatggt gtggttgccg gttctgcatc gggtcgcagc tgctgagact
9181 gcaaaacatc aggccaaatg caacatctgc aaagaatgcc cgattgttgg gttcagatac
9241 aggagcctaa agcattttaa ttatgatgtc tgccagagtt gcttctttc tggaagaaca
9301 gcaaagggcc acaagttaca ttacccgatg gtagaatact gcataccgac aacatctggg
9361 gaagatgtga gagatttcac taaggtgctg aagaacaagt tcaggtccaa gaaatatttt
9421 gccaaacatc ctcggcttgg ctacctgcct gtccagaccg tgctggaagg ggacaactta
9481 gaaactccta tcacgctcat cagtatgtgg ccagagcact atgaccctc ccagtcccct
9541 cagctgtttc atgatgacac ccactcaaga atagagcaat acgctacacg actggcccag
9601 atggaaagga caaacgggtc cttcctaact gatagcagct ctacaacagg aagcgtggag
9661 gatgagcatg ccctcatcca gcagtactgc cagaccctgg gcggggagtc acctgtgagt
9721 cagccgcaga gtccagctca gatcctgaag tccgtggaga gggaagagcg tggggaactg
9781 gagcggatca ttgctgactt ggaggaagag caaagaaatc tgcaggtgga gtatgagcag
9841 ctgaaggagc agcacctaag aagggtctc cctgtgggct cccctccaga ctccatcgta
9901 tctcctcacc acacatctga ggactcagaa cttatagcag aagctaaact cctgcggcag
9961 cacaaagggc ggctggaggc gaggatgcaa attttggaag atcacaataa acagctggag
10021 tctcagctgc accgcctcag acagctcctg gagcagcctg actctgactc ccgcatcaat
10081 ggtgtctccc ctgggcttc cccacagcat tctgcattga gctactcact tgacactgac
10141 ccaggcccac agttccacca ggcagcatct gaggacctgc tggccccacc tcacgacact
10201 agcacggacc tcacggacgt gatggagcag atcaacagca cgtttccctc ttgcagctca
10261 aatgtcccca gcaggccaca ggcaatgtga gcatctatcc agccagccaa catttcccga
10321 ccttcagtat tgccctcttc tgcaaatgcc aatcccaaga cccattcaac cccaaagctc
10381 cgtggctcca cgacacaagc tgttgagtgc ttactgggtg ttctactgag ggaaccaaac
10441 actgactatc caaagatatt ttggtttttct aataacgtat attattgttt tctttctccc
10501 ctttctatgc aactgtaaat taatgaacag agaagtattt ggaggtggta aagcatttgt
10561 cactgatttg tataatatat acagccatgg gaaagtgggt ggggcttttc taatatgaaa
10621 ctgtcttttt aataaccaag agaaaaaatt gcataagaat tagaccactt tacattatta
10681 cattccttct gctgttcaca ttaaccttgt acaataactt cacttattat ttgactgttt
10741 taccattatg ttttggttat ttataaattt atcagccata ccaaacgaat agattctatg
10801 tatttggttt ctataatctg gccaaattcc taagttcata tatttgaatc aaatatttta
10861 catatgtgga gtaggcaggc attctgaaga tactatttaa ctttagttga cgtcacacac
10921 accatccttt agtaaccact ggatgactac actaaaaatc ctgtggactt taacggcaag
10981 ctgctggggt atttttcctc ctgtttttat tccttttttg taagtagatc ttgacgtctt
11041 tatttatttc atcttgcaat ctctataata aagaagactg tattgtaata gtcccc
```

FIGURE 5

SEQ ID NO:5 (5' UTR, 1-208))
```
   1 gggattccct cactttcccc ctacaggact cagatctggg aggcaattac cttcggagaa
  61 aaacgaatag gaaaaactga agtgttactt tttttaaagc tgctgaagtt tgttggtttc
 121 tcattgtttt taagcctact ggagcaataa agtttgaaga acttttacca ggttttttt
 181 atcgctgcct tgatatacac ttttcaaa
```

SEQ ID NO:6 (N terminus, 209-964)
```
 209 at gctttggtgg gaagaagtag aggactgtta
 241 tgaaagagaa gatgttcaaa agaaaacatt cacaaatgg gtaaatgcac aattttctaa
 301 gtttgggaag cagcatattg agaacctctt cagtgaccta caggatggga ggcgcctcct
 361 agacctcctc gaaggcctga cagggcaaaa actgccaaaa gaaaaaggat ccacaagagt
 421 tcatgccctg aacaatgtca acaaggcact gcgggttttg cagaacaata atgttgattt
 481 agtgaatatt ggaagtactg acatcgtaga tggaaatcat aaactgactc ttggtttgat
 541 ttggaatata atcctccact ggcaggtcaa aaatgtaatg aaaaatatca tggctggatt
 601 gcaacaaacc aacagtgaaa agattctcct gagctgggtc cgacaatcaa ctcgtaatta
 661 tccacaggtt aatgtaatca acttcaccac cagctggtct gatggcctgg ctttgaatgc
 721 tctcatccat agtcataggc cagaccatt tgactggaat agtgtggttt gccagcagtc
 781 agccacacaa cgactggaac atgcattcaa catcgccaga tatcaattag catagagaa
 841 actactcgat cctgaagatg ttgataccac ctatccagat aagaagtcca tcttaatgta
 901 catcacatca ctcttccaag ttttgcctca acaagtgagc attgaagcca tccaggaagt
 961 ggaa
```

SEQ ID NO:7 (Hinge 1, 965-1219)
```
 965 atgttg ccaaggccac ctaaagtgac taaagaagaa cattttcagt tacatcatca
1021 aatgcactat tctcaacaga tcacggtcag tctagcacag ggatatgaga gaacttcttc
1081 ccctaagcct cgattcaaga gctatgccta cacacaggct gcttatgtca ccacctctga
1141 ccctacacgg agcccatttc cttcacagca tttggaagct cctgaagaca agtcatttgg
1201 cagttcattg atggagagt
```

SEQ ID NO:8 (Repeat 1, 1220-1546)
```
1220 g aagtaaacct ggaccgttat caaacagctt tagaagaagt
1261 attatcgtgg cttctttctg ctgaggacac attgcaagca caaggagaga tttctaatga
1321 tgtggaagtg gtgaaagacc agtttcatac tcatgagggg tacatgatgg atttgacagc
1381 ccatcagggc cgggttggta atattctaca attgggaagt aagctgattg gaacaggaaa
1441 attatcagaa gatgaagaaa ctgaagtaca agagcagatg aatctcctaa attcaagatg
1501 ggaatgcctc agggtagcta gcatggaaaa acaaagcaat ttacat
```

SEQ ID NO:9 (Repeat 2, 1547-1879)
```
1547 agag ttttaatgga
1561 tctccagaat cagaaactga aagagttgaa tgactggcta acaaaaacag aagaaagaac
1621 aaggaaaatg gaggaagagc ctcttggacc tgatcttgaa gacctaaaac gccaagtaca
1681 acaacataag gtgcttcaag aagatctaga acaagaacaa gtcagggtca ttctctcac
1741 tcacatggtg gtggtagttg atgaatctag tggagatcac gcaactgctg ctttggaaga
1801 acaacttaag gtattgggag atcgatgggc aaacatctgt agatggacag aagaccgctg
1861 ggttctttta caagacatc
```

SEQ ID NO:10 (Repeat 3, 1880-2212)
```
1880 c ttctcaaatg gcaacgtctt actgaagaac agtgcctttt
1921 tagtgcatgg ctttcagaaa aagaagatgc agtgaacaag attcacacaa ctggctttaa
1981 agatcaaaat gaaatgttat caagtcttca aaaactggcc gttttaaaag cggatctaga
2041 aagaaaaag caatccatgg gcaaactgta ttcactcaaa caagatcttc tttcaacact
2101 gaagaataag tcagtgaccc agaagacgga agcatggctg gataactttg cccggtgttg
2161 ggataattta gtccaaaaac ttgaaagag tacagcacag atttcacagg ct
```

SEQ ID NO:11 (Hinge 2, 2213-2359)
```
2213 gtcaccac
2221 cactcagcca tcactaacac agacaactgt aatggaaaca gtaactacgg tgaccacaag
2281 ggaacagatc ctggtaaagc atgctcaaga ggaacttcca ccaccacctc cccaaaagaa
2341 gaggcagatt actgtggat
```

FIGURE 6

```
SEQ ID NO:12 (Repeat 4, 2360-2692)
2360 t ctgaaattag gaaaaggttg gatgttgata taactgaact
2401 tcacagctgg attactcgct cagaagctgt gttgcagagt cctgaatttg caatctttcg
2461 gaaggaaggc aacttctcag acttaaaaga aaaagtcaat gccatagagc gagaaaaagc
2521 tgagaagttc agaaaactgc aagatgccag cagatcagct caggccctgg tggaacagat
2581 ggtgaatgag ggtgttaatg cagatagcat caaacaagcc tcagaacaac tgaacagccg
2641 gtggatcgaa ttctgccagt tgctaagtga gagacttaac tggctggagt at SEQ ID NO:13 (Repeat 5, 2693-3019)
2693 cagaacaa
2701 catcatcgct ttctataatc agctacaaca attggagcag atgacaacta ctgctgaaaa
2761 ctggttgaaa atccaaccca ccacccatc agagccaaca gcaattaaaa gtcagttaaa
2821 aatttgtaag gatgaagtca accggctatc aggtcttcaa cctcaaattg aacgattaaa
2881 aattcaaagc atagccctga aagagaaagg acaaggaccc atgttcctgg atgcagactt
2941 tgtggccttt acaaatcatt ttaagcaagt cttttctgat gtgcaggcca gagagaaaga
3001 gctacagaca attttgac SEQ ID NO:14 (Repeat 6, 3020-3346)
3020 a ctttgccacc aatgcgctat caggagacca tgagtgccat
3061 caggacatgg gtccagcagt cagaaaccaa actctccata cctcaacta gtgtcaccga
3121 ctatgaaatc atggagcaga gactcgggga attgcaggct ttacaaagtt ctctgcaaga
3181 gcaacaaagt ggcctatact atctcagcac cactgtgaaa gagatgtcga agaaagcgcc
3241 ctctgaaatt agccggaaat atcaatcaga atttgaagaa attgagggac gctggaagaa
3301 gctctcctcc cagctggttg agcattgtca aagctagag gagcaa SEQ ID NO:15 (Repeat 7, 3347-3673)
3347 atga ataaactccg
3361 aaaaattcag aatcacatac aaaccctgaa gaaatggatg gctgaagttg atgtttttct
3421 gaaggaggaa tgcctgccc ttggggattc agaaattcta aaaaagcagc tgaaacagtg
3481 cagacttta gtcagtgata ttcagacaat tcagcccagt ctaaacagtg tcaatgaagg
3541 tgggcagaag ataagaatg aagcagagcc agagtttgct tcgagacttg agacagaact
3601 caaagaactt aacactcagt gggatcacat gtgccaacag gtctatgcca gaaaggaggc
3661 cttgaaggga ggt SEQ ID NO:16 (Repeat 8, 3674-4000)
3674 ttggaga aaactgtaag cctccagaaa gatctatcag agatgcacga
3721 atggatgaca caagctgaag aagagtatct tgagagagat tttgaatata aaactccaga
3781 tgaattacag aaagcagttg aagagatgaa gagagctaaa gaagaggccc aacaaaaaga
3841 agcgaaagtg aaactcctta ctgagtctgt aaatagtgtc atagctcaag ctccacctgt
3901 agcacaagag gccttaaaaa aggaacttga aactctaacc accaactacc agtggctctg
3961 cactaggctg aatgggaaat gcaagacttt ggaagaagtt SEQ ID NO:17 (Repeat 9, 4001-4312)
4001 tgggcatgtt ggcatgagtt
4021 attgtcatac ttggagaaag caaacaagtg gctaaatgaa gtagaattta aacttaaaac
4081 cactgaaaac attcctgcg gagctgagga aatctctgag gtgctagatt cacttgaaaa
4141 tttgatgcga cattcagagg ataacccaaa tcagattcgc atattggcac agaccctaac
4201 agatggcgga gtcatggatg agctaatcaa tgaggaactt gagacattta attctcgttg
4261 gagggaacta catgaagagg ctgtaaggag gcaaaagttg cttgaacaga gc SEQ ID NO:18 (Repeat 10, 4313-4588)
4313 atccagtc
4321 tgcccaggag actgaaaaat ccttacactt aatccaggag tccctcacat tcattgacaa
4381 gcagttggca gcttatattg cagacaaggt ggacgcagct caatgcctc aggaagccca
4441 gaaatccaa tctgatttga caagtcatga gatcagttta gaagaaatga gaaacataa
4501 tcaggggaag gaggctgccc aaagagtcct gtctcagatt gatgttgcac agaaaaaatt
4561 acaagatgtc tccatgaagt ttcgatta
```

FIGURE 7

SEQ ID NO:19 (Repeat 11, 4589-4915)
```
4589 tt ccagaaacca gccaattttg agctgcgtct
4621 acaagaaagt aagatgattt tagatgaagt gaagatgcac ttgcctgcat tggaaacaaa
4681 gagtgtggaa caggaagtag tacagtcaca gctaaatcat tgtgtgaact tgtataaaag
4741 tctgagtgaa gtgaagtctg aagtggaaat ggtgataaag actggacgtc agattgtaca
4801 gaaaaagcag acggaaaatc ccaaagaact tgatgaaaga gtaacagctt tgaaattgca
4861 ttataatgag ctgggagcaa aggtaacaga aagaaagcaa cagttggaga aatgc
```

SEQ ID NO:20 (Repeat 12, 4916-5239)
```
4916 ttgaa
4921 attgtcccgt aagatgcgaa aggaaatgaa tgtcttgaca gaatggctgg cagctacaga
4981 tatggaattg acaaagagat cagcagttga aggaatgcct agtaatttgg attctgaagt
5041 tgcctgggga aaggctactc aaaaagagat tgagaaacag aaggtgcacc tgaagagtat
5101 cacagaggta ggagaggcct tgaaaacagt tttgggcaag aaggagacgt tggtggaaga
5161 taaactcagt cttctgaata gtaactggat agctgtcacc tcccgagcag aagagtggtt
5221 aaatcttttg ttggaatac
```

SEQ ID NO:21 (Repeat 13, 5240-5551)
```
5240 c agaaacacat ggaaactttt gaccagaatg tggaccacat
5281 cacaaagtgg atcattcagg ctgacacact tttggatgaa tcagagaaaa agaaacccca
5341 gcaaaaagaa gacgtgctta agcgtttaaa ggcagaactg aatgacatac gcccaaaggt
5401 ggactctaca cgtgaccaag cagcaaactt gatggcaaac cgcggtgacc actgcaggaa
5461 attagtagag ccccaaatct cagagctcaa ccatcgattt gcagccattt cacacagaat
5521 taagactgga aaggcctcca ttcctttgaa g
```

SEQ ID NO:22 (Repeat 14, 5552-5833)
```
5552 gaattggag cagtttaact cagatataca
5581 aaaattgctt gaaccactgg aggctgaaat tcagcagggg gtgaatctga aagaggaaga
5641 cttcaataaa gatatgaatg aagacaatga gggtactgta aaagaattgt tgcaaagagg
5701 agacaactta caacaaagaa tcacagatga gagaagaga gaggaaataa agataaaaca
5761 gcagctgtta cagacaaaac ataatgctct caaggatttg aggtctcaaa gaagaaaaaa
5821 ggctctagaa att
```

SEQ ID NO:23 (Repeat 15, 5834-6127)
```
5834 tctcatc agtggtatca gtacaagagg caggctgatg atctcctgaa
5881 atgcttggat gacattgaaa aaaattagc cagcctacct gagcccagag atgaaaggaa
5941 aataaaggaa attgatcggg aattgcagaa gaagaaagag gagctgaatg cagtgcgtag
6001 gcaagctgag ggcttgtctg aggatggggc cgcaatggca gtggagccaa ctcagatcca
6061 gctcagcaag cgctggcggg aaattgagag caaattgct cagtttcgaa gactcaactt
6121 tgcacaa
```

SEQ ID NO:24 (Repeat 16, 6188-6514)
```
6128 tct tatgtgcctt ctacttattt gactgaaatc actcatgtct cacaagccct
6241 attagaagtg gaacaacttc tcaatgctcc tgacctctgt gctaaggact ttgaagatct
6301 ctttaagcaa gaggagtctc tgaagaatat aaaagatagt ctacaacaaa gctcaggtcg
6361 gattgacatt attcatagca agaagacagc agcattgcaa agtgcaacgc ctgtggaaag
6421 ggtgaagcta caggaagctc tctcccagct tgatttccaa tgggaaaaag ttaacaaaat
6481 gtacaaggac cgacaagggc gatttgacag atct
```

SEQ ID NO:25 (Repeat 17, 6515-6835)
```
6515 gttgag aaatggcggc gttttcatta
6541 tgatataaag atatttaatc agtggctaac agaagctgaa cagtttctca gaaagacaca
6601 aattcctgag aattgggaac atgctaaata caaatggtat cttaaggaac tccaggatgg
6661 cattgggcag cggcaaactg ttgtcagaac attgaatgca actggggaag aaataattca
6721 gcaatcctca aaaacagatg ccagtattct acaggaaaaa ttgggaagcc tgaatctgcg
6781 gtggcaggag gtctgcaaac agctgtcaga cagaaaaaag aggctagaag aacaa
```

FIGURE 8

```
SEQ ID NO:26 (Repeat 18, 6836-7186)
6836 aagaa
6841 tatcttgtca gaatttcaaa gagatttaaa tgaatttgtt ttatggttgg aggaagcaga
6901 taacattgct agtatcccac ttgaacctgg aaaagagcag caactaaaag aaaagcttga
6961 gcaagtcaag ttactggtgg aagagttgcc cctgcgccag ggaattctca aacaattaaa
7021 tgaaactgga ggacccgtgc ttgtaagtgc tcccataagc ccagaagagc aagataaact
7081 tgaaaataag ctcaagcaga caaatctcca gtggataaag gtttccagag ctttacctga
7141 gaaacaagga gaaattgaag ctcaaataaa agaccttggg cagctt SEQ ID NO:27 (Repeat 19, 7187-7489)
7187 gaaa aaaagcttga
7201 agaccttgaa gagcagttaa atcatctgct gctgtggtta tctcctatta ggaatcagtt
7261 ggaaatttat aaccaaccaa accaagaagg accatttgac gttcaggaaa ctgaaatagc
7321 agttcaagct aaacaaccgg atgtggaaga gattttgtct aaagggcagc atttgtacaa
7381 ggaaaaacca gccactcagc cagtgaagag gaagttagaa gatctgagct ctgagtggaa
7441 ggcggtaaac cgtttacttc aagagctgag ggcaaagcag cctgaccta SEQ ID NO:28 (Hinge 3, 7490-7612)
7490 g ctcctggact
7501 gaccactatt ggagcctctc ctactcagac tgttactctg gtgacacaac ctgtggttac
7561 taaggaaact gccatctcca aactagaaat gccatcttcc ttgatgttgg ag SEQ ID NO:29 (Repeat 20, 7613-7942)
7613 gtacctgc
7621 tctggcagat ttcaaccggg cttggacaga acttaccgac tggctttctc tgcttgatca
7681 agttataaaa tcacagaggg tgatggtggg tgaccttgag gatatcaacg agatgatcat
7741 caagcagaag gcaacaatgc aggatttgga acagaggcgt ccccagttgg aagaactcat
7801 taccgctgcc caaaatttga aaaacaagac cagcaatcaa gaggctagaa caatcattac
7861 ggatcgaatt gaaagaattc agaatcagtg ggatgaagta caagaacacc ttcagaaccg
7921 gaggcaacag ttgaatgaaa tg SEQ ID NO:30 (Repeat 21, 7943-8269)
7943 ttaaagga ttcaacacaa tggctggaag ctaaggaaga
7981 agctgagcag gtcttaggac aggccagagc caagcttgag tcatggaagg agggtcccta
8041 tacagtagat gcaatccaaa agaaaatcac agaaaccaag cagttggcca aagacctccg
8101 ccagtggcag acaaatgtag atgtggcaaa tgacttggcc ctgaaacttc tccgggatta
8161 ttctgcagat gataccagaa aagtccacat gataacagag aatatcaatg cctcttggag
8221 aagcattcat aaaagggtga gtgagcgaga ggctgctttg gaagaaact SEQ ID NO:31 (Repeat 22, 8270-8617)
8270 c atagattact
8281 gcaacagttc cccctggacc tggaaaagtt tcttgcctgg cttacagaag ctgaaacaac
8341 tgccaatgtc ctacaggatg ctaccgtaa ggaaaggctc ctagaagact ccaagggagt
8401 aaaagagctg atgaaacaat ggcaagacct ccaaggtgaa attgaagctc acacagatgt
8461 ttatcacaac ctggatgaaa acagccaaaa aatcctgaga tccctggaag gttccgatga
8521 tgcagtcctg ttacaaagac gtttggataa catgaacttc aagtggagtg aacttcggaa
8581 aaagtctctc aacattaggt cccatttgga agccagt SEQ ID NO:32 (Repeat 23, 8618-9004)
8618 tct gaccagtgga agcgtctgca
8641 cctttctctg caggaacttc tggtgtggct acagctgaaa gatgatgaat taagccggca
8701 ggcacctatt ggaggcgact tccagcagt tcagaagcag aacgatgtac atagggcctt
8761 caagagggaa ttgaaaacta agaacctgt aatcatgagt actcttgaga ctgtacgaat
8821 atttctgaca gagcagcctt tggaaggact agagaaactc taccaggagc ccagagagct
8881 gcctcctgag gagagagccc agaatgtcac tcggcttcta cgaaagcagg ctgaggaggt
8941 caatactgag tgggaaaaat tgaacctgca ctccgctgac tggcagagaa aaatagatga
9001 gacc
```

FIGURE 9

SEQ ID NO:33 (Repeat 24, 9005-9328)
```
9005 cttgaa agactccagg aacttcaaga ggccacggat gagctggacc tcaagctgcg
9061 ccaagctgag gtgatcaagg gatcctggca gcccgtgggc gatctcctca ttgactctct
9121 ccaagatcac ctcgagaaag tcaaggcact tcgaggagaa attgcgcctc tgaaagagaa
9181 cgtgagccac gtcaatgacc ttgctcgcca gcttaccact ttgggcattc agctctcacc
9241 gtataacctc agcactctgg aagacctgaa caccagatgg aagcttctgc aggtggccgt
9301 cgaggaccga gtcaggcagc tgcatgaa
```

SEQ ID NO:34 (Hinge 4, 9329-9544)
```
9329 c ccacagggac tttggtccag catctcagca
9361 ctttctttcc acgtctgtcc agggtccctg ggagagagcc atctcgccaa acaaagtgcc
9421 ctactatatc aaccacgaga ctcaaacaac ttgctgggac catcccaaaa tgacagagct
9481 ctaccagtct ttagctgacc tgaataatgt cagattctca gcttatagga ctgccatgaa
9541 actc
```

SEQ ID NO:35 (Start of C terminus, 9545-10431)
```
9545 cgaaga ctgcagaagg ccctttgctt ggatctcttg agcctgtcag ctgcatgtga
9601 tgccttggac cagcacaacc tcaagcaaaa tgaccagccc atggatatcc tgcagattat
9661 taattgtttg accactattt atgaccgcct ggagcaagag cacaacaatt tggtcaacgt
9721 ccctctctgc gtggatatgt gtctgaactg gctgctgaat gtttatgata cgggacgaac
9781 agggaggatc cgtgtcctgt cttttaaaac tggcatcatt tccctgtgta agcacattt
9841 ggaagacaag tacagatacc ttttcaagca agtggcaagt tcaacaggat tttgtgacca
9901 gcgcaggctg ggcctccttc tgcatgattc tatccaaatt ccaagacagt tgggtgaagt
9961 tgcatccttt ggggcagta acattgagcc aagtgtccgg agctgcttcc aatttgctaa
10021 taataagcca gagatcgaag cggccctctt cctagactgg atgagactgg aaccccagtc
10081 catggtgtgg ctgccgtcc tgcacagagt ggctgctgca gaaactgcca agcatcaggc
10141 caaatgtaac atctgcaaag agtgtccaat cattggattc aggtacagga gtctaaagca
10201 cttttaattat gacatctgcc aaagctgctt tttttctggt cgagttgcaa aaggccataa
10261 aatgcactat cccatggtgg aatattgcac tccgactaca tcaggagaag atgttcgaga
10321 ctttgccaag gtactaaaaa acaaatttcg aaccaaaagg tatttttgcga agcatccccg
10381 aatgggctac ctgccagtgc agactgtctt agagggggac aacatggaaa c
```

SEQ ID NO:36 (alternatively spliced exons 71-78, 10432-11254)
```
10432 tccgttac
10441 tctgatcaac ttctggccag tagattctgc gcctgcctcg tcccctcagc tttcacacga
10501 tgatactcat tcacgcattg aacattatgc tagcaggcta gcagaaatgg aaaacagcaa
10561 tggatcttat ctaaatgata gcatctctcc taatgagagc atagatgatg aacatttgtt
10621 aatccagcat tactgccaaa gtttgaacca ggactccccc ctgagccagc ctcgtagtcc
10681 tgcccagatc ttgatttcct tagagagtga ggaaagaggg gagctagaga gaatcctagc
10741 agatcttgag gaagaaaaca ggaatctgca agcagaatat gaccgtctaa agcagcagca
10801 cgaacataaa ggcctgtccc cactgccgtc ccctcctgaa atgatgccca cctctcccca
10861 gagtccccgg gatgctgagc tcattgctga ggccaagcta ctgcgtcaac acaaaggccg
10921 cctggaagcc aggatgcaaa tcctggaaga ccacaataaa cagctggagt cacagttaca
10981 caggctaagg cagctgctgg agcaacccca ggcagaggcc aaagtgaatg gcacaacggt
11041 gtcctctcct tctacctctc tacagaggtc cgacagcagt cagcctatgc tgctccgagt
11101 ggttggcagt caaacttcgg actccatggg tgaggaagat cttctcagtc ctccccagga
11161 cacaagcaca gggttagagg aggtgatgga gcaactcaac aactccttcc ctagttcaag
11221 aggaagaaat acccctggaa agccaatgag agag
```

SEQ ID NO:37 (End of coding region, 11255-11266)
```
11255 gacaca atgtag
```

FIGURE 10

```
SEQ ID NO:38 (3' UTR, 11267-13957)
11267 gaag tcttttccac
11281 atggcagatg atttgggcag agcgatggag tccttagtat cagtcatgac agatgaagaa
11341 ggagcagaat aaatgtttta caactcctga ttcccgcatg gttttttataa tattcataca
11401 acaaagagga ttagacagta agagtttaca agaaataaat ctatattttt gtgaagggta
11461 gtggtattat actgtagatt tcagtagttt ctaagtctgt tattgttttg ttaacaatgg
11521 caggttttac acgtctatgc aattgtacaa aaaagttata agaaaactac atgtaaaatc
11581 ttgatagcta aataacttgc catttcttta tatggaacgc attttgggtt gtttaaaaat
11641 ttataacagt tataaagaaa gattgtaaac taaagtgtgc tttataaaaa aaagttgttt
11701 ataaaaaccc ctaaaaacaa aacaaacaca cacacacaca catacacaca cacacacaaa
11761 actttgaggc agcgcattgt tttgcatcct tttggcgtga tatccatatg aaattcatgg
11821 cttttttcttt ttttgcatat taaagataag acttcctcta ccaccacacc aaatgactac
11881 tacacactgc tcatttgaga actgtcagct gagtggggca ggcttgagtt ttcatttcat
11941 atatctatat gtctataagt atataaatac tatagttata tagataaaga gatacgaatt
12001 tctatagact gacttttttcc attttttaaa tgttcatgtc acatcctaat agaaagaaat
12061 tacttctagt cagtcatcca ggcttacctg cttggtctag aatggatttt tcccggagcc
12121 ggaagccagg aggaaactac accacactaa aacattgtct acagctccag atgtttctca
12181 ttttaaacaa ctttccactg acaacgaaag taaagtaaag tattggatttt ttttaaaggg
12241 aacatgtgaa tgaatacaca ggacttatta tatcagagtg agtaatcggt tggttggttg
12301 attgattgat tgattgatac attcagcttc ctgctgctag caatgccacg atttagattt
12361 aatgatgctt cagtggaaat caatcagaag gtattctgac cttgtgaaca tcagaaggta
12421 tttttttaact cccaagcagt agcaggacga tgatagggct ggagggctat ggattccag
12481 cccatccctg tgaaggagta ggccactctt taagtgaagg attggatgat tgttcataat
12541 acataaagtt ctctgtaatt acaactaaat tattatgccc tcttctcaca gtcaaaagga
12601 actgggtggt ttggttttttg ttgcttttttt agatttattg tcccatgtgg gatgagtttt
12661 taaatgccac aagacataat ttaaaataaa taaactttgg gaaaaggtgt aagacagtag
12721 ccccatcaca tttgtgatac tgacaggtat caacccagaa gcccatgaac tgtgtttcca
12781 tcctttgcat ttctctgcga gtagttccac acaggtttgt aagtaagtaa gaaagaaggc
12841 aaattgattc aaatgttaca aaaaaaccct tcttggtgga ttagacaggt taaatatata
12901 aacaaacaaa caaaaattgc tcaaaaaaga ggagaaaagc tcaagaggaa aagctaagga
12961 ctggtaggaa aaagctttac tctttcatgc catttttattt cttttttgatt tttaaatcat
13021 tcattcaata gataccaccg tgtgacctat aattttgcaa atctgttacc tctgacatca
13081 agtgtaatta gcttttggag agtgggctga catcaagtgt aattagcttc tggagagtgg
13141 gttttgtcca ttattaataa ttaattaatt aacatcaaac acggcttctc atgctatttc
13201 tacctcactt tggtttttggg gtgttcctga taattgtgca cacctgagtt cacagcttca
13261 ccacttgtcc attgcgttat ttttcttttc ctttataatt ctttctttttt ccttcataat
13321 tttcaaaaga aaacccaaag ctctaaggta acaaattacc aaattacatg aagatttggt
13381 ttttgtcttg catttttttc ctttatgtga cgctggacct tttctttacc caaggatttt
13441 taaaactcag atttaaaaca aggggttact ttacatccta ctaagaagtt taagtaagta
13501 agtttcattc taaaatcaga ggtaaataga gtgcataaat aattttgttt taatcttttt
13561 gttttttcttt tagacacatt agctctggag tgagtctgtc ataatatttg aacaaaaatt
13621 gagagcttta ttgctgcatt ttaagcataa ttaatttgga cattatttcg tgttgtgttc
13681 tttataacca ccgagtatta aactgtaaat cataatgtaa ctgaagcata aacatcacat
13741 ggcatgtttt gtcattgttt tcaggtactg agttcttact tgagtatcat aatatattgt
13801 gttttaacac caacactgta acatttacga attattttttt taaacttcag ttttactgca
13861 ttttcacaac atatcagact tcaccaaata tatgccttac tattgtatta tagtactgct
13921 ttactgtgta tctcaataaa gcacgcagtt atgttac
```

FIGURE 11

Query=Human Dystrophin 1220-9328; Sbjt=Mouse Dystrophin 1238-9319

```
Query:  1220  gaagtaaacctggaccgtta 1239
              ||||||||  |||||  ||||
Sbjct:  1238  gaagtaaatctggatagtta 1257

Query:  1240  tcaaacagctttagaagaagtattatcgtggcttctttctgctgaggacacattgcaagc 1299
              |||||  |||||||||||||||  || ||||||||||||||| ||||| ||||||| |||
Sbjct:  1258  ccaaactgctttagaagaagtactttcatggcttctttctgccgaggatacattgcgagc 1317

Query:  1300  acaaggagagatttctaatgatgtggaagtggtgaaagaccagtttcatactcatgaggg 1359
              |||||||||||||| ||||||||| ||||| |||||||| |||||||| |||||||||||
Sbjct:  1318  acaaggagagatttcaaatgatgttgaagaagtgaaagaacagtttcatgctcatgaggg 1377

Query:  1360  gtacatgatggatttgacagcccatcagggccgggttggtaatattctacaattgggaag 1419
              | ||||||||| || |||| | ||||| || ||  ||||||| |||||||| || |||||
Sbjct:  1378  attcatgatggatctgacatctcatcaaggacttgttggtaatgttctacagttaggaag 1437

Query:  1420  taagctgattggaacaggaaaattatcagaagatgaagaaactgaagtacaagagcagat 1479
              | | || |||||| ||| |||||||||||||||||||||| ||||||| |||||| | ||
Sbjct:  1438  tcaactagttggaaaagggaaattatcagaagatgaagaagctgaagtgcaagaacaaat 1497

Query:  1480  gaatctcctaaattcaagatgggaatgcctcagggtagctagcatggaaaaacaaagcaa 1539
              ||||||||||||||||||||||||||| | ||||||||||||||||||||| ||||||||
Sbjct:  1498  gaatctcctaaattcaagatgggaatgtctcagggtagctagcatggaaaaacaaagcaa 1557

Query:  1540  tttacat agagttttaatggatctccagaatcagaaactgaaagagttgaatgactggct 1599
              ||||| |  | ||| |||||||||||||||||||||| |  ||||| |  |||||||| |
Sbjct:  1558  attacac aaagttctaatggatctccagaatcagaaattaaaagaactagatgactggtt 1617

Query:  1600  aacaaaaacagaagaaagaacaaggaaaatggaggaagagcctcttggacctgatcttga 1659
              ||||||||  |||||  |||||   |   |||||||| ||||| ||||||||||||||||
Sbjct:  1618  aacaaaaactgaagagagaactaagaaaatggaggaagagcccttggacctgatcttga 1677

Query:  1660  agacctaaaacgccaagtacaacaacataaggtgcttcaagaagatctagaacaagaaca 1719
              |||  ||||| |||||||||||||||||||||||||||||||||||||||||||  || |
Sbjct:  1678  agatctaaaatgccaagtacaacaacataaggtgcttcaagaagatctagaacaggagca 1737

Query:  1720  agtcagggtcaattctctcactcacatggtggtggtagttgatgaatctagtggagatca 1779
              ||||||||||||  | ||||||||||||||||  |  ||||||||||||| | || |||
Sbjct:  1738  ggtcagggtcaactcgctcactcacatggtagtagtggttgatgaatccagcggtgatca 1797

Query:  1780  cgcaactgctgctttggaagaacaacttaaggtattgggagatcgatgggcaaacatctg 1839
              |||||||||||||||||||||||||||||||||| |||||||||||||||||| ||||||
Sbjct:  1798  tgcaacagctgctttggaagaacaacttaaggtactgggagatcgatgggcaaatatctg 1857

Query:  1840  tagatggacagaagaccgctgggttcttttacaagacatc cttctcaaatggcaacgtct 1899
              ||| ||| |||||||||||||| ||||||||||||| |||  ||||| ||||||| | |
Sbjct:  1858  cagatggactgaagaccgctggattgttttacaagatatt cttctaaaatggcagcattt 1917

Query:  1900  tactgaagaacagtgccttttagtgcatggctttcagaaaaagaagatgcagtgaacaa 1959
              |||||||||||||||||||||||| |||||||||||||| ||||||||||| |||| ||
Sbjct:  1918  tactgaagaacagtgccttttagtacatggctttcagaaaaagaagatgcaatgaagaa 1977

Query:  1960  gattcacacaactggctttaaagatcaaaatgaaatgttatcaagtcttcaaaaactggc 2019
              ||||| ||||   ||||||||||||||||||||||||| ||||||||||||| | | |
Sbjct:  1978  cattcagacaagtggctttaaagatcaaaatgaaatgatgtcaagtcttcacaaaatatc 2037

Query:  2020  cgtttaaaagcggatctagaaaagaaaaagcaatccatgggcaaactgtattcactcaa 2079
              |||||||    ||||||||||||||||||| ||||||| |||||    |||||||||||
Sbjct:  2038  tactttaaaaatagatctagaaaagaaaaagccaaccatggaaaaactaagttcactcaa 2097

Query:  2080  acaagatcttctttcaacactgaagaataagtcagtgacccagaagacggaagcatggct 2139
              |||||||| |||||  |||||| ||||||||||||||||||    || |||| |  | |
Sbjct:  2098  tcaagatctactttcggcactgaaaaataagtcagtgactcaaaagatggaaatctggat 2157

Query:  2140  ggataactttgcccggtgttgggataatttagtccaaaaacttgaaaagagtacagcaca 2199
              ||| ||||||||| ||| |   |||||||| |||||||||||||||||||||| ||||||
Sbjct:  2158  ggaaaactttgcacaacgttgggacaatttaaccccaaaaacttgaaaagagttcagcaca 2217
```

FIGURE 11 (cont.)

```
Query: 2200  gatttcacaggct gtcaccaccactcagccatcactaacacagacaactgtaatggaaac  2259
             ||||||||||||| |||||||||||||| |||||  |||||||||||||||||||||||
Sbjct: 2218  aatttcacaggct gtcaccaccactcaaccatccctaacacagacaactgtaatggaaac  2277

Query: 2260  agtaactacggtgaccacaagggaacagatcctggtaaagcatgctcaagaggaacttcc  2319
             |||||||  ||||||||||||||||||||  ||| ||||||||  ||||  |||||||||||||
Sbjct: 2278  ggtaactatggtgaccacaagggaacaaatcatggtaaaacatgcccaagaggaacttcc  2337

Query: 2320  accaccacctcccaaaagaagaggcagattactgtggat tctgaaattaggaaaaggtt  2379
             ||||||||||| |||||||||||||||||| ||||||||| ||||||  |  |||||||||||
Sbjct: 2338  accaccacctcctcaaaagaagaggcagataactgtggat tctgaactcaggaaaaggtt  2397

Query: 2380  ggatgttgatataactgaacttcacagctggattactcgctcagaagctgtgttgcagag  2439
             |||||| |||||||||||||||||||| ||||||||||  ||||||||||||| || |||||
Sbjct: 2398  ggatgtcgatataactgaacttcacagttggattactcgttcagaagctgtattacagag  2457

Query: 2440  tcctgaatttgcaatctttcggaaggaaggcaacttctcagacttaaaagaaaaagtcaa  2499
             |  ||||||||||| ||| || |||||||||||||| ||  |||||||||  |||||||||||
Sbjct: 2458  ttctgaatttgcagtctatcgaaaagaaggcaacatctcagacttgcaagaaaaagtcaa  2517

Query: 2500  tgccatagagcgagaaaaagctgagaagttcagaaaactgcaagatgccagcagatcagc  2559
             |||||||  ||||||||||||  |||||||||||||||||||||||||||||||||||||||
Sbjct: 2518  tgccatagcacgagaaaaagcagagaagttcagaaaactgcaagatgccagcagatcagc  2577

Query: 2560  tcaggccctggtggaacagatggtgaatgagggtgttaatgcagatagcatcaaacaagc  2619
             ||||||||||||||||||||||| ||||||||||||||||||| || || |||| ||||||
Sbjct: 2578  tcaggccctggtggaacagatggcaaatgagggtgttaatgctgaaagtatcagacaagc  2637

Query: 2620  ctcagaacaactgaacagccggtggatcgaattctgccagttgctaagtgagagacttaa  2679
             |||||||||||||||||||||||||| ||||||||||| ||||||||||||||||| ||||
Sbjct: 2638  ttcagaacaactgaacagccggtggacagaattctgccaattgctgagtgagagagttaa  2697

Query: 2680  ctggctggagtat cagaacaacatcatcgctttctataatcagctacaacaattggagca  2739
             |||||| |||||| ||  |||||||||| ||| || ||||||||||||||||||||||| ||
Sbjct: 2698  ctggctagagtat caaaccaacatcattacctttataatcagctacaacaattggaaca  2757

Query: 2740  gatgacaactactgctgaaaactggttgaaaatccaacccaccacccatcagagccaac  2799
             |||||||||||||||| |||||| |||||||||  | |||||||| |||||||||||||||
Sbjct: 2758  gatgacaactactgccgaaaacttgttgaaaacccagtctaccaccctatcagagccaac  2817

Query: 2800  agcaattaaaagtcagttaaaaatttgtaaggatgaagtcaaccggctatcaggtcttca  2859
             |||||||||||| |||||||||||||||||||||||||||||||  | | |||| ||||||
Sbjct: 2818  agcaattaaaagccagttaaaaatttgtaaggatgaagtcaacagattgtcagctcttca  2877

Query: 2860  acctcaaattgaacgattaaaaattcaaagcatagccctgaaagagaaaggacaaggacc  2919
             |||||||||||| | |||||||||||| ||  ||||||  ||||||| ||  |||| || ||
Sbjct: 2878  gcctcaaattgagcaattaaaaattcagagtctacaactgaaagaaaagggacaggggcc  2937

Query: 2920  catgttcctggatgcagactttgtggcctttacaaatcatttaagcaagtcttttctga  2979
             ||||| |||||||||||||||||||||||||||| ||||||||  | |||| ||  ||
Sbjct: 2938  aatgtttctggatgcagactttgtggcctttactaatcatttaaccacatctttgatgg  2997

Query: 2980  tgtgcaggccagagagaaagagctacagacaattttgac actttgccaccaatgcgcta  3039
             ||||  ||||| ||||||||||||||||||||||||||| |||| ||||||||||||||
Sbjct: 2998  tgtgagggccaaagagaaagagctacagacaattttgac actttaccaccaatgcgcta  3057

Query: 3040  tcaggagaccatgagtgccatcaggacatgggtccagcagtcagaaaccaaactctccat  3099
             |||||||| ||||| |||||||||||| ||| |||||||||||||||| ||||||||| |
Sbjct: 3058  tcaggagacaatgagtagcatcaggacgtggatccagcagtcagaaagcaaactctctgt  3117

Query: 3100  acctcaacttagtgtcaccgactatgaaatcatggagcagagactcggggaattgcaggc  3159
             |||| | |||||||| || || ||||||| |||||| |||||||||||||| |||| ||||
Sbjct: 3118  accttatcttagtgttactgaatatgaaataatggaggagagactcgggaattacaggc  3177

Query: 3160  tttacaaagttctctgcaagagcaacaaagtggcctatactatctcagcaccactgtgaa  3219
             | | |||||||||||| || ||||||||||| |||| ||||||| || |||||||||
Sbjct: 3178  tctgcaaagttctttgaaagagcaacaaaatggcttcaactatctgagtgacactgtgaa  3237
```

FIGURE 11 (cont.)

```
Query: 3220  agagatgtcgaagaaagcgccctctgaaattagccggaaatatcaatcagaatttgaaga  3279
             ||||||  |  |||||||||  ||  |||||   |||  ||||||    ||||||||||||
Sbjct: 3238  ggagatggccaagaaagcaccttcagaaatatgccagaaatatctgtcagaatttgaaga  3297

Query: 3280  aattgagggacgctggaagaagctctcctcccagctggttgagcattgtcaaaagctaga  3339
             ||||||||  |  |||||||||  ||  ||||||||||  ||    ||  ||||||||||
Sbjct: 3298  gattgaggggcactggaagaaacttctcctcccagttggtggaaagctgccaaaagctaga  3357

Query: 3340  ggagcaa atgaataaactccgaaaaattcagaatcacatacaaaccctgaagaaatggat  3399
             || ||   |||||||||| |||||| |||||||||||||  |  ||| |  ||||||||||
Sbjct: 3358  agaacat atgaataaacttcgaaaatttcagaatcacataaaaaccttacagaaatggat  3417

Query: 3400  ggctgaagttgatgtttttctgaaggaggaatggcctgcccttggggattcagaaattct  3459
             |||||||||||||||||  ||||| ||||||||||||||  ||||||| |  |||| |||
Sbjct: 3418  ggctgaagttgatgttttcctgaaagaggaatggcctgccctgggggatgctgaaatcct  3477

Query: 3460  aaaaaagcagctgaaacagtgcagactttagtcagtgatattcagacaattcagcccag   3519
             |||||  |||||  |||||  |||||||||||  |||||||||  ||||||||||||||
Sbjct: 3478  gaaaaacagctcaaacaatgcagactttagttggtgatattcaaacaattcagcccag    3537

Query: 3520  tctaaacagtgtcaatgaaggtgggcagaagataaagaatgaagcagagccagagtttgc  3579
             |  ||||  |||||||||||||||||||||||||||| |||||||| ||   ||||||||
Sbjct: 3538  tttaaatagtgttaatgaaggtgggcagaagataaagagtgaagctgaacttgagtttgc  3597

Query: 3580  ttcgagacttgagacagaactcaaagaacttaacactcagtgggatcacatgtgccaaca  3639
             || |||||  |||||||||| | ||| ||||||||||||||||||||||||  ||||  ||
Sbjct: 3598  atccagactggagacagaacttagagagcttaacactcagtgggatcacatatgccgcca  3657

Query: 3640  ggtctatgccagaaaggaggccttgaagggaggt tggagaaaactgtaagcctccagaa  3699
             ||||||  |||||||||||  ||| |||| ||||  |||| |||| |||||||||||| ||
Sbjct: 3658  ggtctacaccagaaaggaagccttaaaggcaggt tggataaaaccgtaagcctccaaaa  3717

Query: 3700  agatctatcagagatgcacgaatggatgacacaagctgaagaagagtatcttgagagaga  3759
             |||||||||||||||||| || ||||||||||||||||||||||| |||||| |||||||
Sbjct: 3718  agatctatcagagatgcatgagtggatgacacaagctgaagaagaatatctagagagaga  3777

Query: 3760  ttttgaatataaaactccagatgaattacagaaagcagttgaagagatgaagagagctaa  3819
             ||||||||||||||||||||||||||||||||  ||  ||| ||||||| |||||||||||
Sbjct: 3778  ttttgaatataaaactccagatgaattacagactgctgttgaagaaatgaagagagctaa  3837

Query: 3820  agaagaggcccaacaaaaagaagcgaaagtgaaactccttactgagtctgtaaatagtgt  3879
             ||||||||| | |  ||||||||| |||||||||||||||||||| |||||||||||||||
Sbjct: 3838  agaagaggcactacaaaaagaaactaaagtgaaactccttactgagactgtaaatagtgt  3897

Query: 3880  catagctcaagctccacctgtagcacaagaggccttaaaaaaggaacttgaaactctaac  3939
             ||||||||  |||||||    ||||||||||||||||||||||||||||||||||||| ||
Sbjct: 3898  aatagctcacgctccaccctcagcacaagaggccttaaaaaaggaacttgaaactctgac  3957

Query: 3940  caccaactaccagtggctctgcactaggctgaatgggaaatgcaagactttggaagaagt  3999
             |||||||||||| ||||| ||||| | ||||||||| |||||||||| ||||||||||||
Sbjct: 3958  caccaactaccaatggctgtgcaccaggctgaatggaaaatgcaaactttggaagaagt  4017

Query: 4000  t tgggcatgttggcatgagttattgtcatacttggagaaagcaaacaagtggctaaatga  4059
             | |||||||||||||||||||||||||||| |||||||||||||||||||||||| ||||
Sbjct: 4018  t tgggcatgttggcatgagttattgtcatatttagagaaagcaaacaagtggctcaatga  4077

Query: 4060  agtagaatttaaacttaaaaccactgaaaacattcctggcggagctgaggaaatctctga  4119
             |||||||| |||||||||| ||| |||||| |||  ||| ||| |||||||||| ||||
Sbjct: 4078  agtagaattgaaacttaaaaccatggaaaatgttcctgcaggacctgaggaaatcactga  4137

Query: 4120  ggtgctagattcacttgaaaatttgatgcgacattcagaggataacccaaatcagattcg  4179
             |||||||| || ||||||||||| ||||| |  |||||||| ||||||||||||||||||
Sbjct: 4138  agtgctagaatctcttgaaaatctgatgcatcattcagaggagaacccaaatcagattcg  4197

Query: 4180  catattggcacagaccctaacagatggcggagtcatggatgagctaatcaatgaggaact  4239
             |||||||||||||| || || |||||||||||||||||||||| || ||||||||||| |
Sbjct: 4198  tctattggcacagactcttacagatggaggagtcatggatgaactgatcaatgaggagct  4257
```

FIGURE 11 (cont.)

```
Query: 4240 tgagacatttaattctcgttggagggaactacatgaagaggctgtaaggaggcaaaagtt 4299
             ||||||  |||||||||||||||||||||||||||||||||||||||| ||||  |||||||
Sbjct: 4258 tgagacgtttaattctcgttggagggaactacatgaagaggctgtgaggaaacaaaagtt 4317

Query: 4300 gcttgaacagagc atccagtctgcccaggagactgaaaaatccttacacttaatccagga 4359
             |||||||||||||  |||||||||||||||| | ||||||  ||||| |||||||| |||||
Sbjct: 4318 gcttgaacagagt atccagtctgcccaggaaattgaaaagtccttgcacttaattcagga 4377

Query: 4360 gtccctcacattcattgacaagcagttggcagcttatattgcagacaaggtggacgcagc 4419
             ||| ||  ||||||||||||||||||||||||||||||| | ||||||||||| |||||
Sbjct: 4378 gtcgcttgaattcattgacaagcagttggcagcttatatcactgacaaggtggatgcagc 4437

Query: 4420 tcaaatgcctcaggaagcccagaaaatccaatctgatttgacaagtcatgagatcagttt 4479
             |||||||||||||||||||||||||||||||| |||||||||||||||||||||  |||||
Sbjct: 4438 tcaaatgcctcaggaagcccagaaaatccaatcagatttgacaagtcatgagataagttt 4497

Query: 4480 agaagaaatgaagaaacataatcaggggaaggaggctgcccaaagagtcctgtctcagat 4539
             ||||||||||||||||||| ||||||||||||| || ||||||||||  || || || ||
Sbjct: 4498 agaagaaatgaagaaacataaccaggggaaggatgccaaccaaagggttctttcacaaat 4557

Query: 4540 tgatgttgcacagaaaaaattacaagatgtctccatgaagtttcgatta ttccagaaacc 4599
             |||||||||||||||| |||||||||||||||||||||| ||||||||| |||||  |||
Sbjct: 4558 tgatgttgcacagaaaaaattacaagatgtctccatgaaatttcgatta ttccaaaaacc 4617

Query: 4600 agccaattttgagctgcgtctacaagaaagtaagatgatttagatgaagtgaagatgca 4659
             ||||||||||| |  ||||| | |||||||||||||||||||||||||||  |||||||
Sbjct: 4618 agccaattttgaacaacgtctagaggaaagtaagatgatttagatgaagtcaagatgca 4677

Query: 4660 cttgcctgcattggaaacaaagagtgtggaacaggaagtagtacagtcacagctaaatca 4719
             |||||||||||||||||| |||||||| ||||||||||| | ||| |||||||| || |||
Sbjct: 4678 tttgcctgcattggaaaccaagagtgttgaacaggaagtaattcagtcacaactaagtca 4737

Query: 4720 ttgtgtgaacttgtataaaagtctgagtgaagtgaagtctgaagtggaaatggtgataaa 4779
             |||||||||||||||||||| |||||||||||| ||||||||||||||||||||||| ||
Sbjct: 4738 ttgtgtgaacttgtataaaagcctgagtgaagtcaagtctgaagtggaaatggtgattaa 4797

Query: 4780 gactggacgtcagattgtacagaaaaagcagacggaaaatcccaaagaacttgatgaaag 4839
             ||  ||||||||  ||||||||||||||||||||  |||||||||||||| ||||||||  |
Sbjct: 4798 aaccggacgtcaaattgtacagaaaaagcagacagaaaatcccaaagagcttgatgaacg 4857

Query: 4840 agtaacagctttgaaattgcattataatgagctgggagcaaaggtaacagaaagaaagca 4899
             |||||||||||||||||||||||| |||||| ||||| | || |||||||||| ||||||
Sbjct: 4858 agtaacagctttgaaattgcattacaatgagttgggtgcgaaggtaacagagagaaagca 4917

Query: 4900 acagttggagaaatgc ttgaaattgtcccgtaagatgcgaaaggaaatgaatgtcttgac 4959
             |||||||||||||||| ||||| |||||||||||||| | |||||||||||||||||| ||
Sbjct: 4918 acagttggagaaatgc ttgaagttgtcccgtaagatgagaaaggaaatgaatgtcttaac 4977

Query: 4960 agaatggctggcagctacagatatggaattgacaaagagatcagcagttgaaggaatgcc 5019
             |||||||||||||||| ||||||| |||||||| |||||||||||||||||||||||||
Sbjct: 4978 agaatggctggcagcaacagatacagaattgacgaagagatcagcagttgaaggaatgcc 5037

Query: 5020 tagtaatttggattctgaagttgcctggggaaaggctactcaaaaagagattgagaaaca 5079
             |||||||||||||||||||||||||||||||||||||||||||||||||||| |||||||
Sbjct: 5038 aagtaatttggattctgaagttgcctggggaaaggctactcaaaaagagattgagaaaca 5097

Query: 5080 gaaggtgcacctgaagagtatcacagaggtaggagaggccttgaaaacagttttgggcaa 5139
             |||||    ||||||||| |||||| | ||||||| | ||||||| ||  |||||||||
Sbjct: 5098 gaaggctcacttgaagagtgttacagaattaggagagtctttgaaaatggtgttgggcaa 5157

Query: 5140 gaaggagacgttggtggaagataaactcagtcttctgaatagtaactggatagctgtcac 5199
             ||| || || ||||| |||||||||||||||||||||||| ||||||||||||||||||
Sbjct: 5158 gaaagaaaccttggtagaagataaactgagtcttctgaacagtaactggatagctgtcac 5217

Query: 5200 ctcccgagcagaagagtggttaaatctttttgttggaatac cagaaacacatggaaacttt 5259
             |||| ||| |||||| ||| ||||||||||||||||||||| |||||||||||||||| ||
Sbjct: 5218 ctccagagtagaagaatggctaaatctttttgttggaatac cagaaacacatggaaaccttt 5277
```

FIGURE 11 (cont.)

```
Query: 5260  tgaccagaatgtggaccacatcacaaagtggatcattcaggctgacacactttggatga  5319
             |||  ||||| | || ||  |||||||||||||||||||  || ||   |||||| |||||
Sbjct: 5278  tgatcagaacatagaacaaatcacaaagtggatcattcatgcagatgaacttttagatga  5337

Query: 5320  atcagagaaaagaaacccagcaaaaagaagacgtgcttaagcgtttaaaggcagaact   5379
             || || || ||||||||| ||  ||||| ||||||| | |||||||||||||||| ||| |
Sbjct: 5338  gtctgaaaagaagaaacccacaacaaaaggaagacattcttaagcgtttaaaggctgaaat  5397

Query: 5380  gaatgacatacgcccaaaggtggactctacacgtgaccaagcagcaaacttgatggcaaa  5439
             |||||||| ||||||||||||||||||| ||||||||||||||||||||| ||||||||||
Sbjct: 5398  gaatgacatgcgcccaaaggtggactccacacgtgaccaagcagcaaaattgatggcaaa  5457

Query: 5440  ccgcggtgaccactgcaggaaattagtagagccccaaatctcagagctcaaccatcgatt  5499
             |||||||||||||||||||||||| |||||||||||||||||| ||||||||| ||||||
Sbjct: 5458  ccgcggtgaccactgcaggaaagtagtagagccccaaatctctgagctcaaccgtcgatt  5517

Query: 5500  tgcagccatttcacacagaattaagactggaaaggcctccattcctttgaag gaattgga  5559
             ||||||  ||||  ||||||||||||||||||||||||||||||||||||||| ||||||||
Sbjct: 5518  tgcagctatttctcacagaattaagactggaaaggcctccattcctttgaag gaattgga  5577

Query: 5560  gcagtttaactcagatatacaaaaattgcttgaaccactggaggctgaaattcagcaggg  5619
             |||||||||||||||||||||||||||||||||||||||||||||||||||||||||||
Sbjct: 5578  gcagtttaactcagatatacaaaaattgcttgaaccactggaggctgaaattcagcaggg  5637

Query: 5620  ggtgaatctgaaagaggaagacttcaataaagatatgaatgaagacaatgagggtactgt  5679
             |||||||||||||||||||||||||||||||||||||||| |||||||||||||||||||
Sbjct: 5638  ggtgaatctgaaagaggaagacttcaataaagatatgagtgaagacaatgagggtactgt  5697

Query: 5680  aaaagaattgttgcaaagaggagacaacttacaacaaagaatcacagatgagagaaagag  5739
             ||| ||||||||||||||||||||||||||||||||||||||||||||||||||||||| |
Sbjct: 5698  aaatgaattgttgcaaagaggagacaacttacaacaaagaatcacagatgagagaaagcg  5757

Query: 5740  agaggaaataaagataaaacagcagctgttacagacaaaacataatgctctcaaggattt  5799
             ||||||||||||||||||||||||||||||||||||||||||||||||||||||||||||
Sbjct: 5758  agaggaaataaagataaaacagcagctgttacagacaaaacataatgctctcaaggattt  5817

Query: 5800  gaggtctcaaagaagaaaaaaggctctagaaatt tctcatcagtggtatcagtacaagag  5859
             ||||||||||||||||||||||| ||||||||| |||| |||||||||||||||||||||
Sbjct: 5818  gaggtctcaaagaagaaaaaaggccctagaaatt tctcaccagtggtatcagtacaagag  5877

Query: 5860  gcaggctgatgatctcctgaaatgcttggatgacattgnnnnnnnnnttagccagcctacc  5919
             ||||||||||||||||||||||||||||||||||||| ||||           |||||||||||||
Sbjct: 5878  gcaggctgatgatctcctgaaatgcttggatgaaattgaaaaaaaattagccagcctacc  5937

Query: 5920  tgagcccagagatgaaaggaaaataaaggaaattgatcgggaattgcagaagaagaaaga  5979
             |||  |||||||||||||| ||| |||||||||||||| |||||||||||||||||||||
Sbjct: 5938  tgaacccagagatgaaagaaaattaaaggaaattgatcgtgaattgcagaagaagaaaga  5997

Query: 5980  ggagctgaatgcagtgcgtaggcaagctgagggcttgtctgaggatggggccgcaatggc  6039
             |||||||||||||||||| |||||||||||||||||||||||| |||||||||||||||
Sbjct: 5998  ggagctgaatgcagtgcgcaggcaagctgagggcttgtctgagaatggggccgcaatggc  6057

Query: 6040  agtggagccaactcagatccagctcagcaagcgctggcgggaaattgagagcaaatttgc  6099
             ||||||||||||||||||||||||||||||||||||||||| |||||||||||| |||||
Sbjct: 6058  agtggagccaactcagatccagctcagcaagcgctggcggcaaattgagagcaatttgc  6117

Query: 6100  tcagtttcgaagactcaactttgcacaa attcacactgtccgtgaagaaacgatgatggt  6159
             |||||||||||||||||||||||||||| ||||||||| ||| || ||||| || || ||
Sbjct: 6118  tcagtttcgaagactcaactttgcacaa attcacactctccatgaagaaactatggtagt  6177

Query: 6160  gatgactgaagacatgcctttggaaatttcttatgtgccttctacttatttgactgaaat  6219
             || |||||||||| ||||||||| |||||||||||||||||||||||||||||| || ||
Sbjct: 6178  gacgactgaagatatgcctttggatgtttcttatgtgccttctacttatttgaccgagat  6237

Query: 6220  cactcatgtctcacaagcccattagaagtggaacaacttctcaatgctcctgacctctg  6279
             || |||| ||| |||||| ||| | ||||||| || || |||||| ||| |||||| |||||
Sbjct: 6238  cagtcatatcttacaagctctttcagaagttgatcatcttctaaatactcctgaactctg  6297
```

FIGURE 11 (cont.)

```
Query:  6280  tgctaaggactttgaagatctctttaagcaagaggagtctctgaagaatataaaagatag  6339
              ||||||  ||  |||||||||||  ||||||||||||||||||  |||||||||||||  |
Sbjct:  6298  tgctaaagatttgaagatcttttt aagcaagaggagtctcttaagaatataaaagacaa  6357

Query:  6340  tctacaacaaagctcaggtcggattgacattattcatagcaagaagacagcagcattgca  6399
              |  |||||||| ||||||||||||||||||| ||||||||| |  ||||||||||||||| |||||
Sbjct:  6358  tttgcaacaaatctcaggtcggattgatattattcacaagaagaagacagcagccttgca  6417

Query:  6400  aagtgcaacgcctgtggaaagggtgaagctacaggaagctctctcccagcttgatttcca  6459
              |||||  ||  |  ||||||  ||||||   ||||||||||  |   |||  |  ||||||||
Sbjct:  6418  aagtgccacctccatggaaaaggtgaaagtacaggaagccgtggcacagatggatttcca  6477

Query:  6460  atgggaaaaagttaacaaaatgtacaaggaccgacaaggggcgatttgacagatct gttga  6519
              |||||||| ||  |  | |||||||||||| |||||||||| |||| |||||||||   |||||
Sbjct:  6478  gggggaaaaacttcatagaatgtacaaggaacgacaagggcgattcgacagatca gttga  6537

Query:  6520  gaaatggcggcgttttcattatgatataaagatatttaatcagtggctaacagaagctga  6579
              |||||||| |  |||||||||||||||||| ||| ||||||||||| |  |||| |||
Sbjct:  6538  aaaatggcgacactttcattatgatatgaaggtatttaatcaatggctgaatgaagttga  6597

Query:  6580  acagttctcagaaagacacaaattcctgagaattgggaacatgctaaatacaaatggta  6639
              ||||||| ||| |||||||||||||||||| ||  |||||||||||||||||||||||||||||||
Sbjct:  6598  acagttttcaaaaagacacaaaatcctgaaaactgggaacatgctaaatacaaatggta  6657

Query:  6640  tcttaaggaactccaggatggcattgggcagcggcaaactgttgtcagaacattgaatgc  6699
              |||||||||||||||||||||||||||||||| ||| |||||||||||||||| ||||||
Sbjct:  6658  tcttaaggaactccaggatggcattgggcagcgtcaagctgttgtcagaacactgaatgc  6717

Query:  6700  aactggggaagaaataattcagcaatcctcaaaaacagatgccagtattctacaggaaaa  6759
              |||||||||||||||||||| |  ||  ||||||||||||||  || ||||||||| |||||
Sbjct:  6718  aactggggaagaaataattcaacagtcttcaaaaacagatgtcaatattctacaagaaaa  6777

Query:  6760  attgggaagcctgaatctgcggtggcaggaggtctgcaaacagctgtcagacagaaaaaa  6819
              |||  ||||| |||  |||||||||||  ||||||| |||| |||| || |  |||
Sbjct:  6778  attaggaagcttgagtctgcggtggcacgacatctgcaaagagctggcagaaggagaaa  6837

Query:  6820  gaggctagaagaacaa aagaatatcttgtcagaatttcaaagagatttaaatgaatttgt  6879
              ||||  |  ||||||||| |||||| ||||||||||||||||| |||||||||||||||||||||
Sbjct:  6838  gaggattgaagaacaa aagaatgtcttgtcagaatttcaaagagatttaaatgaatttgt  6897

Query:  6880  tttatggttggaggaagcagataacattgctagtatcccacttgaacctggaaaagagca  6939
              |||  |||  ||||||||||||||||||||| ||  |||||      |||| |  |||||
Sbjct:  6898  tttgtggctggaagaagcagataacattgctattactccact------tggagatgagca  6951

Query:  6940  gcaactaaaagaaaagcttgagcaagtcaagttactggtggaagagttgcccctgcgcca  6999
              |||  |||||||||  |  ||||| |||||||||||||| |||||||||||||||||||||
Sbjct:  6952  gcagctaaaagaacaacttgaacaagtcaagttactggcagaagagttgcccctgcgcca  7011

Query:  7000  gggaattctcaaacaattaaatgaaactggaggacccgtgcttgtaagtgctcccataag  7059
              |||||||||  ||||||||||||||  || || || |||||  |||||||||||||||||
Sbjct:  7012  gggaattctaaaacaattaaatgaaacaggaggagcagtacttgtaagtgctcccataag  7071

Query:  7060  cccagaagagcaagataaacttgaaaataagctcaagcagacaaatctccagtggataaa  7119
              |||||||||||||||| ||||||| ||||| |||| ||||||||||||||||||||||||
Sbjct:  7072  gccagaagagcaagataaacttgaaaagaagctcaaacagacaaatctccagtggataaa  7131

Query:  7120  ggtttccagagctttacctgagaaacaaggagaaattgaagctcaaataaaagaccttgg  7179
              |||  ||||||||||||||||||||||||||||  ||||| | ||| |||||||   |
Sbjct:  7132  ggtctccagagctttacctgagaaacaaggagagcttgaggttcacttaaaagatttag  7191

Query:  7180  gcagctt gnnnnnnngcttgaagaccttgaagagcagttaaatcatctgctgctgtggtt  7239
              ||||                  ||||||||||||  |||| ||||| ||||| |
Sbjct:  7192  gcag--- -----------------cttgaagagcagctggatcacctgcttctgtggct  7230

Query:  7240  atctcctattaggaatcagttggaaatttataaccaaccaaaccaagaaggaccatttga  7299
              ||||||||||| || ||||||||||||||||||||||||||| || | ||||| |||||
Sbjct:  7231  ctctcctattagaaaccagttggaaatttataaccaaccaagtcaggcaggaccgtttga  7290
```

FIGURE 11 (cont.)

```
Query: 7300  cgttcaggaaactgaaatagcagttcaagctaaacaaccggatgtggaagagattttgtc 7359
             |  ||||  ||||  || ||||||| | |||||||  |||||||||||  |  ||||||
Sbjct: 7291  cataaaggagattgaagtaacagttcacggtaaacaagcggatgtggaaaggcttttgtc 7350

Query: 7360  taaagggcagcatttgtacaaggaaaaaccagccactcagccagtgaagaggaagttaga 7419
             ||||||||||||||||||| ||||||||||| ||||||||||||||||||||||||||||
Sbjct: 7351  gaaagggcagcatttgtataaggaaaaaccaagcactcagccagtgaagaggaagttaga 7410

Query: 7420  agatctgagctctgagtggaaggcggtaaaccgtttacttcaagagctgagggcaaagca 7479
             ||||||||  ||||||||| |||| |||||| ||| ||||| |||||||||| |||||||
Sbjct: 7411  agatctgaggtctgagtgggaggctgtaaaccatttacttcgggagctgaggacaaagca 7470

Query: 7480  gcctgaccta gctcctggactgaccactattggagcctctcctactcagactgttactct 7539
             |||||||    || ||||||||||   |||||| |||||||| ||||||||||||||||||
Sbjct: 7471  gcctgaccgt gccctggactgagcactactggagcctctgccagtcagactgttactct 7530

Query: 7540  ggtgacacaacctgtggttactaaggaaactgccatctccaaactagaaatgccatcttc 7599
             |||||||||  ||||||||||||||||||||| |||||||||||||||||||||||||||
Sbjct: 7531  agtgacacaatctgtggttactaaggaaactgtcatctccaaactagaaatgccatcttc 7590

Query: 7600  cttgatgttggag gtacctgctctggcagatttcaaccgggcttggacagaacttaccga 7659
             ||| ||||||||| ||||||| ||||||| ||||||||| |||||||||||||||| ||
Sbjct: 7591  tttgctgttggag gtacctgcactggcagacttcaaccgagcttggacagaacttacaga 7650

Query: 7660  ctggctttctctgcttgatcaagttataaaatcacagagggtgatggtgggtgaccttga 7719
             |||||| ||||||||||||| |||||||||||||||||| ||||||||||||||  ||
Sbjct: 7651  ctggctgtctctgcttgatcgagttataaaatcacagagtgatggtgggtgatctgga 7710

Query: 7720  ggatatcaacgagatgatcatcaagcagaaggcaacaatgcaggatttggaacagaggcg 7779
             || |||||  || |||||||||| |||||||||||||  ||||| ||||||||||||| ||
Sbjct: 7711  agacatcaatgaaatgatcatcaaacagaaggcaacactgcaagatttggaacagagacg 7770

Query: 7780  tccccagttggaagaactcattaccgctgcccaaaatttgaaaaacaagaccagcaatca 7839
             |||||  |||||||||||||||| ||||||||| ||||||||||||||   ||||||||
Sbjct: 7771  ccccccaattggaagaactcattactgctgcccagaatttgaaaaacaaaaccagcaatca 7830

Query: 7840  agaggctagaacaatcattacggatcgaattgaaagaattcagaatcagtgggatgaagt 7899
             ||| |||||||||||||||| ||||||||||||||||||||||| ||||||||||||  ||
Sbjct: 7831  agaagctagaacaatcattactgatcgaattgaaagaattcagattcagtgggatgaggt 7890

Query: 7900  acaagaacaccttcagaaccggaggcaacagttgaatgaaatg ttaaaggattcaacaca 7959
             |||||||||  || |||||  ||||  |||||||||||||||| |||||||||||||||||
Sbjct: 7891  tcaagaacagctgcagaacaggagacaacagttgaatgaaatg ttaaaggattcaacaca 7950

Query: 7960  atggctggaagctaaggaagaagctgagcaggtcttaggacaggccagagccaagcttga 8019
             |||||||||||||||||||||||| || |||||| ||||||| ||||| ||||||||||
Sbjct: 7951  atggctggaagctaaggaagaagccgaacaggtcataggacaggtcagaggcaagcttga 8010

Query: 8020  gtcatggaaggagggtccctatacagtagatgcaatccaaaagaaaatcacagaaaccaa 8079
             |||||||  ||||| | |||||||||||||||||||||||||||| |||||||||||||
Sbjct: 8011  ctcatggaaagaaggtcctcacacagtagatgcaatccaaaagaagatcacagaaaccaa 8070

Query: 8080  gcagttggccaaagacctccgccagtggcagacaaatgtagatgtggcaaatgacttggc 8139
             ||||||||||||||||||||| |  ||||||  || |||||  |||||||||||  ||||  |||||
Sbjct: 8071  gcagttggccaaagacctccgtcaacggcagataagtgtagacgtggcaaatgatttggc 8130

Query: 8140  cctgaaacttctccgggattattctgcagatgataccagaaaagtccacatgataacaga 8199
             |||||||||||||  ||||| |||||||| |||||||||||||||| ||||||||||||||
Sbjct: 8131  actgaaacttcttcgggactattctgctgatgataccagaaaagtacacatgataacaga 8190

Query: 8200  gaatatcaatgcctcttggagaagcattcataaaagggtgagtgagcgagaggctgcttt 8259
             |||||||||| | |||||| |||  |||||||||||||| || ||||||||||||||||||
Sbjct: 8191  gaatatcaatacttcttggggaaacattcataaaagagtaagtgagcaagaggctgcttt 8250

Query: 8260  ggaagaaact catagattactgcaacagttccccctggacctggaaaagtttcttgcctg 8319
             ||||||||||| ||||||||||||| ||||| ||| |||||||||| |||||||| ||||
Sbjct: 8251  ggaagaaact catagattactgcagcagttccctctggacctggagaagtttctttcctg 8310
```

FIGURE 11 (cont.)

```
Query: 8320  gcttacagaagctgaaacaactgccaatgtcctacaggatgctacccgtaaggaaaggct 8379
             | |||| |||||  ||||||||||||||||||||||||| ||| ||||||||| | |||
Sbjct: 8311  gattacggaagcagaaacaactgccaatgtcctacaggacgcttcccgtaaggagaagct 8370

Query: 8380  cctagaagactccaaggggagtaaaagagctgatgaaacaatggcaagacctccaaggtga 8439
             ||||||||||||||||| ||||||  | ||||||||||| ||||||||||| ||||||| 
Sbjct: 8371  cctagaagactccagggggagtcagagagctgatgaaaccatggcaagatctccaaggaga 8430

Query: 8440  aattgaagctcacacagatgtttatcacaacctggatgaaaacagccaaaaaatcctgag 8499
             |||||||  ||||||||||  | ||||||| || |||||||  |||||||||||||||
Sbjct: 8431  aattgaaactcacacagatatctatcacaatcttgatgaaaatggccaaaaaatcctgag 8490

Query: 8500  atccctggaaggttccgatgatgcagtcctgttacaaagacgtttggataacatgaactt 8559
             |||||||||||||| ||||| |||  || ||||||||||||||||||||||||||| ||
Sbjct: 8491  atccctggaaggttcggatgaagcaccctgttacaaagacgtttggataacatgaatttt 8550

Query: 8560  caagtggagtgaacttcggaaaaagtctctcaacattaggtcccatttggaagccagt tc 8619
             ||||||||||||||||| |||||||||||||||||||||||||||||||||||| ||  
Sbjct: 8551  caagtggagtgaacttcagaaaaagtctctcaacattaggtcccatttggaagcaagt tc 8610

Query: 8620  tgaccagtggaagcgtctgcacctttctctgcaggaacttctggtgtggctacagctgaa 8679
             |||||||||||||||| ||||  ||||||||  ||||||||| ||  |||||||||||| 
Sbjct: 8611  tgaccagtggaagcgtttgcatctttctcttcaggaacttcttgtttggctacagctgaa 8670

Query: 8680  agatgatgaattaagccggcaggcacctattggaggcgactttccagcagttcagaagca 8739
             |||||||||  | |||||| |||||||  | |||| ||  ||| ||||||||||||||| 
Sbjct: 8671  agatgatgaactgagccgtcaggcacccatcggtggtgatttcccagcagttcagaagca 8730

Query: 8740  gaacgatgtacatagggccttcaagagggaattgaaaactaaagaacctgtaatcatgag 8799
             ||| ||  |||||||||||||||||||||||||||||||||||||||||||||||||||
Sbjct: 8731  gaatgatatacatagggccttcaagagggaattgaaaactaaagaacctgtaatcatgag 8790

Query: 8800  tactcttgagactgtacgaatatttctgacagagcagcctttggaaggactagagaaact 8859
             ||||| ||||||||   |||||||||||||||||||||||||||||||||||||||||| 
Sbjct: 8791  tactctggagactgtgagaatatttctgacagagcagcctttggaaggactagagaaact 8850

Query: 8860  ctaccaggagcccagagagctgcctcctgaggagagagcccagaatgtcactcggcttct 8919
             ||||||||||||||||||| ||||||||||  ||||| |||||||||||||||||| ||
Sbjct: 8851  ctaccaggagcccagagaactgcctcctgaagaaagagctcagaatgtcactcggctcct 8910

Query: 8920  acgaaagcaggctgaggaggtcaatactgagtggggaaaaattgaacctgcactccgctga 8979
             |||||||||||||||| |||||||  |||   |||| |||||||||||||| ||| ||| 
Sbjct: 8911  acgaaagcaggctgaagaggtcaacgctgaatgggacaaattgaacctgcgctcagctga 8970

Query: 8980  ctggcagagaaaaatagatgagaca cttgaaagactccaggaacttcaagaggccacgga 9039
             ||||||||||||||||||||| |   |||||||||||||||||||||| || || | || 
Sbjct: 8971  ttggcagagaaaaatagatgaagct cttgaaagactccaggaacttcaggaagctgccga 9030

Query: 9040  tgagctggacctcaagctgcgccaagctgaggtgatcaagggatcctggcagcccgtggg 9099
             ||| ||||||||||||| |||||||||||||||||||||||||||||||||||| ||||
Sbjct: 9031  tgaactggacctcaagttgcgccaagctgaggtgatcaagggatcctggcagccagtggg 9090

Query: 9100  cgatctcctcattgactctctccaagatcacctcgagaaagtcaaggcacttcgaggaga 9159
             |||||||||||||||||||||| |||||||||| ||  |||||||||||||||| ||||
Sbjct: 9091  ggatctcctcattgactctctgcaagatcaccttgaaaaagtcaaggcacttcggggaga 9150

Query: 9160  aattgcgcctctgaaagagaacgtgagccacgtcaatgaccttgctcgccagcttaccac 9219
             ||||| ||| || |||||||| ||||| | ||||||||||||||  |  ||||| |||| 
Sbjct: 9151  aattgcacctcttaaagagaatgtcaatcgtgtcaatgaccttgcacatcagctgaccac 9210

Query: 9220  tttgggcattcagctctcaccgtataacctcagcactctggaagacctgaacaccagatg 9279
             |||||||||||||||||||| ||||||||||||||| ||||||||  ||||  ||||||
Sbjct: 9211  actgggcattcagctctcacccttataacctcagcactttggaagatctgaataccagatg 9270

Query: 9280  gaagcttctgcaggtggccgtcgaggaccgagtcaggcagctgcatgaa
             || |||||| ||||||||  |||||||||| || ||||||||||||||
Sbjct: 9271  gaggcttctacaggtggctgtggaggaccgtgtcagacagctgcatgaa
```

FIGURE 12 (ΔR4-R23, SEQ ID NO:39)

```
GGGATTCCCTCACTTTCCCCCTACAGGACTCAGATCTGGGAGGCAATTACCTTCGGAGAAAAACGAATAGGA
AAAACTGAAGTGTTACTTTTTTTAAAGCTGCTGAAGTTTGTTGGTTTCTCATTGTTTTTAAGCCTACTGGAG
CAATAAAGTTTGAAGAACTTTTACCAGGTTTTTTTTATCGCTGCCTTGATATACACTTTTCAAAATGCTTTG
GTGGGAAGAAGTAGAGGACTGTTATGAAAGACAAGATGTTCAAAAGAAAACATTCACAAAATGGGTAAATGC
ACAATTTTCTAAGTTTGGGAAGCAGCATATTGAGAACCTCTTCAGTGACCTACAGGATGGGAGGCGCCTCCT
AGACCTCCTCGAAGGCCTGACAGGGCAAAAACTGCCAAAAGAAAAAGGATCCACAAGAGTTCATGCCCTGAA
CAATGTCAACAAGGCACTGCGGGTTTTGCAGAACAATAATGTTGATTTAGTGAATATTGGAAGTACTGACAT
CGTAGATGGAAATCATAAACTGACTCTTGGTTTGATTTGGAATATAATCCTCCACTGGCAGGTCAAAAATGT
AATGAAAAATATCATGGCTGGATTGCAACAAACCAACAGTGAAAAGATTCTCCTGAGCTGGGTCCGACAATC
AACTCGTAATTATCCACAGGTTAATGTAATCAACTTCACCACCAGCTGGTCTGATGGCCTGGCTTTGAATGC
TCTCATCCATAGTCATAGGCCAGACCTATTTGACTGGAATAGTGTGGTTTGCCAGCAGTCAGCCACACAACG
ACTGGAACATGCATTCAACATCGCCAGATATCAATTAGGCATAGAGAAACTACTCGATCCTGAAGATGTTGA
TACCACCTATCCAGATAAGAAGTCCATCTTAATGTACATCACATCACTCTTCCAAGTTTTGCCTCAACAAGT
GAGCATTGAAGCCATCCAGGAAGTGGAAATGTTGCCAAGGCCACCTAAAGTGACTAAAGAAGAACATTTTCA
GTTACATCATCAAATGCACTATTCTAACAGATCACGGTCAGTCTAGCACAGGGATATGAGAGAACTTCTTC
CCCTAAGCCTCGATTCAAGAGCTATGCCTACACACAGGCTGCTTATGTCACCACCTCTGACCCTACACGGAG
CCCATTTCCTTCACAGCATTTGGAAGCTCCTGAAGACAAGTCATTTGGCAGTTCATTGATGGAGAGTGAAGT
AAACCTGGACCGTTATCAAACAGCTTTAGAAGAAGTATTATCGTGGCTTCTTTCTGCTGAGGACACATTGCA
AGCACAAGGAGAGATTTCTAATGATGTGGAAGTGGTGAAAGACCAGTTTCATACTCATGAGGGGTACATGAT
GGATTTGACAGCCCATCAGGGCCGGGTTGGTAATATTCTACAATTGGGAAGTAAGCTGATTGGAACAGGAAA
ATTATCAGAAGATGAAGAAACTGAAGTACAAGAGCAGATGAATCTCCTAAATTCAAGATGGGAATGCCTCAG
GGTAGCTAGCATGGAAAAACAAAGCAATTTACATAGAGTTTTAATGGATCTCCAGAATCAGAAACTGAAAGA
GTTGAATGACTGGCTAACAAAAACAGAAGAAAGAACAAGGAAAATGGAGGAAGAGCCTCTTGGACCTGATCT
TGAAGACCTAAAACGCCAAGTACAACAACATAAGGTGCTTCAAGAAGATCTAGAACAAGAACAAGTCAGGGT
CAATTCTCTCACTCACATGGTGGTGGTAGTTGATGAATCTAGTGGAGATCACGCAACTGCTGCTTTGGAAGA
ACAACTTAAGGTATTGGGAGATCGATGGGCAAACATCTGTAGATGGACAGAAGACCGCTGGGTTCTTTTACA
AGACATCCTTCTCAAATGGCAACGTCTTACTGAAGAACAGTGCCTTTTTAGTGCATGGCTTTCAGAAAAAGA
AGATGCAGTGAACAAGATTCACACAACTGGCTTTAAAGATCAAAATGAAATGTTATCAAGTCTTCAAAAACT
GGCCGTTTTAAAAGCGGATCTAGAAAAGAAAAAGCAATCCATGGGCAAACTGTATTCACTCAAACAAGATCT
TCTTTCAACACTGAAGAATAAGTCAGTGACCCAGAAGACGGAAGCATGGCTGGATAACTTTGCCCGGTGTTG
GGATAATTTAGTCCAAAAACTTGAAAAGAGTACAGCACAGATTTCACAGGCTGTCACCACCACTCAGCCATC
ACTAACACAGACAACTGTAATGGAAACAGTAACTACGGTGACCACAAGGGAACAGATCCTGGTAAAGCATGC
TCAAGAGGAACTTCCACCACCACCTGCCCAAAAGAAGAGGCAGATTACTGTGGATCTTGAAAGACTCCAGGA
ACTTCAAGAGGCCACGGATGAGCTGGACCTCAAGCTGCGCCAAGCTGAGGTGATCAAGGGATCCTGGCAGCC
CGTGGGCGATCTCCTCATTGACTCTCTCCAAGATCACCTCGAGAAAGTCAAGGCACTTCGAGGAGAAATTGC
GCCTCTGAAAGAGAACGTGAGCCACGTCAATGACCTTGCTCGCCAGCTTACCACTTTGGCATTCAGCTCTC
ACCGTATAACCTCAGCACTCTGGAAGACCTGAACACCAGATGGAAGCTTCTGCAGGTGGCCGTCGAGGACCG
AGTCAGGCAGCTGCATGAAGCCCACAGGGACTTTGGTCCAGCATCTCAGCACTTTCTTTCCACGTCTGTCCA
GGGTCCCTGGGAGAGAGCCATCTCGCCAAACAAAGTGCCCTACTATATCAACCACGAGACTCAAACAACTTG
CTGGGACCATCCCAAAATGACAGAGCTCTACCAGTCTTTAGCTGACCTGAATAATGTCAGATTCTCAGCTTA
TAGGACTGCCATGAAACTCCGAAGACTGCAGAAGGCCCTTTGCTTGGATCTCTTGAGCCTGTCAGCTGCATG
TGATGCCTTGGACCAGCACAACCTCAAGCAAAATGACCAGCCCATGGATATCCTGCAGATTATTAATTGTTT
GACCACTATTTATGACCGCCTGGAGCAAGAGCACAACAATTTGGTCAACGTCCCTCTCTGCCGTGGATATGTG
TCTGAACTGGCTGCTGAATGTTTATGATACGGGACGAACAGGGAGGATCCGTGTCCTGTCTTTTAAAACTGG
CATCATTTCCCTGTGTAAAGCACATTTGGAAGACAAGTACAGATACCTTTTCAAGCAAGTGGCAAGTTCAAC
AGGATTTTGTGACCAGCGCAGGCTGGGCCTCCTTCTGCATGATTCTATCCAAATTCCAAGACAGTTGGGTGA
AGTTGCATCCTTTGGGGGCAGTAACATTGAGCCAAGTGTCCGGAGCTGCTTCCAATTTGCTAATAATAAGCC
AGAGATCGAAGCGGCCCTCTTCCTAGACTGGATGAGACTGGAACCCCAGTCCATGGTGTGGCTGCCCGTCCT
GCACAGAGTGGCTGCTGCAGAAACTGCCAAGCATCAGGCCAAATGTAACATCTGCAAAGAGTGTCCAATCAT
TGGATTCAGGTACAGGAGTCTAAAGCACTTTAATTATGACATCTGCCAAAGCTGCTTTTTTTCTGGTCGAGT
TGCAAAAGGCCATAAAATGCACTATCCCATGGTGGAATATTGCACTCCGACTACATCAGGAGAAGATGTTCG
AGACTTTGCCAAGGTACTAAAAAACAAATTTCGAACCAAAAGGTATTTTGCGAAGCATCCCCGAATGGGCTA
CCTGCCAGTGCAGACTGTCTTAGAGGGGGACAACATGGAAACGCCTGCCTCGTCCCCTCAGCTTTCACACGA
```

FIGURE 12 (cont.)

```
TGATACTCATTCACGCATTGAACATTATGCTAGCAGGCTAGCAGAAATGGAAAACAGCAATGGATCTTATCT
AAATGATAGCATCTCTCCTAATGAGAGCATAGATGATGAACATTTGTTAATCCAGCATTACTGCCAAAGTTT
GAACCAGGACTCCCCCCTGAGCCAGCCTCGTAGTCCTGCCCAGATCTTGATTTCCTTAGAGAGTGAGGAAAG
AGGGGAGCTAGAGAGAATCCTAGCAGATCTTGAGGAAGAAAACAGGAATCTGCAAGCAGAATATGACCGTCT
AAAGCAGCAGCACGAACATAAAGGCCTGTCCCCACTGCCGTCCCTCCTGAAATGATGCCCACCTCTCCCCA
GAGTCCCCGGGATGCTGAGCTCATTGCTGAGGCCAAGCTACTGCGTCAACACAAAGGCCGCCTGGAAGCCAG
GATGCAAATCCTGGAAGACCACAATAAACAGCTGGAGTCACAGTTACACAGGCTAAGGCAGCTGCTGGAGCA
ACCCCAGGCAGAGGCCAAAGTGAATGGCACAACGGTGTCCTCTCCTTCTACCTCTCTACAGAGGTCCGACAG
CAGTCAGCCTATGCTGCTCCGAGTGGTTGGCAGTCAAACTTCGGACTCCATGGGTGAGGAAGATCTTCTCAG
TCCTCCCCAGGACACAAGCACAGGGTTAGAGGAGGTGATGGAGCAACTCAACAACTCCTTCCCTAGTTCAAG
AGGAAGAAATACCCCTGGAAAGCCAATGAGAGAGGACACAATGTAGGAAGTCTTTTCCACATGGCAGATGAT
TTGGGCAGAGCGATGGAGTCCTTAGTATCAGTCATGACAGATGAAGAAGGAGCAGAATAAATGTTTTACAAC
TCCTGATTCCCGCATGGTTTTTATAATATTCATACAACAAAGAGGATTAGACAGTAAGAGTTTACAAGAAAT
AAATCTATATTTTTGTGAAGGGTAGTGGTATTATACTGTAGATTTCAGTAGTTTCTAAGTCTGTTATTGTTT
TGTTAACAATGGCAGGTTTTACACGTCTATGCAATTGTACAAAAAAGTTATAAGAAAACTACATGTAAAATC
TTGATAGCTAAATAACTTGCCATTTCTTTATATGGAACGCATTTTGGGTTGTTTAAAAATTTATAACAGTTA
TAAAGAAAGATTGTAAACTAAAGTGTGCTTTATAAAAAAAAGTTGTTTATAAAAACCCCTAAAAACAAAACA
AACACACACACACACACATACACACACACACACAAAACTTTGAGGCAGCGCATTGTTTTGCATCCTTTTGGC
GTGATATCCATATGAAATTCATGGCTTTTTCTTTTTTTGCATATTAAAGATAAGACTTCCTCTACCACCACA
CCAAATGACTACTACACACTGCTCATTTGAGAACTGTCAGCTGAGTGGGGCAGGCTTGAGTTTTCATTTCAT
ATATCTATATGTCTATAAGTATATAAATACTATAGTTATATAGATAAAGAGATACGAATTTCTATAGACTGA
CTTTTTCCATTTTTTAAATGTTCATGTCACATCCTAATAGAAAGAAATTACTTCTAGTCAGTCATCCAGGCT
TACCTGCTTGGTCTAGA
```

FIGURE 13 (ΔR2-R21, SEQ ID NO:40)

```
GGGATTCCCTCACTTTCCCCCTACAGGACTCAGATCTGGGAGGCAATTACCTTCGGAGAAAAACGAATAGGA
AAAACTGAAGTGTTACTTTTTTTAAAGCTGCTGAAGTTTGTTGGTTTCTCATTGTTTTTAAGCCTACTGGAG
CAATAAAGTTTGAAGAACTTTTACCAGGTTTTTTTTATCGCTGCCTTGATATACACTTTTCAAAATGCTTTG
GTGGGAAGAAGTAGAGGACTGTTATGAAAGAGAAGATGTTCAAAAGAAAACATTCACAAAATGGGTAAATGC
ACAATTTTCTAAGTTTGGGAAGCAGCATATTGAGAACCTCTTCAGTGACCTACAGGATGGGAGGCGCCTCCT
AGACCTCCTCGAAGGCCTGACAGGGCAAAAACTGCCAAAAGAAAAAGGATCCACAAGAGTTCATGCCCTGAA
CAATGTCAACAAGGCACTGCGGGTTTTGCAGAACAATAATGTTGATTTAGTGAATATTGGAAGTACTGACAT
CGTAGATGGAAATCATAAACTGACTCTTGGTTTGATTTGGAATATAATCCTCCACTGGCAGGTCAAAAATGT
AATGAAAAATATCATGGCTGGATTGCAACAAACCAACAGTGAAAAGATTCTCCTGAGCTGGGTCCGACAATC
AACTCGTAATTATCCACAGGTTAATGTAATCAACTTCACCACCAGCTGGTCTGATGGCCTGGCTTTGAATGC
TCTCATCCATAGTCATAGGCCAGACCTATTTGACTGGAATAGTGTGGTTTGCCAGCAGTCAGCCACACAACG
ACTGGAACATGCATTCAACATCGCCAGATATCAATTAGGCATAGAGAAACTACTCGATCCTGAAGATGTTGA
TACCACCTATCCAGATAAGAAGTCCATCTTAATGTACATCACATCACTCTTCCAAGTTTTGCCTCAACAAGT
GAGCATTGAAGCCATCCAGGAAGTGGAAATGTTGCCAAGGCCACCTAAAGTGACTAAAGAAGAACATTTTCA
GTTACATCATCAAATGCACTATTCTCAACAGATCACGGTCAGTCTAGCACAGGGATATGAGAGAACTTCTTC
CCCTAAGCCTCGATTCAAGAGCTATGCCTACACACAGGCTGCTTATGTCACCACCTCTGACCCTACACGGAG
CCCATTTCCTTCACAGCATTTGGAAGCTCCTGAAGACAAGTCATTTGGCAGTTCATTGATGGAGAGTGAAGT
AAACCTGGACCGTTATCAAACAGCTTTAGAAGAAGTATTATCGTGGCTTCTTTCTGCTGAGGACACATTGCA
AGCACAAGGAGAGATTTCTAATGATGTGGAAGTGGTGAAAGACCAGTTTCATACTCATGAGGGGTACATGAT
GGATTTGACAGCCCATCAGGGCCGGGTTGGTAATATTCTACAATTGGGAAGTAAGCTGATTGGAACAGGAAA
ATTATCAGAAGATGAAGAAACTGAAGTACAAGAGCAGATGAATCTCCTAAATTCAAGATGGGAATGCCTCAG
GGTAGCTAGCATGGAAAAACAAAGCAATTTACATCATAGATTACTGCAACAGTTCCCCCTGGACCTGGAAAA
GTTTCTTGCCTGGCTTACAGAAGCTGAAACAACTGCCAATGTCCTACAGGATGCTACCCGTAAGGAAAGGCT
CCTAGAAGACTCCAAGGGAGTAAAAGAGCTGATGAAACAATGGCAAGACCTCCAAGGTGAAATTGAAGCTCA
CACAGATGTTTATCACAACCTGGATGAAAACAGCCAAAAAATCCTGAGATCCCTGGAAGGTTCCGATGATGC
AGTCCTGTTACAAAGACGTTTGGATAACATGAACTTCAAGTGGAGTGAACTTCGGAAAAAGTCTCTCAACAT
TAGGTCCCATTTGGAAGCCAGTTCTGACCAGTGGAAGCGTCTGCACCTTTCTCTGCAGGAACTTCTGGTGTG
GCTACAGCTGAAAGATGATGAATTAAGCCGGCAGGCACCTATTGGAGGCGACTTTCCAGCAGTTCAGAAGCA
GAACGATGTACATAGGGCCTTCAAGAGGGAATTGAAAACTAAAGAACCTGTAATCATGAGTACTCTTGAGAC
TGTACGAATATTTCTGACAGAGCAGCCTTTGGAAGGACTAGAGAAACTCTACCAGGAGCCCAGAGAGCTGCC
TCCTGAGGAGAGAGCCCAGAATGTCACTCGGCTTCTACGAAAGCAGGCTGAGGAGGTCAATACTGAGTGGGA
AAAATTGAACCTGCACTCCGCTGACTGGCAGAGAAAAATAGATGAGACCCTTGAAAGACTCCAGGAACTTCA
AGAGGCCACGGATGAGCTGGACCTCAAGCTGCGCCAAGCTGAGGTGATCAAGGGATCCTGGCAGCCCGTGGG
CGATCTCCTCATTGACTCTCTCCAAGATCACCTCGAGAAAGTCAAGGCACTTCGAGGAGAAATTGCGCCTCT
GAAAGAGAACGTGAGCCACGTCAATGACCTTGCTCGCCAGCTTACCACTTTGGGCATTCAGCTCTCACCGTA
TAACCTCAGCACTCTGGAAGACCTGAACACCAGATGGAAGCTTCTGCAGGTGGCCGTCGAGGACCGAGTCAG
GCAGCTGCATGAAGCCCACAGGGACTTTGGTCCAGCATCTCAGCACTTTCTTTCCACGTCTGTCCAGGGTCC
CTGGGAGAGAGCCATCTCGCCAAACAAAGTGCCCTACTATATCAACCACGAGACTCAAACAACTTGCTGGGA
CCATCCCAAAATGACAGAGCTCTACCAGTCTTTAGCTGACCTGAATAATGTCAGATTCTCAGCTTATAGGAC
TGCCATGAAACTCCGAAGACTGCAGAAGGCCCTTTGCTTGATCTCTTGAGCCTGTCAGCTGCATGTGATGC
CTTGGACCAGCACAACCTCAAGCAAAATGACCAGCCCATGGATATCCTGCAGATTATTAATTGTTTGACCAC
TATTTATGACCGCCTGGAGCAAGAGCACAACAATTTGGTCAACGTCCCTCTCTGCGTGGATATGTGTCTGAA
CTGGCTGCTGAATGTTTATGATACGGGACGAACAGGGAGGATCCGTGTCCTGTCTTTTAAAACTGGCATCAT
TTCCCTGTGTAAAGCACATTTGGAAGACAAGTACAGATACCTTTTCAAGCAAGTGGCAAGTTCAACAGGATT
TTGTGACCAGCGCAGGCTGGGCCTCCTTCTGCATGATTCTATCCAAATTCCAAGACAGTTGGGTGAAGTTGC
ATCCTTTGGGGGCAGTAACATTGAGCCAAGTGTCCGGAGCTGCTTCCAATTTGCTAATAATAAGCCAGAGAT
CGAAGCGGCCCTCTTCCTAGACTGGATGAGACTGGAACCCCAGTCCATGGTGTGGCTGCCCGTCCTGCACAG
AGTGGCTGCTGCAGAAACTGCCAAGCATCAGGCCAAATGTAACATCTGCAAAGAGTGTCCAATCATTGGATT
CAGGTACAGGAGTCTAAAGCACTTTAATTATGACATCTGCCAAAGCTGCTTTTTTTCTGGTCGAGTTGCAAA
AGGCCATAAAATGCACTATCCCATGGTGGAATATTGCACTCCGACTACATCAGGAGAAGATGTTCGAGACTT
TGCCAAGGTACTAAAAAACAAATTTCGAACCAAAAGGTATTTTGCGAAGCATCCCCGAATGGGCTACCTGCC
AGTGCAGACTGTCTTAGAGGGGACAACATGGAAACGCCTGCCTCGTCCCCTCAGCTTTCACACGATGATAC
TCATTCACGCATTGAACATTATGCTAGCAGGCTAGCAGAAATGGAAAACAGCAATGGATCTTATCTAAATGA
```

FIGURE 13 (cont.)

```
TAGCATCTCTCCTAATGAGAGCATAGATGATGAACATTTGTTAATCCAGCATTACTGCCAAAGTTTGAACCA
GGACTCCCCCCTGAGCCAGCCTCGTAGTCCTGCCCAGATCTTGATTTCCTTAGAGAGTGAGGAAAGAGGGGA
GCTAGAGAGAATCCTAGCAGATCTTGAGGAAGAAAACAGGAATCTGCAAGCAGAATATGACCGTCTAAAGCA
GCAGCACGAACATAAAGGCCTGTCCCCACTGCCGTCCCCTCCTGAAATGATGCCCACCTCTCCCCAGAGTCC
CCGGGATGCTGAGCTCATTGCTGAGGCCAAGCTACTGCGTCAACACAAAGGCCGCCTGGAAGCCAGGATGCA
AATCCTGGAAGACCACAATAAACAGCTGGAGTCACAGTTACACAGGCTAAGGCAGCTGCTGGAGCAACCCCA
GGCAGAGGCCAAAGTGAATGGCACAACGGTGTCCTCTCCTTCTACCTCTCTACAGAGGTCCGACAGCAGTCA
GCCTATGCTGCTCCGAGTGGTTGGCAGTCAAACTTCGGACTCCATGGGTGAGGAAGATCTTCTCAGTCCTCC
CCAGGACACAAGCACAGGGTTAGAGGAGGTGATGGAGCAACTCAACAACTCCTTCCCTAGTTCAAGAGGAAG
AAATACCCCTGGAAAGCCAATGAGAGAGGACACAATGTAGGAAGTCTTTTCCACATGGCAGATGATTTGGGC
AGAGCGATGGAGTCCTTAGTATCAGTCATGACAGATGAAGAAGGAGCAGAATAAATGTTTTACAACTCCTGA
TTCCCGCATGGTTTTTATAATATTCATACAACAAAGAGGATTAGACAGTAAGAGTTTACAAGAAATAAATCT
ATATTTTTGTCAAGGGTAGTGGTATTATACTGTAGATTTCAGTAGTTTCTAAGTCTGTTATTGTTTTGTTAA
CAATGGCAGGTTTTACACGTCTATGCAATTGTACAAAAAAGTTATAAGAAAACTACATGTAAAATCTTGATA
GCTAAATAACTTGCCATTTCTTTATATGGAACGCATTTTGGGTTGTTTAAAAATTTATAACAGTTATAAAGA
AAGATTGTAAACTAAAGTGTGCTTTATAAAAAAAAGTTGTTTATAAAAACCCCTAAAAACAAAACAAACACA
CACACACACACATACACACACACACAAAACTTTGAGGCAGCGCATTGTTTTGCATCCTTTTGGCGTGATA
TCCATATGAAATTCATGGCTTTTTCTTTTTTTGCATATTAAAGATAAGACTTCCTCTACCACCACACCAAAT
GACTACTACACACTGCTCATTTGAGAACTGTCAGCTGAGTGGGGCAGGCTTGAGTTTTCATTTCATATATCT
ATATGTCTATAAGTATATAAATACTATAGTTATATAGATAAAGAGATACGAATTTCTATAGACTGACTTTTT
CCATTTTTTAAATGTTCATGTCACATCCTAATAGAAAGAAATTACTTCTAGTCAGTCATCCAGGCTTACCTG
CTTGGTCTAGA
```

FIGURE 14 (ΔR2-R21+H3, SEQ ID NO:41)

```
GGGATTCCCTCACTTTCCCCCTACAGGACTCAGATCTGGGAGGCAATTACCTTCGGAGAAAAACGAATAGGA
AAAACTGAAGTGTTACTTTTTTTAAAGCTGCTGAAGTTTGTTGGTTTCTCATTGTTTTTAAGCCTACTGGAG
CAATAAAGTTTGAAGAACTTTTACCAGGTTTTTTTTATCGCTGCCTTGATATACACTTTTCAAAATGCTTTG
GTGGGAAGAAGTAGAGGACTGTTATGAAAGAGAAGATGTTCAAAAGAAAACATTCACAAAATGGGTAAATGC
ACAATTTTCTAAGTTTGGGAAGCAGCATATTGAGAACCTCTTCAGTGACCTACAGGATGGGAGGCGCCTCCT
AGACCTCCTCGAAGGCCTGACAGGGCAAAAACTGCCAAAAGAAAAAGGATCCACAAGAGTTCATGCCCTGAA
CAATGTCAACAAGGCACTGCGGGTTTTGCAGAACAATAATGTTCATTTAGTGAATATTGGAAGTACTGACAT
CGTAGATGGAAATCATAAACTGACTCTTGGTTTGATTTGGAATATAATCCTCCACTGGCAGGTCAAAAATGT
AATGAAAAATATCATGGCTGGATTGCAACAAACCAACAGTGAAAAGATTCTCCTGAGCTGGGTCCGACAATC
AACTCGTAATTATCCACAGGTTAATGTAATCAACTTCACCACCAGCTGGTCTGATGGCCTGGCTTTGAATGC
TCTCATCCATAGTCATAGGCCAGACCTATTTGACTGGAATAGTGTGGTTTGCCAGCAGTCAGCCACACAACG
ACTGGAACATGCATTCAACATCGCCAGATATCAATTAGGCATAGAGAAACTACTCGATCCTGAAGATGTTGA
TACCACCTATCCAGATAAGAAGTCCATCTTAATGTACATCACATCACTCTTCCAAGTTTTGCCTCAACAAGT
GAGCATTGAAGCCATCCAGGAAGTGGAAATGTTGCCAAGGCCACCTAAAGTGACTAAAGAAGAACATTTTCA
GTTACATCATCAAATGCACTATTCTCAACAGATCACGGTCAGTCTAGCACAGGGATATGAGAGAACTTCTTC
CCCTAAGCCTCGATTCAAGAGCTATGCCTACACACAGGCTGCTTATGTCACCACCTCTGACCCTACACGGAG
CCCATTTCCTTCACAGCATTTGGAAGCTCCTGAAGACAAGTCATTTGGCAGTTCATTGATGGAGAGTGAAGT
AAACCTGGACCGTTATCAAACAGCTTTAGAAGAAGTATTATCGTGGCTTCTTTCTGCTGAGGACACATTGCA
AGCACAAGGAGAGATTTCTAATGATGTGGAAGTGGTGAAAGACCAGTTTCATACTCATGAGGGGTACATGAT
GGATTTGACAGCCCATCAGGGCCGGGTTGGTAATATTCTACAATTGGGAAGTAAGCTGATTGGAACAGGAAA
ATTATCAGAAGATGAAGAAACTGAAGTACAAGAGCAGATGAATCTCCTAAATTCAAGATGGGAATGCCTCAG
GGTAGCTAGCATGAAAAACAAAGCAATTTACATGCTCCTGGACTGACCACTATTGGAGCCTCTCCTACTCA
GACTGTTACTCTGGTGACACAACCTGTGGTTACTAAGGAAACTGCCATCTCCAAACTAGAAATGCCATCTTC
CTTGATGTTGGAGCATAGATTACTGCAACAGTTCCCCCTGGACCTGGAAAAGTTTCTTGCCTGGCTTACAGA
AGCTGAAACAACTGCCAATGTCCTACAGGATGCTACCCGTAAGGAAAGGCTCCTAGAAGACTCCAAGGGAGT
AAAAGAGCTGATGAAACAATGGCAAGACCTCCAAGGTGAAATTGAAGCTCACACAGATGTTTATCACAACCT
GGATGAAAACAGCCAAAAAATCCTGAGATCCCTGGAAGGTTCCGATGATGCAGTCCTGTTACAAAGACGTTT
GGATAACATGAACTTCAAGTGGAGTGAACTTCGGAAAAAGTCTCTCAACATTAGGTCCCATTTGGAAGCCAC
TTCTGACCAGTGGAAGCGTCTGCACCTTTCTCTGCAGGAACTTCTGGTGTGGCTACAGCTGAAAGATGATGA
ATTAAGCCGGCAGGCACCTATTGGAGGCGACTTTCCAGCAGTTCAGAAGCAGAACGATGTACATAGGGCCTT
CAAGAGGGAATTGAAAACTAAAGAACCTGTAATCATGAGTACTCTTGAGACTGTACGAATATTTCTGACAGA
GCAGCCTTTGGAAGGACTAGAGAAACTCTACCAGGAGCCCAGAGAGCTGCCTCCTGAGGAGAGAGCCCAGAA
TGTCACTCGGCTTCTACGAAAGCAGGCTGAGGAGGTCAATACTGAGTGGGAAAAATTGAACCTGCACTCCGC
TGACTGGCAGAGAAAAATAGATGAGACCCTTGAAAGACTCCAGGAACTTCAAGAGGCCACGGATGAGCTGGA
CCTCAAGCTGCGCCAAGCTGAGGTGATCAAGGGATCCTGGCAGCCCGTGGGCGATCTCCTCATTGACTCTCT
CCAAGATCACCTCGAGAAAGTCAAGGCACTTCGAGGAGAAATTGCGCCTCTGAAAGAGAACGTGAGCCACGT
CAATGACCTTGCTCGCCAGCTTACCACTTTGGGCATTCAGCTCTCACCGTATAACCTCAGCACTCTGGAAGA
CCTGAACACCAGATGGAAGCTTCTGCAGGTGGCCGTCGAGGACCGAGTCAGGCAGCTGCATGAAGCCCACAG
GGACTTTGGTCCAGCATCTCAGCACTTTCTTTCCACGTCTGTCCAGGGTCCCTGGGAGAGAGCCATCTCGCC
AAACAAAGTGCCCTACTATATCAACCACGAGACTCAAACAACTTGCTGGGACCATCCCAAAATGACAGAGCT
CTACCAGTCTTTAGCTGACCTGAATAATGTCAGATTCTCAGCTTATAGGACTGCCATGAAACTCCGAAGACT
GCAGAAGGCCCTTTGCTTGGATCTCTTGAGCCTGTCAGCTGCATGTGATGCCTTGGACCAGCACAACCTCAA
GCAAAATGACCAGCCCATGGATATCCTGCAGATTATTAATTGTTTGACCACTATTTATGACCGCCTGGAGCA
AGAGCACAACAATTTGGTCAACGTCCCTCTCTGCGTGGATATGTGTCTGAACTGGCTGCTGAATGTTTATGA
TACGGGACGAACAGGGAGGATCCGTGTCCTGTCTTTTAAAACTGGCATCATTTCCCTGTGTAAAGCACATTT
GGAAGACAAGTACAGATACCTTTTCAAGCAAGTGGCAAGTTCAACAGGATTTTGTGACCAGCGCAGGCTGGG
CCTCCTTCTGCATGATTCTATCCAAATTCCAAGACAGTTGGGTGAAGTTGCATCCTTTGGGGCAGTAACAT
TGAGCCAAGTGTCCGGAGCTGCTTCCAATTTGCTAATAATAAGCCAGAGATCGAAGCGGCCCTCTTCCTAGA
CTGGATGAGACTGGAACCCCAGTCCATGGTGTGGCTGCCCGTCCTGCACAGAGTGGCTGCTGCAGAAACTGC
CAAGCATCAGGCCAAATGTAACATCTGCAAAGAGTGTCCAATCATTGGATTCAGGTACAGGAGTCTAAAGCA
CTTTAATTATGACATCTGCCAAAGCTGCTTTTTTTCTGGTCGAGTTGCAAAAGGCCATAAAATGCACTATCC
CATGGTGGAATATTGCACTCCGACTACATCAGGAGAAGATGTTCGAGACTTTGCCAAGGTACTAAAAAACAA
ATTTCGAACCAAAAGGTATTTTGCGAAGCATCCCCGAATGGGCTACCTGCCAGTGCAGACTGTCTTAGAGGG
```

FIGURE 14 (cont.)

```
GGACAACATGGAAACGCCTGCCTCGTCCCCTCAGCTTTCACACGATGATACTCATTCACGCATTGAACATTA
TGCTAGCAGGCTAGCAGAAATGGAAAACAGCAATGGATCTTATCTAAATGATAGCATCTCTCCTAATGAGAG
CATAGATGATGAACATTTGTTAATCCAGCATTACTGCCAAAGTTTGAACCAGGACTCCCCCCTGAGCCAGCC
TCGTAGTCCTGCCCAGATCTTGATTTCCTTAGAGAGTGAGGAAAGAGGGGAGCTAGAGAGAATCCTAGCAGA
TCTTGAGGAAGAAAACAGGAATCTGCAAGCAGAATATGACCGTCTAAAGCAGCAGCACGAACATAAAGGCCT
GTCCCCACTGCCGTCCCCTCCTGAAATGATGCCCACCTCTCCCCAGAGTCCCCGGGATGCTGAGCTCATTGC
TGAGGCCAAGCTACTGCGTCAACACAAAGGCCGCCTGGAAGCCAGGATGCAAATCCTGGAAGACCACAATAA
ACAGCTGGAGTCACAGTTACACAGGCTAAGGCAGCTGCTGGAGCAACCCCAGGCAGAGGCCAAAGTGAATGG
CACAACGGTGTCCTCTCCTTCTACCTCTCTACAGAGGTCCGACAGCAGTCAGCCTATGCTGCTCCGAGTGGT
TGGCAGTCAAACTTCGGACTCCATGGGTGAGGAAGATCTTCTCAGTCCTCCCCAGGACACAAGCACAGGGTT
AGAGGAGGTGATGGAGCAACTCAACAACTCCTTCCCTAGTTCAAGAGGAAGAAATACCCCTGGAAAGCCAAT
GAGAGAGGACACAATGTAGGAAGTCTTTTCCACATGGCAGATGATTTGGGCAGAGCGATGGAGTCCTTAGTA
TCAGTCATGACAGATGAAGAAGGAGCAGAATAAATGTTTTACAACTCCTGATTCCCGCATGGTTTTTATAAT
ATTCATACAACAAAGAGGATTAGACAGTAAGAGTTTACAAGAAATAAATCTATATTTTTGTGAAGGGTAGTG
GTATTATACTGTAGATTTCAGTAGTTTCTAAGTCTGTTATTGTTTTGTTAACAATGGCAGGTTTTACACGTC
TATGCAATTGTACAAAAAGTTATAAGAAAACTACATGTAAAATCTTGATAGCTAAATAACTTGCCATTTCT
TTATATGGAACGCATTTTGGGTTGTTTAAAAATTTATAACAGTTATAAAGAAAGATTGTAAACTAAAGTGTG
CTTTATAAAAAAAAGTTGTTTATAAAAACCCCTAAAAAACAAAACAAACACACACACACACACATACACACAC
ACACACAAAACTTTGAGGCAGCGCATTGTTTTGCATCCTTTTGGCGTGATATCCATATGAAATTCATGGCTT
TTTCTTTTTTTGCATATTAAAGATAAGACTTCCTCTACCACCACACCAAATGACTACTACACACTGCTCATT
TGAGAACTGTCAGCTGAGTGGGGCAGGCTTGAGTTTTCATTTCATATATCTATATGTCTATAAGTATATAAA
TACTATAGTTATATAGATAAAGAGATACGAATTTCTATAGACTGACTTTTTCCATTTTTTAAATGTTCATGT
CACATCCTAATAGAAAGAAATTACTTCTAGTCAGTCATCCAGGCTTACCTGCTTGGTCTAGA
```

FIGURE 15 (AH2-R19, SEQ ID NO:42)

```
gggattccct cactttcccc ctacaggact cagatctggg aggcaattac cttcggagaa
aaacgaatag gaaaaactga agtgttactt tttttaaagc tgctgaagtt tgttggtttc
tcattgtttt taagcctact ggagcaataa agtttgaaga acttttacca ggttttttt
atcgctgcct tgatatacac ttttcaaaat gctttggtgg gaagaagtag aggactgtta
tgaaagagaa gatgttcaaa agaaaacatt cacaaaatgg gtaaatgcac aattttctaa
gtttgggaag cagcatattg agaacctctt cagtgaccta caggatggga ggcgcctcct
agacctcctc gaaggcctga cagggcaaaa actgccaaaa gaaaaaggat ccacaagagt
tcatgccctg aacaatgtca acaaggcact gcgggttttg cagaacaata atgttgattt
agtgaatatt ggaagtactg acatcgtaga tggaaatcat aaactgactc ttggtttgat
ttggaatata atcctccact ggcaggtcaa aaatgtaatg aaaaatatca tggctggatt
gcaacaaacc aacagtgaaa agattctcct gagctgggtc cgacaatcaa ctcgtaatta
tccacaggtt aatgtaatca acttcaccac cagctggtct gatggcctgg ctttgaatgc
tctcatccat agtcataggc cagacctatt tgactggaat agtgtggttt gccagcagtc
agccacacaa cgactggaac atgcattcaa catcgccaga tatcaattag catagagaa
actactcgat cctgaagatg ttgataccac ctatccagat aagaagtcca tcttaatgta
catcacatca ctcttccaag ttttgcctca acaagtgagc attgaagcca tccaggaagt
ggaaatgttg ccaaggccac ctaaagtgac taaagaagaa catttcagt tacatcatca
aatgcactat tctcaacaga tcacggtcag tctagcacag ggatatgaga gaacttcttc
ccctaagcct cgattcaaga gctatgccta cacacaggct gcttatgtca ccacctctga
ccctacacgg agcccatttc cttcacagca tttggaagct cctgaagaca agtcatttgg
cagttcattg atggagagtg aagtaaacct ggaccgttat caaacagctt tagaagaagt
attatcgtgg cttctttctg ctgaggacac attgcaagca caaggagaga tttctaatga
tgtggaagtg gtgaaagacc agtttcatac tcatgagggg tacatgatgg atttgacagc
ccatcagggc cgggttggta atattctaca attgggaagt aagctgattg gaacaggaaa
attatcagaa gatgaagaaa ctgaagtaca agagcagatg aatctcctaa attcaagatg
ggaatgcctc agggtagcta gcatggaaaa acaaagcaat ttacatagag ttttaatgga
tctccagaat cagaaactga aagagttgaa tgactggcta acaaaaacag aagaaagaac
aaggaaaatg gaggaagagc ctcttggacc tgatcttgaa gacctaaaac gccaagtaca
acaacataag gtgcttcaag aagatctaga acaagaacaa gtcagggtca attctctcac
tcacatggtg gtggtagttg atgaatctag tggagatcac gcaactgctg ctttggaaga
acaacttaag gtattgggag atcgatgggc aaacatctgt agatggacag aagaccgctg
ggttctttta caagacatcc ttctcaaatg gcaacgtctt actgaagaac agtgcctttt
tagtgcatgg ctttcagaaa aagaagatgc agtgaacaag attcacacaa ctggctttaa
agatcaaaat gaaatgttat caagtcttca aaaactggcc gttttaaaag cggatctaga
aaagaaaaag caatccatgg gcaaactgta ttcactcaaa caagatcttc tttcaacact
gaagaataag tcagtgaccc agaagacgga agcatggctg gataactttg cccggtgttg
ggataattta gtccaaaaac ttgaaaagag tacagcacag atttcacag
cag cctgacctag ctcctggact
gaccactatt ggagcctctc ctactcagac tgttactctg gtgacacaac ctgtggttac
taaggaaact gccatctcca aactagaaat gccatcttcc ttgatgttgg aggtacctgc
tctggcagat ttcaaccggg cttggacaga acttaccgac tggctttctc tgcttgatca
agttataaaa tcacagaggg tgatggtggg tgaccttgag gatatcaacg agatgatcat
caagcagaag gcaacaatgc aggatttgga acagaggcgt ccccagttgg aagaactcat
taccgctgcc caaaatttga aaaacaagac cagcaatcaa gaggctagaa caatcattac
ggatcgaatt gaaagaattc agaatcagtg ggatgaagta caagaacacc ttcagaaccg
gaggcaacag ttgaatgaaa tgttaaagga ttcaacacaa tggctggaag ctaaggaaga
agctgagcag gtcttaggac aggccagagc caagcttgag tcatggaagg agggtcccta
tacagtagat gcaatccaaa agaaaatcac agaaaccaag cagttggcca aagacctccg
ccagtggcag acaaatgtag atgtggcaaa tgacttggcc ctgaaacttc tccgggatta
ttctgcagat gataccagaa aagtccacat gataacagag aatatcaatg cctcttggag
aagcattcat aaaagggtga gtgagcgaga ggctgctttg gaagaaactc atagattact
gcaacagttc ccctggacc tggaaaagtt tcttgcctgg cttacagaag ctgaacaac
tgccaatgtc ctacaggatg ctacccgtaa ggaaaggctc ctagaagact ccaagggagt
aaaagagctg atgaaacaat ggcaagacct ccaaggtgaa attgaagctc acacagatgt
ttatcacaac ctggatgaaa acagccaaaa aatcctgaga tccctggaag gttccgatga
tgcagtcctg ttacaaagac gtttggatata catgaacttc aagtggagtg aacttcggaa
aaagtctctc aacattaggt cccatttgga agccagttct gacgatgtga agcgtctgca
cctttctctg caggaacttc tggtgtggct acagctgaaa gatgatgaat taagccggca
ggcacctatt ggaggcgact tccagcagt tcagaagcag aacgatgtac atagggcctt
caagagggaa ttgaaaacta agaacctgt aatcatgagt actcttgaga ctgtacgaat
atttctgaca gagcagcctt tggaaggact agagaaactc taccaggagc ccagagagct
```

FIGURE 15 (cont.)

```
gcctcctgag gagagagccc agaatgtcac tcggcttcta cgaaagcagg ctgaggaggt
caatactgag tgggaaaaat tgaacctgca ctccgctgac tggcagagaa aaatagatga
gacccttgaa agactccagg aacttaaga ggccacggat gagctggacc tcaagctgcg
ccaagctgag gtgatcaagg gatcctggca gcccgtgggc gatctcctca ttgactctct
ccaagatcac ctcgagaaag tcaaggcact tcgaggagaa attgcgcctc tgaaagagaa
cgtgagccac gtcaatgacc ttgctcgcca gcttaccact ttgggcattc agctctcacc
gtataacctc agcactctgg aagacctgaa caccagatgg aagcttctgc aggtggccgt
cgaggaccga gtcaggcagc tgcatgaagc ccacagggac tttggtccag catctcagca
ctttctttcc acgtctgtcc agggtccctg ggagagagcc atctcgccaa acaaagtgcc
ctactatatc aaccacgaga ctcaaacaac ttgctgggac catcccaaaa tgacagagct
ctaccagtct ttagctgacc tgaataatgt cagattctca gcttatagga ctgccatgaa
actccgaaga ctgcagaagg cccttttgctt ggatctcttg agcctgtcag ctgcatgtga
tgccttggac cagcacaacc tcaagcaaaa tgaccagccc atggatatcc tgcagattat
taattgtttg accactattt atgaccgcct ggagcaagag cacaacaatt tggtcaacgt
ccctctctgc gtggatatgt gtctgaactg gctgctgaat gtttatgata cgggacgaac
agggaggatc cgtgtcctgt cttttaaaac tggcatcatt tccctgtgta aagcacattt
ggaagacaag tacagatacc ttttcaagca agtggcaagt tcaacaggat tttgtgacca
gcgcaggctg ggcctccttc tgcatgattc tatccaaatt ccaagacagt tgggtgaagt
tgcatccttt gggggcagta acattgagcc aagtgtccgg agctgcttcc aatttgctaa
taataagcca gagatcgaag cggccctctt cctagactgg atgagactgg aaccccagtc
catggtgtgg ctgcccgtcc tgcacagagt ggctgctgca gaaactgcca agcatcaggc
caaatgtaac atctgcaaag agtgtccaat cattggattc aggtacagga gtctaaagca
ctttaattat gacatctgcc aaagctgctt ttttttctggt cgagttgcaa aaggccataa
aatgcactat cccatggtgg aatattgcac tccgactaca tcaggagaag atgttcgaga
ctttgccaag gtactaaaaa acaaatttcg aaccaaaagg tatttgcga agcatccccg
aatgggctac ctgccagtgc agactgtctt agaggggggac aacatggaaa ctcccgttac
tctgatcaac ttctggccag tagattctgc gcctgcctcg tccctcagc tttcacacga
tgatactcat tcacgcattg aacattatgc tagcaggcta gcagaaatgg aaaacagcaa
tggatcttat ctaaatgata gcatctctcc taatgagagc atagatgatg aacatttgtt
aatccagcat tactgccaaa gtttgaacca ggactccccc ctgagccagc ctcgtagtcc
tgcccagatc ttgatttcct tagagagtga ggaaagaggg gagctagaga gaatcctagc
agatcttgag gaagaaaaca ggaatctgca agcagaatat gaccgtctaa agcagcagca
cgaacataaa ggcctgtccc cactgccgtc ccctcctgaa atgatgccca cctctcccca
gagtccccgg gatgctgagc tcattgctga ggccaagcta ctgcgtcaac acaaaggccg
cctggaagcc aggatgcaaa tcctggaaga ccacaataaa cagctggagt cacagttaca
caggctaagg cagctgctgg agcaacccca ggcagaggcc aaagtgaatg gcacaacggt
gtcctctcct tctacctctc tacagaggtc cgacagcagt cagcctatgc tgctccgagt
ggttggcagt caaacttcgg actccatggg tgaggaagat cttctcagtc ctccccagga
cacaagcaca gggttagagg aggtgatgga gcaactcaac aactccttcc ctagttcaag
aggaagaaat acccctggaa agccaatgag agaggacaca atgtaggaag tcttttccac
atggcagatg atttgggcag agcgatggag tccttagtat cagtcatgac agatgaagaa
ggagcagaat aaatgtttta caactcctga ttcccgcatg gtttttataa tattcataca
acaaagagga ttagacagta agagtttaca agaaataaat ctatattttt gtgaagggta
gtggtattat actgtagatt tcagtagttt ctaagtctgt tattgttttg ttaacaatgg
caggttttac acgtctatgc aattgtacaa aaaagttata agaaaactac atgtaaaatc
ttgatagcta aataacttgc catttcttta tatggaacgc attttgggtt gtttaaaaat
ttataacagt tataaagaaa gattgtaaac taaagtgtgc tttataaaaa aaagttgttt
ataaaaaccc ctaaaaacaa aacaaacaca cacacacaca catacacaca cacacacaaa
actttgaggc agcgcattgt tttgcatcct tttggcgtga tatccatatg aaattcatgg
cttttcttt tttgcatat taaagataag acttcctcta ccaccacacc aaatgactac
tacacactgc tcatttgaga actgtcagct gagtggggca ggcttgagtt ttcatttcat
atatctatat gtctataagt atataaatac tatagttata tagataaaga gatacgaatt
tctatagact gacttttttcc atttttttaaa tgttcatgtc acatcctaat agaaagaaat
tacttctagt cagtcatcca ggcttacctg cttggtctag aatggatttt tcccggagcc
ggaagccagg aggaaactac accacactaa aacattgtct acagctccag atgtttctca
ttttaaacaa cttttccactg acaacgaaag taaagtaaag tattggattt tttttaaaggg
aacatgtgaa tgaatacaca ggacttatta tatcagagtg agtaatcggt tggttggttg
attgattgat tgattgatac attcagcttc ctgctgctag caatgccacg atttagattt
aatgatgctt cagtggaaat caatcagaag gtattctgac cttgtgaaca tcagaaggta
ttttttaact cccaagcagt agcaggacga tgatagggct ggagggctat ggattcccag
cccatccctg tgaaggagta ggccactctt taagtgaagg attggatgat tgttcataat
acataaagtt ctctgtaatt acaactaaat tattatgccc tcttctcaca gtcaaaagga
```

FIGURE 15 (cont.)

```
actgggtggt ttggtttttg ttgctttttt agatttattg tcccatgtgg gatgagtttt
taaatgccac aagacataat ttaaaataaa taaactttgg gaaaaggtgt aagacagtag
ccccatcaca tttgtgatac tgacaggtat caacccagaa gcccatgaac tgtgtttcca
tcctttgcat ttctctgcga gtagttccac acaggtttgt aagtaagtaa gaaagaaggc
aaattgattc aaatgttaca aaaaaccct tcttggtgga ttagacaggt taaatatata
aacaaacaaa caaaaattgc tcaaaaaaga ggagaaaagc tcaagaggaa aagctaagga
ctggtaggaa aaagctttac tctttcatgc catttattt cttttgatt tttaaatcat
tcattcaata gataccaccg tgtgacctat aatttgcaa atctgttacc tctgacatca
agtgtaatta gcttttggag agtgggctga catcaagtgt aattagcttt tggagagtgg
gttttgtcca ttattaataa ttaattaatt aacatcaaac acggcttctc atgctatttc
tacctcactt tggttttggg gtgttcctga taattgtgca cacctgagtt cacagcttca
ccacttgtcc attgcgttat tttctttttc ctttataatt ctttcttttt ccttcataat
tttcaaaaga aacccaaag ctctaaggta acaaattacc aaattacatg aagatttggt
ttttgtcttg cattttttc ctttatgtga cgctggacct tttctttacc caaggatttt
taaaactcag atttaaaaca aggggttact ttacatccta ctaagaagtt taagtaagta
agtttcattc taaaatcaga ggtaaataga gtgcataaat aatttgttt taatctttt
gttttctttt tagacacatt agctctggag tgagtctgtc ataatatttg aacaaaaatt
gagagcttta ttgctgcatt ttaagcataa ttaatttgga cattatttcg tgttgtgttc
tttataacca ccgagtatta aactgtaaat cataatgtaa ctgaagcata aacatcacat
ggcatgtttt gtcattgttt tcaggtactg agttcttact tgagtatcat aatatattgt
gttttaacac caacactgta acatttacga attatttttt taaacttcag ttttactgca
ttttcacaac atatcagact tcaccaaata tatgccttac tattgtatta tagtactgct
ttactgtgta tctcaataaa gcacgcagtt atgttac
```

FIGURE 16 (SEQ ID NO:87)

Human skeletal muscle alpha actinin, complete cDNA sequence:

Genbank accession # M86406; 4181 base pairs

```
GGAACTCCGCTTCGCCCGAGACCCAGCGCCCAGGCGTGTCGCCCGAGAGGAGCCGCGCGAAG
GTCACCCCGCGCCCGCCGCCCGCCGCCCGCCGCCTCCGTGGGTCCGTTTGCCAGTCAGCCCGT
GCGTCCGAGCCCCTCGCGCCCCGCCGCAGCCCCGGCCAACCGAGCGCCATGAACCAGATAGA
GCCCGGCGTGCAGTACAACTACGTGTACGACGAGGATGAGTACATGATCCAGGAGGAGGAGT
GGGACCGCGACCTGCTCCTGGACCCAGCCGGCACCCAGATTGAGAACATCGAGGAAGACTTCAG
TGGTGTAACTCCCACCTAAGGAAAGCCGGCACCCAGATTGAGAACATCGAGGAAGACTTCAG
GAATGGCCTTAAGCTCATGCTGCTTTTGGAAGTCATCTCAGGGGAAAGGCTGCCCAAACCTGA
CCGGGGAAAAATGCGGTTCCACAAAATTGCTAATGTCAACAAAGCTTTGGATTACATAGCCA
GCAAAGGGGTGAAACTGGTGTCCATCGGCGCTGAAGAAATTGTTGATGGCAATGTGAAAATG
ACCCTGGGTATGATCTGGACCATCATCCTTCGCTTTGCTATTCAGGATATTTCGGTTGAAGAAA
CATCTGCCAAAGAAGGTCTGCTGCTTTGGTGTCAGAGGAAAACTGCTCCTTATAGAAATGTGA
ACATTCAGAACTTCCATACTAGCTGGAAAGATGGCCTTGGACTCTGTGCCCTCATCCACCGAC
ACCGGCCTGACCTCATTGACTACTCAAAGCTTAACAAGGATGACCCCATAGGAAATATTAACC
TGGCCATGGAAATCGCTGAGAAGCACCTGGATATTCCTAAAATGTTGGATGCTGAAGACATCG
TGAACACCCCTAAACCCGATGAAAGAGCCATCATGACGTACGTCTCTTGCTTCTACCACGCTT
TTGCGGGCGCGGAGCAGGCCGAGACAGCGGCTAACAGGATATGTAAGGTTCTTGCTGTGAAT
CAAGAGAATGAGAGGCTGATGGAAGAATATGAGAGGCTAGCGAGTGAGCTTTTGGAATGGAT
TCGTCGCACGATCCCCTGGCTGGAGAACCGGACTCCCGAGAAGACCATGCAAGCCATGCAGA
AGAAGCTGGAGGACTTCCGGGATTACCGCCGGAAGCACAAGCCACCCAAGGTGCAGGAGAA
ATGCCAGCTGGAGATCAACTTCAACACGCTGCAGACCAAGCTGCGGATCAGCAACCGTCCTG
CCTTCATGCCCTCCGAGGGCAAGATGGTGTCGGATATTGCTGGTGCCTGGCAGAGGCTGGAGC
AGGCTGAGAAGGGTTACGAGGAGTGGTTGCTCAATGAGATTCGGAGACTGGAGCGCTTGGAA
CACCTGGCTGAGAAGTTCAGGCAGAAGGCCTCAACGCACGAGACTTGGGCTTATGGCAAAGA
GCAGATCTTGCTGCAGAAGGATTACGAGTCGGCGTCGCTGACAGAGGTGCGGGCTCTGCTGC
GGAAGCACGAGGCGTTCGAGAGCGACCTGGCAGCGCACCAGGACCGCGTGGAGCAGATCGC
AGCCATCGCGCAGGAGCTCAATGAACTGGACTATCACGACGCTGTGAATGTCAATGATCGGT
GCCAGAAAATTTGTGACCAGTGGGACCGACTGGGAACGCTTACTCAGAAGAGGAGAGAAGCC
CTAGAGAGAATGGAGAAATTGCTAGAAACCATTGATCAGCTTCACCTGGAGTTTGCCAAGAG
GGCTGCTCCTTTCAACAATTGGATGGAGGGCGCTATGGAGGATCTGCAAGATATGTTCATTGT
CCACAGCATTGAGGAGATCCAGAGTCTGATCACTGCGCATGAGCAGTTCAAGGCCACGCTGC
CCGAGGCGGACGGAGAGCGGCAGTCCATCATGGCCATCCAGAACGAGGTGGAGAAGGTGATT
CAGAGCTACAACATCAGAATCAGCTCAAGCAACCCGTACAGCACTGTCACCATGGATGAGCT
CCGGACCAAGTGGGACAAGGTGAAGCAACTCGTGCCCATCCGCGATCAATCCCTGCAGGAGG
AGCTGGCTCGCCAGCATGCTAACGAGCGTCTGAGGCGCCAGTTTGCTGCCCAAGCCAATGCCA
TTGGGCCCTGGATCCAGAACAAGATGGAGGAGATTGCCCGGAGCTCCATCCAGATCACAGGA
GCCCTGGAAGACCAGATGAACCAGCTGAAGCAGTATGAGCACAACATCATCAACTATAAGAA
CAACATCGACAAGCTGGAGGGAGACCATCAGCTCATCCAGGAGGCCCTTGTCTTTGACAACA
AGCACACGAACTACACGATGGAGCACATTCGTGTTGGATGGGAGCTGCTGCTGACAACCATC
GCCAGAACCATCAATGAGGTGGAGACTCAGATCCTGACGAGAGATGCGAAGGGCATCACCCA
GGAGCAGATGAATGAGTTCAGAGCCTCCTTCAACCACTTTGACAGGAGGAAGAATGGCCTGA
TGGATCATGAGGATTTCAGAGCCTGCCTGATTTCCATGGGTTATGACCTGGGTGAAGCCGAAT
TTGCCCGCATTATGACCCTGGTAGATCCCAACGGGCAAGGCACCGTCACCTTCCAATCCTTCA
TCGACTTCATGACTAGAGAGACGGCTGACACCGACACTGCCGAGCAGGTCATCGCCTCCTTCC
GGATCCTGGCTTCTGATAAGCCATACATCCTGGCGGAGGAGCTGCGTCGGGAGCTGCCCCGG
ATCAGGCCCAGTACTGCATCAAGAGGATGCCCGCCTACTCGGGCCCAGGCAGTGTGCCTGGTG
CACTGGATTACGCTGCGTTCTCTTCCGCACTCTACGGGGAGAGCGATCTGTGATGCTGAGCTT
CTGTAATCACTCATCCCATCAGAATGCAATAAAAGCGGAAGTCACAGTTTGTTTCCTGGAAAC
TTTGACAAGCTTTATTAAGTTGAGAGAGAGAGAGGGGGAAAAAAAAAAAGCCTTTCGTAGTT
CAGTAATTGCCAGCAATATAACACGGCTAAAATGAAGTTTTTACAGTATATGACATAGTGCGC
```

FIGURE 16 (cont.)

```
TTCATAAATAGGTTTATTTCTGAGTTTTTAGCAAAATGTAATGAAATATCAGGTTGATTTCTTT
GATTAAACAGAACAAATTACTTGAGTAATAGGAAATTAGGAGGATCTAGGGACAGAAGGAAA
GTGAAAAATGTGAAAATACAAAATACCCAAGATTTAAGACCGGGGGGAAAAAACCACAAATT
GGTAAATAAAGGTTTGCTATTTGTAAAAAATTTCATTTATCTCTAATATGCTTATGTGATTGGC
CCTAGGGGAGTATATTTGGGATTCTAATGTTTTATTTTCATGCTTATCCAAAGATTACTATTGT
ATCTTCAAATGAACTTAATATTGTGAGATGGAACTGCCGGGGATTAAAAAGACTACCCAAAA
GATTTTTGGCACTTACAATTTTTAAAATAGTTTATGTCATCTCTTCATTATTTAGGGCTGGATG
GTCAACTCAGTCAGTGATTTTTTGATGCTTCTCTTATCCTCCAGAATAGAGACCTAAGGACACG
TGGAAGTCAGTTTAATTGCCAGAGAGAAGGATGCAATCACTAGGTGAAATGAGGTTTTTAGG
ATTATTTATTGATTCCAGGTTCCCATGCTTTTTGTTAGAGCTTATTAGTACAGGTTCTCAAGAG
ATGACCACATAAAAGTGCTCTGTTTATAAATAAGCAGGTTTCTGTAGTACTGACTGGTTCATC
ACAAGGCAAGTCAGAAACCAGTATCCTTCTAGCTCTCCAGTCAGGACTTCCTTATGCCTCTAG
TTTTATGACCGGTTAAGGAGAAGCCAGAGTTAGAGTAGGAGAGGACTAATTCTCAGCAGCAG
TGGAGGTGAGTTCTTTCTTTTGCGGAAGCTTTACATATGTTTTGTGTAGTAGGAATAACTAGAT
ATTTTAGCTAGTGTGCGGTGTGTGTTCACCCCTGGGATTGGACAGTGTATCCTAACAAGTCCC
ATGTCTGGTTCTGTGTCTAAAGGCCTGCTCCATGACACAGGATGCTACATGCACTCCTGCTAG
CACATCTTGATCTGTTGAATGTTCATTCTTTCTTTTTGCTCATACTGCTGTAGGCTATAATTCCC
CCCTGTTTTTCCATCTTGTTGACAGCTTGTAGAGAATAAAGCAGGAATTC
```

FIGURE 17  (16-repeat construct, SEQ ID NO:44) (numbering corresponds to the numbering of human dystrophin, acc. no. M185330

```
   1 gggattccct cactttcccc ctacaggact cagatctggg aggcaattac cttcggagaa
  61 aaacgaatag gaaaaactga agtgttactt tttttaaagc tgctgaagtt tgttggtttc
 121 tcattgtttt taagcctact ggagcaataa agtttgaaga acttttacca ggttttttt
 181 atcgctgcct tgatatacac ttttcaaaat gctttggtgg gaagaagtag aggactgtta
 241 tgaaagagaa gatgttcaaa agaaaacatt cacaaaatgg gtaaatgcac aatttcctaa
 301 gtttgggaag cagcatattg agaacctctt cagtgaccta caggatggga ggcgcctcct
 361 agacctcctc gaaggcctga cagggcaaaa actgccaaaa gaaaaggat ccacaagagt
 421 tcatgccctg aacaatgtca acaaggcact gcgggttttg cagaacaata atgttgattt
 481 agtgaatatt ggaagtactg acatcgtaga tggaaatcat aaactgactc ttggtttgat
 541 ttggaatata atcctccact ggcaggtcaa aaatgtaatg aaaaatatca tggctggatt
 601 gcaacaaacc aacagtgaaa agattctcct gagctgggtc cgacaatcaa ctcgtaatta
 661 tccacaggtt aatgtaatca acttcaccac cagctggtct gatggcctgg ctttgaatgc
 721 tctcatccat agtcataggc cagacctatt tgactggaat agtgtggttt gccagcagtc
 781 agccacacaa cgactggaac atgcattcaa catcgccaga tatcaattag gcatagagaa
 841 actactcgat cctgaagatg ttgataccac ctatccagat aagaagtcca tcttaatgta
 901 catcacatca ctcttccaag ttttgcctca acaagtgagc attgaagcca tccaggaagt
 961 ggaaatgttg ccaaggccac ctaaagtgac taagaagaa catttcagt tacatcatca
1021 aatgcactat tctcaacaga tcacggtcag tctagcacag ggatatgaga gaacttcttc
1081 ccctaagcct cgattcaaga gctatgccta cacacaggct gcttatgtca ccacctctga
1141 ccctacacgg agcccatttc cttcacagca tttggaagct cctgaagaca agtcatttgg
1201 cagttcattg atggagagtg aagtaaacct ggaccgttat caaacagctt tagaagaagt
1261 attatcgtgg cttctttctg ctgaggacac attgcaagca caaggagaga tttctaatga
1321 tgtggaagtg gtgaaagacc agtttcatac tcatgagggg tacatgatgg atttgacagc
1381 ccatcagggc cgggttggta atattctaca attgggaagt aagctgattg gaacaggaaa
1441 attatcagaa gatgaagaaa ctgaagtaca agagcagatg aatctcctaa attcaagatg
1501 ggaatgcctc agggtagcta gcatggaaaa acaaagcaat ttacatagag tttaatgga
1561 tctccagaat cagaaactga aagagttgaa tgactggcta acaaaaacag aagaagaac
1621 aagqaaaatg gaggaagagc ctctttggacc tgatcttgaa gacctaaaac gccaagtaca
1681 acaacataag gtgcttcaag aagatctaga acaagaacaa gtcagggtca attctctcac
1741 tcacatggtg gtggtagttg atgaatctag tggagatcac gcaactgctg ctttggaaga
1801 acaacttaag gtattgggag atcgatggc aaacatctgt agatggacag aagaccgctg
1861 ggttcttta caagacatcc ttctcaaatg gcaacgtctt actgaagaac agtgcctttt
1921 tagtgcatgg ctttcagaaa aagaagatgc agtgaacaag attcacacaa ctggctttaa
1981 agatcaaaat gaaatgttat caagtcttca aaaactggcc gttttaaaag cggatctaga
2041 aagaaaaaag caatccatgg gcaaactgta ttcactcaaa caagatcttc tttcaacact
2101 gaagaataag tcagtgaccc agaagacgga agcatggctg gataactttg cccggtgttg
2161 ggataattta gtccaaaaac ttgaaagag tacagcacag atttcacagg ctgtcaccac
2221 cactcagcca tcactaacac agacaactgt aatggaaaca gtaactacgg tgaccacaag
2281 ggaacagatc ctggtaaagc atgctcaaga ggaacttcca ccaccacctc cccaaaagaa
2341 gaggcagatt actgtggatt ctgaaattag gaaaaggttg gatgttgata taactgaact
2401 tcacagctgg attactcgct cagaagctgt gttgcagagt cctgaatttg caatctttcg
2461 gaaggaaggc aacttctcag acttaaaaga aaagtcaat gccatagagc gagaaaaagc
2521 tgagaagttc agaaaactgc aagatgccag cagatcagct caggcctgg tggaacagat
2581 ggtgaatgag ggtgttaatg cagatagcat caaacaagcc tcagaacaac tgaacagccg
2641 gtggatcgaa ttctgccagt tgctaagtga gagacttaac tggctggagt atcagaacaa
2701 catcatcgct ttctataatc agctacaaca attggagcag atgacaacta ctgctgaaaa
2761 ctggttgaaa atccaaccca ccacccatc agagccaaca gcaattaaaa gtcagttaaa
2821 aatttgtaag gatgaagtca accggctatc aggtcttcaa cctcaaattg aacgattaaa
2881 aattcaaagc atagccctga aagagaaagg acaaggaccc atgttcctgg atgcagactt
2941 tgtggccttt acaaatcatt ttaagcaagt cttttctgat gtgcaggcca gagagaaaga
3001 gctacagaca attttgaca ctttgccacc aatgcgctat caggagacca tgagtgccat
3061 caggacatgg gtccagcagt cagaaaccaa actctccata cctcaactta gtgtcaccga
3121 ctatgaaatc atggagcaga gactcgggga attgcaggct ttacaaagtt ctctgcaaga
3181 gcaacaaagt ggcctatact atcagcac cactgtgaaa gagatgtcga agaaagcgcc
3241 ctctgaaatt agccggaaat atcaatcaga atttgaagaa attgagggac gctggaagaa
3301 gctctcctcc cagctggttt agcattgtca aaagtagag gagcaaatga ataaactccg
3361 aaaaattcag aatcacatac aaaccctgaa gaaatggatg gctgaagttg atgtttttct
3421 gaaggaggaa tggcctgccc ttggggattc agaaattcta aaaagcagc tgaaacagtg
3481 cagacttttta gtcagtgata ttcagacaat tcagcccagt ctaaacagtg tcaatgaagg
3541 tgggcagaag ataaagaatg aagcagagcc agagtttgct tcgagacttg agacagaact
3601 caaagaactt aacactcagt gggatcacat gtgccaacag gtctatgcca gaaaggaggc
```

FIGURE 17 (cont.)

```
3661 cttgaaggga ggtttggaga aaactgtaag cctccagaaa gatctatcag agatgcacga
3721 atggatgaca caagctgaag aagagtatct tgagagagat tttgaatata aaactccaga
3781 tgaattacag aaagcagttg aagagatgaa gagagctaaa gaagaggccc aacaaaaaga
3841 agcgaaagtg aaactcctta ctgagtctgt aaatagtgtc atagctcaag ctccacctgt
3901 agcacaagag gccttaaaaa aggaacttga aactctaacc accaactacc agtggctctg
3961 cactaggctg aatgggaaat gcaagacttt ggaagaa
6512 tctgttgag aaatggcggc gttttcatta
6541 tgatataaag atatttaatc agtggctaac agaagctgaa cagtttctca gaaagacaca
6601 aattcctgag aattgggaac atgctaaata caaatggtat cttaaggaac tccaggatgg
6661 cattgggcag cggcaaactg ttgtcagaac attgaatgca actggggaag aaataattca
6721 gcaatcctca aaaacagatg ccagtattct acaggaaaaa ttgggaagcc tgaatctgcg
6781 gtggcaggag gtctgcaaac agctgtcaga cagaaaaaag aggctagaag aacaaaagaa
6841 tatcttgtca gaatttcaaa gagatttaaa tgaatttgtt ttatggttgg aggaagcaga
6901 taacattgct agtatcccac ttgaacctgg aaaagagcag caactaaaag aaaagcttga
6961 gcaagtcaag ttactggtgg aagagttgcc cctgcgccag ggaattctca aacaattaaa
7021 tgaaactgga ggaccgtgc ttgtaagtgc tcccataagc ccagaagagc aagataaact
7081 tgaaaataag ctcaagcaga caaatctcca gtggataaag gtttccagag ctttacctga
7141 gaaacaagga gaaattgaag ctcaaataaa agaccttggg cagcttgaaa aaaagcttga
7201 agaccttgaa gagcagttaa atcatctgct gctgtggtta tctcctatta ggaatcagtt
7261 ggaaatttat aaccaaccaa accaagaagg accatttgac gttcaggaaa ctgaaatagc
7321 agttcaagct aaacaaccgg atgtggaaga gattttgtct aaagggcagc atttgtacaa
7381 ggaaaaacca gccactcagc cagtgaagag gaagttagaa gatctgagct ctgagtggaa
7441 ggcggtaaac cgtttacttc aagagctgag ggcaaagcag cctgacctag ctcctggact
7501 gaccactatt ggagcctctc ctactcagac tgttactctg gtgacacaac ctgtggttac
7561 taaggaaact gccatctcca aactagaaat gccatcttcc ttgatgttgg aggtacctgc
7621 tctggcagat ttcaaccggg cttggacaga acttaccgac tggctttctc tgcttgatca
7681 agttataaaa tcacagaggg tgatggtggg tgaccttgag gatatcaacg agatgatcat
7741 caagcagaag gcaacaatgc aggatttgga acagaggcgt ccccagttgg aagaactcat
7801 taccgctgcc caaaatttga aaaacaagac cagcaatcaa gaggctagaa caatcattac
7861 ggatcgaatt gaaagaattc agaatcagtg ggatgaagta caagaacacc ttcagaaccg
7921 gaggcaacag ttgaatgaaa tgttaaagga ttcaacacaa tggctggaag ctaaggaaga
7981 agctgagcag gtcttaggac aggccagagc caagcttgag tcatggaagg agggtcccta
8041 tacagtagat gcaatccaaa agaaaatcac agaaccaag cagttggcca aagacctccg
8101 ccagtggcag acaaatgtag atgtggcaaa tgacttggcc ctgaaacttc tccgggatta
8161 ttctgcagat gataccagaa aagtccacat gataacagag aatatcaatg cctcttggag
8221 aagcattcat aaaaggtga gtgagcgaga ggctgctttg gaagaactc atagattact
8281 gcaacagttc cccctggacc tggaaaagtt tcttgcctgg cttacagaag ctgaaacaac
8341 tgccaatgtc ctacaggatg ctacccgtaa ggaaaggctc ctagaagact caagggagt
8401 aaaagagctg atgaaacaat ggcaagacct ccaaggtgaa attgaagctc acacagatgt
8461 ttatcacaac ctggatgaaa acagccaaaa aatcctgaga tccctggaag gttccgatga
8521 tgcagtcctg ttacaaagac gtttggataa catgaacttc aagtggagtg aacttcggaa
8581 aaagtctctc aacattaggt cccatttgga agccagttct gaccagtgga gcgtctgca
8641 cctttctgca caggaacttc tggtgtggct acagctgaaa gatgatgaat taagccggca
8701 ggcacctatt ggaggcgact ttccagcagt tcagaagcag aacgatgtac ataggccctt
8761 caagagggaa ttgaaaacta agaacctgt aatcatgagt actcttgaga ctgtacgaat
8821 atttctgaca gagcagcctt tggaaggact agagaaactc taccaggagc ccagagagct
8881 gcctcctgag gagagagccc agaatgtcac tcggcttcta cgaaagcagg ctgaggaggt
8941 caatactgag tgggaaaaat tgaacctgca ctccgctgac tggcagagaa aaatagatga
9001 gacccttgaa agactccagg aacttcaaga ggccacggat gagctggacc tcaagctgcg
9061 ccaagctgga gtgatcaagg gatcctggca gcccgatggc gatctccctca ttgactctct
9121 ccaagatcac ctcgagaaag tcaaggcact tcgaggagaa attgcgcctc tgaaagagaa
9181 cgtgagccac gtcaatgacc ttgctcgcca gcttaccact tgggcattc agctctcacc
9241 gtataacctc agcactctgg aagacctgaa caccagatgg aagcttctgc aggtggccgt
9301 cgaggaccga gtcaggcagc tgcatgaagc ccacagggac tttggtccag catctcagca
9361 ctttctttcc acgtctgtcc agggtccctg ggagagcc atctcgccaa acaaagtgcc
9421 ctactatatc aaccagaga ctcaaacaac ttgctgggac. catcccaaaa tgacagagct
9481 ctaccagtct ttagctgacc tgaataatgt cagattctca gcttataga ctgccatgaa
9541 actccgaaga ctgcagaagg ccctttgctt ggatctcttg agcctgtcag ctgcatgtga
9601 tgccttggac cagcacaacc tcaagcaaaa tgaccagccc atggatatcc tgcagattat
9661 taattgtttg accactattt atgaccgcct ggagcaagag cacaacaatt tggtcaacgt
9721 ccctctctgc gtggatatgt gtctgaactg gctgctgaat gtttatgata cgggacgaac
9781 agggaggatc cgtgtcctgt ctttcaagaac tggcatcatt tccctgtgta agcacattt
9841 ggaagacaga tacagatacc tttcaagca agttggcaagt tcaacaggat tttgtgacca
9901 gcgcaggctg ggcctccttc tgcatgattc tatccaaatt ccaagacagt tgggtgaagt
9961 tgcatccttt ggggcagta acattgagcc aagtgtccgg agctgcttcc aatttgctaa
10021 taataagcca gagatcgaag cggcctctct cctagactgg atgagactgg aacccagtc
10081 catggtgtgg ctcccgtcc tgcacagagt ggctgctgca gaaactgcca agcatcaggc
10141 caaatgtaac atctgcaaag agtgtccaat cattggattc aggtacagga gtctaaagca
```

FIGURE 17 (cont.)

```
10201 ctttaattat gacatctgcc aaagctgctt tttttctggt cgagttgcaa aaggccataa
10261 aatgcactat cccatggtgg aatattgcac tccgactaca tcaggagaag atgttcgaga
10321 ctttgccaag gtactaaaaa acaaatttcg aaccaaaagg tattttgcga agcatccccg
10381 aatgggctac ctgccagtgc agactgtctt agaggggygac aacatggaaa ctcccgttac
10441 tctgatcaac ttctggccag tagattctgc gcctgcctcg tcccctcagc tttcacacga
10501 tgatactcat tcacgcattg aacattatgc tagcaggcta gcagaaatgg aaaacagcaa
10561 tggatcttat ctaaatgata gcatctctcc taatgagagc atagatgatg aacatttgtt
10621 aatccagcat tactgccaaa gtttgaacca ggactccccc ctgagccagc ctcgtagtcc
10681 tgcccagatc ttgatttcct tagagagtga ggaaagaggg gagctagaga gaatcctagc
10741 agatcttgag gaagaaaaca ggaatctgca agcagaatat gaccgtctaa agcagcagca
10801 cgaacataaa ggcctgtccc cactgccgtc ccctcctgaa atgatgccca cctctcccca
10861 gagtcccgg gatgctgagc tcattgctga ggccaagcta ctgcgtcaac acaaaggccg
10921 cctggaagcc aggatgcaaa tcctggaaga ccacaataaa cagctggagt cacagttaca
10981 caggctaagg cagctgctgg agcaaccca ggcagaggcc aaagtgaatg gcacaacggt
11041 gtcctctcct tctacctctc tacagaggtc cgacagcagt cagcctatgc tgctccgagt
11101 ggttggcagt caaacttcgg actccatggg tgaggaagat cttctcagtc ctccccagga
11161 cacaagcaca gggttagagg aggtgatgga gcaactcaac aactccttcc ctagttcaag
11221 aggaagaaat acccctggaa agccaatgag agaggacaca atgtaggaag tctttttccac
11281 atggcagatg atttgggcag agcgatggag tccttagtat cagtcatgac agatgaagaa
11341 ggagcagaat aaatgtttta caactcctga ttcccgcatg gtttttataa tattcataca
11401 acaaagagga ttagacagta agagtttaca agaaatataa ctatatttt gtgaagggta
11461 gtggtattat actgtagatt tcagtagttt ctaagtctgt tattgttttg ttaacaatgg
11521 caggttttac acgtctatgc aattgtacaa aaaagttata agaaaactac atgtaaaatc
11581 ttgatagcta aataacttgc catttcttta tatggaacgc atttgggtt gtttaaaaat
11641 ttataacagt tataaagaaa gattgtaaac taaagtgtgc tttataaaaa aaagttgttt
11701 ataaaaaccc ctaaaaacaa aacaaacaca cacacacaca catacacaca cacacacaaa
11761 actttgaggc agcgcattgt tttgcatcct tttggcgtga tatccatatg aaattcatgg
11821 ctttttcttt ttttgcatat taaagataag acttcctcta ccaccacacc aaatgactac
11881 tacacactgc tcatttgaga actgtcagct gagtggggca ggcttgagtt ttcatttcat
11941 atatctatat gtctataagt atataaatac tatagttata tagataaaga gatacgaatt
12001 tctatagact gactttttcc atttttttaaa tgttcatgtc acatcctaat agaaagaaat
12061 tacttctagt cagtcatcca ggcttacctg cttggtctag aatggatttt tcccggagcc
12121 ggaagccagg aggaaactac accacactaa aacattgtct acagctccag atgtttctca
12181 ttttaaacaa ctttccactg acaacgaaag taaagtaaag tattggattt ttttaaaggg
12241 aacatgtgaa tgaatacaca ggacttatta tatcagagtg agtaatcggt tggttggttg
12301 attgattgat tgattgatac attcagcttc ctgctgctag caatgccacg atttagattt
12361 aatgatgctt cagtggaaat caatcagaag gtattctgac cttgtgaaca tcagaaggta
12421 ttttttaact cccaagcagt agcaggacga tgatagggct ggagggctat ggattcccag
12481 cccatccctg tgaaggagta ggccactctt taagtgaagg attggatgat tgttcataat
12541 acataaagtt ctctgtaatt acaactaaat tattatgccc tcttctcaca gtcaaaagga
12601 actgggtggt ttggttttttg ttgcttttt agatttattg tcccatgtgg gatgagtttt
12661 taaatgccac aagacataat ttaaaataaa taaactttgg gaaaaggtgt aagacagtag
12721 ccccatcaca tttgtgatac tgacaggtat caacccagaa gcccatgaac tgtgtttcca
12781 tcctttgcat ttctctgcga gtagttccac acaggtttgt aagtaagtaa gaaagaaggc
12841 aaattgattc aaatgttaca aaaaaccct tcttggtgga ttagacaggt taaatatata
12901 aacaaacaaa caaaaattgc tcaaaaaaga ggagaaaagc tcaagaggaa aagctaagga
12961 ctggtaggaa aaagctttac tcttcatgc catttattt ctttttgatt tttaaatcat
13021 tcattcaata gataccaccg tgtgacctac aattttgcaa atctgttacc tctgacatca
13081 agtgtaatta gcttttggag agtgggctga catcaagtgt aattagcttt tggagagtgg
13141 gttttgtcca ttattaataa ttaattaatt aacatcaaac acggcttctc atgctatttc
13201 tacctcactt tggtttggg gtgttcctga taattgtgca cacctgagtt cacagcttca
13261 ccacttgtcc attgcgttat ttctttttc ctttataatt ctttctttt ccttcataat
13321 tttcaaaaga aaacccaaag ctctaaggta acaaattacc aaattacatg aagatttggt
13381 ttttgtcttg catttttttc ctttatgtga cgctggacct tttctttacc caaggatttt
13441 taaaactcag atttaaaaca aggggttact ttacatccta ctaagaagtt taagtaagta
13501 agtttcattc taaaatcaga ggtaaataga gtgcataaat aatttgttt taatctttt
13561 gtttttcttt tagacacatt agctctggag tgagtctgtc ataatatttg aacaaaaatt
13621 gagagcttta ttgctgcatt ttaagcataa ttaatttgga cattatttcg tgttgtgttc
13681 tttataacca ccgagtatta aactgtaaat cataatgtaa ctgaagcata aacatcacat
13741 ggcatgtttt gtcattgttt tcaggtactg agttcttact tgagtatcat aatatattgt
13801 gttttaacac caacactgta acatttacga attatttttt taaacttcag ttttactgca
13861 ttttcacaac atatcagact tcaccaaata tatgccttac tattgtatta tagtactgct
13921 ttactgtgta tctcaataaa gcacgcagtt atgttac
```

FIGURE 18 (WW domain, SEQ ID NO:45)

```
9371 acgtctgtcc agggtccctg ggagagagcc atctcgccaa acaaagtgcc
9421 ctactatatc aaccacgaga ctcaaacaac ttgctgggac catcccaaaa tgacagagct
9481 ctac
```

Contractile properties of EDL, soleus, and diaphragm muscles in wild-type, mdx, and dystrophin Δ71–78 mice. Muscle mass and specific force for mdx (A) and Δ71–78 (B) muscles were charted as a percentage of wild-type values. Significant differences ($P < 0.05$) are marked with an asterisk (*).

FIGURE 21 (pBSX sequence, SEQ ID NO:46)

```
CTAAATTGTAAGCGTTAATATTTTGTTAAAATTCGCGTTAAATTTTTGTTAAATCAGCTCATTTTTTAACCAATAG
GCCGAAATCGGCAAAATCCCTTATAAATCAAAAGAATAGACCGAGATAGGGTTGAGTGTTGTTCCAGTTTGGAACA
AGAGTCCACTATTAAAGAACGTGGACTCCAACGTCAAAGGGCGAAAAACCGTCTATCAGGGCGATGGCCCACTACG
TGAACCATCACCCTAATCAAGTTTTTTGGGGTCGAGGTGCCGTAAAGCACTAAATCGGAACCCTAAAGGGAGCCCC
CGATTTAGAGCTTGACGGGGAAAGCCGGCGAACGTGGCGAGAAAGGAAGGGAAGAAAGCGAAAGGAGCGGGCGCTA
GGGCGCTGGCAAGTGTAGCGGTCACGCTGCGCGTAACCACCACACCCGCCGCGCTTAATGCGCCGCTACAGGGCGC
GTCCCATTCGCCATTCAGGCTGCGCAACTGTTGGGAAGGGCGATCGGTGCGGGCCTCTTCGCTATTACGCCAGCTG
GCGAAAGGGGGATGTGCTGCAAGGCGATTAAGTTGGGTAACGCCAGGGTTTTCCCAGTCACGACGTTGTAAAACGA
CGGCCAGTGAGCGCGCGTAATACGACTCACTATAGGGCGAATTGGAGCTTACGTATTAATTAAGGCGCCGCGGTGG
CGGCCGCTCTAGAACTAGTGGATCCCCCGGGCTGCAGGAATTCGGCCGCCTAGGCCACGCGTAAGCTTATCGATAC
CGTCGACCTCGAGGGGGGGCCCGGTACCCAGCTTTTGTTCCCTTTAGTGAGGGTTAATTGCGCGCTTGGCGTAATC
ATGGTCATAGCTGTTTCCTGTGTGAAATTGTTATCCGCTCACAATTCCACACAACATACGAGCCGGAAGCATAAAG
TGTAAAGCCTGGGGTGCCTAATGAGTGAGCTAACTCACATTAATTGCGTTGCGCTCACTGCCCGCTTTCCAGTCGG
GAAACCTGTCGTGCCAGCTGCATTAATGAATCGGCCAACGCGCGGGGAGAGGCGGTTTGCGTATTGGGCGCTCTTC
CGCTTCCTCGCTCACTGACTCGCTGCGCTCGGTCGTTCGGCTGCGGCGAGCGGTATCAGCTCACTCAAAGGCGGTA
ATACGGTTATCCACAGAATCAGGGGATAACGCAGGAAAGAACATGTGAGCAAAAGGCCAGCAAAAGGCCAGGAACC
GTAAAAAGGCCGCGTTGCTGGCGTTTTTCCATAGGCTCCGCCCCCCTGACGAGCATCACAAAAATCGACGCTCAAG
TCAGAGGTGGCGAAACCCGACAGGACTATAAAGATACCAGGCGTTTCCCCCTGGAAGCTCCCTCGTGCGCTCTCCT
GTTCCGACCCTGCCGCTTACCGGATACCTGTCCGCCTTTCTCCCTTCGGGAAGCGTGGCGCTTTCTCATAGCTCAC
GCTGTAGGTATCTCAGTTCGGTGTAGGTCGTTCGCTCCAAGCTGGGCTGTGTGCACGAACCCCCCGTTCAGCCCGA
CCGCTGCGCCTTATCCGGTAACTATCGTCTTGAGTCCAACCCGGTAAGACACGACTTATCGCCACTGGCAGCAGCC
ACTGGTAACAGGATTAGCAGAGCGAGGTATGTAGGCGGTGCTACAGAGTTCTTGAAGTGGTGGCCTAACTACGGCT
ACACTAGAAGGACAGTATTTGGTATCTGCGCTCTGCTGAAGCCAGTTACCTTCGGAAAAAGAGTTGGTAGCTCTTG
ATCCGGCAAACAAACCACCGCTGGTAGCGGTGGTTTTTTTGTTTGCAAGCAGCAGATTACGCGCAGAAAAAAAGGA
TCTCAAGAAGATCCTTTGATCTTTTCTACGGGGTCTGACGCTCAGTGGAACGAAAACTCACGTTAAGGGATTTTGG
TCATGAGATTATCAAAAAGGATCTTCACCTAGATCCTTTTAAATTAAAAATGAAGTTTTAAATCAATCTAAAGTAT
ATATGAGTAAACTTGGTCTGACAGTTACCAATGCTTAATCAGTGAGGCACCTATCTCAGCGATCTGTCTATTTCGT
TCATCCATAGTTGCCTGACTCCCCGTCGTGTAGATAACTACGATACGGGAGGGCTTACCATCTGGCCCCAGTGCTG
CAATGATACCGCGAGACCCACGCTCACCGGCTCCAGATTTATCAGCAATAAACCAGCCAGCCGGAAGGGCCGAGCG
CAGAAGTGGTCCTGCAACTTTATCCGCCTCCATCCAGTCTATTAATTGTTGCCGGGAAGCTAGAGTAAGTAGTTCG
CCAGTTAATAGTTTGCGCAACGTTGTTGCCATTGCTACAGGCATCGTGGTGTCACGCTCGTCGTTTGGTATGGCTT
CATTCAGCTCCGGTTCCCAACGATCAAGGCGAGTTACATGATCCCCCATGTTGTGCAAAAAAGCGGTTAGCTCCTT
CGGTCCTCCGATCGTTGTCAGAAGTAAGTTGGCCGCAGTGTTATCACTCATGGTTATGGCAGCACTGCATAATTCT
CTTACTGTCATGCCATCCGTAAGATGCTTTTCTGTGACTGGTGAGTACTCAACCAAGTCATTCTGAGAATAGTGTA
TGCGGCGACCGAGTTGCTCTTGCCCGGCGTCAATACGGGATAATACCGCGCCACATAGCAGAACTTTAAAAGTGCT
CATCATTGGAAAACGTTCTTCGGGGCGAAAACTCTCAAGGATCTTACCGCTGTTGAGATCCAGTTCGATGTAACCC
ACTCGTGCACCCAACTGATCTTCAGCATCTTTTACTTTCACCAGCGTTTCTGGGTGAGCAAAAACAGGAAGGCAAA
ATGCCGCAAAAAAGGGAATAAGGGCGACACGGAAATGTTGAATACTCATACTCTTCCTTTTTCAATATTATTGAAG
CATTTATCAGGGTTATTGTCTCATGAGCGGATACATATTTGAATGTATTTAGAAAAATAAACAAATAGGGGTTCCG
CGCACATTTCCCCGAAAAGTGCCAC
```

FIGURE 23   ("full-length" HDMD, SEQ ID NO:47)
-numbering corresponds to human dystrophin SEQ ID NO:1

```
   1 gggattccct cactttcccc ctacaggact cagatctggg aggcaattac cttcggagaa
  61 aaacgaatag gaaaaactga agtgttactt tttttaaagc tgctgaagtt tgttggtttc
 121 tcattgtttt taagcctact ggagcaataa agtttgaaga acttttacca ggttttttt
 181 atcgctgcct tgatatacac ttttcaaaat gctttggtgg gaagaagtag aggactgtta
 241 tgaaagagaa gatgttcaaa agaaaacatt cacaaaatgg gtaaatgcac aattttctaa
 301 gtttgggaag cagcatattg agaacctctt cagtgaccta caggatggga ggcgcctcct
 361 agacctcctc gaaggcctga cagggcaaaa actgccaaaa gaaaaaggat ccacaagagt
 421 tcatgccctg aacaatgtca acaaggcact gcgggttttg cagaacaata atgttgattt
 481 agtgaatatt ggaagtactg acatcgtaga tggaaatcat aaactgactc ttggtttgat
 541 ttggaatata atcctccact ggcaggtcaa aaatgtaatg aaaaatatca tggctggatt
 601 gcaacaaacc aacagtgaaa agattctcct gagctgggtc cgacaatcaa ctcgtaatta
 661 tccacaggtt aatgtaatca acttcaccac cagctggtct gatggcctgg ctttgaatgc
 721 tctcatccat agtcataggc cagacctatt tgactggaat agtgtggttt gccagcagtc
 781 agccacacaa cgactggaac atgcattcaa catcgccaga tatcaattag catagagaa
 841 actactcgat cctgaagatg ttgataccac ctatccagat aagaagtcca tcttaatgta
 901 catcacatca ctcttccaag ttttgcctca acaagtgagc attgaagcca tccaggaagt
 961 ggaaatgttg ccaaggccac ctaaagtgac taaagaagaa cattttcagt tacatcatca
1021 aatgcactat tctcaacaga tcacggtcag tctagcacag ggatatgaga gaacttcttc
1081 ccctaagcct cgattcaaga gctatgccta cacacaggct gcttatgtca ccacctctga
1141 ccctacacgg agcccatttc cttcacagca tttgaagct cctgaagaca agtcatttgg
1201 cagttcattg atggagagtg aagtaaacct ggaccgttat caaacagctt tagaagaagt
1261 attatcgtgg cttctttctg ctgaggacac attgcaagca caggagaga tttctaatga
1321 tgtggaagtg gtgaaagacc agtttcatac tcatgagggg tacatgatgg atttgacagc
1381 ccatcagggc cgggttggta atattctaca attgggaagt aagctgattg gaacaggaaa
1441 attatcagaa gatgaagaaa ctgaagtaca agagcagatg aatctcctaa attcaagatg
1501 ggaatgcctc agggtagcta gcatggaaaa acaaagcaat ttacatagag ttttaatgga
1561 tctccagaat cagaaactga aagagttgaa tgactggcta acaaaaacag aagaagaac
1621 aaggaaaatg gaggaagagc ctcttggacc tgatcttgaa gacctaaaac gccaagtaca
1681 acaacataag gtgcttcaag aagatctaga acaagaacaa gtcagggtca attctctcac
1741 tcacatggtg gtggtagttg atgaatctag tggagatcac gcaactgctg ctttggaaga
1801 acaacttaag gtattgggag atcgatgggc aaacatctgt agatggacag aagaccgctg
1861 ggttctttta caagacatcc ttctcaaatg gcaacgtctt actgaagaac agtgcctttt
1921 tagtgcatgg ctttcagaaa aagaagatgc agtgaacaag attcacacaa ctggctttaa
1981 agatcaaaat gaaatgttat caagtcttca aaaactggcc gttttaaaag cggatctaga
2041 aaagaaaaag caatccatgg gcaaactgta ttcactcaaa caagatcttc tttcaacact
2101 gaagaataag tcagtgaccc agaagacgga agcatgcgct gataactttg cccggtgttg
2161 ggataattta gtccaaaaac ttgaaaagag tacagcacag atttcacagg ctgtcaccac
2221 cactcagcca tcactaacac agacaactgt aatggaaaca gtaactacgg tgaccacaag
2281 ggaacagatc ctggtaaagc atgctcaaga ggaacttcca ccaccacctc cccaaagaa
2341 gaggcagatt actgtggatt ctgaaattag gaaaaggttg gatgttgata aactgaact
2401 tcacagctgg attactcgct cagaagctgt gttgcagagt cctgaatttg caatctttcg
2461 gaaggaaggc aacttctcag acttaaaaga aaagtcaat gccatagagc gagaaaaagc
2521 tgagaagttc agaaaactgc aagatgccag cagatctgct caggcctgg tggacagat
2581 ggtgaatgag ggtgttaatg cagatagcat caaacaagcc tcagaacaac tgaacagccg
2641 gtggatcgaa ttctgccagt tgctaagtga gagacttaac tggctggagt atcagaacaa
2701 catcatcgct ttctataatc agctacaaca attggagcag atgacaacta ctgctgaaaa
2761 ctggttgaaa atccaaccca ccacccatc agagccaaca gcaattaaaa gtcagttaaa
2821 aatttgtaag gatgaagtca accggctcaa ggtcttcaa cctcaaattg aacgattaaa
2881 aattcaaagc atagccctga aagaaaagg acaaggaccc atgttcctgg atgcagactt
2941 tgtggccttt acaaatcatt ttaagcaagt cttttctgat gtgcaggcca gagagaaaga
3001 gctacagaca atttttgaca cttttgccacc aatgcgctat caggagacca tgagtgccat
3061 caggacatgg tccagcagt cagaaaccaa actctccata cctcaactta gtgtcaccga
3121 ctatgaaatc atggagcaga gactcgggga ttgcaggct ttacaaagtt ctctgcaaga
3181 gcaacaagt ggcctatact atctcagcac cactgtgaaa gagatgtcga agaagcgcc
3241 ctctgaaatt agccggaaat atcaatcaga tttgaagaa attgagggac gctggaagaa
3301 gctctcctcc cagctggttg agcattgtca aaagctagag gagcaaatga ataaactccg
3361 aaaattcag aatcacatac aaaccctgaa gaatggatg gctgaagttg atgttttctct
3421 gaaggaggaa tggcctgccc ttgggggatc agaaattcta aaaagcagc tgaaacagtg
3481 cagacttta gtcagtgata ttcagacaat tcagcccagt ctaaacagtg tcaatgaagg
3541 tgggcagaag ataaagaatg aagcagagcc agagtttgct tcgagacttg agacagaact
```

FIGURE 23 (cont.)

```
3601 caaagaactt aacactcagt gggatcacat gtgccaacag gtctatgcca gaaaggaggc
3661 cttgaaggga ggtttggaga aaactgtaag cctccagaaa gatctatcag agatgcacga
3721 atggatgaca caagctgaag aagagtatct tgagagagat tttgaatata aaactccaga
3781 tgaattacag aaagcagttg aagagatgaa gagagctaaa gaagaggccc aacaaaaaga
3841 agcgaaagtg aaactcctta ctgagtctgt aaatagtgtc atagctcaag ctccacctgt
3901 agcacaagag gccttaaaaa aggaacttga aactctaacc accaactacc agtggctctg
3961 cactaggctg aatgggaaat gcaagacttt ggaagaagtt tgggcatgtt ggcatgagtt
4021 attgtcatac ttggagaaag caaacaagtg gctaatgaa gtagaattta aacttaaaac
4081 cactgaaaac attcctggcg gagctgagga aatctctgag gtgctagatt cacttgaaaa
4141 tttgatgcga cattcagagg ataacccaaa tcagattcgc atattggcac agaccctaac
4201 agatggcgga gtcatggatg agctaatcaa tgaggaactt gagacattta attctcgttg
4261 gagggaacta catgaagagg ctgtaaggag gcaaaagttg cttaacaga gcatccagtc
4321 tgcccaggag actgaaaaat ccttacactt aatccaggag tccctcacat tcattgacaa
4381 gcagttggca gcttatattg cagacaaggt ggacgcagct caaatgcctc aggaagccca
4441 gaaaatccaa tctgatttga caagtcatga gatcagttta gaagaaatga agaaacataa
4501 tcaggggaag gaggctgccc aaagagtcct gtctcagatt gatgttcac agaaaaaatt
4561 acaagatgtc tccatgaagt ttcgattatt ccagaaacca gccaattttg agctgcgtct
4621 acaagaaagt aagatgattt tagatgaagt gaagatgcac ttgcctgcat tggaaacaaa
4681 gagtgtggaa caggaagtag tacagtcaca gctaaatcat tgtgtgaact tgtataaaag
4741 tctgagtgaa gtgaagtctg aagtggaaat ggtgataaag actggacgtc agattgtaca
4801 gaaaaagcag acggaaaatc ccaagaact tgatgaaaga gtaacagctt tgaaattgca
4861 ttataatgag ctgggagcaa aggtaacaga aagaaagcaa cagttggaga aatgcttgaa
4921 attgtcccgt aagatgcgaa aggaaatgaa tgtcttgaca gaatggctgg cagctacaga
4981 tatggaattg acaaagagat cagcagttga aggaatgcct agtaatttgg attctgaagt
5041 tgcctgggga aaggctactc aaaaagagat tgagaaacag aaggtgcacc tgaagagtat
5101 cacagaggta ggagaggcct tgaaaacagt tttgggcaag aaggagacgt tggtggaaga
5161 taaactcagt cttctgaata gtaactggat agctgtcacc tcccgacga aagagtgtt
5221 aaatcttttg ttggaatacc agaaacacat ggaaactttt gaccagaatg tggaccacat
5281 cacaaagtgg atcattcagg ctgacacact tttggatgaa tcagagaaaa agaaaccca
5341 gcaaaaagaa gacgtgctta agcgtttaaa ggcagaactg aatgacatac gcccaaaggt
5401 ggactctaca cgtgaccaag cagcaaactt gatggcaaac cgcggtgacc actgcaggaa
5461 attagtagag ccccaaatct cagagctcaa ccatcgattt gcagccattt cacacagaat
5521 taagactgga aaggcctcca ttcctttgaa ggaattggag cagtttaact cagatataca
5581 aaaattgctt gaaccactgg aggctgaaat tcagcagggg gtgaatctga agaggaaga
5641 cttcaataaa gatatgaatg aagacaatga gggtactgta aaagaattgt gcaaagagg
5701 agacaactta caacaaagaa tcacagatga gagaaagaga gaggaaataa agataaaaca
5761 gcagctgtta cagacaaaac ataatgctct caaggatttg aggtctcaaa gaagaaaaaa
5821 ggctctagaa atttctcatc agtggtatca gtacaagagc caggctgatg atctcctgaa
5881 atgcttggat gacattgaaa aaaattagc cagcctacct gagcccagag atgaaaggaa
5941 aataaaggaa attgatcgg aattcagaa gaagaaagag gagctgaatg cagtgcgtag
6001 gcaagctgag ggcttgtctg aggatgggggc cgcaatgca gtggagccaa ctcagatcca
6061 gctcagcaag cgctggcggg aaattgagag caaatttgct cagtttcgaa gactcaactt
6121 tgcacaaatt cacactgtcc gtgaagaaac gatgatggtg atgactgaag acatgccttt
6181 ggaaatttct tatgtgcctt ctacttattt gactgaaatc actcatgtct cacaagccct
6241 attagaagtg gaacaactc tcaatgctcc tgacctctgt gctaaggact ttgaagatct
6301 ctttaagcaa gaggagtctc tgaagaatat aaaagatagt ctacaacaaa gctcaggtcg
6361 gattgacatt attcatagca agaagacagc agcattgcaa agtgcaacgc ctgtggaaag
6421 ggtgaagcta caggaagctc tctcccagct tgatttccaa tgggaaaaag ttaacaaaat
6481 gtacaaggac cgacaagggc gatttgacag atctgttgag aaatgcggc gttttcatta
6541 tgatataaag atatttaatc agtggctaac agaagctgaa cagtttctca gaaagacaca
6601 aattcctgag aattgggaac atgctaaata caatggtat cttaaggaac tccaggatgg
6661 cattgggcag cggcaaactg ttgtcagaac attgaatgca actggggaag aaataattca
6721 gcaatcctca aaaacagatg ccagtattct acaggaaaaa ttgggaagcc tgaatctgcg
6781 gtggcaggag gtctgcaaac agctgtcaga cagaaaaaag aggctagaag aacaaaagaa
6841 tatcttgtca gaatttcaaa gagatttaaa tgaatttgtt ttatggttgg aggaagcaga
6901 taacattgct agtatcccac ttgaacctgg aaaagagcag caactaaaag aaaagcttga
6961 gcaagtcaag ttactggtgg aagagttgcc cctgcgccag ggaattctca acaattaaaa
7021 tgaaactgga ggacccgtgc ttgtaagtgc tcccataagc ccagaagagc aagataaact
7081 tgaaaataag ctcaagcaga caaatctcca gtggataaag gttccagag ctttacctga
7141 gaaacaagga gaaattgaag ctcaaataaa agacttgggg cagcttgaaa aaaagcttga
7201 agaccttgaa gagcagttcaa atcatctgct gctgtggtta tctcctatta ggaatcagtt
7261 ggaaatttat aaccaaccaa accaagaagg accatttgac gttcaggaaa ctgaaatagc
7321 agttcaagct aaacaaccgg atgtggaaga gattttgtct aaagggcagc atttgtacaa
7381 ggaaaaacca gccactcagc cagtgaagag gaagttagaa gatctgagct ctgagtggaa
```

FIGURE 23 (cont.)

```
7441 ggcggtaaac cgtttacttc aagagctgag ggcaaagcag cctgacctag ctcctggact
7501 gaccactatt ggagcctctc ctactcagac tgttactctg gtgacacaac ctgtggttac
7561 taaggaaact gccatctcca aactagaaat gccatcttcc ttgatgttgg aggtacctgc
7621 tctggcagat ttcaaccggg cttggacaga acttaccgac tggctttctc tgcttgatca
7681 agttataaaa tcacagaggg tgatggtggg tgaccttgag gatatcaacg agatgatcat
7741 caagcagaag gcaacaatgc aggatttgga acagaggcgt ccccagttgg aagaactcat
7801 taccgctgcc caaaatttga aaaacaagac cagcaatcaa gaggctagaa caatcattac
7861 ggatcgaatt gaaagaattc agaatcagtg ggatgaagta caagaacacc ttcagaaccg
7921 gaggcaacag ttgaatgaaa tgttaaagga ttcaacacaa tggctggaag ctaaggaaga
7981 agctgagcag gtcttaggac aggccagagc caagcttgag tcatggaagg agggtcccta
8041 tacagtagat gcaatccaaa agaaaatcac agaaaccaag cagttggcca aagacctccg
8101 ccagtggcag acaaatgtag atgtggcaaa tgacttggcc ctgaaacttc tccgggatta
8161 ttctgcagat gataccagaa aagtccacat gataacagag aatatcaatg cctcttggag
8221 aagcattcat aaaagggtga gtgagcgaga ggctgctttg gaagaaactc atagattact
8281 gcaacagttc cccctggacc tggaaaagtt tcttgcctgg cttacagaag ctgaaacaac
8341 tgccaatgtc ctacaggatg ctacccgtaa ggaaaggctc ctagaagact ccaagggagt
8401 aaaagagctg atgaaacaat ggcaagacct ccaaggtgaa attgaagctc acacagatgt
8461 ttatcacaac ctggatgaaa acagccaaaa aatcctgaga tccctggaag gttccgatga
8521 tgcagtcctg ttacaaagac gtttggataa catgaacttc aagtggagtg aacttcggaa
8581 aaagtctctc aacattaggt cccatttgga agccagttct gaccagtgga agcgtctgca
8641 cctttctctg caggaacttc tggtgtggct acagctgaaa gatgatgaat taagccggca
8701 ggcacctatt ggaggcgact ttccagcagt tcagaagcag aacgatgtac atagggcctt
8761 caagagggaa ttgaaaacta agaacctgt aatcatgagt actcttgaga ctgtacgaat
8821 atttctgaca gagcagcctt tggaaggact agagaaactc taccaggagc ccagagagct
8881 gcctcctgag gagagagccc agaatgtcac tcggcttcta cgaaagcagg ctgaggaggt
8941 caatactgga tgggaaaaat tgaacctgca ctccgctgac tggcagagaa aaatagatga
9001 gaccttgaa agactccagg aacttcaaga ggccacggat gagctggacc tcaagctgcg
9061 ccaagctgag gtgatcaagg gatcctggca gcccgtgggc gatctcctca ttgactctct
9121 ccaagatcac ctcgagaaag tcaaggcact tcgaggagaa attgcgcctc tgaaagagaa
9181 cgtgagccac gtcaatgacc ttgctcgcca gcttaccact ttgggcattc agctctcacc
9241 gtataacctc agcactctgg aagacctgaa caccagatgg aagcttctgc aggtggccgt
9301 cgaggaccga gtcaggcagc tgcatgaagc ccacagggac tttggtccag catctcagca
9361 cttctttcc acgtctgtcc agggtccctg ggagagagcc atctcgccaa acaaagtgcc
9421 ctactatatc aaccacgaga ctcaaacacc ttgctgggac catcccaaaa tgacagagct
9481 ctaccagtct ttagctgacc tgaataatgt cagattctca gcttatagga ctgccatgaa
9541 actccgaaga ctgcagaagg ccctttgctt ggatctcttg agcctgtcag ctgcatgtga
9601 tgccttggac cagcacaacc tcaagcaaaa tgaccagccc atggatatcc tgcagattat
9661 taattgtttg accactattt atgaccgcct ggagcaagag cacaacaatt tggtcaacgt
9721 ccctctctgc gtggatatgt gtctgaactg gctgctgaat gtttatgata cgggacgaac
9781 agggaggatc cgtgtcctgt cttttaaaac tggcatcatt tcctgtgta aagcacattt
9841 ggaagacaag tacagatacc ttttcaagca agtggcaagt tcaacaggat tttgtgacca
9901 gcgcaggctg ggcctccttc tgcatgattc tatccaaatt ccaagacagt tgggtgaagt
9961 tgcatcctt gggggcagta acattgagcc aagtgtccgg agctgcttcc aatttgctaa
10021 taataagcca gagatcgaag cggccctctt cctagactgg atgagactgg aaccccagtc
10081 catggtgtgg ctgcccgtcc tgcacagagt ggctgctgca gaaactgcca agcatcaggc
10141 caaatgtaac atctgcaaag agtgtccaat cattggattc aggtacagga gtctaaagca
10201 ctttaattat gacatctgcc aaagctgctt ttttctggt cgagttgcaa aaggccataa
10261 aatgcactat cccatggtgg aatattgcac tccgactaca tcaggagaag atgttcgaga
10321 ctttgccaag gtactaaaaa acaaatttcg aaccaaaagg tatttttgcga agcatccccg
10381 aatgggctac ctgccagtgc agactgtctt agagggggac aacatggaaa c
10471 gcctgcctcg tcccctcagc tttcacacga
10501 tgatactcat tcacgcattg aacattatgc tagcaggcta gcagaaatgg aaaacagcaa
10561 tggatcttat ctaaatgata gcatctctcc taatgagagc atagatgatg aacatttgtt
10621 aatccagcat tactgccaaa gttgaacca ggactccccc ctgagccagc ctcgtagtcc
10681 tgcccagatc ttgatttcct tagagagtga ggaaagaggg gagctagaga gaatcctagc
10741 agatcttgag gaagaaaaca ggaatctgca agcagaatat gaccgtctaa agcagcagca
10801 cgaacataaa ggcctgtccc cactgccgtc ccctcctgaa atgatgccca cctctcccca
10861 gagtccccgg gatgctgagc tcattgctga ggccaagcta ctgcgtcaac acaaaggccg
10921 cctggaagcc aggatgcaaa tcctggaaga ccacaataaa cagcaggagt cacagttaca
10981 caggctaagg cagctgctgg agcaacccca ggcagaggcc aaagtgaatg gcacaacggt
11041 gtcctctcct tctacctctc tacagaggtc cgacagcagt cagcctatgc tgctccgagt
11101 ggttggcagt caaacttcgg actccatggg tgaggaagat cttctcagtc ctcccagga
11161 cacaagcaca gggttagagg aggtgatgga gcaactcaac aactccttcc ctagttcaag
11221 aggaagaaat acccctggaa agccaatgag agaggacaca atgtaggaag tcttttccac
```

FIGURE 23 (cont.)

```
11281 atggcagatg atttgggcag agcgatggag tccttagtat cagtcatgac agatgaagaa
11341 ggagcagaat aaatgtttta caactcctga ttcccgcatg gtttttataa tattcataca
11401 acaaagagga ttagacagta agagtttaca agaaataaat ctatattttt gtgaagggta
11461 gtggtattat actgtagatt tcagtagttt ctaagtctgt tattgttttg ttaacaatgg
11521 caggttttac acgtctatgc aattgtacaa aaaagttata agaaaactac atgtaaaatc
11581 ttgatagcta aataacttgc catttcttta tatggaacgc attttgggtt gtttaaaaat
11641 ttataacagt tataaagaaa gattgtaaac taaagtgtgc tttataaaaa aaagttgttt
11701 ataaaaaccc ctaaaaacaa aacaaacaca cacacacaca catacacaca cacacacaaa
11761 actttgaggc agcgcattgt tttgcatcct tttggcgtga tatccatatg aaattcatgg
11821 cttttctttt ttttgcatat taaagataag acttcctcta ccaccacacc aaatgactac
11881 tacacactgc tcatttgaga actgtcagct gagtggggca ggcttgagtt ttcatttcat
11941 atatctatat gtctataagt atataaatac tatagttata tagataaaga gatacgaatt
12001 tctatagact gacttttttcc atttttttaaa tgttcatgtc acatcctaat agaaagaaat
12061 tacttctagt cagtcatcca ggcttacctg cttggt
```

FIGURE 29
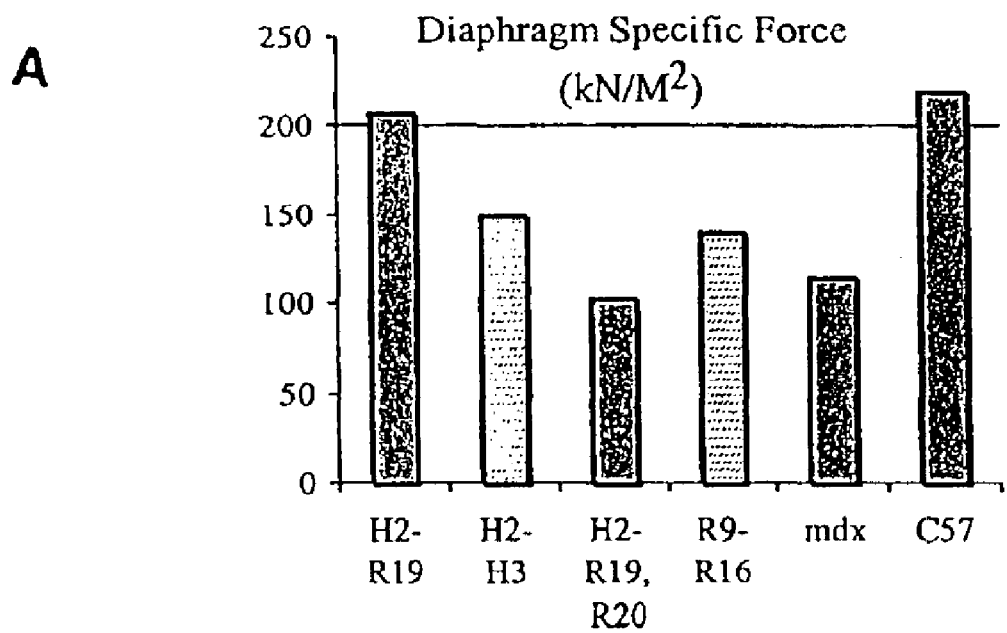
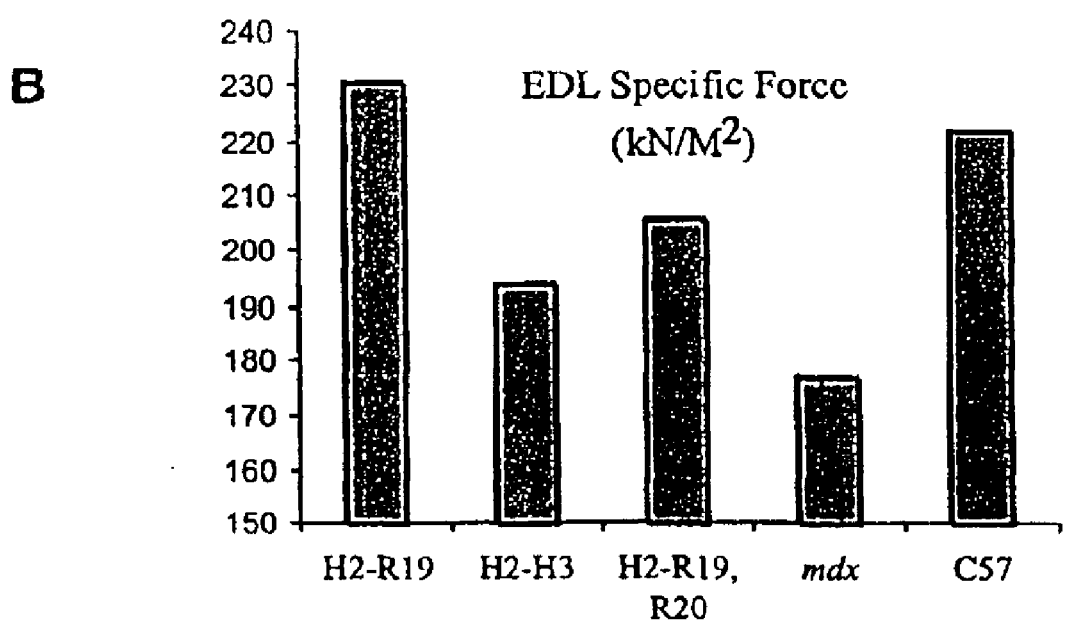

FIGURE 30
A. Specific Force in the TA Muscle
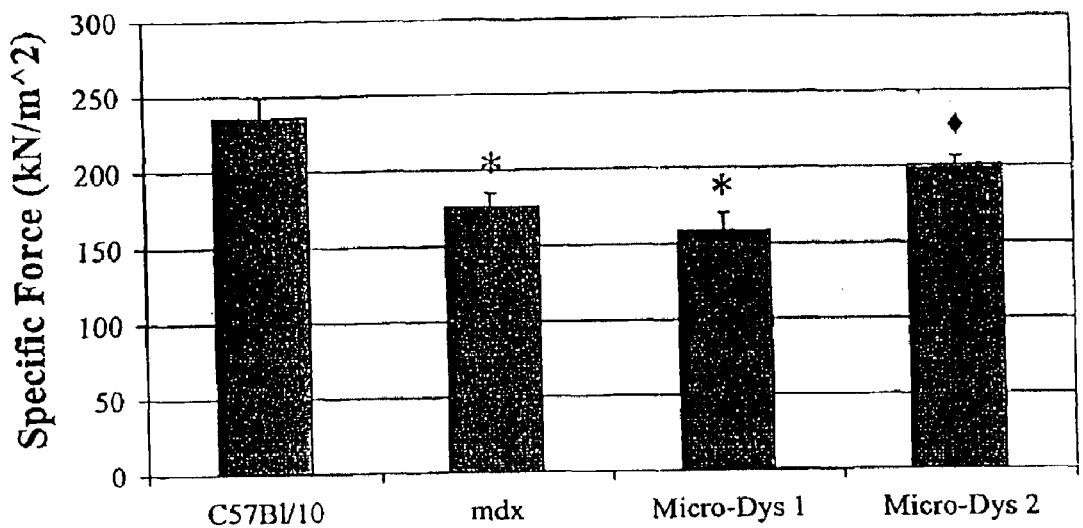
B. Specific Force in the Diaphragm
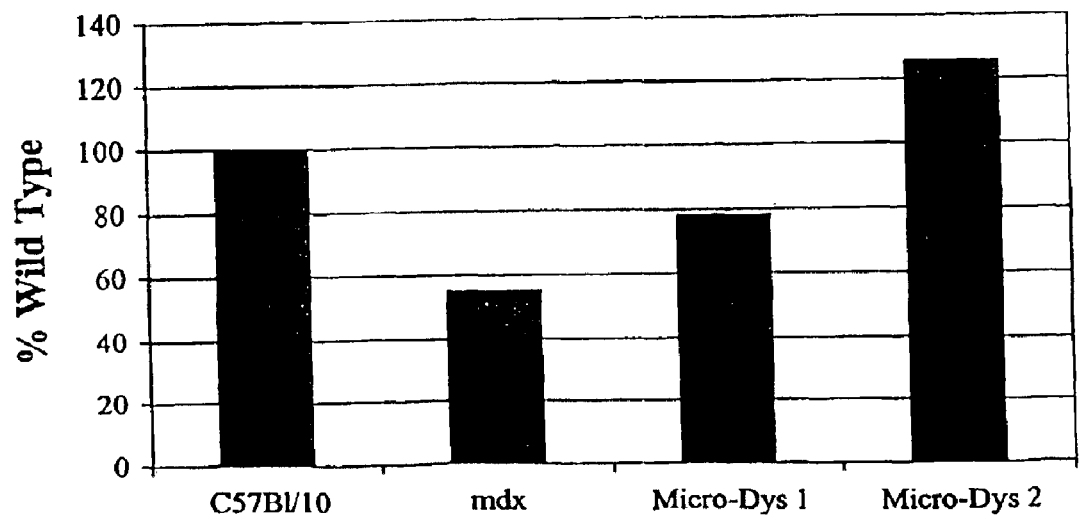

FIGURE 33
A. Body Mass
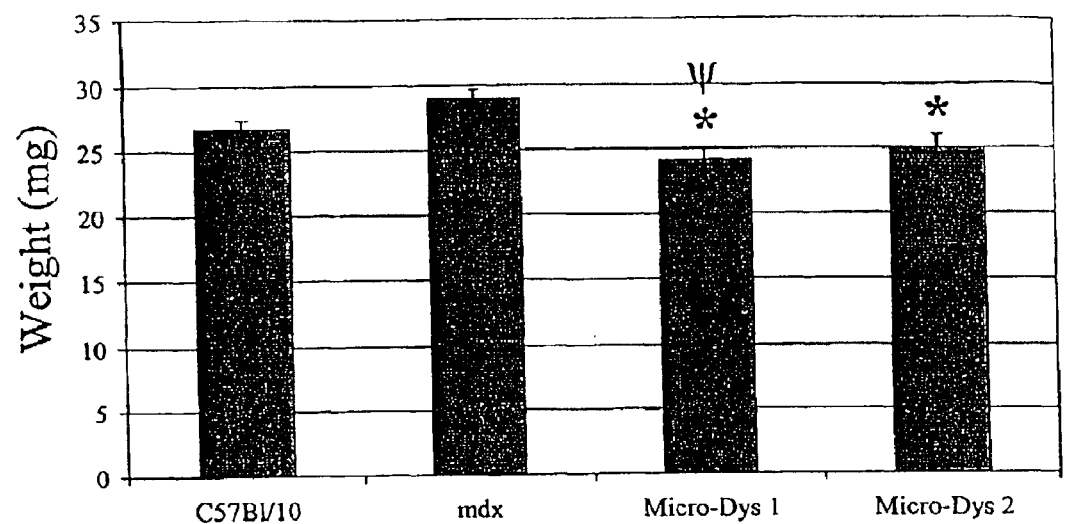
B. Tibialis Anterior Muscle Mass
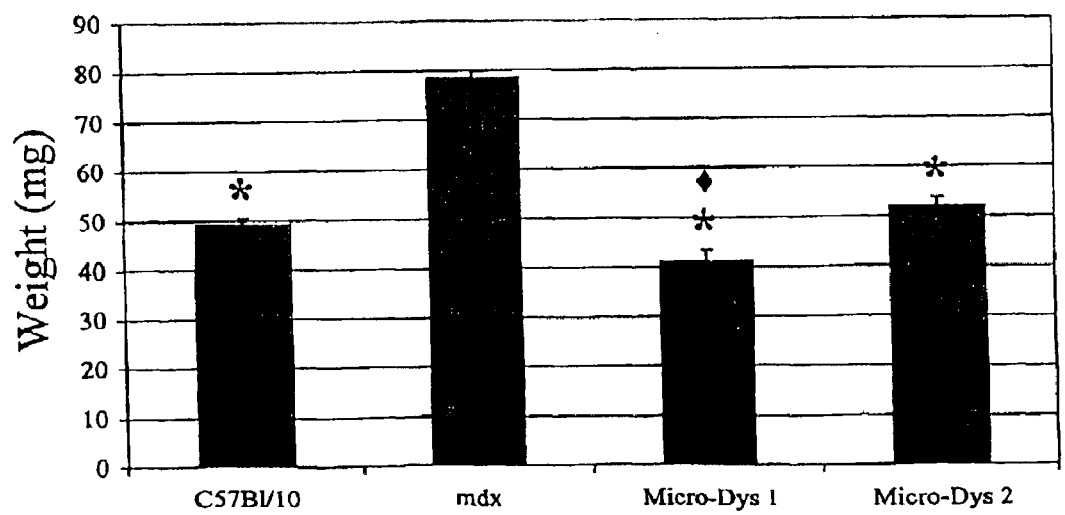

FIGURE 36

SEQ ID NO: 87 wild type mouse enhancer) - CCACTA

```
              2150                                              2200
CGGGTCTAGGCTGCCCATGTAAGGAGGCAAGGCCTGGGGACACCCGAGATGCCTGGTTATAATTAACCCAGACATGTGGCTGCCCCCCCCCCCCCAACAC
              2250                                              2300
CTGCTGCCTGAGCCTCACCCCCACCCCGGTGCCTGGGTCTTAGGCTCTGTACACCATGGAGGAGAAGCTCGCTCTAAAAATAACCCTGTCCCTGGTGGAT
```

SEQ ID NO: 88 ('2R' mouse mutant enhancer) - CCACTA

```
              2150                                              2200
CGGGTCTAGGCTGCCCATGTAAGGAGGCAAGGCCTGGGGACACCCGAGATGCCTGGTTATAATTAACCCCAACACCTGCTGCCCCCCCCCCCCCAACAC
              2250                                              2300
CTGCTGCCTGAGCCTCACCCCCACCCCGGTGCCTGGGTCTTAGGCTCTGTACACCATGGAGGAGAAGCTCGCTCTAAAAATAACCCTGTCCCTGGTGGAT
```

SEQ ID NO: 89 ('S5' mouse mutant enhancer) - CCACTA

```
              2150                                              2200
CGGGTCTAGGCTGCCCATGTAAGGAGGCAAGGCCTGGGGACACCCGAGATGCCTGGTTATAATTAACCCAGACATGTGGCTGCCCCCCCCCCCCCAACAC
              2250                                              2300
CTGCTGCCTGAGCCTGAGCGGTTACCCCACCCCGGTGCCTGGGTCTTAGGCTCTGTACACCATGGAGGAGAAGCTCGCTCTAAAAATAACCCTGTCCCTG
GTGGAT
```

SEQ ID NO: 90 ('2RS5' mouse mutant enhancer) - CCACTA

```
              2150                                              2200
CGGGTCTAGGCTGCCCATGTAAGGAGGCAAGGCCTGGGGACACCCGAGATGCCTGGTTATAATTAACCCCAACACCTGCTGCCCCCCCCCCCCCAACAC
              2250                                              2300
CTGCTGCCTGAGCCTGAGCGGTTACCCCACCCCGGTGCCTGGGTCTTAGGCTCTGTACACCATGGAGGAGAAGCTCGCTCTAAAAATAACCCTGTCCCTG
GTGGAT
```

SEQ ID NO: 91 ('truncated 2RS5' mouse mutant enhancer) - CCACTA

```
              2150                                              2200
CGGGTCTAGGCTGCCCATGTAAGGAGGCAAGGCCTGGGGACACCCGAGATGCCTGGTTATAATTAACCCCAACACCTGCTGCCCCCCCCCCCCCAACAC
              2250
CTGCTGCCTGAGCCTGAGCGGTTACCCCACCCCGGTGCCTGGGTCTTAGGCTCTGTACACCATGG
```

FIGURE 37

SEQ ID NO 92 (mouse promoter sequence, -944 to +7)

GTGGAGCAGCCTGCACTGGGCTTCTGGGAGAAACCAAACCGGGTTCTAACCTTTCAGCTACAGTTATTGCCTTTCCTGTAGATGGGCGACTACAGCCCCACC
CCCACCCCGTCTCCTGTATCCTTCCTGGGCCTGGGGATCCTAGGCTTTCACTGGAAATTTCCCCCCAGGTGCTGTAGGCTAGAGTCACGGCTCCCAAGAAC
AGTCCTTGCCTGGCATGCATGGTTCTGAACCTCCAACTGCAAAAAATGACACATACCTTGACCCTTGGAAGGCTGAGGCAGGGGATTGCCATGAGTGCAAA
GCCAGACTGGGTGGCATAGTTAGACCCTGTCTCAAAAAACCAAAAACAATTAAATAACTAAAGTCAGGCAAGTAATCCTACTCGGGAGACTGAGGCAGAGGG
ATTGTTACATGTCTGAGGCCAGCCTGGACTACATAGGGTTTCAGGCTAGCCCTGTCTACAGAGTAAGGCCCTATTTCAAAAACACAAACAAAATGGTTCTCC
CAGCTGCTAATGCTCACCAGGCAATGAAGCCTGGTGAGCATTAGCAATGAAGGCAATGAAGGAGGGTGCTGGCTACAATCAAGGCTGTGGGGGACTGAGGGC
AGGCTGTAACAGGCTTGGGGGCCAGGGCTTATACGTGCCTGGGACTCCCAAAGTATTACTGTTCCATGTTCCCGGCGAAGGGCCAGCTGTCCCCCGCCAGCT
AGACTCAGCACTTAGTTTAGGAACCAGTGAGCAAGTCAGCCCTTGGGGCAGCCCATACAAGGCCATGGGGCTGGCAAGCTGCACGCCTGGGTCCGGGGTGG
GCACGGTGCCCGGGCAAOGAGCTGAAAGCTCATCTGCTCTCAGGGGCCCCTCCCTGGGACAGCCCCTCCTGGCTAGTCACACCCTGTAGGCTCCTCTATAT
AACCCAGGGGCACAGGGGCTGCCCCTGGGTCAC

SEQ ID NO: 93 mouse promoter sequence, -358 to +7)

AATCAAGGCTGTGGGGGACTGAGGGCAGGCTGTAACAGGCTTGGGGGCCAGGGCTTATACGTGCCTGGGACTCCCAAAGTATTACTGTTCCATGTTCCCGGC
GAAGGGCCAGCTGTCCCCCGCCAGCTAGACTCAGCACTTAGTTTAGGAACCAGTGAGCAAGTCAGCCCTTGGGGCAGCCCATACAAGGCCATGGGGCTGGC
AAGCTGCACGCCTGGGTCCGGGGTGGGCACGGTGCCCGGGCAAOGAGCTGAAAGCTCATCTGCTCTCAGGGGCCCCTCCCTGGGACAGCCCCTCCTGGCTA
GTCACACCCTGTAGGCTCCTCTATATAACCCAGGGGCACAGGGGCTGCCCCCGGGTCAC

SEQ ID NO: 94 (mouse promoter sequence, -80 to +7)

CCTCCCTGGGACAGCCCCTCCTGGCTAGTCACACCCTGTAGGCTCCTCTATATAACCCAGGGGCACAGGGGCTGCCCCCGGGTCAC

MINI-DYSTROPHIN NUCLEIC ACID SEQUENCES

The present Application is a National State Entry under 35 U.S.C. 371 of PCT application PCT/US01/31126, filed Oct. 4, 2001, which claims priority to U.S. Provisional application Ser. No. 60/238,848, filed Oct. 6, 2000, both of which are herein incorporated by reference.

This invention was made with Government support under contract NIH R01AR40864-10. The government has certain rights in this invention.

FIELD OF THE INVENTION

The present invention relates to compositions and methods for expressing mini-dystrophin peptides. In particular, the present invention provides compositions comprising nucleic acid sequences that are shorter than wild-type dystrophin cDNA and that express mini-dystrophin peptides that function in a similar manner as wild-type dystrophin proteins. The present invention also provides compositions comprising mini-dystrophin peptides, and methods for expressing mini-dystrophin peptides in target cells.

BACKGROUND OF THE INVENTION

Muscular dystrophy is a group of inherited disorders characterized by progressive muscle weakness and loss of muscle tissue. Muscular dystrophies includes many inherited disorders, including Becker's muscular dystrophy and Duchenne's muscular dystrophy, which are both caused by mutations in the dystrophin gene. Both of the disorders have similar symptoms, although Becker's muscular dystrophy is a slower progressing form of the disease. Duchenne's muscular dystrophy is a rapidly progressive form of muscular dystrophy.

Both disorders are characterized by progressive muscle weakness of the legs and pelvis which is associated with a loss of muscle mass (wasting). Muscle weakness also occurs in the arms, neck, and other areas, but not as severely as in the lower half of the body. Calf muscles initially enlarge (an attempt by the body to compensate for loss of muscle strength), the enlarged muscle tissue is eventually replaced by fat and connective tissue (pseudohypertrophy). Muscle contractions occur in the legs and heels, causing inability to use the muscles because of shortening of muscle fibers and fibrosis of connective tissue. Bones develop abnormally, causing skeletal deformities of the chest and other areas. Cardiomyopathy occurs in almost all cases. Mental retardation may accompany the disorder but it is not inevitable and does not worsen as the disorder progresses. The cause of this impairment is unknown. Becker's muscular dystrophy occurs in approximately 3 out of 100,000 people. Symptoms usually appear in men between the ages of 7 and 26. Women rarely develop symptoms. There is no known cure for Becker's muscular dystrophy. Treatment is aimed at control of symptoms to maximize the quality of life. Activity is encouraged. Inactivity (such as bed rest) can worsen the muscle disease. Physical therapy may be helpful to maintain muscle strength. Orthopedic appliances such as braces and wheelchairs may improve mobility and self-care. Becker's muscular dystrophy results in slowly progressive disability. A normal life span is possible; however, death usually occurs after age 40.

Duchenne's muscular dystrophy occurs in approximately 2 out of 10,000 people. Symptoms usually appear in males 1 to 6 years old. Females are carriers of the gene for this disorder but rarely develop symptoms. There is no known cure for Duchenne's muscular dystrophy. Treatment is aimed at control of symptoms to maximize the quality of life. Activity is encouraged. Inactivity (such as bed rest) can worsen the muscle disease. Physical therapy may be helpful to maintain muscle strength and function. Orthopedic appliances such as braces and wheelchairs may improve mobility and the ability for self-care. Duchenne's muscular dystrophy results in rapidly progressive disability. By age 10, braces may be required for walking, and by age 12, most patients are confined to a wheelchair. Bones develop abnormally, causing skeletal deformities of the chest and other areas. Muscular weakness and skeletal deformities contribute to frequent breathing disorders. Cardiomyopathy occurs in almost all cases. Intellectual impairment is common but is not inevitable and does not worsen as the disorder progresses. Death usually occurs by age 15, typically from respiratory (lung) disorders.

Although there are no available treatments for muscular dystrophy, the usefulness of gene replacement as therapy for the disease has been established in transgenic mouse models. Unfortunately, progress toward therapy for human patients has been limited by lack of a suitable technique for delivery of such vectors to large masses of muscle cells. What is needed in the art is a vector that can carry most of the dystrophin coding sequence, that can be cheaply produced in large quantities, that can be delivered to a large mass of muscle cells, and that provides stable expression of dystrophin after delivery.

SUMMARY OF THE INVENTION

The present invention provides compositions and methods for expressing mini-dystrophin peptides. In particular, the present invention provides compositions comprising nucleic acid sequences that are shorter than wild-type dystrophin cDNA and that express mini-dystrophin peptides that function in a similar manner as wild-type dystrophin proteins. The present invention also provides compositions comprising mini-dystrophin peptides, and methods for expressing mini-dystrophin peptides in target cells.

The present invention provides such shortened nucleic acid sequences in a variety of ways. For example, the present invention provides nucleic acids encoding only 4, 8, 10, 12, 14, 16, 18, 20 and 22 spectrin-like repeat encoding sequences (i.e. nucleic acids encoding an exact number of spectrin-like repeats). As wild-type dystrophin has 24 spectrin-like repeat encoding sequences, providing nucleic acids encoding fewer numbers of repeats reduces the size of the dystrophin gene (e.g. allowing the nucleic acid sequence to fit into vectors with limited cloning capacity). Another example of such shortened nucleic acid sequences are those that lack at least a portion of the carboxy-terminal domain of wild-type dystrophin nucleic acid. A further example of such shortened nucleic acid sequences are those that lack at least a portion of the 3' untranslated region, or 5' untranslated region, or both. In certain embodiments, the present invention provides compositions comprising the peptides expressed by the nucleic acid sequences of the present invention.

In certain embodiments, the present invention provides compositions comprising nucleic acid encoding a mini-dystrophin peptide, wherein the mini-dystrophin peptide comprises a spectrin-like repeat domain, and wherein the spectrin-like repeat domain consists of n spectrin-like repeats, wherein n is an even number less than 24. In particular embodiments, the present invention provides nucleic acid encoding a mini-dystrophin peptide, wherein the mini-dystrophin peptide comprises a spectrin-like repeat domain comprising n spectrin-like repeats, wherein the mini-dystrophin peptide contains no more than n spectrin-like repeats, and wherein n is an even number that is less than 24 and at least 4. In some embodiments, the present invention provides nucleic acid encoding a mini-dystrophin peptide, wherein the mini-dystrophin peptide comprises n spectrin-like repeats, wherein the mini-dystrophin peptide contains no more than n spectrin-like repeats, and wherein n is an even number that is less than 24 and at least 4.

In some embodiments, n is 20 or less. In other embodiments, n is 16 or less. In particular embodiments, n is 12 or less. In additional embodiments, n is 8 or less. In preferred embodiments, n is 4. In certain embodiments, n is selected from 4, 8, 10, 12, 14, 16, 18, 20 and 22. In some embodiments, the present invention provides compositions comprising nucleic acid encoding a mini-dystrophin peptide, wherein the mini-dystrophin peptide comprises a spectrin-like repeat domain, and wherein the spectrin-like repeat domain consists of n spectrin-like repeats, wherein n is 4, 8, 12, 16, or 20. In certain embodiments, the present invention provides the peptides encoded by the nucleic acid sequences encoding the mini-dystrophin peptides.

In certain embodiments, the present invention provides compositions comprising nucleic acid encoding a mini-dystrophin peptide, wherein the mini-dystrophin peptide comprises i) a spectrin-like repeat domain comprising 4 dystrophin spectrin-like repeats, ii) an actin-binding domain, and iii) a β-dystroglycan binding domain; and wherein the mini-dystrophin peptide contains no more than 4 dystrophin spectrin-like repeats.

In some embodiments, the present invention provides compositions comprising a mini-dystrophin peptide, wherein the mini-dystrophin peptide comprises a spectrin-like repeat domain comprising n spectrin-like repeats, wherein the mini-dystrophin peptide contains no more than n spectrin-like repeats, and wherein n is an even number that is less than 24 and at least 4. In particular embodiments, the present invention provides a cell (or cell line) containing the nucleic acid and peptide sequences of the present invention.

In certain embodiments, the mini-dystrophin peptide is capable of altering a measurable muscle value in a DMD animal model by at least approximately 10% of the wild type value. In other embodiments, the mini-dystrophin peptide is capable of altering a measurable muscle value in a DMD animal model by at least approximately 20% of the wild type value. In particular embodiments, the mini-dystrophin peptide is capable of altering a measurable muscle value in a DMD animal model by at least approximately 30% of the wild type value. In preferred embodiments, the mini-dystrophin peptide is capable of altering a measurable muscle value in a DMD animal model to a level similar to the wild-type value (e.g. ±4%). In certain embodiments, the nucleic acid comprises at least 2, or at least 4, spectrin-like repeat encoding sequences. In some embodiments, the spectrin-like repeat encoding sequences are precise spectrin-like repeat encoding sequences. In certain embodiments, the nucleic acid is less than 5 kilo-bases in length. In other embodiments, the nucleic acid is less than 6 kilo-bases in length. In particular embodiments, the nucleic acid comprises viral DNA (e.g. adenovirus DNA). In preferred embodiments, the viral DNA comprises adeno-associated viral DNA.

In certain embodiments, the present invention provides compositions comprising nucleic acid encoding a mini-dystrophin peptide, wherein the mini-dystrophin peptide comprises a spectrin-like repeat domain, and wherein the spectrin-like repeat domain consists of n spectrin-like repeats, wherein n is an even number less than 24; and wherein the nucleic acid comprises an actin-binding domain encoding sequence, a β-dystroglycan-binding domain encoding sequence, and at least 2, or at least 4, spectrin-like repeat encoding sequences. In some embodiments, the nucleic acid comprises at least 4 spectrin-like repeat encoding sequences.

In certain embodiments, the present invention provides compositions comprising nucleic acid, wherein the nucleic acid comprises at least 2 spectrin-like repeat encoding sequences, and wherein the nucleic acid encodes a mini-dystrophin peptide comprising a spectrin-like repeat domain, wherein the spectrin-like repeat domain consists of n spectrin-like repeats, and wherein n is an even number less than 24. In some embodiments, the nucleic acid comprises at least 4 spectrin-like repeat encoding sequences.

In some embodiments, the nucleic acid comprises SEQ ID NO:39 (i.e. ΔR4–R23). In other embodiments, the nucleic acid comprises SEQ ID NO:40 (i.e. ΔR2–R21). In certain embodiments, the nucleic acid comprises SEQ ID NO:41 (i.e. ΔR2–R21+H3). In still other embodiments, the nucleic acid comprises SEQ ID NO:42 (i.e. ΔH2–R19).

In certain embodiments, the nucleic acid comprises an expression vector (e.g. plasmid, virus, etc). In some embodiments, the expression vector comprises viral DNA. In certain embodiments, the viral DNA comprises adeno-viral DNA. In some embodiments, the viral DNA comprises lentiviral DNA. In other embodiments, the viral DNA comprises helper-dependent adeno-viral DNA. In preferred embodiments, the viral DNA comprises adeno-associated viral DNA. In some embodiments, the nucleic acid is inserted in a virus (e.g. adeno-associated virus, adenovirus, helper-dependent adeno-associated virus, lentivirus).

In certain embodiments, the nucleic acid comprises an actin-binding domain encoding sequence. In particular embodiments, the actin binding domain comprises at least a portion of SEQ ID NO:6 (e.g. 5%, 10%, 20%, 40%, 50%, or 75% of SEQ ID NO:6). In other embodiments, the actin binding domain comprises at least a portion of a homolog or mutated version of SEQ ID NO:6 (e.g. 5%, 10%, 20%, 40%, 50%, or 75% of a SEQ ID NO:6 homolog or mutated version of SEQ ID NO:6). In certain embodiments, the nucleic acid comprises a β-dystroglycan binding domain. In certain embodiments, the β-dystroglycan binding domain comprises at least a portion of a dystrophin hinge 4 encoding sequence (e.g. the 3' 50% of SEQ ID NO:34), and at least a portion of dystrophin cysteine-rich domain encoding sequence (e.g. the 5' 75% of SEQ ID NO:35). In particular embodiments, at least a portion of hinge 4 is the WW domain (SEQ ID NO:45), or a homolog or mutation thereof.

In particular embodiments, the spectrin-like repeat encoding sequences are selected from the group consisting of SEQ ID NOS:8–10, 12–27, and 29–33. In some embodiments, the spectrin-like repeat encoding sequences are selected from the group consisting of SEQ ID NOS:8–10, 12–27, and 29–33, and homologs or mutations of SEQ ID NOS:8–10, 12–27, and 29–33. In preferred embodiments, the spectrin-like repeat encoding sequences are selected from the group consisting of SEQ ID NOS:8–10 and 29–33. In some embodiments, the spectrin-like repeat encoding sequences are identical (e.g. all the sequences are SEQ ID NO:8). In preferred embodiments, the spectrin-like repeat encoding sequences are all different (e.g. the nucleic acid sequence has only 4 spectrin-like repeat encoding sequences, and these 4 are: SEQ ID NO:8, SEQ ID NO:9, SEQ ID NO:10, and SEQ ID NO:33). In certain embodiments, nucleic acid sequence comprises at least one spectrin-like repeat encoding sequence selected from the group consisting of SEQ ID NOS:8–10, and at least one spectrin-like repeat encoding sequence selected from the group consisting of SEQ ID NOS:29–33.

In certain embodiments, the nucleic acid (or the resulting peptide) comprises at least one dystrophin hinge region. In some embodiments, the nucleic acid comprises at least one dystrophin hinge region selected from hinge region 1, hinge region 2, hinge region 3 and hinge region 4. In some embodiments, the nucleic acid comprises at least one dystrophin hinge region selected from hinge region 1, hinge region 2, and hinge region 3. In particular embodiments, dystrophin hinge region 1 is SEQ ID NO:7, or a homolog (See, e.g. FIG. 11), or a mutant version thereof. In particular embodiments, dystrophin hinge region 2 is SEQ ID NO:11, or a homolog (See, e.g. FIG. 11), or a mutant version thereof. In certain embodiments, dystrophin hinge region 3 is SEQ ID NO:28, or a homolog (See, e.g. FIG. 11), or a mutant version thereof. In other embodiments, dystrophin hinge region 4 is SEQ ID NO:34, or a homolog (See, e.g. FIG. 11), or a mutant version thereof.

In some embodiments, the nucleic acid comprises a sequence encoding at least a portion of wild-type dystrophin C-terminal protein. In other embodiments, the nucleic acid comprises at least a portion of the 5' untranslated region. In particular embodiments, the nucleic acid comprises at least a portion of the 3' untranslated region. In different embodiments, the nucleic acid sequence comprises regulatory sequences (e.g. MCK enhancer and promoter elements). In particular embodiments, the nucleic acid sequence is operably linked to regulatory sequences (e.g. MCK enhancer and promoter elements). In certain embodiments, the nucleic acid sequence comprises a mutant muscle-specific enhancer region.

In particular embodiments, the nucleic acid has less than 75% of a wild type dystrophin 5' untranslated region. In other embodiments, the nucleic acid has less than 50% or 20% or 1% (e.g. 0, 1, 2 nucleotides from a wild type dystrophin 5' untranslated region). In particularly preferred embodiments, the nucleic acid sequence does not contain any of the wild-type dystrophin 5' untranslated region. In certain embodiments, the nucleic acid has less than 75% of a wild type dystrophin 3' untranslated region. In other embodiments, the nucleic acid has less than 50%, preferably less than 40%, more preferably less than 35% of a wild type dystrophin 3' untranslated region. In certain embodiments, the nucleic acid does not contain a wild-type dystrophin 3' untranslated region (or, in some embodiments, any type of 3' untranslated region).

In particular embodiments, the mini-dystrophin peptide (e.g. encoded by the nucleic acid of the present invention) comprises a substantially deleted dystrophin C-terminal domain. In some embodiments, the mini-dystrophin peptide comprises less than 40% of wild type dystrophin C-terminal domain, preferably less than 30%, more preferably less than 20%, even more preferably less than 1%, and most preferably approximately 0% (e.g. 0, 1, 2, 3 or 4 amino acids from the wild type dystrophin C-terminal domain). In some embodiments, the nucleic acid sequence comprises at least one intron sequence.

In some embodiments, the present invention provides methods for expressing a mini-dystrophin peptide in a target cell, comprising; a) providing; i) a vector comprising nucleic acid encoding a mini-dystrophin peptide, wherein the mini-dystrophin peptide comprises a spectrin-like repeat domain, and wherein the spectrin-like repeat domain consists of n spectrin-like repeats, wherein n is an even number less than 24, and ii) a target cell, and b) contacting the vector with the target cell under conditions such that the mini-dystrophin peptide is expressed in the target cells. In certain embodiments, the contacting comprises transfecting. In some embodiments, the contacting is performed in-vitro. In particular embodiments, the contacting is done in-vivo. In other embodiments, the target cell is a muscle cell. In particular embodiments, the target cell further comprises a subject (e.g. with Duchenne muscular dystrophy (DMD) or Becker muscular dystrophy (BMD)). In preferred embodiment, the mini-dystrophin peptide is expressed in the cells of a subject (e.g. such that symptoms of DMD or BMD are reduced or eliminated).

In certain embodiments, the present invention provides methods comprising; a) providing; i) a vector comprising nucleic acid encoding a mini-dystrophin peptide, wherein the mini-dystrophin peptide comprises a spectrin-like repeat domain comprising n spectrin-like repeats, wherein the mini-dystrophin peptide contains no more than n spectrin-like repeats, and wherein n is an even number that is less than 24 and at least 4, and ii) a subject comprising a target cells (e.g. a subject with symptoms of a muscle disease, such as Muscular Dystrophy); and b) contacting the vector with the subject under conditions such that the mini-dystrophin peptide is expressed in the target cell (e.g. such that the symptoms are reduced or eliminated). In preferred embodiments, the nucleic acid encoding the mini-dystrophin peptide is contained within an viral vector (e.g. adeno-associated viral vector), and the contacting is done by means of injecting the viral vector into the subject.

In particular embodiments, the present invention provides compositions comprising nucleic acid, wherein the nucleic acid encodes a mini-dystrophin peptide, and wherein the mini-dystrophin peptide comprises a substantially deleted dystrophin C-terminal domain. In some embodiments, the present invention provides the peptides encoded by the nucleic acid of the present invention. In certain embodiments, the substantially deleted dystrophin C-terminal domain is less than 40% of a wild type dystrophin C-terminal domain. In other embodiments, the substantially deleted dystrophin C-terminal domain is less than 30%, 20%, or 1% of a wild type dystrophin C-terminal domain. In preferred embodiments, the substantially deleted dystrophin C-terminal domain is approximately 0% of a wild type dystrophin C-terminal domain. In certain embodiments, the mini-dystrophin peptide does not contain any portion of the wild type dystrophin C-terminal domain (i.e. it is completely deleted).

In certain embodiments, the mini-dystrophin peptide is capable of altering a measurable muscle value in a DMD animal model by at least 10% of the wild type value. In other embodiments, the mini-dystrophin peptide is capable of altering a measurable muscle value in a DMD animal model by at least 20% of the wild type value. In particular embodiments, the mini-dystrophin-peptide is capable of altering a measurable muscle value in a DMD animal model by at least 30% of the wild type value. In preferred embodiments, the mini-dystrophin peptide is capable of altering a measurable muscle value in a DMD animal model to a level similar to the wild-type value (e.g. ±4%).

In certain embodiments, the nucleic acid comprises an expression vector (e.g. plasmid, virus, etc). In some embodiments, the expression vector comprises viral DNA.

In certain embodiments, the viral DNA comprises adenoviral DNA. In some embodiments, the viral DNA comprises lentiviral DNA. In other embodiments, the viral DNA comprises helper-dependent adeno-viral DNA. In preferred embodiments, the viral DNA comprises adeno-associated viral DNA. In some embodiments, the nucleic acid is inserted in a virus (e.g. adeno-associated virus, adenovirus, helper-dependent adeno-associated virus, lentivirus).

In certain embodiments, the nucleic acid comprises an actin-binding domain encoding sequence. In particular embodiments, the actin binding domain comprises at least a portion of SEQ ID NO:6 (e.g. 5%, 10%, 20%, 40%, 50%, or 75% of SEQ ID NO:6). In other embodiments, the actin binding domain comprises at least a portion of a homolog or mutated version of SEQ ID NO:6 (e.g. 5%, 10%, 20%, 40%, 50%, or 75% of a SEQ ID NO:6 homolog or mutated version of SEQ ID NO:6). In certain embodiments, the nucleic acid comprises a β-dystroglycan binding domain. In certain embodiments, the β-dystroglycan binding domain comprises at least a portion of a dystrophin hinge 4 encoding sequence (e.g. the 3' 50% of SEQ ID NO:34), and at least a portion of dystrophin cysteine-rich domain encoding sequence (e.g. the 5' 75% of SEQ ID NO:35). In particular embodiments, at least a portion of hinge 4 is the WW domain (SEQ ID NO:45), or a homolog or mutation thereof.

In certain embodiments, the nucleic acid comprises at least one dystrophin hinge region. In some embodiments, the nucleic acid comprises at least one dystrophin hinge region selected from hinge region 1, hinge region 2, hinge region 3 and hinge region 4. In some embodiments, the nucleic acid comprises at least one dystrophin hinge region selected from hinge region 1, hinge region 2, and hinge region 3. In particular embodiments, dystrophin hinge region 1 is SEQ ID NO:7, or a homolog (See, e.g. FIG. 11), or a mutant version thereof. In particular embodiments, dystrophin hinge region 2 is SEQ ID NO:11, or a homolog (See, e.g. FIG. 11), or a mutant version thereof. In certain embodiments, dystrophin hinge region 3 is SEQ ID NO:28, or a homolog (See, e.g. FIG. 11), or a mutant version thereof. In other embodiments, dystrophin hinge region 4 is SEQ ID NO:34, or a homolog (See, e.g. FIG. 11), or a mutant version thereof.

In other embodiments, the nucleic acid comprises at least a portion of the 5' untranslated region. In particular embodiments, the nucleic acid comprises at least a portion of the 3' untranslated region. In different embodiment, the nucleic acid sequence comprises regulatory sequences (e.g. MCK enhancer and promoter elements). In particular embodiments, the nucleic acid sequence is operably linked to regulatory sequences (e.g. MCK enhancer and promoter elements). In certain embodiments, the nucleic acid sequence comprises a mutant muscle-specific enhancer region.

In particular embodiments, the nucleic acid contains less that 75% of a wild type dystrophin 5' untranslated region. In other embodiments, the nucleic acid contains less than 50% or 20% or 1% (e.g. 0, 1, 2 nucleotides from a wild type dystrophin 5' untranslated region). In particularly preferred embodiments, the nucleic acid sequence does not contain any of the wild-type dystrophin 5' untranslated region. In certain embodiments, the nucleic acid has less than 75% of a wild type dystrophin 3' untranslated region. In other embodiments, the nucleic acid has less than 50%, preferably less than 40%, more preferably less than 35% of a wild type dystrophin 3' untranslated region. In certain embodiments, the nucleic acid does not contain a wild-type dystrophin 3' untranslated region (or, in some embodiments, any type of 3' untranslated region).

In some embodiments, the present invention provides methods for expressing a mini-dystrophin peptide in a target cell, comprising; a) providing; i) a vector comprising nucleic acid, wherein the nucleic acid encodes a mini-dystrophin peptide comprising a substantially deleted dystrophin C-terminal domain, and ii) a target cell, and b) contacting the vector with the target cell under conditions such that the mini-dystrophin peptide is expressed in the target cells. In certain embodiments, the contacting comprises transfecting. In other embodiments, the target cell is a muscle cell.

In certain embodiments, the present invention provides systems and kits with the mini-dystrophin nucleic acid and/or peptide sequences described herein. In certain embodiments, the systems and kits of the present invention comprise a nucleic acid sequence encoding a mini-dystrophin peptide (and/or the mini-dystrophin peptide) and one other component (e.g. an insert component with written instructions for using the mini-dystrophin nucleic acid, or a nucleic acid encoding a vector, or a component for delivering the nucleic acid to a subject, cells for expressing the mini-dystrophin peptide, a buffer, etc.). In certain embodiments, the present invention provides a computer readable medium (e.g. CD, hard drive, floppy disk, magnetic tape, etc.) that contains the nucleic acid or amino acid sequences of the present invention (e.g. a computer readable representation of the nucleotide bases used to make a mini-dystrophin nucleic acid sequence).

In some embodiments, the present invention provides mini-dystrophin nucleic acid sequences for use as a medicament. In other embodiments, the present invention provides mini-dystrophin peptides for use as a medicament. In particular embodiments, the present invention provides the use of mini-dystrophin nucleic acid sequences for preparing a drug for a therapeutic application. In additional embodiments, the present invention provides the use of mini-dystrophin peptides for preparing a drug for a therapeutic application. In some embodiments, the present invention provides mini-dystrophin nucleic acid sequences for the preparation of a composition for the treatment of a muscle disease (e.g. DMD). In other embodiments, the present invention provides mini-dystrophin peptides for the preparation of a composition for the treatment of a muscle disease (e.g. DMD).

DESCRIPTION OF THE FIGURES

FIG. 1 shows the nucleic acid sequence for wild-type human dystrophin cDNA.

FIG. 2 shows the nucleic acid sequence for wild-type mouse dystrophin cDNA.

FIG. 3 shows the nucleic acid sequence for wild-type human utrophin cDNA.

FIG. 4 shows the nucleic acid sequence for wild-type mouse utrophin cDNA

FIG. 5 shows various domains of the nucleic acid sequence for wild-type human dystrophin cDNA.

FIG. 6 shows various domains of the nucleic acid sequence for wild-type human dystrophin cDNA.

FIG. 7 shows various domains of the nucleic acid sequence for wild-type human dystrophin cDNA.

FIG. 8 shows various domains of the nucleic acid sequence for wild-type human dystrophin cDNA.

FIG. 9 shows various domains of the nucleic acid sequence for wild-type human dystrophin cDNA.

FIG. 10 shows the 3' UTR domain nucleic acid sequence for wild-type human dystrophin cDNA.

FIG. 11 shows a sequence alignment between wild-type human dystrophin cDNA (bases 1220–9328 of SEQ ID NO:1) and wild-type mouse dystrophin cDNA (bases 1238–9319 of SEQ ID NO:2). The various domains in the human dystrophin sequence have spaces between them with the ends highlighted in bold. In this regard, homologous sequences for various domains in the mouse cDNA sequence are seen.

FIG. 12 shows the nucleic acid sequence for ΔR4–R23, a nucleic acid sequence encoding a mini-dystrophin peptide.

FIG. 13 shows the nucleic acid sequence for ΔR2–R21, a nucleic acid sequence encoding a mini-dystrophin peptide.

FIG. 14 shows the nucleic acid sequence for ΔR2–R21+H3, a nucleic acid sequence encoding a mini-dystrophin peptide.

FIG. 15 shows the nucleic acid sequence for ΔH2–R19, a nucleic acid sequence encoding a mini-dystrophin peptide.

FIG. 16 shows the complete cDNA sequence for human skeletal muscle alpha actinin.

FIG. 17 shows the nucleic acid sequence for ΔR9–R16, a nucleic acid sequence encoding a mini-dystrophin peptide.

FIG. 18 shows the nucleic acid sequence for the WW domain.

FIG. 21 show the nucleic acid sequence for pBSX.

FIG. 23 shows the 'full-length' HDMD sequence.

FIG. 29 shows graphs depicting the force generating capacity in diaphragm (A) or EDL (B) muscles of the indicated strains of dystrophin transgenic mdx mice and control mice.

FIG. 30 shows a graph depicting the force generating capacity in EDL (A) or diaphragm (B) muscles of the indicated strains of dystrophin transgenic mdx mice and control mice.

FIG. 33 shows a graph depicting the total body mass (A) and mass of the tibialis anterior muscle (B) of the indicated strains of dystrophin transgenic mdx mice and control mice.

FIG. 36 shows the nucleic acid sequence of various MCK enhancer regions (wild-type and mutant).

FIG. 37 shows the nucleic acid sequence of various MCK promoter regions.

DEFINITIONS

Figure 19:
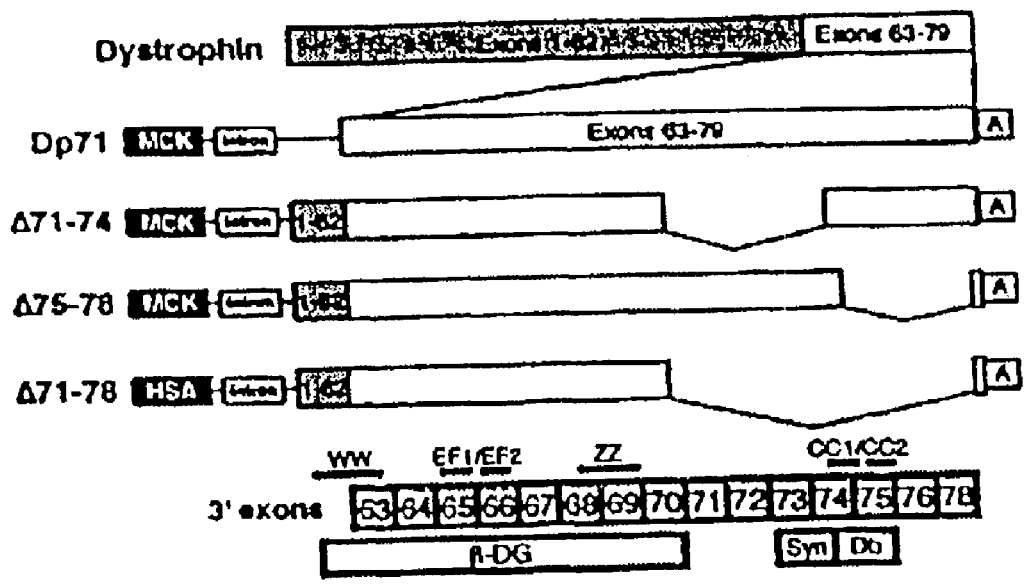
FIG. 19 shows various transgenic expression constructs tested in Example 1.

To facilitate an understanding of the present invention, a number of terms and phrases are defined below:

As used herein, the term "measurable muscle values" refers to measurements of dystrophic symptoms (e.g. fibrosis, an increased proportion of centrally located nuclei, reduced force generation by skeletal muscle, etc.) in an animal. These measurements may be taken, for example, to determine the wild-type value (i.e. the value in a control animal), to determine the value in a DMD (Duchenne muscular dystrophy) animal model (e.g. in an mdx mouse model), and to determine the value in a DMD animal model expressing the mini-dystrophin peptides of the present invention. Various assays may be employed to determine measurable muscle values in an animal including, but not limited to, assays measuring fibrosis, phagocytic infiltration of muscle tissue, variation in myofiber size, an increased proportion of myofibers with centrally located nuclei, elevated serum levels of muscle pyruvate kinase, contractile properties assays, DAP (dystrophin associated protein) assays, susceptibility to contraction induced injuries and measured force assays (See Examples 1 and 4).

As used herein, the term "mini-dystrophin peptide" refers to a peptide that is smaller in size than the full-length wild-type dystrophin peptide, and that is capable of altering (increasing or decreasing) a measurable muscle value in a DMD animal model by at least approximately 10% such that the value is closer to the wild-type value (e.g. a mdx mouse has a measurable muscle value that is 50% of the wild-type value, and this value is increased to at least 60% of the wild-type value; or a mdx mouse has a measurable muscle value that is 150% of the wild-type value, and this value is decreased to at most 140% of the wild-type value). In some embodiments, the mini-dystrophin-peptide is capable of altering a measurable muscle value in a DMD animal model by at least approximately 20% of the wild type value. In certain embodiments, the mini-dystrophin-peptide is capable of altering a measurable muscle value in a DMD animal model by at least approximately 30% of the wild type value. In preferred embodiments, the mini-dystrophin peptide is capable of altering a measurable muscle value in a DMD animal model to a level similar to the wild-type value (e.g. ±4%).

As used herein, the term "wild-type dystrophin cysteine-rich domain" refers to a peptide encoded by the nucleic acid sequences in SEQ ID NO:35 (e.g. in human), as well as wild type peptide homologs encoded by nucleic acid homologs of SEQ ID NO:35 (See, FIG. 11).

As used herein, the term "wild type dystrophin C-terminal domain" refers to a peptide encoded by the nucleic acid sequences in SEQ ID NO:36 (e.g. in human), as well as wild type peptide homologs encoded by nucleic acid homologs of SEQ ID NO:36 (See, FIG. 11).

As used herein, the term "mini-dystrophin peptide comprising a substantially deleted dystrophin C-terminal domain" refers to a mini-dystrophin peptide that has less than 45% of a wild type dystrophin C-terminal domain. In some embodiments, the mini-dystrophin peptide comprises less than 40% of wild type dystrophin C-terminal domain, preferably less than 30%, more preferably less than 20%, even more preferably less than 1%, and most preferably approximately 0% (e.g. 0, 1, 2, 3 or 4 amino acids from the wild type dystrophin C-terminal domain). The construction of mini-dystrophin peptides with a substantially deleted dystrophin C-terminal domain may be accomplished, for example, by deleting all or a portion of SEQ ID NO:36 from human dystrophin SEQ ID NO:1 (See, e.g. Example 3C).

As used herein, the term "wild type dystrophin 5' untranslated region" refers to the nucleic acid sequence at the very 5' end of a wild type dystrophin nucleic acid sequence (e.g. SEQ ID NOS:1 and 2) that immediately precedes the amino acid coding regions. For example, for human dystrophin, SEQ ID NO:5 (the first 208 bases) is the 5' untranslated region (a homolog in mouse may be seen in FIG. 11).

As used herein, the term "wild type dystrophin 3' untranslated region" refers to the nucleic acid sequence at the very 3' end of a wild type dystrophin nucleic acid sequence (e.g. SEQ ID NOS:1 and 2) that immediately proceeds the amino acid coding regions. For example, for human dystrophin, SEQ ID NO:38 (the last 2690 bases of the human dystrophin gene) is the 3' untranslated region (a homolog in mouse may be seen in FIG. 11).

As used herein, the term "actin-binding domain encoding sequence" refers to the portion of a dystrophin nucleic sequence that encodes a peptide-domain capable of binding actin in vitro (e.g. SEQ ID NO:6), as well as homologs (See, FIG. 11), conservative mutations, and truncations of such sequences that encode peptide-domains that are capable of binding actin in vivo. Determining whether a particular nucleic acid sequence encodes a peptide-domain (e.g. homolog, mutation, or truncation of SEQ ID NO:6) that will bind actin in vitro may be performed, for example, by screening the ability of the peptide-domain to bind actin in vitro in a simple actin binding assay (See, Corrado et al., FEBS Letters, 344:255–260 [1994], describing the expression of candidate dystrophin peptides as fusion proteins, absorbing F-actin on to microtiter plates, incubating the candidate peptides in the F-actin coated microtiter plates, washing the plates, adding anti-fusion protein rabbit antibody, and adding an anti-rabbit antibody conjugated to a detectable marker).

As used herein, the term "β-dystroglycan-binding domain encoding sequence" refers to the portion of a dystrophin nucleic sequence that encodes a peptide-domain capable of binding β-dystroglycan in vivo (e.g. SEQ ID NOS:34 and 35), as well as homologs (See, FIG. 11), conservative mutations, and truncations of such sequences that encode peptide-domains that are capable of binding β-dystroglycan in vivo. In preferred embodiments, the β-dystroglycan-binding domain encoding sequence includes at least a portion of a hinge 4 encoding region (e.g. SEQ ID NO:45, the WW domain) and at least a portion of a wild-type dystrophin cysteine-rich domain (e.g. at least a portion of SEQ ID NO:35) (See, e.g. Jung et al., *JBC*, 270 (45):27305 [1995]). Determining whether a particular nucleic acid sequence encodes a peptide-domain (e.g. homolog, mutation, or truncation) that will bind β-dystroglycan in vivo may be performed, for example, by first screening the ability of the peptide-domain to bind β-dystroglycan in vitro in a simple β-dystroglycan binding assay (See, Jung et al., pg 27306—constructing peptide-domain dystrophin-GST fusion peptides and radioactively labelled β-dystroglyean, immobilizing the fusion proteins on glutathione-agarose beads, incubating the beads with the radioactively labelled β-dystroglycan, pelleting the beads, washing the beads, and resolving the sample on an SDS-polyacrylamide gel, staining with Coomasie blue, exposing to film, and quantifying the amount of radioactivity present). Nucleic acid sequences found to express peptides capable of binding β-dystroglycan in such assays may then, for example, be tested in vivo by transfecting a cell line (e.g., COS cells) with two expression vectors, one expressing the dystroglycan peptide and the other expressing the candidate peptide domain (as a fusion protein). After culturing the cells, the protein is then extracted and a co-immunoprecipitation is performed for one of the proteins, followed by a Western blot for the other.

As used herein, the term "spectrin-like repeats" refers to peptides composed of approximately 100 amino acids that are responsible for the rod-like shape of many structural proteins including, but not limited to, dystrophin, utrophin, fodrin, alpha-actin, and spectrin, when the spectrin-like repeats are present in multiple copies (e.g. dystrophin-24, utrophin-22, alpha-actin-4, spectrin-16, etc). Spectrin-like repeats also refers to mutations of these natural peptides, such as conservative changes in amino acid sequence, as well as the addition or deletion of up to 5 amino acids to/from the end of a spectrin-like repeat. Spectrin-like repeats includes 'precise spectrin-like repeats' (see below). Examples of spectrin-like repeats include, but are not limited to, peptides encoded by nucleic acid sequences found in wild-type human dystrophin (e.g. SEQ ID NOS:8–10, 12–27, and 29–33).

As used herein, the term "spectrin-like repeat encoding sequences" refers to nucleic acid sequences encoding spectrin-like repeat peptides. This term includes natural and synthetic nucleic acid sequences encoding the spectrin-like repeats (e.g. both the naturally occurring and mutated spectrin-like repeat peptides). Examples of spectrin-like repeat encoding sequences include, but are not limited to, SEQ ID NOS:8–10, 12–27, and 29–33.

As used herein, the term "precise spectrin-like repeat encoding sequences" refers to nucleic acid sequences encoding spectrin-like repeat peptides with up to 1 additional amino acid added to, or deleted from, the spectrin-like repeat.

As used herein, the term "spectrin-like repeat domain" refers to the region in a mini-dystrophin peptide that contains the spectrin-like repeats of the mini-dystrophin peptide.

The term "gene" refers to a DNA sequence that comprises control and coding sequences necessary for the production of a polypeptide or precursor thereof. The polypeptide can be encoded by a full length coding sequence or by any portion of the coding sequence so long as the desired enzymatic activity is retained. The term "gene" encompasses both cDNA and genomic forms of a given gene.

The tern "wild-type" refers to a gene, gene product, or other sequence that has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene, gene product, or other sequence that displays modifications in sequence and or functional properties (e.g. altered characteristics) when compared to the wild-type gene or gene product. It is noted that naturally-occurring mutants can be isolated; these are identified by the fact that they have altered characteristics when compared to the wild-type gene or gene product.

The term "oligonucleotide" as used herein is defined as a molecule comprised of two or more deoxyribonucleotides or ribonucleotide, usually more than three (3), and typically more than ten (10) and up to one hundred (100) or more (although preferably between twenty and thirty). The exact size will depend on many factors, which in turn depends on the ultimate function or use of the oligonucleotide. The oligonucleotide may be generated in any manner, including chemical synthesis, DNA replication, reverse transcription, or a combination thereof.

As used herein, the term "regulatory sequence" refers to a genetic sequence or element that controls some aspect of the expression of nucleic acid sequences. For example, a promoter is a regulatory element that facilitates the initiation of transcription of an operably linked coding region. Other regulatory elements are enhancers, splicing signals, polyadenylation signals, termination signals, etc. Examples include, but are not limited to, the 5' UTR of the dystrophin gene (SEQ ID NO:5), MCK promoters and enhancers (both wild type and mutant, See U.S. provisional app. Ser No. 60/218,436, filed Jul. 14, 2000, and International Application PCT/US01/22092, filed Jul. 13, 2001, both of which are hereby incorporated by reference).

Transcriptional control signals in eucaryotes comprise "promoter" and "enhancer" elements. Promoters and enhancers consist of short arrays of DNA sequences that interact specifically with cellular proteins involved in transcription. The present invention contemplates modified enhancer regions.

The term "recombinant DNA vector" as used herein refers to DNA sequences containing a desired coding sequence and appropriate DNA sequences necessary for the expression of the operably linked coding sequence in a particular host organism (e.g., mammal). DNA sequences necessary for expression in procaryotes include a promoter, optionally an operator sequence, a ribosome binding site and possibly other sequences. Eukaryotic cells are known to utilize promoters, polyadenlyation signals and enhancers.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

"Hybridization" methods involve the annealing of a complementary sequence to the target nucleic acid (the sequence to be detected). The ability of two polymers of nucleic acid containing complementary sequences to find each other and anneal through base pairing interaction is a well-recognized phenomenon.

The "complement" of a nucleic acid sequence as used herein refers to an oligonucleotide which, when aligned with the nucleic acid sequence such that the 5' end of one sequence is paired with the 3' end of the other, is in "antiparallel association." Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

The term "homology" refers to a degree of complementarity. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (ie., selective) interaction. The absence of non-specific binding may be tested by the use of a second target that lacks even a partial degree of complementarity (e.g., less than about 30% identity); in the absence of non-specific binding the probe will not hybridize to the second non-complementary target.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85–100% identity, preferably about 70–100% identity). With medium stringency conditions, nucleic acid base pairing will occur between nucleic acids with an intermediate frequency of complementary base sequences (e.g., hybridization under "medium stringency" conditions may occur between homologs with about 50–70% identity). Thus, conditions of "weak" or "low" stringency are often required with nucleic acids that are derived from organisms that are genetically diverse, as the frequency of complementary sequences is usually less.

Low stringency conditions when used in reference to nucleic acid hybridization comprise conditions equivalent to binding or hybridization at 42° C. in a solution consisting of 5×SSPE (43.8 g/l NaCL, 6.9 g/l $NaH_2PO_4$—$H_2O$ and 1.85 g/l EDTA, pH adjusted to 7.4 with NaOH), 0.1% SDA, 5× Denhardt's reagent [50× Denhardt's contains per 500 ml: 5 g Ficoll (Type 400, Pharmacia), 5 g BSA (Fraction V, Sigma)] and 100 µg/ml denatured salmon sperm DNA followed by washing in solution comprising 5×SSPE, 0.1% SDS at 42° C. when a probe of about 500 nucleotides in length is employed.

High stringency conditions when used in reference to nucleic acid hybridization comprises conditions equivalent to binding or hybridizing at 42° C. in a solution consisting of 5×SSPE (43.8 g/l NaCL, 6.9 g/l $NaH_2PO_4$—$H_2O$ and 1.85 g/l EDTA, pH adjusted to 7.4 with NaOH), 0.5% SDS, 5× Denhardt's reagent and 100 µg/ml denatured salmon sperm DNA, followed by washing in a solution comprising 0.1×SSPE, 1.0% SDS at 42° C. when a probe of about 500 nucleotides is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell which has stably integrated foreign DNA into the genomic DNA.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "muscle cell" refers to a cell derived from muscle tissue, including, but not limited to, cells derived from skeletal muscle, smooth muscle (e.g. from the digestive tract, urinary bladder, and blood vessels), and cardiac muscle. The term includes muscle cells in vitro, ex vivo, and in vivo. Thus, for example, an isolated cardiomyocyte would constitute a muscle cell, as would a cell as it exists in muscle tissue present in a subject in vivo. This term also encompasses both terminally differentiated and nondifferentiated muscle cells, such as myocytes, myotubes, myoblasts, cardiomyocytes, and cardiomyoblasts.

As used herein, the term "muscle-specific" in reference to an regulatory element (e.g. enhancer region, promoter region) means that the transcriptional activity driven by these regions is mostly in muscle cells or tissue (e.g. 20:1) compared to the activity conferred by the regulatory sequences in other tissues. An assay to determine the muscle-specificity of a regulatory region is provided in Example 5 below (measuring beta-galactoside in muscle cells and liver cells from a mouse transfected with an expression vector).

As used herein, the term "mutant muscle-specific enhancer region" refers to a wild-type muscle-specific enhancer region that has been modified (e.g. deletion, insertion, addition, substitution), and in particular, has been modified to contain an additional MCK-R control element (See U.S. Prov. App. Ser. No. 60/218,436, hereby incorporated by reference, and section IV below).

DESCRIPTION OF THE INVENTION

The present invention provides compositions and methods for expressing mini-dystrophin peptides. In particular, the present invention provides compositions comprising nucleic acid sequences that are shorter than wild-type dystrophin cDNA and that express mini-dystrophin peptides that function in a similar manner as wild-type dystrophin proteins. The present invention also provides compositions comprising mini-dystrophin peptides, and methods for expressing mini-dystrophin peptides in target cells.

The present invention provides such shortened nucleic acid sequences (and resulting peptides) in a variety of ways. For example, the present invention provides nucleic acid encoding only 4, 8, 12, 16, and 20 spectrin-like repeat encoding sequences (i.e. nucleic acid encoding an exact number of spectrin-like repeats that are multiples of 4). As wild-type dystrophin has 24 spectrin-like repeat encoding sequences, providing nucleic acid encoding fewer numbers of repeats reduces the size of the dystrophin gene (e.g. allowing the nucleic acid sequence to fit into vectors with limited cloning capacity). Another example of such shortened nucleic acid sequences are those that lack at least a portion of the carboxy-terminal domain of wild-type dystrophin nucleic acid. A further example of such shortened nucleic acid sequences are those that lack at least a portion of the 3' untranslated region, or 5' untranslated region, or both.

I. Dystrophin

A. Dystrophin Structure

In some embodiments, the present invention provides gene constructs comprising spectrin-like repeats from human dystrophin. Dystrophin is a 427 kDa cytoskeletal protein and is a member of the spectrin/αactinin superfamily (See e.g., Blake et al., Brain Pathology, 6:37 [1996]; Winder, J. Muscle Res. Cell. Motil., 18:617 [1997]; and Tinsley el al., PNAS, 91:8307 [1994]). The N-terminus of dystrophin binds to actin, having a higher affinity for non-muscle actin than for sarcomeric actin. Dystrophin is involved in the submembraneous network of non-muscle actin underlying the plasma membrane. Dystrophin is associated with an oligomeric, membrane spanning complex of proteins and glycoproteins, the dystrophin-associated protein complex (DPC). The N-terminus of dystrophin has been shown in vitro to contain a functional actin-binding domain. The C-terminus of dystrophin binds to the cytoplasmic tail of β-dystroglycan, and in concert with actin, anchors dystrophin to the sarcolemma. Also bound to the C-terminus of dystrophin are the cytoplasmic members of the DPC. Dystrophin thereby provides a link between the actin-based cytoskeleton of the muscle fiber and the extracellular matrix. It is this link that is disrupted in muscular dystrophy.

The central rod domain of dystrophin is composed of a series of 24 weakly repeating units of approximately 110 amino acids, similar to those found in spectrin (i.e., spectrin-like repeats). This domain constitutes the majority of dystrophin and gives dystrophin a flexible rod-like structure. The rod-domain is interrupted by four hinge regions that are rich in proline. It is contemplated that the rod-domain provides a structural link between member of the DPC. Table 1 shows an overview of the structural and functional domains of human dystrophin.

TABLE 1

| Full Length Human Dystrophin cDNA | | |
|---|---|---|
| Nucleotides | Feature | SEQ ID NO: |
| 1–208 | 5' untranslated region | SEQ ID NO:5 |
| 209–211 | Start codon (ATG) | — |
| 209–964 | N terminus | SEQ ID NO:6 |
| 965–1219 | Hinge 1 | SEQ ID NO:7 |
| 1220–1546 | Spectrin-like repeat No. 1 | SEQ ID NO:8 |
| 1547–1879 | Spectrin-like repeat No. 2 | SEQ ID NO:9 |
| 1880–2212 | Spectrin-like repeat No. 3 | SEQ ID NO:10 |
| 2213–2359 | Hinge 2 | SEQ ID NO:11 |
| 2360–2692 | Spectrin-like repeat No. 4 | SEQ ID NO:12 |
| 2693–3019 | Spectrin-like repeat No. 5 | SEQ ID NO:13 |
| 3020–3346 | Spectrin-like repeat No. 6 | SEQ ID NO:14 |

TABLE 1-continued

Full Length Human Dystrophin cDNA

| Nucleotides | Feature | SEQ ID NO: |
|---|---|---|
| 3347–3673 | Spectrin-like repeat No. 7 | SEQ ID NO:15 |
| 3674–4000 | Spectrin-like repeat No. 8 | SEQ ID NO:16 |
| 4001–4312 | Spectrin-like repeat No. 9 | SEQ ID NO:17 |
| 4313–4588 | Spectrin-like repeat No. 10 | SEQ ID NO:18 |
| 4589–4915 | Spectrin-like repeat No. 11 | SEQ ID NO:19 |
| 4916–5239 | Spectrin-like repeat No. 12 | SEQ ID NO:20 |
| 5340–5551 | Spectrin-like repeat No. 13 | SEQ ID NO:21 |
| 5552–5833 | Spectrin-like repeat No. 14 | SEQ ID NO:22 |
| 5834–6127 | Spectrin-like repeat No. 15 | SEQ ID NO:23 |
| 6128–6187 | 20 amino acid insert (not hinge) | — |
| 6188–6514 | Spectrin-like repeat No. 16 | SEQ ID NO:24 |
| 6515–6835 | Spectrin-like repeat No. 17 | SEQ ID NO:25 |
| 6836–7186 | Spectrin-like repeat No. 18 | SEQ ID NO:26 |
| 7187–7489 | Spectrin-like repeat No. 19 | SEQ ID NO:27 |
| 7490–7612 | Hinge 3 | SEQ ID NO:28 |
| 7613–7942 | Spectrin-like repeat No. 20 | SEQ ID NO:29 |
| 7943–8269 | Spectrin-like repeat No. 21 | SEQ ID NO:30 |
| 8270–8617 | Spectrin-like repeat No. 22 | SEQ ID NO:31 |
| 8618–9004 | Spectrin-like repeat No. 23 | SEQ ID NO:32 |
| 9005–9328 | Spectrin-like repeat No. 24 | SEQ ID NO:33 |
| 9329–9544 | Hinge 4 | SEQ ID NO:34 |
| 9545–10431 | Start of C terminus | SEQ ID NO:35 |
| 10432–11254 | Alternatively spliced exons 71–78 | SEQ ID NO:36 |
| 11255–11266 | End of Coding Region | SEQ ID NO:37 |
| 11267–13957 | 3' untranslated region | SEQ ID NO:38 |

*Domain structure based on Winder et al., Febs Letters, 369:27–33 (1995)

B. Spectrin-Like Repeats

Spectrin-like repeats are about 100 amino acids long and are found in a number of proteins, including the actin binding proteins spectrin, fodrin, α-actinin, and dystrophin, but their function remains unclear (Dhermy, 1991. Biol. Cell, 71:249–254). These domains may be involved in connecting functional domains and/or mediate protein-protein interactions. The many tandem, spectrin-like motifs that comprise most of the mass of the proteins in this superfamily are responsible for their similar flexible, rod-like molecular shapes. Although these homologous motifs are frequently called repeats or repetitive segments, adjacent segments in each protein are only distantly related evolutionarily.

Spectrin is a cytoskeletal protein of red blood cells that is associated with the cytoplasmic side of the lipid bilayer (See e.g., Speicher and Ursitti, Current Biology, 4:154 [1994]). Spectrin is a long-thin flexible rod-shaped protein that constitutes about 25% of the membrane-associated protein mass. Spectrin is composed of two large polypeptide chains, α-spectrin (~240 kDa) and β-spectrin (~220 kDa) and serves to cross-link short actin oligomers to form a dynamic two-dimensional submembrane latticework. Spectrin isoforms have been found in numerous cell types and have been implicated in a variety of functions.

The recent determination of the crystal structure of a single domain of spectrin provides insight into the structure function of an entire class of large actin cross-linking proteins (Yan et al., Science, 262:2027 [1993]). The domain is an example of a spectrin-like repeat. Early analysis of spectrin-like repeats by partial peptide sequence analysis demonstrated that most of the antiparallel spectrin heterodimer is made up of homologous 106 residue motifs. Subsequent sequence analyses of cDNAs confirmed that this small motif is the major building block for all spectrin isoforms, as well as for the related actinins and dystrophins (Matsudaira, Trends Biochem Sci, 16:87 [1991]).

Given their similar sequences, all spectrin motifs are expected to have related, but not identical, three-dimensional structures. The structure of a single Drosophila spectrin motif, 14, which has now been determined (Yan et al., Science, 262:2027 [1993]), should therefore provide insight into the overall conformation of spectrins in particular and, to a more limited extent, the other members of the spectrin superfamily. The structure shows that the spectrin motif forms a three-helix bundle, similar to the earliest conformational prediction based on the analysis of multiple homologous motifs (Speicher and Marchesi, Nature, 311:177 [1984]).

II. Variants and Homologs of Dystrophin

The present invention is not limited to the spectrin-like repeat encoding sequences SEQ ID NOS:8–10, 12–27, and 29–33, but specifically includes nucleic acid sequences capable of hybridizing to the spectrin-like repeat encoding sequences SEQ ID NOS:8–10, 12–27, and 29–33, (e.g. capable of hybridizing under high stringent conditions). Those skilled in the art know that different hybridization stringencies may be desirable. For example, whereas higher stringencies may be preferred to reduce or eliminate non-specific binding between the spectrin-like repeat encoding sequences SEQ ID NOS:8–10, 12–27, and 29–33, and other nucleic acid sequences, lower stringencies may be preferred to detect a larger number of nucleic acid sequences having different homologies to the nucleotide sequence of SEQ ID NOS:8–10, 12–27, and 29–33.

Accordingly, in some embodiments, the dystrophin spectrin-like repeats of the compositions of the present invention (e.g., SEQ ID NOs:8–10, 12–27, and 29–33) are replaced with different spectrin-like repeats, including, but not limited to, variants, homologs, truncations, and additions of dystrophin spectrin-like repeats. Candidate spectrin-like repeats are screened for activity using any suitable assay, including, but not limited to, those described below and in illustrative Examples 1 and 5.

A. Homologs

1. Dystrophin From other Species

In some embodiments, the spectrin-like repeats of the gene constructs of the present invention are replaced with spectrin-like repeats of dystrophin from other species (e.g., homologs of dystrophin), including, but not limited to, those described herein. Homologs of dystrophin have been identified in a variety of organisms, including mouse (Genbank accession number M68859); dog (Genbank accession number AF070485); and chicken (Genbank accession number X13369). The spectrin-like repeats of the mouse dystrophin gene were compared to the human gene (See FIG. 11) and were shown to have significant homology. Similar comparisons can be generated with homologs from other species, including but not limited to, those described above, by using a variety of available computer programs (e.g., BLAST, from NCBI). Candidate homologs can be screened for biological activity using any suitable assay, including, but not limited to, those described herein.

2. Utrophin

Figure 38:
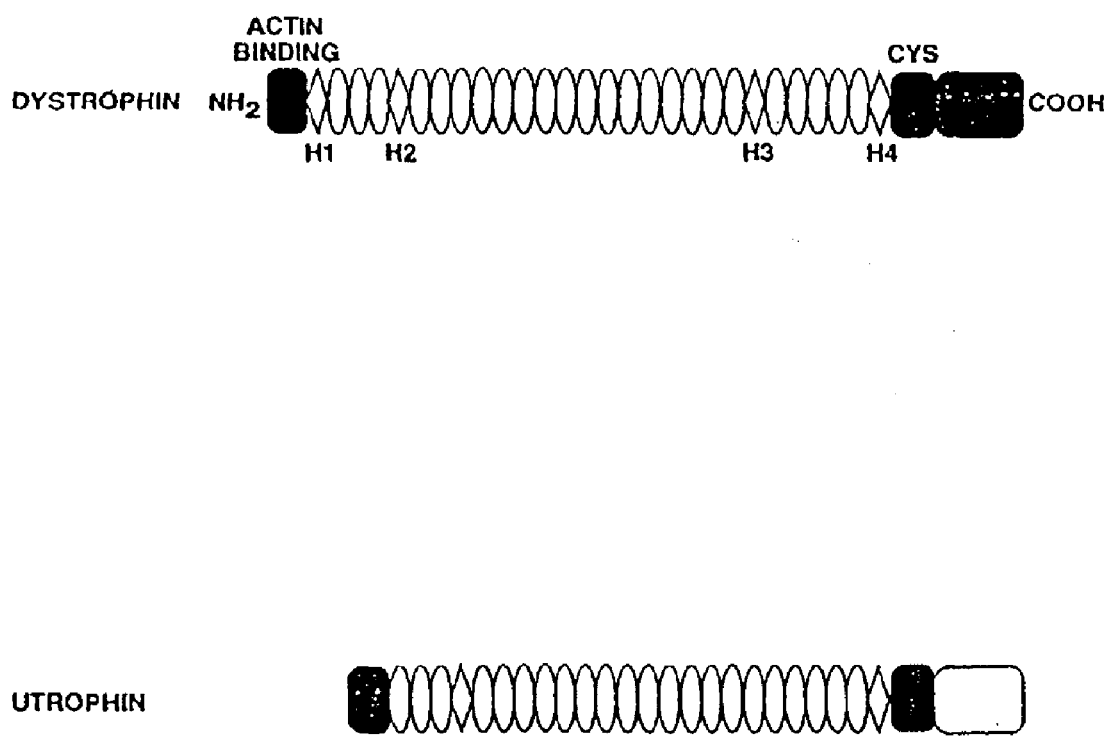
FIG. 38 shows a comparison between domains in dystrophin and utrophin.

In some embodiments, the spectrin-like repeats of the gene constructs of the present invention are replaced with spectrin-like repeats from another peptide (e.g., homologs of dystrophin). For example, in some embodiments, spectrin-like repeats from the utrophin protein (See e.g., Genbank accession number X69086; SEQ ID NO:3; FIG. 3) are utilized. Utrophin is an autosomally-encoded homolog of dystrophin and has been postulated that the proteins play a similar physiological role (For a recent review, See e.g., Blake et al., Brain Pathology, 6:37 [1996]). Human utrophin shows substantial homology to dystrophin, with the major difference occurring in the rod domain, where utrophin lacks repeats 15 and 19 and two hinge regions (See e.g., Love et al., Nature 339:55 [1989]; Winder et al., FEBS Lett., 369:27 [1995]). Utrophin thus contains 22 spectrin-like repeats and two hinge regions. A comparison of the rod domain of Utrophin and Dystrophin is shown in FIG. 38.

In addition, in some embodiments, spectrin-like repeats from a homolog of utrophin are utilized. Homologs of utrophin have been identified in a variety of organisms, including mouse (Genbank accession number Y12229; SEQ ID NO:4; FIG. 4) and rat (Genbank accession number AJ002967). The nucleic acid sequence of these or additional homologs can be compared to the nucleic acid sequence of human utrophin using any suitable methods, including, but not limited to, those described above. Candidate spectrin-like repeats from human utrophin or utrophin homologs can be screened for biological activity using any suitable assay, including, but not limited to, those described herein.

3. Alpha-actinin

In some embodiments, spectrin-like repeats from Dystrophin are replaced with spectrin-like repeats from alpha-actinin. The microfilament protein alpha-actinin exists as a dimer. The N-terminal regions of both polypeptides, arranged in antiparallel orientation, comprise the actin-binding regions, while the C-terminal, larger parts consist of four spectrin-like repeats that interact to form a rod-like structure (See e.g., Winkler et al., Eur. J. Biochem., 248:193 [1997]). In some embodiments, human alpha-actinin spectrin-like repeats are utilized (Genbank accession number M86406; SEQ ID NO:87; FIG. 16). In other embodiments, alpha-actinin homologs from other organisms are utilized (e.g., mouse (Genbank accession number AJ289242); Xenopus (Genbank accession number BE576799); and rat (Genbank accession number AF190909).

B. Variants

Still other embodiments of the present invention provide mutant or variant forms of spectrin-like repeats (ie., muteins). It is possible to modify the structure of a peptide having an activity of spectrin-like repeats for such purposes as enhancing therapeutic or prophylactic efficacy, or stability (e.g., ex vivo shelf life, and/or resistance to proteolytic degradation in vivo). Such modified peptides provide additional peptides having a desired activity of the subject spectrin-like repeats as defined herein. A modified peptide can be produced in which the amino acid sequence has been altered, such as by amino acid substitution, deletion, or addition.

Moreover, as described above, variant forms (e.g., mutants) of the subject spectrin-like repeats are also contemplated as finding use in the present invention. For example, it is contemplated that an isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of spectrin-like repeats containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (See e.g., Stryer (ed.), *Biochemistry*, 2nd ed, W H Freeman and Co. [1981]). Whether a change in the amino acid sequence of a peptide results in a functional homolog can be readily determined by assessing the ability of the variant peptide to function in a fashion similar to the wild-type protein. Peptides in which more than one replacement has taken place can readily be tested in the same manner.

The present invention further contemplates a method of generating sets of combinatorial mutants of the present spectrin-like repeats, as well as truncation mutants, and is especially useful for identifying potential variant sequences (i.e., homologs) that possess the biological activity of spectrin-like repeats (e.g., a decrease in muscle necrosis). In addition, screening such combinatorial libraries is used to generate, for example, novel spectrin-like repeat homologs that possess novel biological activities all together.

Therefore, in some embodiments of the present invention, spectrin-like repeat homologs are engineered by the present method to produce homologs with enhanced biological activity. In other embodiments of the present invention, combinatorially-derived homologs are generated which provide spectrin-like repeats that are easier to express and transfer to host cells. Such spectrin-like repeats, when expressed from recombinant DNA constructs, can be used in therapeutic embodiments of the invention described below.

Still other embodiments of the present invention provide spectrin-like repeat homologs which have intracellular half-lives dramatically different than the corresponding wild-type protein. For example, the altered proteins comprising the spectrin-like repeat homologs are rendered either more stable or less stable to proteolytic degradation or other cellular process that result in destruction of, or otherwise inactivate spectrin-like repeats. Such homologs, and the genes that encode them, can be utilized to alter the pharmaceutical activity of constructs expressing spectrin-like repeats by modulating the half-life of the protein. For instance, a short half-life can give rise to more transient biological effects. As above, such proteins find use in pharmaceutical applications of the present invention.

In some embodiments of the combinatorial mutagenesis approach of the present invention, the amino acid sequences for a population of spectrin-like repeat homologs are aligned, preferably to promote the highest homology possible. Such a population of variants can include, for example, spectrin-like repeat homologs from one or more species, or spectrin-like repeat homologs from different proteins of the same species (e.g., including, but not limited to, those described above). Amino acids that appear at each position of the aligned sequences are selected to create a degenerate set of combinatorial sequences.

In a preferred embodiment of the present invention, the combinatorial spectrin-like repeat library is produced by way of a degenerate library of genes encoding a library of polypeptides that each include at least a portion of candidate spectrin-like repeat sequences. For example, a mixture of synthetic oligonucleotides is enzymatically ligated into gene sequences such that the degenerate set of candidate spectrin-like repeat sequences are expressible as individual polypeptides, or alternatively, as a set of larger fusion proteins (e.g., for phage display) containing the set of spectrin-like repeat sequences therein.

There are many ways by which the library of potential spectrin-like repeat homologs can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential spectrin-like repeat sequences. The synthesis of degenerate oligonucleotides is well known in the art (See e.g., Narang, Tetrahedron Lett., 39:3 9 [1983]; Itakura el al., Recombinant DNA, in Walton (ed.), *Proceedings of the 3rd Cleveland Symposium on Macromolecules*, Elsevier, Amsterdam, pp 273–289 [1981]; Itakura et al., Annu. Rev. Biochem., 53:323 [1984]; Itakura et al., Science 198:1056 [1984]; Ike et al. Nucl. Acid Res., 11:477 [1983]). Such techniques have been employed in the directed evolution of other proteins (See e.g., Scott et al., Science, 249:386–390 [1980]; Roberts et al., Proc. Natl. Acad. Sci. USA, 89:2429–2433 [1992]; Devlin et al., Science, 249: 404–406 [1990]; Cwirla et al., Proc. Natl. Acad. Sci. USA, 87: 6378–6382 [1990]; as well as U.S. Pat. Nos. 5,223,409, 5,198,346, and 5,096,815, each of which is incorporated herein by reference).

A wide range of techniques are known in the art for screening gene products of combinatorial libraries made by point mutations, and for screening cDNA libraries for gene products having a certain property. Such techniques are generally adaptable for rapid screening of the gene libraries generated by the combinatorial mutagenesis of spectrin-like repeat homologs. The most widely used techniques for screening large gene libraries typically comprise cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

Accordingly, in one embodiment of the present invention, the candidate genes comprising altered spectrin-like repeats are displayed on the surface of a cell or viral particle, and the ability of particular cells or viral particles to bind to a another member of the DPC complex (e.g., actin) is assayed. In other embodiments of the present invention, the gene library is cloned into the gene for a surface membrane protein of a bacterial cell, and the resulting fusion protein detected by panning (WO 88/06630; Fuchs et al., BioTechnol., 9:1370 [1991]; and Goward et al., TIBS 18:136 [1992]). In other embodiments of the present invention, fluorescently labeled molecules that bind proteins comprising spectrin like repeats (e.g., actin), can be used to score for potentially functional spectrin-like repeat homologs. Cells are visually inspected and separated under a fluorescence microscope, or, where the morphology of the cell permits, separated by a fluorescence-activated cell sorter.

In an alternate embodiment of the present invention, the gene library is expressed as a fusion protein on the surface of a viral particle. For example, foreign peptide sequences are expressed on the surface of infectious phage in the filamentous phage system, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical *E. coli* filamentous phages M13, fd, and fl are most often used in phage display libraries, as either of the phage gIII or gVIII coat proteins can be used to generate fusion proteins without disrupting the ultimate packaging of the viral particle (See e.g., WO 90/02909; WO 92/09690; Marks et al., J. Biol. Chem., 267:16007 [1992]; Griffths et al., EMBO J., 12:725 [1993]; Clackson et al., Nature, 352:624 [1991]; and Barbas et al., Proc. Natl. Acad. Sci., 89:4457 [1992]).

In another embodiment of the present invention, the recombinant phage antibody system (e.g., RPAS, Pharmacia Catalog number 27-9400-01) is modified for use in expressing and screening of spectrin-like repeat combinatorial libraries. The pCANTAB 5 phagemid of the RPAS kit contains the gene that encodes the phage gIII coat protein. In some embodiments of the present invention, the spectrin-like repeat combinatorial gene library is cloned into the phagemid adjacent to the gIII signal sequence such that it is expressed as a gIII fusion protein. In other embodiments of the present invention, the phagemid is used to transform competent *E. coli* TG1 cells after ligation. In still other embodiments of the present invention, transformed cells are subsequently infected with M13KO7 helper phage to rescue the phagemid and its candidate spectrin-like repeat gene insert. The resulting recombinant phage contain phagemid DNA encoding a specific candidate spectrin-like repeat and display one or more copies of the corresponding fusion coat protein. In some embodiments of the present invention, the phage-displayed candidate proteins that are capable of, for example, binding to actin, are selected or enriched by panning. The bound phage is then isolated, and if the recombinant phage express at least one copy of the wild type gIII coat protein, they will retain their ability to infect *E. coli*. Thus, successive rounds of reinfection of *E. coli* and panning will greatly enrich for spectrin-like repeat homologs, which can then be screened for further biological activities.

In light of the present disclosure, other forms of mutagenesis generally applicable will be apparent to those skilled in the art in addition to the aforementioned rational mutagenesis based on conserved versus non-conserved residues. For example, spectrin-like repeat homologs can be generated and screened using, for example, alanine scanning mutagenesis and the like (Ruf et al., Biochem., 33:1565 [1994]; Wang et al., J. Biol. Chem., 269:3095 [1994]; Balint et al. Gene 137:109 [1993]; Grodberg et al., Eur. J. Biochem., 218:597 [1993]; Nagashima et al., J. Biol. Chem., 268:2888 [1993]; Lowman et al., Biochem., 30:10832 [1991]; and Cunningham et al., Science, 244:1081 [1989]), by linker scanning mutagenesis (Gustin et al., Virol., 193:653 [1993]; Brown et al., Mol. Cell. Biol., 12:2644 [1992]; McKnight et al., Science, 232:316); or by saturation mutagenesis (Meyers et al., Science, 232:613 [1986]).

C. Truncations and Additions

In yet other embodiments of the present invention, the spectrin-like repeats of human dystrophin are replaced by truncation or additions of spectrin-like repeats from dystrophin or another protein, including, but not limited to, those described above. Accordingly, in some embodiments, amino acids are truncated from either end of one or more of the spectrin-like repeats in a given construct. The activity of truncation mutants is determined using any suitable assay, including, but not limited to, those disclosed herein.

In some embodiments, additional amino acids are added to either or both ends of the spectrin-like repeats in a given construct. In some embodiments, single amino acids are added and the activity of the construct is determined. Amino acids may be added to one or more of the spectrin-like repeats in a given construct. The activity of spectrin-like repeats comprising additional amino acids is determined using any suitable assay, including, but not limited to, those disclosed herein.

III. Carboxy-Terminal Domain Truncated Dystrophin Genes

In some embodiments, the present invention provides compositions comprising nucleic acid, wherein the nucleic acid encodes a mini-dystrophin peptide, and wherein the mini-dystrophin peptide comprises a substantially deleted dystrophin C-terminal domain (e.g., 55% of the dystrophin C-terminal domain is missing). In some embodiments, this type of truncation prevents the mini-dystrophin peptide from binding both syntrophin and dystrobrevin.

The dystrophin COOH-terminal domain is located adjacent to the cysteine-rich domain, and contains an alternatively spliced region and two coiled-coil motifs (Blake et al., *Trends Biochem. Sci.*, 20:133, 1995). The alternatively spliced region binds three isoforms of syntrophin in muscle, while the coiled-coil motifs bind numerous members of the dystrobrevin family (Sadoulet-Puccio et al., *PNAS*, 94:12413, 1997). The dystrobrevins display significant homology with the COOH-terminal region of dystrophin, and the larger dystrobrevin isoforms also bind to the syntrophins. The importance and functional significance of syntrophin and dystrobrevin remains largely unknown, although they may be involved in cell signaling pathways (Grady et al., *Nat. Cell. Biol*, 1:215, 1999).

Researchers have previously generated transgenic mdx mouse strains expressing dystrophins deleted for either the syntrophin or the dystrobrevin binding domain (Rafael et al., *Hum. Mol. Genet.*, 3:1725, 1994; and Rafael et al., *J. Cell Biol.*, 134:93 1996). These mice displayed normal muscle function and essentially normal localization of syntrophin, dystrobrevin, and nNOS. Thus, while dystrobrevin appears to protect muscle from damage (Grady et al., *Nat. Cell. Biol*, 1:215, 1999), removal of the dystrobrevin binding site from dystrophin does not result in a dystrophy. Subsequent studies revealed that syntrophin and dystrobrevin bind each other in addition to dystrophin, so that removal of only one of the two binding sites on dystrophin might not sever the link between dystrophin, syntrophin and dystrobrevin. Surprisingly, the transgenic mice according to the present invention (See Example 1) displayed normal muscle function even though they lacked both the syntrophin and dystrobrevin binding sites.

IV. MCK Regulatory Regions

In certain embodiments, nucleic acid encoding mini-dystrophin peptides of the present invention are operably linked to muscle creatine kinase gene (MCK) regulatory regions and control elements, as well as mutated from of these regions and elements (see See U.S. Provisional App. Ser No. 60/218,436, filed Jul. 14, 2000, and International Application PCT/US01/22092, filed Jul. 13, 2001, both of which are hereby incorporated by reference). In some embodiments, the nucleic acid encoding mini-dystrophin peptides is operably linked to these sequences to provide muscle specificity and reduced size such that the resulting construct is able to fit into, for example, a viral vector (e.g. adeno-associated virus). MCK gene regulatory regions (e.g. promoters and enhancers) display striated muscle-specific activity and have been characterized in vitro and in vivo. The major known regulatory regions in the mouse MCK gene include a 206 base pair muscle-specific enhancer located approximately 1.1 kb 5' of the transcription start site in mouse (i.e. SEQ ID NO:87) and a 358 base pair proximal promoter (i.e. SEQ ID NO:93) [Shield, et al., *Mol. Cell. Biol.*, 16:5058 (1996)]. A larger MCK promoter region may also be employed (e.g. SEQ ID NO:92), as well as smaller MCK promoter regions (e.g. SEQ ID NO:94).

The 206 base pair MCK enhancer (SEQ ID NO:87) contains a number of sequence motifs, including two classes of E-boxes (MCK-L and MCK-R), CarG, and AT-rich sites. Similar E-box sequences are found in the enhancers of the human, rat, and rabbit MCK genes [See, Trask, et al., *Nucleic Acids Res.*, 20:2313 (1992)]. Mutation may be made to this sequence by, for example, inserting an additional MCK-R control element into a wild-type enhancer sequence naturally containing one MCK-R control element (such that the resulting sequence has at least two MCK-R control elements). For example, the inserted MCK-R control element replaces the endogenous MCK-L control element. The 206 base pair mouse enhancer (SEQ ID NO:2) may be modified by replacing the left E-box (MCK-L) with a right E-Box (MCK-R) to generate a mutant muscle-specific enhancer region (e.g. to generate SEQ ID NO:88). A similar approximately 200 base pair wild type enhancer region in human may be modified by replacing the left E-box with a MCK-R to generate a mutant muscle-specific enhancer region (e.g. 2R human enhancer regions).

Another modification that may be made to generate mutant muscle-specific enhancer regions by inserting the S5 sequence GAGCGGTTA (SEQ ID NO:95) into wild type mouse, human, and rat enhancer sequence. Making such a modification to the mouse enhancer SEQ ID NO:87, for example, generates S5 mutant muscle-specific enhancer regions (e.g. SEQ ID NO:89). Another modification that may be made, for example, to the wild type mouse enhancer is replacing the left E-box (MCK-L) with a right E-Box (MCK-R), and also inserting the 5S sequence, to generate 2R5S type sequences (e.g in mouse, SEQ ID NO:90). These mutant muscle-specific enhancer regions may have additional sequences added to them or sequences that are taken away. For example, the mutant muscle-specific enhancer regions may have a portion of the sequence removed (e.g. the 3' 41 base pairs). Examples of such mutant truncation 2RS5 sequences in mouse is SEQ ID NO:91 with the 3' 41 base pairs removed, generating mutant truncated 2RS5 muscle-specific enhancer regions.

Any of these wild-type or mutant muscle-specific enhancer regions described above may be further modified to produce additional mutants. These additional mutants include, but are not limited to, muscle-specific enhancer regions having deletions, insertions or substitutions of different nucleotides or nucleotide analogs so long as the transcriptional activity of the enhancer region is maintained. Guidance in determining which and how many nucleotide bases may be substituted, inserted or deleted without abolishing the transcriptional activity may be found using computer programs well known in the art, for example, DNAStar software or GCG (Univ. of Wisconsin) or may be determined empirically using assays provided by the present invention.

V. Expression Vectors

The present invention contemplates the use of expression vectors with the compositions and methods of the present invention (e.g. with the nucleic acid constructs encoding the mini-dystrophin peptides). Vectors suitable for use with the methods and compositions of the present invention, for example, should be able to adequately package and carry the compositions and cassettes described herein. A number of suitable vectors are known in the art including, but are not limited to, the following: 1) Adenoviral Vectors; 2) Second Generation Adenoviral Vectors; 3) Gutted Adenoviral Vectors; 4) Adeno-Associated Virus Vectors; and 5) Lentiviral Vectors.

Those skilled in the art will recognize and appreciate that other vectors are suitable for use with methods and compositions of the present invention. Indeed, the present invention is not intended to be limited to the use of the recited vectors, as such, alternative means for delivering the compositions of the present invention are contemplated. For example, in various embodiments, the compositions of the present invention are associated with retrovirus vectors and herpes virus vectors, plasmids, cosmids, artificial yeast chromosomes, mechanical, electrical, and chemical transfection methods, and the like. Exemplary delivery approaches are discussed below.

1. Adenoviral Vectors

Self-propagating adenovirus (Ad) vectors have been extensively utilized to deliver foreign genes to a great variety of cell types in vitro and in vivo. "Self-propagating viruses" are those which can be produced by transfection of a single piece of DNA (the recombinant viral genome) into a single packaging cell line to produce infectious virus; self-propagating viruses do not require the use of helper virus for propagation. As with many vectors, adenoviral vectors have limitations on the amount of heterologous nucleic acid they are capable of delivering to cells. For example, the capacity of adenovirus is approximately 8–10 kb, the capacity of adeno-associated virus is approximately 4.8 kb, and the capacity of lentivirus is approximately 8.9 kb. Thus, the mutants of the present invention that provide shorter nucleic acid sequences encoding the mini-dystrophin peptides (compared to full length wild-type dystrophin (14 kb)), improve the carrying capacity of such vectors.

2. Second Generation Adenoviral Vectors

In an effort to address the viral replication problems associated with first generation Ad vectors, so called "second generation" Ad vectors have been developed. Second generation Ad vectors delete the early regions of the Ad genome (E2A, E2B, and E4). Highly modified second generation Ad vectors are less likely to generate replication-competent virus during large-scale vector preparation, and complete inhabitation of Ad genome replication should abolish late gene replication. Host immune response against late viral proteins is thus reduced [See Amalfitano et al., "Production and Characterization of Improved Adenovirus Vectors With the E1, E2b, and E3 Genes Deleted," J. Virol. 72:926–933 (1998)]. The elimination of E2A, E2B, and E4 genes from the Ad genome also provide increased cloning capacity. The deletion of two or more of these genes from the Ad genome allows for example, the delivery of full length or cDNA dystrophin genes via Ad vectors [Kumar-Singh et al, *Hum. Mol. Genet.*, 5:913 (1996)].

3. Gutted Adenoviral Vectors

"Gutted," or helper dependent, Ad vectors contain cis-acting DNA sequences that direct adenoviral replication and packaging but do not contain viral coding sequences [See Fisher et al. "Recombinant Adenovirus Deleted of All Viral Genes for Gene Therapy of Cystic Fibrosis," *Virology* 217:11–22 (1996) and Kochanek et al. "A New Adenoviral Vector: Replacement of All Viral Coding Sequences With 28 kb of DNA Independently Expressing Both Full-length Dystrophin and Beta-galactosidase'" *Proc. Nat. Acad. Sci. USA* 93:5731–5736 (1996)]. Gutted vectors are defective viruses produced by replication in the presence of a helper virus, which provides all of the necessary viral proteins in trans. Since gutted vectors do not contain any viral genes, expression of viral proteins is not possible.

Recent developments have advanced the field of gutted vector production [See Hardy et al., "Construction of Adenovirus Vectors Through Cre-lox Recombination," J. Virol. 71:1842–1849 (1997) and Hartigan-O'Conner et al., "Improved Production of Gutted Adenovirus in Cells Expressing Adenovirus Preterminal Protein and DNA Polymerase," *J. Virol.* 73:7835–7841 (1999)]. Gutted Ad vectors are able to maximally accommodate up to about 37 kb of exogenous DNA, however, 28–30 kb is more typical. For example, a gutted Ad vector can accommodate the full length dystrophin or cDNA, but also expression cassettes or modulator proteins.

4. Adeno-Associated Virus Vectors

In preferred embodiments, the nucleic acid encoding the mini-dystrophin peptides of the present invention are inserted in adeno-associated vectors (AAV vectors). AAV vectors evade a host's immune response and achieve persistent gene expression through avoidance of the antigenic presentation by the host's professional APCs such as dendritic cells. Most AAV genomes in muscle tissue are present in the form of large circular multimers. AAV's are only able to carry about 5 kb of exogenous DNA. As such, the nucleic acid of the present invention encoding the mini-dystrophin peptides is well suited, in some embodiments, for insertion into these vectors due the reduced size of the nucleic acid sequences.

The dystrophin expression cassettes of the present invention (containing nucleic acid encoding mini-dystrophin peptides) may be cloned into any of a variety of cis-acting plasmid vectors that contain the adeno-associated virus inverted terminal repeats (ITRs) to allow production of infectious virus. For example, one such plasmid is the cis-acting plasmid (pCisAV) (Yan et al., *PNAS*, 97:6716–6721, 2000). This plasmid contains the AAV-ITRs separated by a NotI cloning site. The ITR elements were derived from pSub201, a recombinant plasmid from which an infectious adeno-associated virus genome can be excised in vitro and used to study viral replication. After ligation of the dystrophin expression cassette (isolated as a NotI fragment from pCK6DysR4–23–71–78An) into NotI-digested pCisAV, rAAV stocks are generated by cotransfection of pCisAV. CK6DysR4–23–71–78An and pRep/Cap (Fisher, et al., *J. Virol.* 70:520–532, 1996) together with coinfection of the recombinant adenovirus Ad.CMVlacZ into 293 cells. Recombinant AAV vector, for example, may then be purified on CsCl gradients as described (Duan, et al., *Virus Res.* 48:41–56, 1997).

5. Lentiviral Vectors

Vectors based on human or feline lentiviruses have emerged as another vector useful for gene therapy applications. Lentivirus-based vectors infect nondividing cells as part of their normal life cycles, and are produced by expression of a package-able vector construct in a cell line that expresses viral proteins. The small size of lentiviral particles constrains the amount of exogenous DNA they are able to carry to about 10 kb. However, once again, the small size nucleic acid encoding the mini-dystrophin peptides of the present invention allow such vectors to be employed.

6. Retroviruses

Vectors based on Moloney murine leukemia viruses (MMLV) and other retroviruses have emerged as useful for gene therapy applications. These vectors stably transduce actively dividing cells as part of their normal life cycles, and integrate into host cell chromosomes. Retroviruses may be employed with the compositions of the present invention (e.g. gene therapy), for example, in the context of infection and transduction of muscle precursor cells such as myoblasts, satellite cells, or other muscle stem cells.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); µM (micromolar); mol (moles); mmol (millimoles); µmol (micromoles); nmol (nanomoles); pmol (picomoles); g (grams); mg (milligrams); µg (micrograms); ng (nanograms); l or L (liters); ml (milliliters); µl (microliters); cm (centimeters); mm (millimeters); µm (micrometers); nm (nanometers); ° C. (degrees Centigrade); and Sigma (Sigma Chemical Co., St. Louis, Mo.).

EXAMPLE 1

Carboxy-Terminal Domain Truncated Dystrophin Genes

This example describes the generation of carboxy-terminal truncated dystrophin nucleic acid sequences. In particular, this examples describes the construction of dystrophin nucleic acid sequence with the entire carboxy-terminal domain deleted, and testing of this sequence in a mouse model for DMD.

A. Methods

The bases encoding amino acids 3402–3675 (corresponding to exons 71–78) were deleted from the full length murine dystrophin cDNA (SEQ ID NO:2, accession No. M68859) by recombinant PCR, leaving the last three amino acids (exon 79) of the dystrophin protein unaltered. This dystrophin Δ71–78 cDNA was cloned into an expression vector containing bases −2139 to +239 of the human-skeletal actin (HSA) promoter (Brennan, et al. *J. Biol. Chem.* 268:719, 1993). A splice acceptor from the SV40 VP1 intron (isolated as a 400 bp HindIII/XbaI fragment from pSVL; Amersham Pharmacia Biotech) was inserted immediately 3' of the HSA fragment, and the SV40 polyadenylation signal (isolated as a BamHI fragment from pCMVβ; MacGregor and Caskey, Nuc. Acid. Res., 17:2365, 1989) was inserted 3' of the dystrophin cDNA. The excised dystrophin Δ71–78 expression cassette was injected into wild-type C57Bl/10× SJL/J F2 hybrid embryos, and $F_o$ mice were screened by PCR. Five positive $F_o$'s were backcrossed onto the C57Bl/10mdx background, and the line with the most uniform expression levels was selected for analysis. Also employed were previously described transgenic mdx mice that express dystrophin constructs deleted approximately for exons 71–74 (Δ71–74) or exons 75–78 (Δ75–78), which remove amino acids 3402–3511 and 3528–3675, respectively, See Rafael et al., *J. Cell Biol.*, 134:93–102, 1996). Transgenic mdx line Dp71 expresses the Dp71 isoform of dystrophin in striated muscle (Cox et al., *Nat. Genet.*, 8:333–339, 1994).

i. Morphology Methods

Quadriceps, soleus, extensor digitorum longus (EDL), tibialis anterior, and diaphragm muscles were removed from the mice, frozen in liquid nitrogen cooled O.C.T. embedding medium (Tissue-Tek), and cut into 7-µm sections. After fixing in 3.7% formaldehyde, sections were stained in hematoxylin and eosin-phloxine. Stained sections were imaged with a Nikon E1000 microscope connected to a Spot-2 CCD camera. To determine the percentage of fibers containing central nuclei, the number of muscle fibers with centrally-located nuclei was divided by the total number of muscle fibers.

ii. Evans Blue Assays 4 month old control mice and Δ71–78 mice were analyzed after injection with Evans blue, as described previously (Straub et al., *J. Cell. Biol.*, 139:375–385, 1997). In brief, mice were tail vein-injected with 150 µl of a solution containing 10 mg/ml Evans blue dye in PBS (150 mM NaCl, 50 mM Tris, pH 7.4). After 3 hours, the animals were euthanized and mouse tissues were either fixed in 3.7% formaldehyde/0.5% glutaraldehyde to observe gross dye uptake, or frozen unfixed in O.C.T. embedding medium. To examine Evans blue uptake by individual fibers, 7-µm-thick frozen sections were fixed in cold acetone and analyzed by fluorescence microscopy.

iii. Immunofluorescence Assays

Quadriceps and diaphragm muscles from C57Bl/10, mdx, and Δ71–78 mice were removed, frozen in O.C.T. embedding medium, and cut into 7-µm sections. Immunofluorescence was performed with previously described antibodies against dystrophin ($NH_2$ terminus), α1-syntrophin (SYN17), β1-syntrophin, α-dystrobrevin-1 (DB670), α-dystrobrevin-2 (DB2), and utrophin. After incubation with primary antibodies, cryosections were incubated with an FITC-conjugated goat anti-rabbit secondary antibody and fluorescent images were viewed on a Nikon E1000 microscope. Antibodies to α-sarcoglycan (Rabbit 98), β-sarcoglycan (Goat 26), γ-sarcoglycan (Rabbit 245), δ-sarcoglycan (Rabbit 215), sarcospan (Rabbit 235), α-dystroglycan (Goat 20), β-dystroglycan (AP 83), or nNOS (Rabbit 200) have been described previously (Duclos e al., *J. Cell. Biol.*, 142:1461, 1998). Cy3-conjugated secondary antibodies were used and images were viewed on a Bio-Rad MRC-600 laser scanning confocal microscope. All digitized images were captured under the same conditions.

iv. Measurements of Contractile Properties Methods

Contractile properties of muscles from 6-month-old Δ71–78 transgenic mice were compared with those of C57Bl/10 wild-type and mdx mice using methods described previously (Lynch et al., *Am. J. Physiol.*, 272:C2063, 1997). The samples included eight muscles each from the EDL, soleus, and diaphragm. Mice were deeply anesthetized with avertin and each muscle was isolated and dissected free from the mouse. After removal of the limb muscles, the mice were euthanized with the removal of the diaphragm muscle. The muscles were immersed in a bath filled with oxygenated buffered mammalian Ringer's solution (137 mM NaCl, 24 mM $NaHCO_3$, 11 mM glucose, 5 mM KCl, 2 mM $CaCl_2$, 1 mM $MgSO_4$, 1 mM $NaH_2PO_4$, and 0.025 mM tubocurarine chloride, pH 7.4). For each muscle, one tendon was tied to a servomotor and the other tendon to a force transducer. Muscles were stretched from slack length to the optimal length for force development and then stimulated at a frequency that produced absolute isometric tetanic force (mN). After the measurements of the contractile properties, the muscles were removed from the bath, blotted and weighed to determine muscle mass. Specific force ($kN/m^2$) was calculated by dividing absolute force by total fiber cross sectional area.

v. Muscle Membrane Isolation Methods

Muscle microsomes from 12–14 month-old C57Bl/10, mdx, Δ71–78, Δ71–74, Δ75–78, and Dp71 mice were prepared as described previously (Ohlendieck et al., *J. Cell.*

Biol., 112:135, 1991). In brief, skeletal muscle was homogenized in 7.5-vol homogenization buffer plus protease inhibitor Complete (Boehringer). The homogenate was centrifuged at 14,000 g for 15 min to remove cellular debris. The supernatant was filtered through cheesecloth and spun at 142,000 g for 37 minutes to collect microsomes. The microsome pellet was resuspended in KCl wash buffer (0.6 M KCl, 0.3 M sucrose, 50 mM Tris-HCl, pH 7.4) plus protease inhibitors and recentrifuged at 142,000 g for 37 minutes to obtain KCl-washed microsomes. The final pellet was resuspended in 0.3 M sucrose and 20 mM Tris-maleate, pH 7.0. Samples were quantified by the Coomassie Plus Protein Assay Reagent (Pierce Chemical Co.) and equivalent protein loading was verified by SDS-PAGE. KCl-washed microsomes were analyzed by Western blot using antibodies against β2-syntrophin, pan syntrophin, nNOS (Transduction Laboratories), β-dystroglycan, α-sarcoglycan (Novocastra Laboratories), and other proteins described above.

B. Results i. Generation of Dystrophin Δ71–78 Transgenic Mice

To test the function of a dystrophin protein lacking both the syntrophin and dystrobrevin binding sites, we prepared a cDNA expression vector deleted for the COOH-terminal domain (corresponding to exons 71–78; See FIG. 19) as described above. The structure of several dystrophin transgenic constructs previously tested are also shown for comparison. Mice expressing the dystrophin Δ71–78 transgene were crossed onto the mdx background and dystrophin levels were analyzed by Western blotting. The expression of the dystrophin Δ71–78 transgene in skeletal muscle was determined to be 10-fold higher than endogenous dystrophin. Immunofluorescent staining of quadriceps muscle using an antibody against the NH$_2$-terminus of dystrophin revealed that the Δ71–78 protein was localized to the sarcolemma, similar to wild-type dystrophin. Dystrophin Δ71–78 expression was also found to be uniform in the diaphragm, EDL, and soleus muscles, but the tibialis anterior muscle displayed a mosaic expression pattern. The human skeletal muscle-actin promoter used in this study was not expressed in either smooth or cardiac muscle.

ii. Morphology of Dystrophin Δ71–78 Mice Appears Normal

We initially analyzed transgenic mdx mouse muscle tissues for morphological signs of dystrophy. Hematoxylin and eosin-stained limb and diaphragm skeletal muscle sections of dystrophin Δ71–78 mice revealed none of the signs of fibrosis, necrotic fibers, or mononuclear cell infiltration that were apparent in age-matched mdx controls. NMJs (neuromuscular junctions) of transgenic mice stained with rhodamine-labeled -bungarotoxin consistently appeared normal in contrast to the varying degrees of postsynaptic folding observed in mdx NMJs. Mdx muscle fibers have previously been shown to be highly permeable to the vital dye Evans blue in vivo, reflecting damage to the dystrophic fiber sarcolemma (Matsuda et al., *J. Biochem.* (Tokyo), 118:959, 1995). Skeletal muscle fibers from dystrophin Δ71–78 mice, like wild-type animals, were found not to be permeable to Evans blue dye.

iii. Analysis of Centrally Nucleated Muscle Fibers

Another hallmark of dystrophy in mdx mice is the presence of large numbers of centrally-nucleated muscle fibers, reflecting cycles of fiber degeneration and regeneration (Torres and Duchen, *Brain*, 110:269, 1987). To estimate the degree of myofiber regeneration occurring in Δ71–78 transgenic mice, centrally nucleated fibers were counted from a variety of muscle groups in age-matched wild-type, mdx, and Δ71–78 mice (See, Table 2). By 4 months of age, 71% of muscle fibers in mdx quadriceps muscles contained central nuclei, whereas wild-type muscles had <1%. Interestingly, 4 month old dystrophin Δ71–78 quadriceps muscles displayed 1% central nuclei, indicating that very little, if any, regeneration was occurring. When 1-year-old mice were compared, a modest increase in centrally nucleated fibers became apparent. Quadriceps muscles from Δ71–78 mice contained 10% centrally nucleated fibers, although diaphragm muscles still displayed <1%. EDL and soleus muscles displayed 5 and 8% centrally nucleated fibers, respectively. For comparison, 1-year-old wild-type mice had <1% centrally nucleated fibers in both limb and diaphragm muscles. Furthermore, 1-year-old mdx limb muscles had 60% centrally nucleated fibers, whereas the diaphragm had 35%.

TABLE 2

Percentage of Centrally Nucleated Fibers in Mouse Skeletal Muscles

| Line | Age | Quad | Dia | TA | EDL | Soleus |
|---|---|---|---|---|---|---|
| C57/B110 | 4 | <1 | <1 | ND | ND | ND |
| mdx | 4 | 71 | 58 | ND | ND | ND |
| Δ71–78 | 4 | 1 | <1 | ND | ND | ND |
| C57/B110 | 12 | <1 | <1 | <1 | <1 | <1 |
| mdx | 12 | 65 | 35 | 58 | 50 | 61 |
| Δ71–78 | 12 | 10 | <1 | ND | 5 | 8 |
| Δ71–74 | 15 | 5 | <1 | <1 | <1 | ND |
| Δ75–78 | 15 | 8 | <1 | 4 | 2 | 7 |

Quad = quadriceps; Dia = diaphragm; TA = tibialis anterior; Age is in months

Previous studies of transgenic mice expressing dystrophins deleted for exons Δ71–74 (Δ71–74) or exons Δ75–78 (Δ75–78) revealed no increase in the numbers of centrally nucleated fibers by 4 months of age (Rafael et al. 1996, see above). To contrast these mice with the 71–78 transgenics, central nuclei counts were performed on 15-month-old Δ71–74 and 75–78 mice. It was determined that these animals had central nuclei counts in between those of wild-type and Δ71–78 mice. The Δ71–74 and Δ75–78 mice had 5 and 8% centrally nucleated fibers in quadriceps, respectively (Table 2).

iv. Contractile Properties

Figure 20:
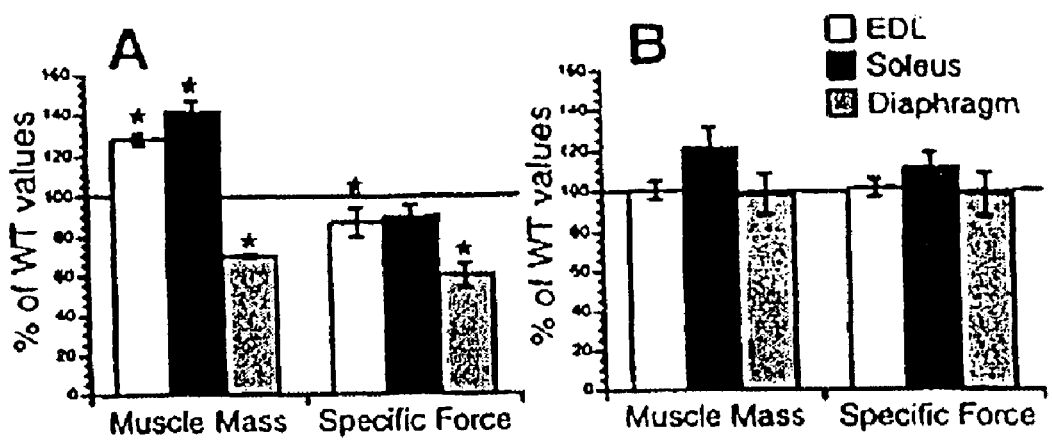
FIG. 20 shows the contractile properties of EDL, soleus, and diaphragm muscles in wild-type, mdx, and dystrophin Δ71–78 mice.

Compared with muscles of wild-type mice, those from mdx mice displayed a significant amount of necrosis, fibrosis, and infiltrating mononuclear cells. mdx skeletal muscles also displayed a loss of specific force-generating capacities when muscles were stimulated to contract in vitro, providing an extremely sensitive and quantitative measurement of the dystrophic process (FIG. 20A). In contrast, dystrophin Δ71–78 mice had no major abnormalities when subjected to the same analysis (FIG. 20B). Muscle mass for both EDL and diaphragm were not significantly different between dystrophin Δ71–78 and wild-type mice, whereas dystrophin Δ71–78 soleus muscles were slightly hypertrophied. When stimulated to contract, all three muscle groups displayed specific forces not significantly different from wild-type ($P<0.05$). These results demonstrate that the dystrophin Δ71–78 protein has essentially the same functional capacity as the full-length protein.

V. Localization of the DAP Complex in Δ71–78 Mice

Immunofluorescent analysis of the peripheral DAP complex revealed α1-syntrophin, β1-syntrophin, α-dystrobrevin-1, and α-dystrobrevin-2 to be localized at the sarcolemma with dystrophin, despite the lack of syntrophin and dystrobrevin binding sites in the transgene-encoded dystrophin. α1-syntrophin levels were similar between wild-type and Δ71–78 mice. However, the levels of β1-syntrophin were elevated at the membrane in Δ71–78 mice, particularly in those fibers that normally express significant levels of this isoform. α-dystrobrevin-1 was primarily located at the NMJ in wild-type mice, and was exclusively located at the NMJs in mdx mice. Surprisingly, in dystrophin Δ71–78 mice, higher levels of α-dystrobrevin-1 were observed at the sarcolemma than in wild-type mice. The Δ71–78 mice also displayed a slight increase in utrophin localization along the sarcolemma, but this increase was less than the increase in mdx fibers. Immunofluorescent localization of the sarcoglycans, α- and β-dystroglycan, sarcospan, and nNOS in Δ71–78 mice revealed no differences in the expression of these proteins when compared with wild-type mice. The proper localization of these proteins to the sarcolemma indicated that membrane targeting of the DAP complex components can proceed in the absence of the COOH-terminal domain of dystrophin.

vi. DAP Complex Protein Levels

To examine the levels of the DAP complex members that associate with dystrophin, muscle microsomes were prepared from wild-type and dystrophin Δ71–78 mice and analyzed by Western blotting. This approach provides information on the relative abundance of individual DAP complex members in muscles of separate lines of mice. Slightly elevated levels of β-dystroglycan were detected in dystrophin Δ71–78 mice, which we have previously observed whenever dystrophin is overexpressed. Isoforms of syntrophin and dystrobrevin were present at slightly different levels when the dystrophin Δ71–78 membranes were compared with those from wild-type mice. α1-syntrophin and β2-syntrophin levels were lower than in wild-type mice, whereas the level of β1-syntrophin was elevated. Although there was approximately the same amount of α-dystrobrevin-2, there were elevated levels of α-dystrobrevin-1 in Δ71–78 microsomes. A reduction in nNOS was observed in dystrophin Δ71–78 muscle, indicating that nNOS binds weakly to the DAP complex in Δ71–78 mice. Levels of α-sarcoglycan were similar in all lines tested, and provided an internal control for protein loading.

Since some DAP complex members exhibited isoform changes in Δ71–78 mice, we examined purified microsomes from dystrophin Δ71–74 and Δ75–78 mice. Transgenic mdx mice that express the dystrophin isoform Dp71 in muscle were also included in this study since these dystrophic mice have the DAP complex present at the sarcolemma. α1-syntrophin levels were lower in all four transgenic lines compared with wild-type mice. Surprisingly, β1-syntrophin was absent in Δ71–74 microsomes but was highly overexpressed in Δ75–78 and Dp71 microsomes. The Δ71–74 microsomes had equivalent β2-syntrophin levels when compared with wild-type microsomes, but this isoform of syntrophin was reduced in both Δ75–78 and Dp71 microsomes. A pan syntrophin antibody, which detects all three isoforms of syntrophin, confirmed the upregulation of syntrophin in Δ75–78 and Dp71 microsomes. Similar to Δ71–78, α-dystrobrevin-1 was elevated in all dystrophin transgenic microsome preparations. However, in comparison with wild-type, α-dystrobrevin-2 was higher in Δ71–74 and Δ75–78, but equal in Dp71 microsomes. Contrary to the Δ71–78 mice, deleting either exons 71–74 or 75–78 restored nNOS to wild-type levels. However, Dp71 mice, which lack the NH$_2$-terminal and rod domains of dystrophin, did not retain nNOS in the microsome fractions. Previous studies have also shown that utrophin is upregulated in mdx and Dp71 mice (Ohlendieck et al., Neuron, 7:499–508, 1991). Therefore, utrophin levels were compared in all transgenic lines and we found that Δ71–78, Δ71–74, and Δ75–78 mice do not have the elevated levels seen in mdx and Dp71 mice.

EXAMPLE 2

Construction of ΔR4–R23, ΔR2–R21+H3, and ΔR2–R1

Figure 22:
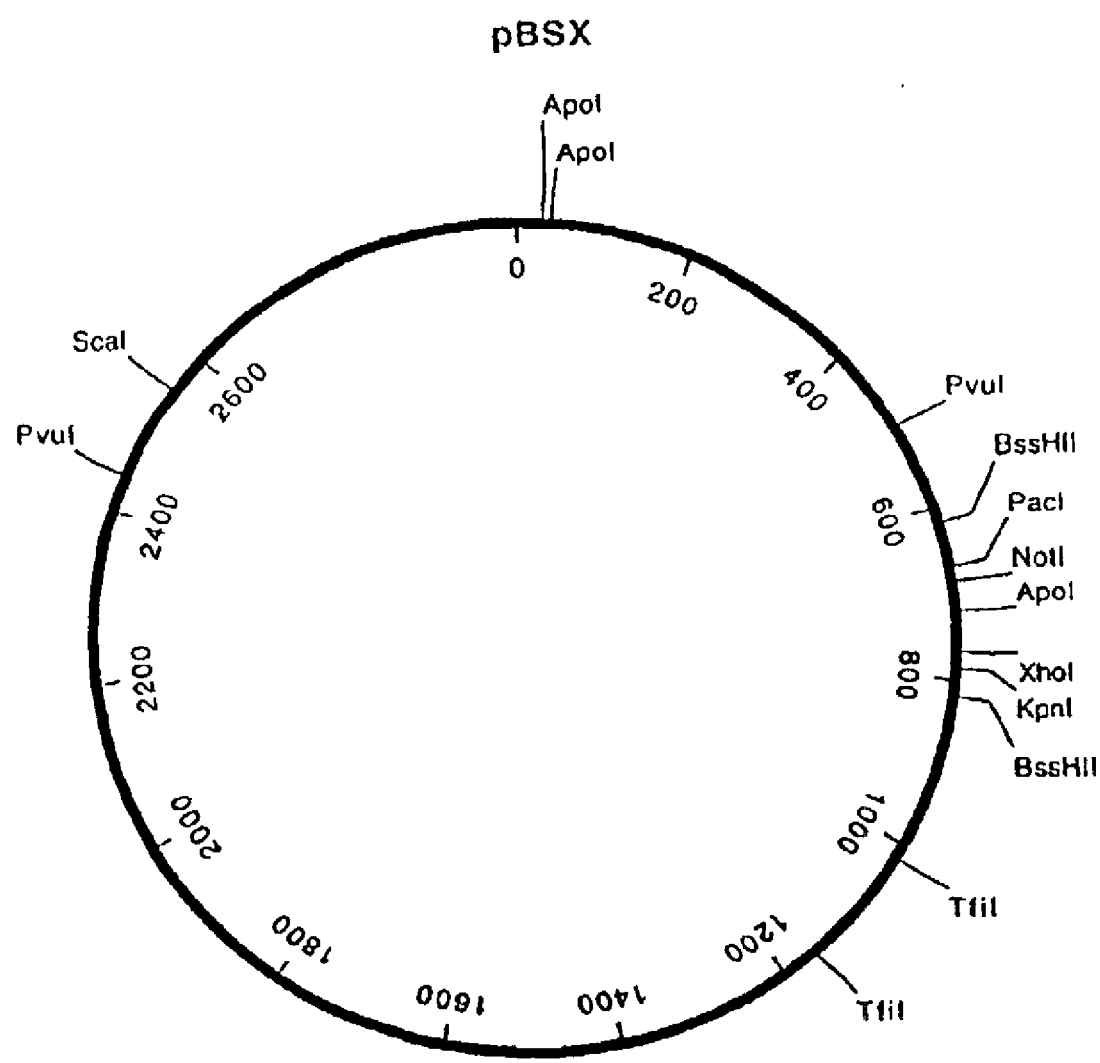
FIG. 22 shows a restriction map for pBSX.

This example describes the construction of R4–R23 (micro-dys1), ΔR2–R21+H3 (micro-dys3), and ΔR2–R1 (micro-dys2), three sequences with 4 spectrin-like repeat encoding sequences. The 'full-length' human dystrophin cDNA that was started with was actually a sequence slightly smaller than the true full-length human dystrophin cDNA. In particular, the starting sequence, called full-length HDMD (SEQ ID NO:47, see FIG. 23) is the same as the wild-type human dystrophin in SEQ ID NO:1, except the 3' 1861 base pairs are deleted (at an XbaI site), and the 39 base pair alternatively spliced exon 71 (bases 10432–10470) are deleted. This sequence (SEQ ID NO:47) is originally in pBSX (SEQ ID NO:46, See FIGS. 21 and 22).

A. Cloning ΔR4–R23

Figure 24:
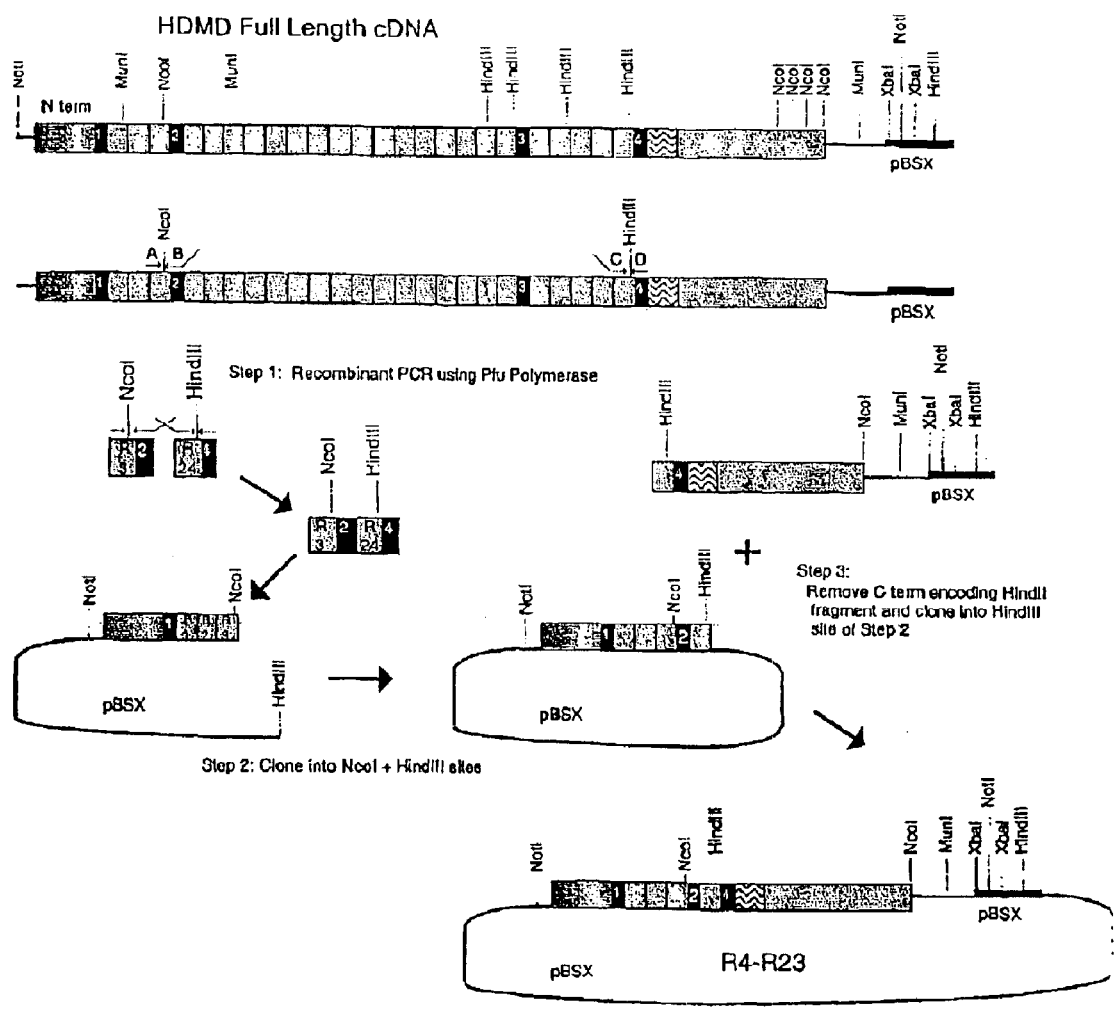
FIG. 24 shows the cloning procedure for ΔR4–R23.

The procedure used for cloning ΔR4–R23 is outlined in FIG. 24. Initially, three PCR reactions were performed (employing Pfu polymerase) to create the deletion shown in FIG. 24. The primers employed in the first reaction were 5' GAA CAA GAT TCA CAC AAC TGG C 3' (SEQ ID NO:48), which anneals to 1954–1975 of the HDMD clone, and 5' <u>GTT CCT GGA GTC TTT CAA GAT</u> CCA CAG TAA TCT GCC TC 3' (SEQ ID NO:49), which is a reversed tailed primer (the bold sequence anneals to 2359–2341 of the HDMD clone, and the underlined sequence anneals to 9023–9005 the HDMD clone. PCR was conducted employing these primers, and a 425 bp PCR product was produced. The first primer employed in the second reaction was 5' GAG GCA GAT TAC TGT GGA T <u>CT TGA AAG ACT CCA GGAAC</u> 3' (SEQ ID NO:50), which is the reverse complement primer of SEQ ID NO:49 (the bold-faced sequence of SEQ ID NO:50) anneals to 2341–2359 of the HDMD clone in the forward direction. The underlined sequence anneals to 9005–9023 of the HDMD clone in the forward direction. The other primer employed for the second reaction was 5' TGT TTG GCG AGA TGG CTC 3' (SEQ ID NO:51) which anneals to 9413–9396 of HDMD in the reverse direction. PCR was conducted employing these primers, and a 427 bp PCR product was produced. The third reaction employed the products from steps 1 and 2 and the outside primers SEQ ID NO:48 and SEQ ID NO:51, producing a 814 bp fragment by PCR. This fragment was then digested with NcoI and HindIII to produce a 581 bp DNA fragment.

This 581 bp fragment was then cloned into a 5016 bp NcoI+Hind III fragment from the HDMD clone. The 581 bp fragment contained part of repeat 3, all of Hinge 2, and part of repeat 24. The NcoI site used in the HDMD clone was located at 2055 bp. The Hind III site was located at 9281 bp. The 5016 fragment contained the pBSX cloning vector sequence, and the entire 5' UTR, the entire N terminus, Hinge 1, Repeats 1, 2, and part of repeat 3 up to the NcoI site of human dystrophin. Ligation of the 5016 bp fragment and 581 bp fragment (step 2) was then performed to created a 5597 bp sequence.

Step 3 was then performed to clone a 2.9 kb HindIII fragment containing part of repeat 24, the C terminus, and the 3' UTR (See FIG. 24). The 5' HindIII site is located at 9281 bp of the HDMD clone. The 3' HindIII site of this fragment is derived from pBSX polylinker. This 2.9 kb fragment was cloned into the HindIII site of the product of Step 2 to yield an 8.5 kb plasmid, composed of the ΔR4–R23 cDNA plus pBSX. The entire ΔR4–R23 cDNA was excised from pBSX with NotI and cloned into the NotI site of the HSA expression vector (HSA promoter—VP1 intron—NotI site—tandem SV40 poly adenylation site).

B. Cloning ΔR2–R21+H3

Figure 25:
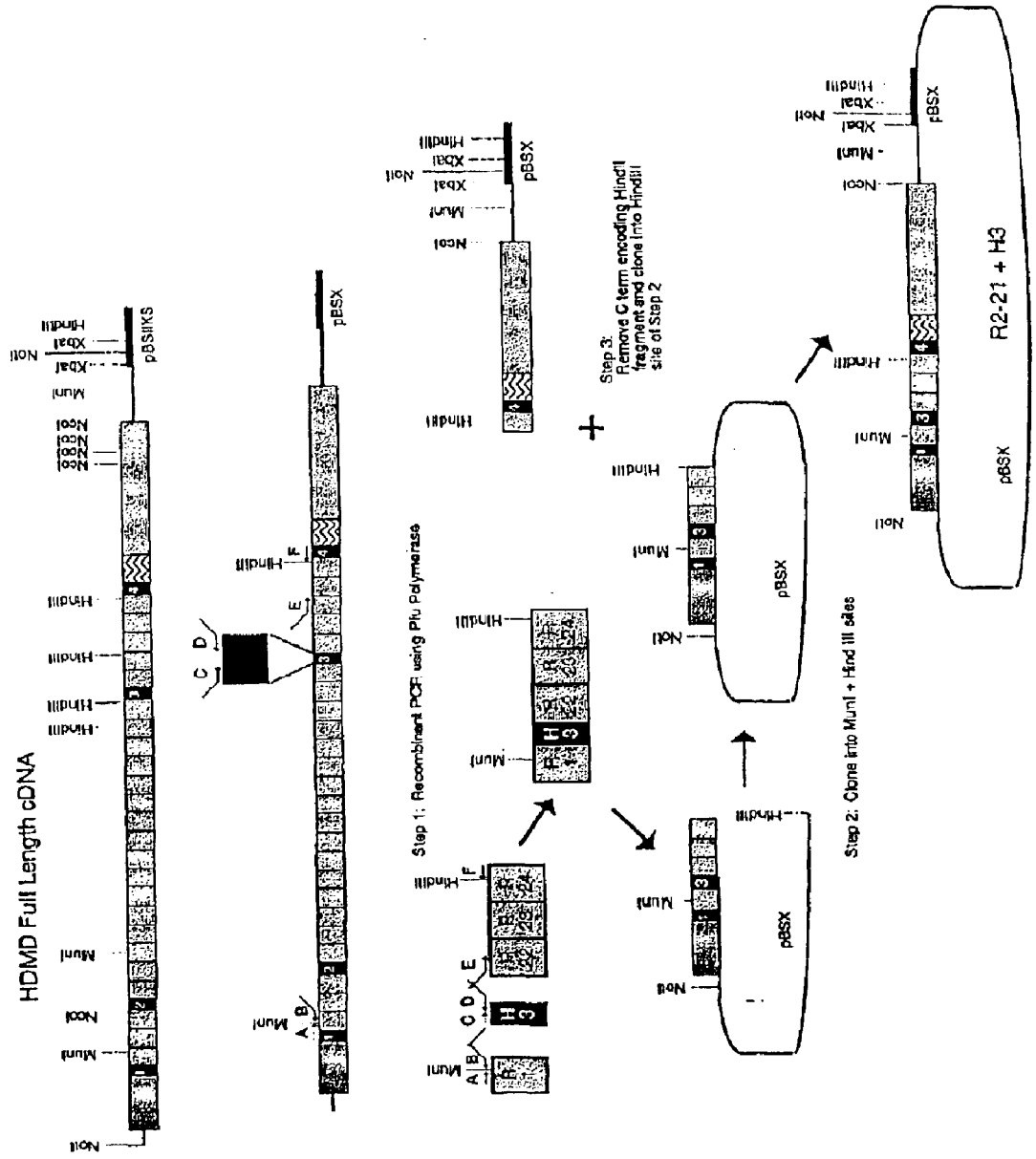
FIG. 25 shows the cloning procedure for ΔR2–R21+H3.
Figure 26:
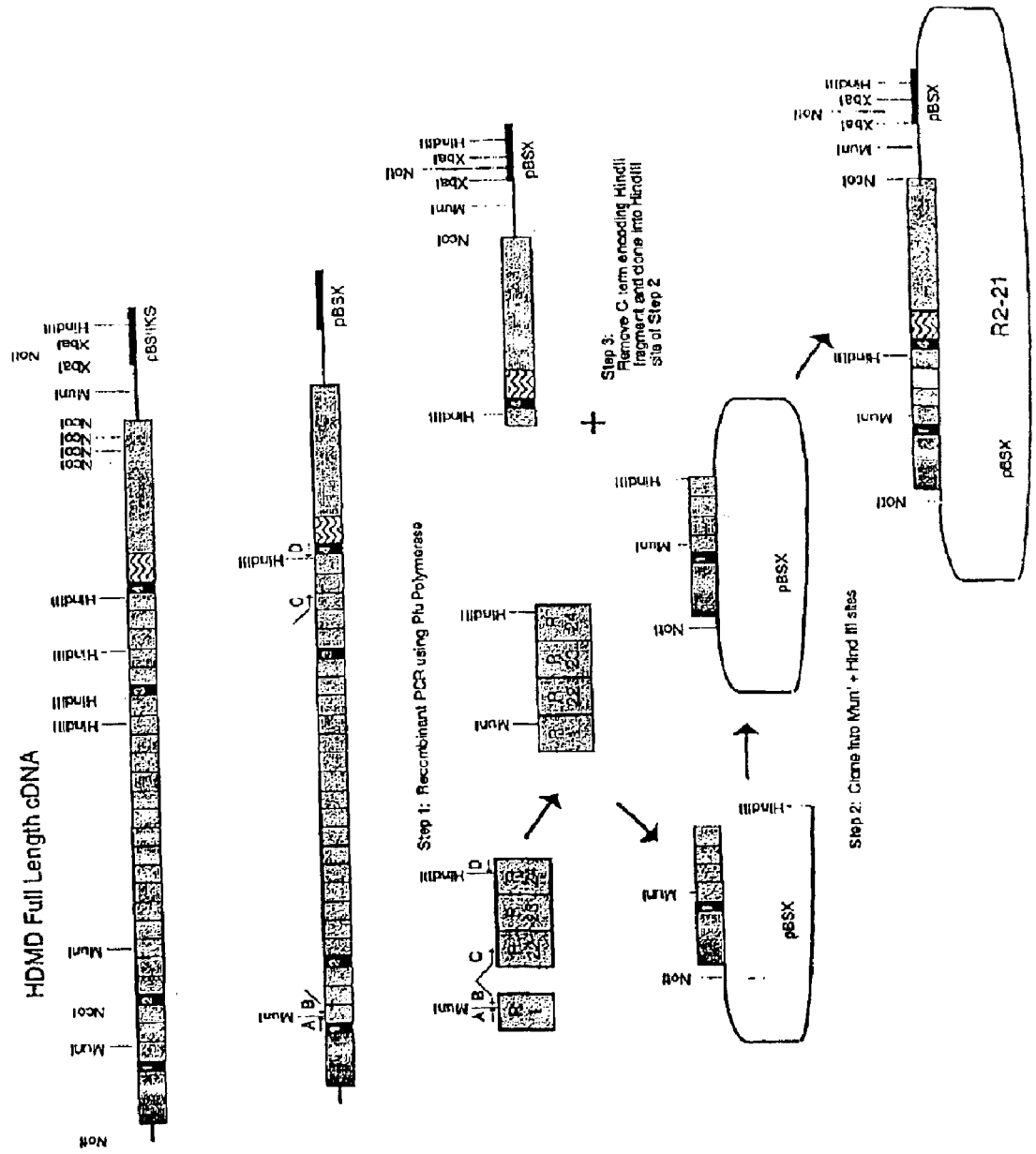
FIG. 26 shows the cloning procedure for ΔR2–R21.

The procedure used for cloning ΔR2–R21+H3 is outlined in FIG. 25. Initially, four PCR reactions were performed (employing Pfu polymerase) to create the deletion shown in FIG. 25. The primers employed in the first reaction were 5' GAT GTG GAA GTG GTG AAA GAC 3' (SEQ ID NO:52), which anneals to 1319–1330 of the HDMD clone, and 5' CCA ATA GTG GTC AGT CCA GGA GCA TGT AAA TTG CTT TG 3' (SEQ ID NO:53), which is a reverse, tailed primer (the bold-faced sequence anneals to 1546–1532 of the HDMD clone and the underlined sequence anneals to 7512–7490 of the HDMD clone. PCR was conducted with these primers and a 228 bp PCR product was produced. The first primer employed in the second reaction was 5' CAA AGC AAT TTA CAT GCT CCT GGA CTG ACC ACT ATTGG 3' (SEQ ID NO:54), which is the reverse complement of SEQ ID NO:53 (the bold-faced sequence of SEQ ID NO:54 anneals to 1532–1546 of the HDMD clone in the forward direction, and the underlined sequence anneals to 7512–7490 of the HDMD clone in the forward direction. The other primer employed in the second reaction was 5' CTG TTG CAG TAA TCT ATG CTC CAA CAT CAA GGA AGATG 3' (SEQ ID NO:55), and the bold-faced sequence anneals to 8287–8270 of the HDMD clone, and the underlined sequence anneals to 7612–7593 of the HDMD clone as a reverse primer. PCR was performed with these primers, and a 123 bp PCR product was produced. The first primer employed in the third reaction was 5' CATCTT CCT TGA TGT TGG AGC ATA GAT TAC TGC AAC AG 3' (SEQ ID NO:56), the underlined sequence anneals to 7593–7612 of the HDMD clone in the forward direction, and the bold-faced sequence anneals to 8270–8287. The second primer employed in the third reaction was SEQ ID NO:51 (see above), which anneals to 9413–9396 in the reverse direction. PCR was performed with these primers, and a 1143 bp fragment was produced. The fourth reaction employed the products from reactions 1, 2, and 3 as template, and the outside primers (SEQ ID NO:52 and SEQ ID NO:51), and a 1494 bp fragment was produced using Pfu polymerase.

This 1494 bp fragment was then digested with MunI and HindIII to produce a 1270 bp band and cloned into a 4320 bp MunI+HindIII fragment from the HDMD clone. The 1270 bp fragment contained the part of repeat 1, all of hinge 3, repeat 22, repeat 23, and part of repeat 24. The 4320 bp fragment contained the 5' UTR of HDMD, the N terminus, Hinge 1, and part of repeat 1 and pBSX. The MunI site in HDMD is located at base 1409. The HindIII site is at 9281 bp. Ligation of the 4320 bp fragment and the 1270 bp fragment was then performed (See FIG. 25) and a 4490 bp fragment was produced. Step 3 was performed as describe above for ΔR4–R23 to generate ΔR2–R21+H3.

C. Cloning ΔR2–R21

The cloning of ΔR2–R21 was performed essentially the same way as for ΔR2–R21+H3, with the exception of the recombinant PCR reaction to assemble the rod domain deletion (See, FIG. 26). All other steps are the same. Three PCR reactions were performed (using Pfu polymerase) to create the deletion. The primers employed in the first reaction were SEQ ID NO:52 (see above), and 5' CTG TTG CAG TAATCT ATG ATG TAA ATT GCT TTG 3' (SEQ ID NO:57), the underlined sequence anneals to 8287–8270 of the HDMD clone in the reverse direction, and the bold-faced sequence anneals to 1546–1532 of the HDMD clone in the reverse direction. PCR was performed with these primers, and a 250 bp product was obtained. The first primer employed in the second reaction was 5' CAA AGC AAT TTA CAT CAT AGA TTACTG CAA CAG 3' (SEQ ID NO:58), which is is the reverse complement of SEQ ID NO:57 (the bold-faced sequence of SEQ ID NO:58 anneals to 1532–1546 of the HDMD clone in the forward direction, and the underlined sequence anneals to 8270–8287 of the HDMD clone in the forward direction. The other primer employed in the second reaction was SEQ ID NO:51, which anneals to 9413–9396 in the reverse direction. PCR was performed with these primers and a 1143 bp product was obtained. The third reaction employed the products from reactions 1 and 2 (as template) and the outside primers (SEQ ID NO:52 and SEQ ID NO:51), and a 1383 bp fragment was produced. This fragment was then digested with MunI and HindIII to produce an 1147 bp fragment containing part of repeat 1, repeat 22, repeat 23, and part of repeat 24. This was then cloned into the same MunI+HindIII HDMD fragment described for the ΔR2–R21+H3 clone and all other steps thereafter were the same.

EXAMPLE 3

ΔR4–R23 Deletions

This example describes the construction of 5' UTR, 3' UTR, and C-terminal deletions of ΔR4–R23 (making it even smaller), as well as the addition of polyadenylation and promoter sequences. This example also describes the alteration of the Kozak sequence (to become more like that of consensus).

A. Deletion of the 3' UTR

In order to delete the 3' UTR, the following two primers were employed 5' TCT CTC CAA GAT CAC CTC G 3' (SEQ ID NO:64), which anneals to 9117–9134 of the HDMD full length clone, and 5' ATG AAG CTT GCG GCC GCA TGC GGG AAT CAG GAG TTG 3' (SEQ ID NO:65) (the underlined site is a HindIII site that was included in this primer and the bold-faced type is a NotI site). SEQ ID NO:65 is a reverse primer that anneals to 11340–11322 of HDMD in the 3' UTR. These primers cause the deletion of 707 bp of the 3' UTR from the XbaI cloning site located at 12057 to the end of this primer (SEQ ID NO:65), leaving 113 bp of native 3' UTR, and introducing NotI and HindIII cloning sites. The PCR product obtained using the primers corresponding to SEQ ID NOS:64 and 65 on the pΔR4–R23 clone was named HdysΔ3'UTR and was saved for use as a template to generate a further deletion of exons 71–78 (see part C below).

B. Deletion of 5' UTR and Alteration of Kozak Sequence

A portion of the 5' UTR was deleted (and the Kozak sequence was altered in the same step). The 'step 2' clone from cloning of ΔR4–R23 was utilized (this was the the product of ligating the step 1 PCR product into the 5016 bp NcoI and HindIII fragment from the HDMD full-length clone, and this clone contained pBSX backbone plus the 5' UTR, N terminus, Hinge 1, Repeats 1, 2, 3, Hinge 2, and part of repeat 24. There is an MunI site located in the first repeat at nucleotide 1409 of the HDMD cDNA. In addition, there is a NotI site that is polylinker derived at the 5' end of the clone. These two sites were employed, MunI+NotI, to clone a new fragment containing a truncated 5' UTR and an altered Kozak sequence as follows. PCR was performed, using Pfu polymerase using the following primers. The first primer was 5' TAG CGG CCG CGG TTT TTT TTA TCG CTG CCT TGA TAT ACA CTT TCC ACC ATG CTT TGG TGG GAA GAA GTA G 3' (SEQ ID NO:59). We created a NotI site (underlined) in this primer so the product could be cloned back into the NotI site from the polylinker. The sequence immediately 3' to this NotI site corresponds to the dystrophin 5' UTR sequence (the original Kozak sequence was changed with this primer, from TCAAAATGC, changed to CCACCATGC. The second primer was 5' TTT TCC TGT TCC AAT CAG C 3' (SEQ ID NO:60) which anneals to sequence 1441–1423 of HDMD full length clone. The final product of this reaction was 1270 bp and was digested with NotI+MunI to produce a 1233 bp fragment that was then cloned into the NotI (polylinker)+MunI site in Repeat 1 of the "Step 2" clones (described above for ΔR4–23). This new clone was named pHDMD5' Kozak.

C. Deletion of Exons 71–78 (C-terminal)

Figure 35:
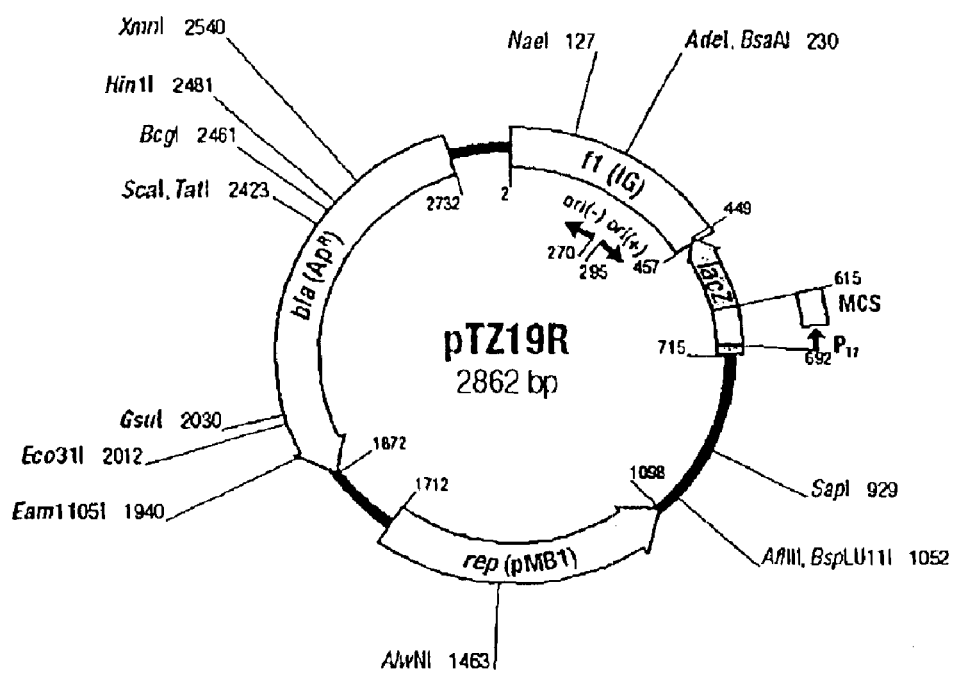
FIG. 35 is a schematic illustration of the structure of plasmid pTZ19R (top) and the sequence of the multiple cloning site in the vector (bottom) (SEQ ID NOS:95 and 96).

Using three PCR reactions, a 71–78 deletion was created. We used the HindIII fragment containing the 3'UTR that was generated by digestion of the HDMD full-length dystrophin cDNA with HindIII as the vector to clone the 71–78 fragment into the HindIII site. The primer employed for the first reaction were 5' GGC TTC CTA CAT TGT GTC AGT TTC CAT GTT GTC CCC 3' (SEQ ID NO:66), and 5' TCT CTC CAA GAT CAC CTC 3' (SEQ ID NO:67) anneals to 9117–9134 of HDMD. PCR was performed employing these primers and a 1334 bp product was produced. The primers for the second reaction were SEQ ID NO:65, and 5' GGG GAC AAC ATG GAA ACT GAC ACA ATG TAG GAA GCC 3' (SEQ ID NO:68), where the bold-face sequence anneals to exon 70 at 10415–10431 in the forward direction, and the underlined sequence anneals to 11216–11233 in the forward direction. PCR was performed and a 150 bp fragment was generated. The product of reactions 1 and 2 were used as template and the outside primers SEQ ID NO:65 and SEQ ID NO:67 were used to prime the reaction which generated the complete 71–78 C terminus (1484 bp). This product was digested with HindIII to produce a 1319 bp fragment and was cloned into the HindIII site of pTZ19R (See FIG. 35). This new clone was named pTZ-HDMD-H3Δ71–78Δ3.

D. Cloning of the SV40 pA Sequence into the Not I Site

The next step was the cloning of the SV 40 pA sequence:

(SEQ ID NO:71)
5'GATCCAGACATGATAAGATACATTGATGAGTTTGGACAAACCACAACT

AGAATGCAGTGAAAAAAATGCTTTATTTGTGAAATTTGTGATGCTATTGC

TTTATTTGTAACCATTATAAGCTGCAATAAACAAGTTAACAACAACAATT

GCATTCATTTTATGTTTCAGGTTCAGGGGGAGGTGTGGGAGGTTTTTTCG

GATC3' into the NotI site of the 3' HindIII fragment that now contains the 3' UTR and 71–78. A PCR reaction was performed on the template pHSA with a reverse primer 5' A GC GGC CGC AAA AAA CCT CCC ACA CCT CC 3' (SEQ ID NO:69, containing a regenerating NotI site— underlined) and 5' TAC GGC CGA TCC AGA CAT GAT AAG ATA C 3' (SEQ ID NO:70, containing a destroying EagI site, in bold). All other sequence (besides the NotI and EagI sites) is SV40 pA. This PCR reaction generated a 195 bp product+cloning sites=209 bp. We then cloned this fragment into the NotI site of pTZ-HDMD-H3Δ71–78Δ3 generated by PCR in the 3' UTR clone. The upstream (5'-most) NotI site in this clone was destroyed by EagI ligation. This new clone was named pTZ-HDMD-H33'A.

E. Cloning of CK6 Promoter into NotI Site

The CK6 promoter—

(SEQ ID NO:61)
5'GGT-
ACTACGGGTCTAGGCTGCCCATGTAAGGAGGCAAGGCCTGGGGACACCCG

AGATGCCTGGTTATAATTAACCCCAACACCTGCTGCCCCCCCCCCCCCAA

CACCTGCTGCCTGAGCCTGAGCGGTTACCCCACCCCGGTGCCTGGGTCTT

AGGCTCTGTACACCATGGAGGAGAAGCTCGCTCTAAAAATAACCCTGTCC

CTGGTGGGCCCAATCAAGGCTGTGGGGGACTGAGGGCAGGCTGTAACAGG

CTTGGGGGCCAGGGCTTATACGTGCCTGGGACTCCCAAAGTATTACTGTT

CCATGTTCCCGGCGAAGGGCCAGCTGTCCCCCGCCAGCTAGACTCAGCAC

TTAGTTTAGGAACCAGTGAGCAAGTCAGCCCTTGGGGCAGCCCATACAAG

GCCATGGGGCTGGGCAAGCTGCACGCCTGGGTCCGGGGTGGGCACGGTGC

CCGGGCAACGAGCTGAAAGCTCATCTGCTCTCAGGGCCCCTCCCTGGGGA

CAGCCCCTCCTGGCTAGTCACACCCTGTAGGCTCCTCTATATAACCCAGG

GGCACAGGGGCTGCCCCCGGGTCACGGGGATCCTCTAGACC-3' was amplified using two tailed primers: 5' AGC GGC CGC GGT ACT ACG GGT CTA GG 3' Forward (SEQ ID NO:62), and 5' ATC GGC CGT CTA GAG GAT CCC CGT GAC C 3' Reverse (SEQ ID NO:63). The underlined sequence is a NotI site added to the end of this primer. The remaining sequence is CK6 sequence. The bold-faced type is an EagI site added to the end of this primer. The remaining sequence is from CK6. The CK6 promoter was amplified this way so we could add the NotI and EagI sites (so the entire cassette could be excised when put back together with NotI). This PCR product was therefore digested with NotI and EagI and ligated into the NotI site of pHDMD5'Kozak. This new clone was named pCK6HDMD5'Kozak. NotI and EagI produce compatible cohesive sites, but when EagI ligates to NotI, it destroys the site. So we placed the EagI site at the 3' end, so that when the final construct was cut with NotI, the entire expression cassette could be excised intact. The same strategy was employed at the 3' end when placing the SV40 poly A sequence into the 3' Not I site.

F. Re-ligating the 5' and 3' Ends.

This step was performed as described above in the microdystrophin transgene constructs. We reconstituted the same cloning sites but with modifications in the fragments, so the modified 3' end, isolated as a HindIII fragment from clone pTZ-HDMD-H33'A (example 3 part D), was able to be cloned into the HindIII site of pCK6HDMD5'Kozak (example 3, part E). This final clone, named pCK6R4–R23KozakΔ3', contains a truncated dystrophin expression cassette that can be excised in its entirety by digestion with NotI. This excised expression cassette can then be used for a variety of purposes. One such purpose is to clone the cassette into a plasmid containing the inverted terminal repeats from adeno-associated virus. By cloning the dystrophin expression cassette HDMD-H33'A into a cloning site between the two ITRs of AAV, a recombinant AAV vector could be produced.

EXAMPLE 4

Construction of Reduced Repeat Dystrophin Constructs

This example describes the construction of ΔH2–R19 (an 8 spectrin-like-repeat sequence), pΔR9R16 (a 16 spectrinlike-repeat sequence), pΔR1R24 (a zero spectrin-like-repeat sequence), pΔH2–H3 (an 8 spectrin-like repeat sequence), and ΔH2–R19,R20 (a 7 spectrin-like repeat sequence). One starting plasmid was pHBMD, a human dystrophin cDNA (full-length HDMD, SEQ ID NO:47) with a further deletion of the sequences encoded by exons 17–48. The cDNA was cloned into the commercially available plasmid vector pTZ19r (MBI Fermentas; Genbank accession number Y14835, See FIG. 35), into which an EcoRI-SalI adapter (prepared by self-annealing of the oligonucleotide 5'-AATTCGTCGACG-3', SEQ ID NO:83) had been ligated into the the EcoRI site. Base number 1 of the cDNA is immediately 3' of the adapter sequence, and the cDNA ends at the XbaI site at base 12,100 of SEQ ID NO:1. This XbaI site had been ligated into the XbaI site of the plasmid ptZ19r. Another starting plasmid is pBSX (SEQ ID NO:46), a modified version of pBluescript KSII+ (Stratagene) which is used to make pBSXA (pBSX into which the SV40 polyadenylation signal (pA) was added). This pA sequence was excised as a 206 bp fragment from pCMVβ (Clonetech), blunt-ended with DNA polymerase I, and ligated into the blunt-ended KpnI site of pBSX.

Another starting plasmid is pCK3, which is pBSX with the 3.3 kb mouse muscle creatine kinase enhancer plus promoter attached to the minx intron (See, Hauser et al., *Mol Ther*., 2:16–25, 2000). Another staring plasmid is pHDSK, which is pHBMD digested with KpnI, to remove the dystrophin sequences 3' of the internal KpnI site (base 7,616 of the human dystrophin cDNA sequence, SEQ ID NO:1). A further starting vector is p44.1, which is pBluescript KS– (Stratagene) carrying a human dystrophin cDNA fragment spanning the EcoRI site at base 7,002 to the EcoRI site at base 7,875 of the full-length human dystrophin cDNA sequence, cloned into the EcoRI site of the vector. Another plasmid employed was p30-2, pBluescribe (Stratagena) containing a fragment from the full-length human dystrophin cDNA spanning bases 1,455 to the EcoRI site at base 2,647, cloned into the EcoRI site of the vector. An additional vector employed was p30–1, pBluescribe (Stratagene) containing an EcoRI fragment from the full-length human dystrophin cDNA spanning bases 2,647 to 4,558, cloned into the EcoRI site of the vector. An further plasmid employed is p47–4, pBluescript KS– (Stratagene) carrying the human dystrophin cDNA EcoRI fragment spanning bases 4,452 to 7,002 of the full-length cDNA sequence, cloned into the EcoRI site of the vector. Another plasmid is p9–7, pBluescribe (Stratagene) containing bases 1–1,538 of the full-length human dystrophin cDNA. Base 1 is attached to a linker of the sequence 5' GAATTC-3' and cloned into the EcoRI site of the vector. Base 1,538 is blunt-end cloned into the PstI site of the vector, which had been destroyed by fill-in with T4 DNA polymerase. Another vector employed is p63–1, pBluescript KS– (Stratagene) carrying the human dystrophin cDNA EcoRI fragment spanning bases 7,875 to the 3' end of the full-length cDNA, cloned into the EcoRI site of the vector (the 3' end of the cDNA is ligated to a linker of the sequence 5'-GAATTC-3').

Initially, the MCK promoter plus enhancer and the minx intron were excised from pCK3 by digestion with EagI, yielding a 3.5 kb fragment that was ligated into EagI-digested pBSXA to make pBSXACK3. Truncated dystrophin cDNAs, derived from pHBMD, containing various deletions of dystrophin domains were prepared as described below. The cDNA inserts were excised from the plasmid backbone with SalI, and ligated into pBSXACK3 at the SalI site, which is located between the minx intron and the pA sequence, such that the 3' end of the cDNA was adjacent to the pA sequence. The isolation of the truncated cDNAs is described below. pBSXACK3-truncated dystrophin plasmids were digested with BssHII to release the expression vectors, which were gel purified and used to generate transgenic mice.

Isolation of ΔH2R19

A PCR product was generated by amplification of plasmid p30-2 with primers (SEQ ID NO:72)
5'-TGTGCTGCAAGGCGATTAAGTTGG-3' and (SEQ ID NO:75)
5'-GAGCTAGGTCAGGCTGCTGTGAAATCTGTGC-3'.

Primers SEQ ID NO:75 overlaps the end of repeat 3 and the beginning of hinge 3. Primer SEQ ID NO:72 corresponds to a sequence in the plasmid vector adjacent to the cloning site. A second PCR product was generated by amplification of plasmid p44-1 using primers 5'-CCAGGCTT-TACACTTTATGCTTCC-3' (SEQ ID NO:73) and 5'-GCACAGATTTCACAGCAGCCTGACCTAGCTC-3' (SEQ ID NO:74). Primer SEQ ID NO:74 is the reverse complement of primer SEQ ID NO:75. Primer SEQ ID NO:73 corresponds to a sequence in the plasmid vector adjacent to the cloning site. The PCR products were then purified by agarose gel electorphoreses, and quantified. A recombinant PCR product was then prepared by mixing together 10 ng of each of the first two PCR products, then re-PCR amplifying using only primers SEQ ID NO:72 and SEQ ID NO:73. This recombinant PCR product was then digested with NheI and KpnI, and ligated into NheI and KpnI digested pHΔSK to generate plasmid pHBMDΔH2 (NheI cuts at cDNA base 1,519, and KpnI cuts at base 7,616 of the full-length human dystrophin cDNA sequence). pHBMDΔH2 was then digested with KpnI and XbaI, and ligated to the KpnI-XbaI fragment from pHBMD (this latter fragment contains the full-length human dystrophin cDNA bases 7,616 to 12,100) to obtain plasmid pΔH2R19.

Isolation of pΔR9R16

Plasmid p44-1 was digested with EcoRI and Asp718 to excise a 610 bp cDNA insert, that was ligated into pBSX digested with EcoRI and Asp718, yielding pBSX44AE. pBSX44AE was digested with EcoRI and XbaI, and ligated to the NheI-EcoRI cDNA-containing fragment from p30-2, yielding pBSX44AE/30-2NE. Plasmid pBSX44AE/30-2NE was linearized by digestion with EcoRI, into which was ligated the EcoRI-digested recombinant PCR product ΔR9–R16. This latter recombinant PCR product was generated as follows. Plasmid p30-1 was amplified with primers SEQ ID NO:72 and 5'-CCATTTCTCAACA-GATCTTCCAAAGTCTTG-3' (SEQ ID NO:77), and plasmid p47-4 was amplified by PCR with primers SEQ ID NO:73 and 5'-CAAGACTTTGGAAGATCT-GTTGAGAAATGG-3 (SEQ ID NO:76). A recombinant PCR product (ΔR9–R16) was then prepared by mixing together 10 ng of each of the first two PCR products, then re-PCR amplifying using only primers SEQ ID NO:72 and SEQ ID NO:73. This recombinant PCR product was then digested with EcoRI, and ligated into EcoRI digested pBSX44AE/30-2NE to generate plasmid pR9R16int. Plasmid pR9R16int was digested with NcoI and Asp718, and the 3 kb cDNA fragment was isolated and ligated into NcoI and Asp718 digested pHΔSK to generate pΔR9R16.

Isolation of pΔR1R24

Plasmid p9-7 was PCR amplified with PCR primers 5'-AGTGTGGTTTGCCAGCAGTC (SEQ ID NO:80) and 5'-CAAAGTCCCTGTGGGCGTCTTCAGGAGCTTCC-3' (SEQ ID NO:79). Plasmid p63-1 was PCR amplified with primers 5' GGAAGCTCCTGAAGACGCCCACA-GGGACTTTG-3' (SEQ ID NO:78) and 5'-TGGTTGATATAGTAGGGCAC-3' (SEQ ID NO:81). A recombinant PCR product (ΔR1–R24) was then prepared by mixing together 10 ng of each of the first two PCR products, then re-PCR amplifying using only primers SEQ ID NO:80 and SEQ ID NO:81. This recombinant PCR product was then digested with SexAI and PpuMI, and ligated into SexAI and PpuMI digested pHBMD to generate plasmid pΔR1R24.

Isolation of pΔH2–H3

This clone was prepared exactly as pΔH2–R19, except that primer 5'-CAGATTTCACAGGCTGCTCTG-GCAGATTTC-3' (SEQ ID NO:82) was used in place of primer SEQ ID NO:74, and primer 5'-GAAATCTGCCAGAGCAGCCTGTGAAATCTG-3' (SEQ ID NO:84) was used in place of primer SEQ ID NO:75.

Isolation of ΔH2–R19,R20

This clone was generated from clone pΔH2R19 as follows. Plasmid p44-1 was amplified with primers SEQ ID NO:72 and 5'-TGAATCCTTTAACATAGGTACCTCCA-ACAT-3' (SEQ ID NO:85). Plasmid 63-1 was amplified with primers 5'-ATGTTGGAGGTACCTATGTTAAAGGATTCA-3' (SEQ ID NO:86) and SEQ ID NO:81. The PCR products were then purified by agarose gel electorphoreses, and quantified. A recombinant PCR product was then prepared by mixing together 10 ng of each of the first two PCR products, then re-PCR amplifying using only primers SEQ ID NO:72 and SEQ ID NO:81. This product was digested with Asp718 and BstXI, and ligated into Asp718 and BstXI digested pHBMD generating clone pBMDΔR20. The Asp718-XbaI cDNA-containing fragment from pBMDΔR20 was isolated and ligated into Asp718 and XbaI digested pΔH2R19 to generate pΔH2–R19,R20.

EXAMPLE 5

Testing Truncated Dystrophin in mdx Mice

Figure 27:
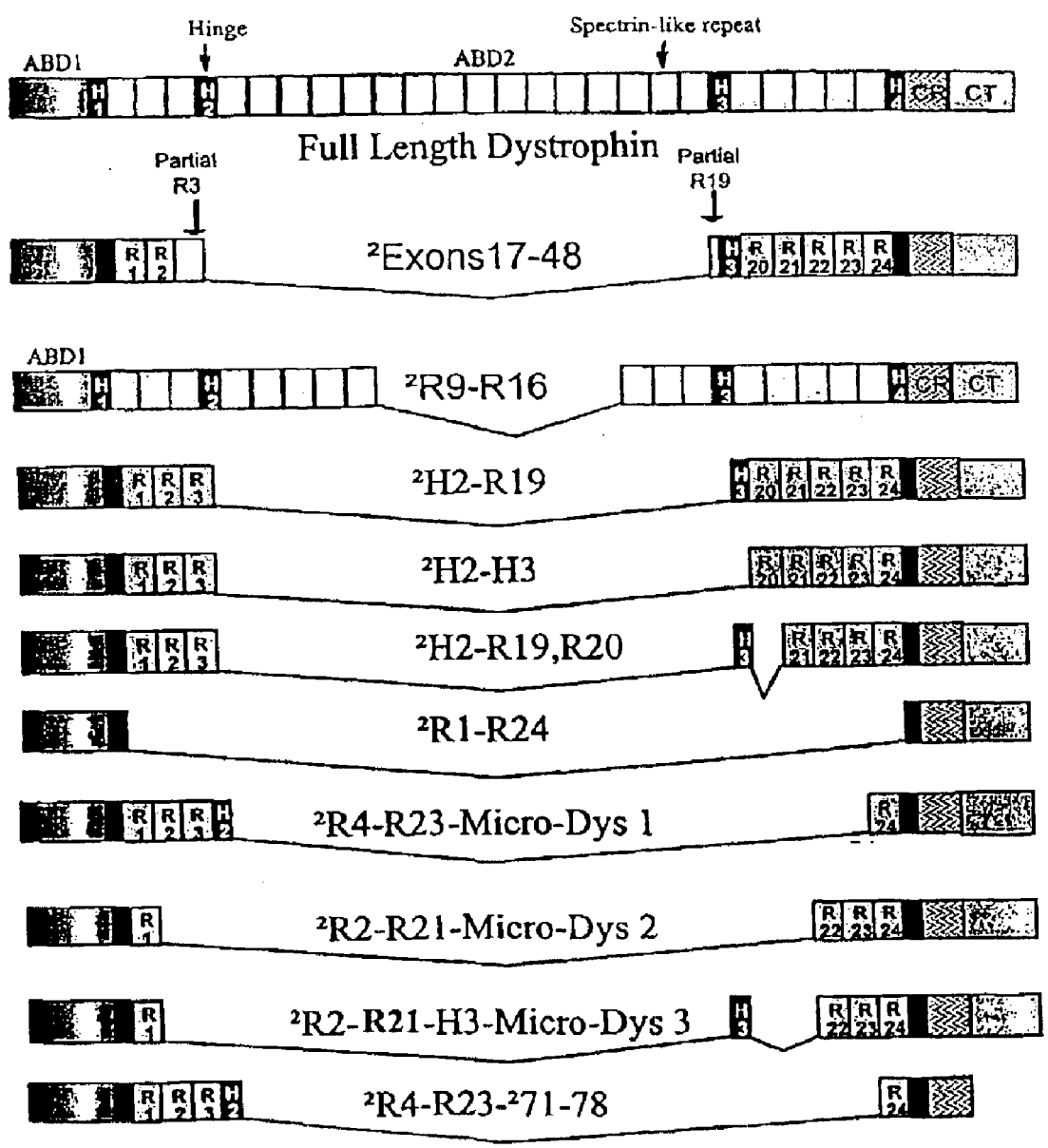
FIG. 27 shows a schematic illustration of the domains encoded by the truncated and full-length dystrophin sequences tested in Example 5.

This example describes the generation of transgenic mdx mice expressing truncated dystrophin cDNA (see above), and testing these mice in various ways to determine various measurable muscle values. A variety of dystrophin expression cassettes (FIG. 27) were used to generate transgenic mice to test their functional capacity in alleviating muscular dystrophy on the dystrophin null mdx background. FIG. 27 depicts the truncated dystrophin cDNA sequences tested, all of which were linked to an regulatory regions, a minx intron, and the SV40 polyadenylation sequence (the 4-repeat constructs employed the HSA actin promoter, See Crawford et al., *J. Cell. Biol.*, 150:1399, 2000; and the remaining sequences employed an MCK enhancer and promoter, see Niwa et al., *Genes Dev.* 4:1552, 1990). Each of these constructs was released by digestion from plasmid hosts, were gel purified, and used to generate transgenic mice.

Excised expression cassettes injected into wild type C57B1/10×SJL/J F2 hybrid embryos, and F[o] mice were screened by PCR analysis of DNA isolated from tail snips. Positive F[o] mice were backcrossed onto the C57B1/10mdx background, and individual mouse lines were tested for dystrophin expression by immunofluorescent analysis with dystrophin antibodies for of expression in skeletal muscle fibers. Lines that displayed uniform expression of dystrophin in muscle fibers were selected for further analysis. These lines were further backcrossed onto the mdx mouse background before analysis of dystrophin expression, muscle function and morphology.

A. Truncated Dystrophin cDNAs are Expressed at Various Levels in Muscles of Transgenic mdx Mice.

Muscle extracts were analyzed by western (immuno) blot analysis to determine the amount of dystrophin made in different muscles of the transgenic mdx mice. For these studies, total protein was extracted from the quadriceps and diaphragm muscles of control and transgenic mice, and protein concentrations were determined using the Coomassie Plus Protein Assay Reagent (Pierce). One hundred micrograms of each sample was electrophoresed on a 6% polyacrylamidc/SDS gel (29.7:0.3/acryl:bis), transferred for 2 hours at 75 volts onto Biotrace Nitrocellulose (Gelman Science) in 1× Tris-Glycine, 20% methanol, 0.05% SDS, using a wet-transfer apparatus (Hoefer). Membranes were blocked in 10% non-fat dry milk, 1% normal goat serum, and 0.1% Tween-20, and hybridized with DYS1 (Novacastra) at a 1/1000 dilution for 2 hours at room temperature, washed, and then probed with horse radish peroxidase conjugated anti-mouse antibodies at a 1/2,000 dilution (Cappel). Blots were developed using the ECL chemiluminescence system (Amersham). All incubations contained 1% normal goat serum and 0.1% Tween-20. The results of the western blot indicated that R9–R16 was poorly expressed in this line of mice, especially in the diaphragm, and that H2–H3 was very poorly expressed in the diaphragm.

B. Truncated Dystrophin cDNAs Confer Various Degrees of Protection on Muscles of Transgenic mdx Mice.

Various muscle groups from the different lines of transgenic mice expressing truncated dystrophins were examined for morphological abnormalities, and for expression of dystrophin by indirect immunofluorescence (IF) in individual fibers. IF analysis was performed as follows. Skeletal muscle was removed from control and transgenic animals, cut into strips, embedded in Tissue-tek OCT mounting media (Miles, Inc.), and frozen quickly in liquid nitrogen-cooled isopentane. Seven micrometer sections were blocked with 1% gelatin in KPBS for 15 minutes, washed in KPBS+0.2% gelatin (KPBSG), and incubated for 2 hours in KPBSG+1% normal goat serum with affinity-purified dystrophin antibody 18-4 (Cox et al., *Nature*, 364:725–729, 1993) at a dilution of 1/1000. After washing, the slides were incubated for 1 hour with either biotin-labeled goat anti-rabbit polyclonal antibodies (Pierce), washed again, and incubated with FITC (fluorescein isothiocynate)-conjugated streptavidin. After a final wash, Vectashield (Vector Laboratories, Inc.) with DAPI was applied and sections were photographed through a dual bandpass filter under 40× magnification using a Nikon E1000 microscope.

Morphological analysis of the muscles was performed as follows. Muscle groups from among the following types were chosen for analysis: Quadriceps (Quad), soleus, extensor digitorum longus (EDL), tibialis anterior (TA), and diaphragm muscles. Selected muscles were removed from mice, frozen in liquid nitrogen cooled O.C.T. embedding medium (Tissue-Tek), and cut into 7 μm sections. After fixing in 3.7% formaldehyde, sections were stained in hematoxylin and eosin-phloxine. Stained sections were imaged with a Nikon E1000 microscope and photographed.

The results of this analysis show that micro-dystrophin expression (ΔR4R23 transgene) in the diaphragm prevents the onset of muscular dystrophy in mdx mice. In particular, micro-dystrophin transgenic and wild-type C57B1/10 diaphragm sections stained with hematoxylin and eosin (H&E) show morphologically healthy muscle without areas of fibrosis, necrosis, mononuclear cell infiltration, or centrally located nuclei. Conversely, the mdx diaphragm displays a high level of dystrophic morphology by H&E. Also, immuno-fluorescence, using anti-dystrophin polyclonal primary antisera, demonstrates that micro-dystrophin transgenes are expressed at the sarcolemmal membrane in a similar fashion to that of wild-type dystrophin, while mdx mice do not express dystrophin.

H & E staining also shows that truncated dystrophins with 8 or 16 spectrin-like repeats have varying abilities to prevent dystrophy in the diaphragm of transgenic mdx mice. The H2R19 maintains normal muscle morphology that is not different from wild-type C57B1/10 muscle. The ΔH2R19 muscle displays a very low percentage of centrally nucleated fibers, while the ΔH2–R19,R20 and ΔR9–16 constructs display percentages intermediate between ΔH2–R19 and mdx (see FIG. 28). The mdx diaphragm had a large number of centrally nucleated fibers, many necrotic fibers, and large areas of mono-nuclear cell infiltration and fibrosis.

The results also show that quadriceps muscle fibers expressing micro-dystrophin transgene (ΔR4R23 transgene) display normal morphology and exclude Evans Blue Dye. Micro-dystrophin transgenic mdx or C57B1/10 quadriceps sections stained with hematoxylin and eosin (H&E) display morphologically healthy muscle without areas of necrosis, fibrosis, mononuclear cell infiltration, or centrally-located nuclei, as opposed to sections of mdx muscle. The high abundance of central nuclei and mononuclear immune cell infiltration are evidence of muscle cell necrosis. Immunofluorescence results indicate that micro-dystrophins display a subsarcolemmal expression pattern like that of wild-type dystrophin, while mdx mice do not express dystrophin. Evans Blue Dye (EBD) uptake is an indication of a damaged myofiber. For analysis of EBD uptake, mice were tail vein injected with 150 μl of a solution containing 10 mg/ml Evans blue dye in PBS (150 mM NaCl, 50 mM Tris pH 7.4). After three hours, the animals were euthanized and mouse tissues were either fixed in 3.7% formaldehyde/0.5% glutaraldehyde to observe gross dye uptake, or frozen unfixed in O.C.T. embedding medium. To examine Evans blue uptake by individual fibers, 7 μm thick frozen sections were fixed in cold acetone and analyzed by fluorescence microscopy. The results of this testing indicate that fibers expressing micro-dystrophin or wild-type dystrophin exclude EBD, and that damaged mdx muscle cell membranes are permeable to Evans Blue dye.

Figure 28:
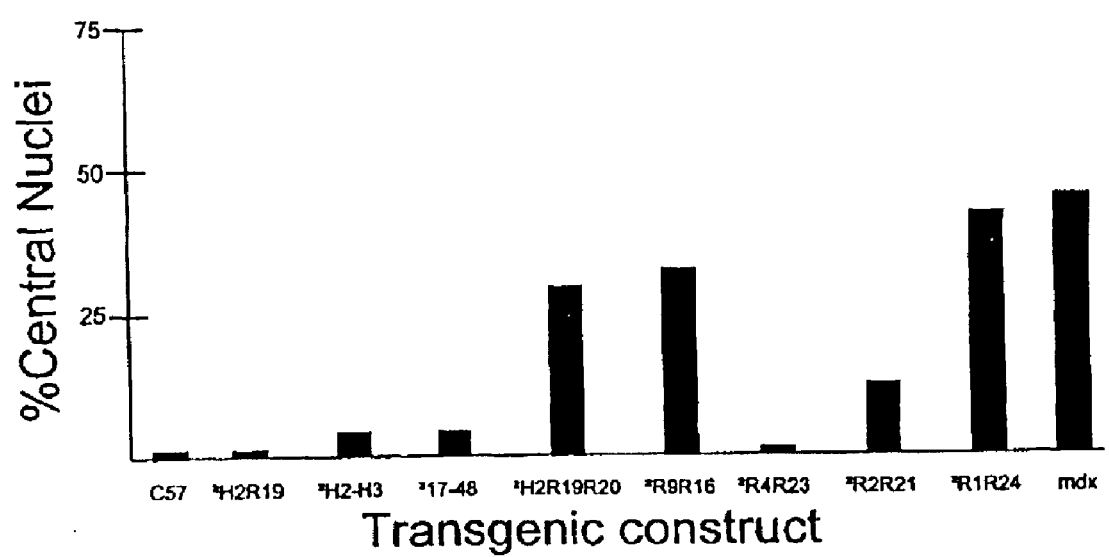
FIG. 28 is a graph showing the percentage of myofibers in quadricep muscles of 3 month old mice that display centrally-located nuclei in the indicated strains of transgenic mice.

A hallmark of dystrophy in mdx mice is the presence of large numbers of centrally-nucleated muscle fibers, reflecting cycles of fiber degeneration and regeneration. To estimate the degree of myofiber regeneration occurring in the transgenic mice, centrally-nucleated fibers were counted from quadriceps muscles in age-matched wild-type, mdx, and transgenic mdx mice (FIG. 28). To determine the percentage of fibers containing central nuclei, the number of muscle fibers with centrally-located nuclei was divided by the total number of muscle fibers.

Expression of 8 or 4 repeat micro-dystrophin transgenes on the mdx background significantly reduces the percentage of fibers with centrally-located nuclei to wild-type or near wild-type levels (FIG. 28). Dystrophin molecules with zero repeats are unable to correct the mdx phenotype by this assay. The best constructs were observed to be the 8 repeat H2–R19 and the 4 repeat R2–R23 constructs. Greater percentages of centrally nucleated fibers were observed in mice expression the exon 17–48 deletion, the 4 repeat R2R21 construct, the 7 repeat H2R19,R20 construct, the 16 repeat R9R16 construct, and the zero repeat R1R24 construct (FIG. 28). The results from the R9R16 construct likely do not reflect the full functional capacity of the 16 repeat dystrophin since this line of mice expressed very low levels of the truncated dystrophin protein. All other muscles expressed levels of dystrophin that have been shown to be capable of preventing dystrophy if the expressed protein is functional (Phelps et al., *Hum Mol Genet*; 4:1251–1258, 1995).

The functional capacity of the truncated dystrophins was also assessed by measuring muscle contractile properties in the transgenic mdx mice. Contractile properties of muscles from transgenic mice were compared with those of C57B1/10 wild type and mdx mice. The samples included 4–8 muscles each from the tibialis anterior (TA), extensor digitorum longus (EDL) or diaphragm. Mice were deeply anesthetized with avertin and each muscle was isolated and dissected free from the mouse. After removal of the limb muscles, the mice were euthanized with the removal of the diaphragm muscle. The muscles were immersed in a bath filled with oxygenated buffered mammalian Ringer's solution (137 mM NaCl, 24 mM NaHCO$_3$, 11 mM glucose, 5 mM KCl, 2 mM CaCl$_2$, 1 mM MgSO$_4$, 1 mM NaH$_2$PO$_4$, and 0.025 mM tubocurarine chloride, pH 7.4). For each muscle, one tendon was tied to a servomotor and the other tendon to a force transducer. Muscles were stretched from slack length to the optimal length for force development and then stimulated at a frequency that produced absolute isometric tetanic force (mN). Following the measurements of the contractile properties, the muscles were removed from the bath, blotted and weighed to determine muscle mass. Specific force (kN/m2) was calculated by dividing absolute force by total fiber cross sectional area.

FIG. 29 shows that the 8 repeat dystrophin encoded by H2–R19 supports normal force development in both the diaphragm (FIG. 29a) and EDL muscle (FIG. 29b). In contrast, previous studies showed that the exon 17–48 construct, which encodes a dystrophin with 8.25 spectrin-like repeats, supports only 90–95% of normal force development in the diaphragm (Phelps et al., *Hum Mol Genet*, 4:1251–1258, 1995). The 8 repeat dystrophin lacking a central hinge (H2–H3), and tile 7 repeat dystrophin (H2–R19,R20) both fail to support significant force generation compared with dystrophic mdx muscles. The results from the R9–R16 construct likely do not reflect the full functional capacity of the 16 repeat dystrophin, since this line of mice expressed very low levels of the truncated dystrophin.

FIG. 30 shows that the micro-dystrophin transgenic mdx mice develop less specific force than do C57B1/10 mice in the TA, but near wild-type levels in the diaphragm. Micro-dys 1 and −2 refer to transgenes ΔR4–R23, and ΔR2–R21, respectively. FIG. 30A shows that C57B1/10 mice display significantly higher specific force than both transgenic lines and mdx mice in the tibialis anterior (TA) muscle. Data are presented as means ±standard error of the means (s.e.m.) with each bar representing 6 to 8 TA muscles. ANOVA statistical testing was performed. (* indicates significance from C57B1/10, $p<0.01$; s indicates significance from C57B1/10, $p<0.05$). FIG. 30B shows that mice expressing Micro-dys 1 develop wild type levels of specific force in the diaphragm, while mice expressing Micro-dys 2 develop ~22% less specific force by the same assay when compared with C57B1/10. Both lines of mice develop more specific force than mdx mice in the diaphragm. Data are presented as the percentage of wild type.

Figure 31:
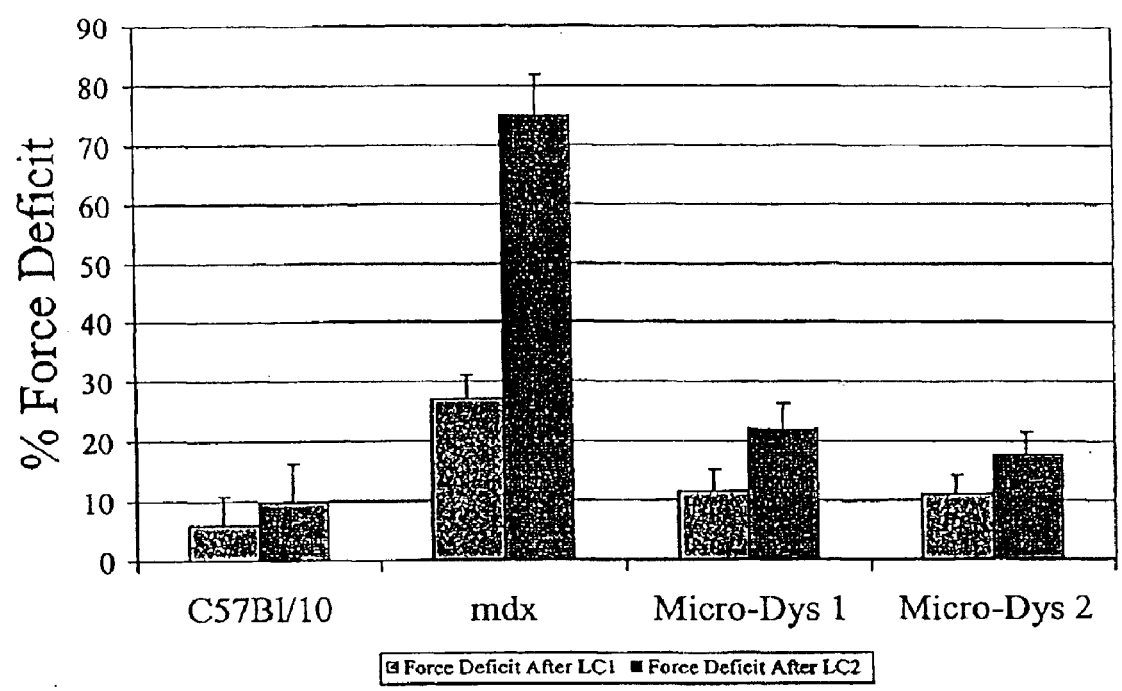
FIG. 31 is a graph showing the percentage of force generating capacity lost after 1 or 2 lengthening contractions of the tibialis anterior muscle of the indicated strains of dystrophin transgenic mdx mice and control mice.

Dystrophic mice are susceptible to contraction-induced injury (Petrof, et al., *Proc. Natl. Acad. Sci. USA.* 90:3710–3714, 1993). In this part of the example tested whether the 4 repeat dystrophin clones would protect muscles of transgenic mdx mice from contraction induced injuries. To test contraction-induced injury, an experimental protocol consisting of two muscle stretches was performed in live, anesthetized animals. The distal tendon of the TA was cut and secured to the lever arm of a servomotor that monitors position and force produced by the muscle. Stimulation voltage and optimal muscle length (L$_o$) for force production were determined. The muscle was maximally stimulated and then stretched 40% greater than L$_o$ (LC1) for 300 milliseconds. A second lengthening contraction was performed 10 seconds later (LC2). The maximum force that the muscle was able to produce after each stretch was measured and expressed as a percentage of the force produced before stretch. Mdx mice expressing micro-dystrophins were significantly protected from the dramatic force deficit produced after a lengthening contraction compared with mdx mice (FIG. 31). Micro-dys 1 and -2 refer to transgenes ΔR4–R23, and ΔR2–R21, respectively. Furthermore, there was no significant difference between either micro-dystrophin construct studied in this assay and C57B1/10 mice following the second, most damaging lengthening contraction. Data are presented as means±s.e.m. with each bar representing between 6 and 8 TA muscles from 9–11 week old mice.

C. Truncated 4 Repeat Dystrophin cDNAs Restore the Ability to Run Long Distances to mdx Mice.

Figure 32:
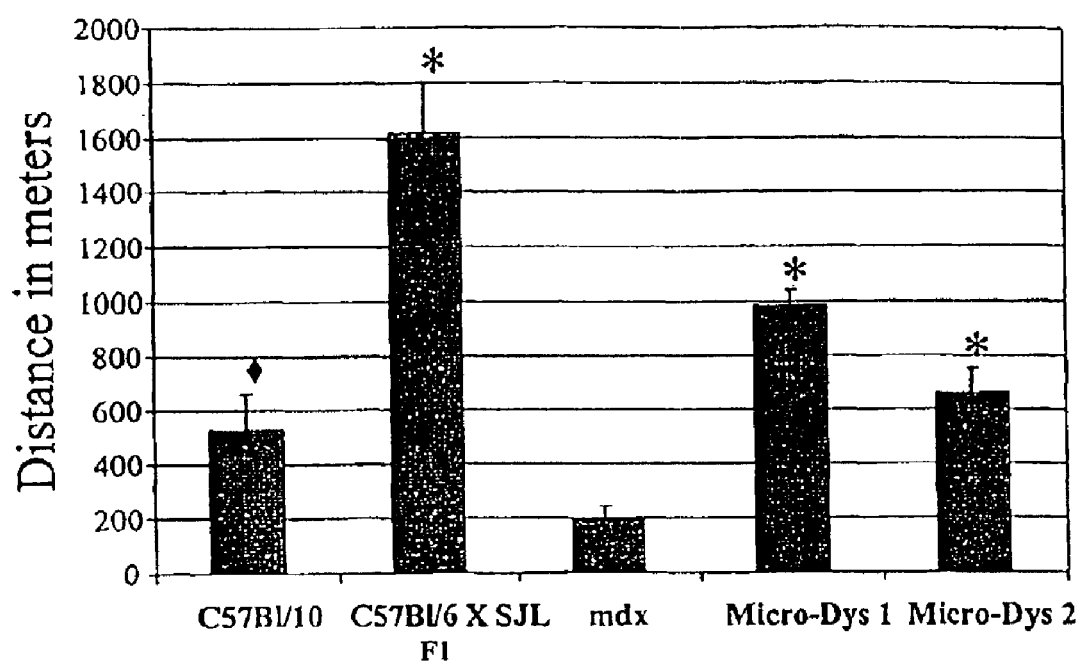
FIG. 32 is a graph showing the total distance run on a treadmill by animals from the indicated strains of dystrophin transgenic mdx mice and control mice.

We have observed that mdx mice are not able to run for long distances on a treadmill, as compared to wild-type mice (see below). Therefore, mice expressing four repeat dystrophins were compared with wild-type and mdx mice for ability to run for extended times on a treadmill. The exercising protocol utilized a six lane, enclosed treadmill with a shock grid to allow forced running at a controlled rate. C57B1/10, C57B1/6×SJL F1, mdx or transgenic mdx mice were run at a 15 degree downward angle to induce damaging eccentric muscle contractions. Mice were given a 15 minute acclimation period prior to exercise, and then ran at 10 meters/minute with a subsequent 5 m/min increase in rate every 10 minutes until exhaustion. Exhaustion was determined to be the time at which a mouse spent more than 5 seconds sitting on the shock grid without attempting a re-entry to the treadmill. As shown in FIG. 32, both lines of four repeat transgenic mice ran significantly farther than mdx mice. Micro-dys 1 and -2 refer to transgenes ΔR4–R23, and ΔR2–R21, respectively. Micro-dystrophin transgenic mice are a genetic mixture of C57B1/6×SJL, and C57B1/10 strains, and ran an intermediate distance between the two wild-type lines. Data are presented as means ±s.e.m. ANOVA statistical analyses were performed. (* indicates values significantly different from mdx line, $p<0.01$; s indicates values significantly different from mdx line, $p<0.05$).

D. Micro-dystrophin Transgenic mdx Mice do not Display Hypertrophy

As a way to measure the functional capacity of the four-repeat dystrophins, we weighed both whole mice and dissected tibialis anterior muscles from age matched transgenic and control mice. The results shown in FIG. 33 show that the micro-dystrophin transgenic mdx mice do not display the muscle hypertrophy normally observed in mdx mice. FIG. 33A shows that three month old micro-dystrophin transgenic mdx mice weighed significantly less than age-matched mdx control mice. FIG. 11B shows that tibialis anterior (TA) muscle masses in mdx mice were significantly higher than control muscle masses in C57B1/10 and in both lines of mdx mice expressing different micro-dystrophin transgenes. Data are presented as means ±s.e.m. with each bar representing between 3 and 4 mice. ANOVA statistical analyses were performed (* indicates difference from mdx line, $p<0.01$; Y indicates difference from C57B1/10 line, $p<0.01$; s indicates difference from C57B1/10 line, $p<0.05$). Micro-dys 1 and -2 refer to transgenes ΔR4–R23, and ΔR2–R21, respectively.

EXAMPLE 6

Mini-dystrophin-containing Adeno-associated Viral Vectors

Figure 34:
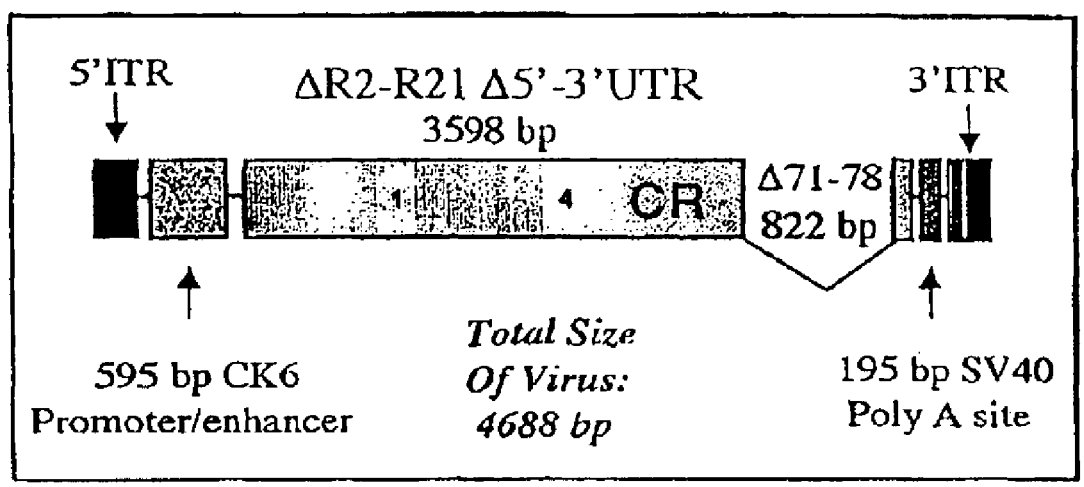
FIG. 34 is a schematic illustration of the structure of a mini-dystrophin expression cassette inserted into an adeno-associated viral vector.

This example describes a construct that could be made in order to allow adeno-associated virus to express a mini-dystrophin peptide in a target muscle cells. FIG. 34 shows a schematic illustration of a plasmid vector containing the adeno-associated virus inverted terminal repeats (AAV-ITRs), the muscle promoter plus enhancer fragment known as CK6 (SEQ ID NO:61, the ΔR2–R21 four repeat dystrophin cDNA (SEQ ID NO:40) with a further deletion of sequences encoded on exons 71–78, plus a 195 base pair SV40 polyadenylation signal that would have a total insert size of approximately 4.7 kb. The cloning capacity of adeno-associated viral vectors is approximately 4.9 kb. As such, the construct could be efficiently packaged into AAV viral particles (e.g. this plasmid construct could be used to transfect cells such that AAV expressing mini-dystrophin peptide is expressed). These AAV then, for example, may be administered to a subject with DMD or BMD (i.e. gene therapy to correct a muscle deficiency in a subject).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in material science, chemistry, and molecular biology or related fields are intended to be within the scope of the following claims.

We claim:

1. A composition comprising nucleic acid encoding a mini-dystrophin peptide, wherein said mini-dystrophin peptide comprises a spectrin-like repeat domain comprising 4 dystrophin spectrin-like repeats, wherein said mini-dystrophin peptide contains no more than 4 dystrophin spectrin-like repeats.

2. The composition of claim 1, wherein said dystrophin spectrin-like repeats are human dystrophin spectrin-like repeats.

3. The composition of claim 1, wherein said mini-dystrophin-peptide is capable of increasing a measurable muscle value in a DMD animal model by at least 20% of the wild type value, wherein said measurable muscle value is a diaphragm specific force value.

4. The composition of claim 3, wherein said mini-dystrophin peptide is capable of increasing said diaphragm specific force value in a DMD animal model by at least 30% of the wild-type value.

5. The composition of claim 1, wherein said nucleic acid comprises an expression vector.

6. The composition of claim 1, wherein said nucleic acid comprises spectrin-like repeat encoding sequences.

7. The composition of claim 6, wherein said spectrin-like repeat encoding sequences are precise spectrin-like repeat encoding sequences.

8. The composition of claim 1, wherein said nucleic acid comprises an actin-binding domain encoding sequence.

9. The composition of claim 8, wherein said actin binding domain comprises at least a portion of SEQ ID NO:6.

10. The composition of claim 1, wherein said nucleic acid comprises a β-dystroglycan binding domain.

11. The composition of claim 10, wherein said β-dystroglycan binding domain comprises at least a portion of a dystrophin hinge 4 encoding sequence, and at least a portion of a dystrophin cysteine-rich domain encoding sequence.

12. The composition of claim 6, wherein said spectrin-like repeat encoding sequences are selected from the group consisting of SEQ ID NOS:8–10, 12–27, and 29–33.

13. The composition of claim 1, wherein said nucleic acid contains less than 75% of a wild type dystrophin 5' untranslated region.

14. The composition of claim 1, wherein said mini-dystrophin peptide further comprises a substantially deleted dystrophin C-terminal domain.

15. The composition of claim 1, wherein said nucleic acid contains less than 50% of a dystrophin 3' untranslated region.

16. A composition comprising nucleic acid encoding a mini-dystrophin peptide, wherein said mini-dystrophin peptide comprises i) a spectrin-like repeat domain comprising 4 dystrophin spectrin-like repeats, ii) an actin-binding domain, and iii) a β-dystroglycan binding domain; and wherein said mini-dystrophin peptide contains no more than 4 dystrophin spectrin-like repeats.

17. The composition of claim 16, wherein said mini-dystrophin-peptide is capable of altering increasing a measurable muscle value in a DIVID animal model by at least 20% of the wild type value wherein said measurable muscle value is a diaphragm specific force value.

18. The composition of claim 17, wherein said mini-dystrophin peptide is capable of increasing said diaphragm specific force value in a DMD animal model by at least 30% of the wild-type value.

19. The composition of claim 16, wherein said nucleic acid is less than 5.0 kb in length.

20. A composition comprising nucleic acid encoding a mim-dystrophin peptide, wherein said mini-dystrophin peptide comprises a spectrin-like repeat domain comprising 8 dystrophin spectrin-like repeats, wherein said mini-dystrophin peptide contains no more than 8 dystrophin spectrin-like repeats.

21. The composition of claim 20, wherein said dystrophin spectrin-like repeats are human dystrophin spectrin-like repeats.

22. The composition of claim 20, wherein said mini-dystrophin-peptide is capable of altering a measurable muscle value in a DMD animal model by at least 20% of the wild type value.

23. The composition of claim 16, wherein said nucleic acid contains less than 50% of a dystrophin 3+ untranslated region.

24. The composition of claim 1, wherein said mini-dystrophin peptide further comprises dystrophin hinge region 1 and dystrophin hinge region 4.

25. The composition of claim 24, wherein said mini-dystrophin further comprises dystrophin hinge region 2 or dystrophin hinge region 3.

26. The composition of claim 16, wherein said mini-dystrophin peptide further comprises dystrophin hinge region 1 and dystrophin hinge region 4.

27. The composition of claim 26, wherein said mini-dystrophin further comprises dystrophin hinge region 2 or dystrophin hinge region 3.

28. The composition of claim 1, wherein said nucleic acid is less than 5.0 kb in length.

29. The composition of claim 5, wherein said expression vector comprises an adeno-associated viral sequence, and wherein said nucleic acid comprises a promoter.

30. The composition of claim 29, wherein said promoter is an MCK promoter.

31. The composition of claim 16, wherein said nucleic acid comprises an adeno-associated viral sequence and a promoter.

32. The composition of claim 31, wherein said promoter comprises an MCK promoter.

33. The composition of claim 1, wherein said 4 dystrophin spectrin-like repeats are selected from the group consisting of: dystrophin spectrin-like repeat number 1, dystrophin spectrin-like repeat number 2, dystrophin spectrin-like repeat number 3, dystrophin spectrin-like repeat number 22, dystrophin spectrin-like repeat number 23, and dystrophin spectrin like repeat number 24.

34. The composition of claim 16, wherein said 4 dystrophin spectrin-like repeats are selected from the group consisting of: dystrophin spectrin-like repeat number 1, dystrophin spectrin-like repeat number 2, dystrophin spectrin-like repeat number 3, dystrophin spectrin-like repeat number 22, dystrophin speetrin-like repeat number 23, and dystrophin spectrin like repeat number 24.

* * * * *

SEQUENCE LISTING

```
<160> NUMBER OF SEQ ID NOS: 96

<210> SEQ ID NO 1
<211> LENGTH: 13957
<212> TYPE: DNA
<213> ORGANISM: Homo sapiens

<400> SEQUENCE: 1
gggattccct cactttcccc ctacaggact cagatctggg aggcaattac cttcggagaa      60
aaacgaatag gaaaaactga agtgttactt tttttaaagc tgctgaagtt tgttggtttc     120
tcattgtttt taagcctact ggagcaataa agtttgaaga acttttacca ggtttttttt     180
```

-continued

```
atcgctgcct tgatatacac ttttcaaaat gctttggtgg aagaagtag aggactgtta    240 tgaaagagaa gatgttcaaa agaaaacatt cacaaaatgg gtaaatgcac aatttctaa    300 gtttgggaag cagcatattg agaacctctt cagtgaccta caggatggga ggcgcctcct    360
agacctcctc gaaggcctga cagggcaaaa actgccaaaa gaaaaaggat ccacaagagt    420
tcatgccctg aacaatgtca acaaggcact gcgggttttg cagaacaata atgttgattt    480
agtgaatatt ggaagtactg acatcgtaga tggaaatcat aaactgactc ttggtttgat    540
ttggaatata atcctccact ggcaggtcaa aaatgtaatg aaaaatatca tggctggatt    600
gcaacaaacc aacagtgaaa agattctcct gagctgggtc cgacaatcaa ctcgtaatta    660
tccacaggtt aatgtaatca acttcaccac cagctggtct gatggcctgg ctttgaatgc    720
tctcatccat agtcataggc cagacctatt tgactggaat agtgtggttt gccagcagtc    780
agccacacaa cgactggaac atgcattcaa catcgccaga tatcaattag gcatagagaa    840
actactcgat cctgaagatg ttgataccac ctatccagat aagaagtcca tcttaatgta    900
catcacatca ctcttccaag ttttgcctca acaagtgagc attgaagcca tccaggaagt    960
ggaaatgttg ccaaggccac ctaaagtgac taaagaagaa catttttcagt tacatcatca   1020 aatgcactat tctcaacaga tcacggtcag tctagcacag ggatatgaga gaacttcttc   1080
ccctaagcct cgattcaaga gctatgccta cacacaggct gcttatgtca ccacctctga   1140
ccctacacgg agcccatttc cttcacagca tttggaagct cctgaagaca agtcatttgg   1200
cagttcattg atggagagtg aagtaaaacct ggaccgttat caaacagctt tagaagaagt   1260
attatcgtgg cttctttctg ctgaggacac attgcaagca caaggagaga tttctaatga   1320
tgtggaagtg gtgaaagacc agtttcatac tcatgagggg tacatgatgg atttgacagc   1380
ccatcagggc cgggttggta atattctaca attgggaagt aagctgattg gaacaggaaa   1440
attatcagaa gatgaagaaa ctgaagtaca agagcagatg aatctcctaa attcaagatg   1500
ggaatgcctc agggtagcta gcatggaaaa acaaagcaat ttacatagag ttttaatgga   1560
tctccagaat cagaaactga aagagttgaa tgactggcta acaaaaacag aagaaagaac   1620
aaggaaaatg gaggaagagc ctcttggacc tgatcttgaa gacctaaaac gccaagtaca   1680
acaacataag gtgcttcaag aagatctaga acaagaacaa gtcagggtca attctctcac   1740
tcacatggtg gtggtagttg atgaatctag tggagatcac gcaactgctg ctttggaaga   1800
acaacttaag gtattgggag atcgatgggc aaacatctgt agatggacag aagaccgctg   1860
ggttctttta caagacatcc ttctcaaatg gcaacgtctt actgaagaac agtgcctttt   1920
tagtgcatgc ctttcagaaa aagaagatgc agtgaacaag attcacacaa ctggctttaa   1980
agatcaaaat gaaatgttat caagtcttca aaaactggcc gttttaaaag cggatctaga   2040
aaagaaaaag caatccatgg gcaaactgta ttcactcaaa caagatcttc tttcaacact   2100
gaagaataag tcagtgaccc agaagacgga agcatggctg ataactttg cccggtgttg   2160 ggataattta gtccaaaaac ttgaaaagag tacagcacag atttcacagg ctgtcaccac   2220
cactcagcca tcactaacac agacaactgt aatggaaaca gtaactacgg tgaccacaag   2280
ggaacagatc ctggtaaagc atgctcaaga ggaacttcca ccaccacctc cccaaaagaa   2340
gaggcagatt actgtggatt ctgaaattag gaaaggttg atgttgata taactgaact   2400 tcacagctgg attactcgct cagaagctgt gttgcagagt cctgaatttg caatcttcg    2460 gaaggaaggc aacttctcag acttaaaaga aaaagtcaat gccatagagc gagaaaaagc   2520
```

```
tgagaagttc agaaaactgc aagatgccag cagatcagct caggccctgg tggaacagat    2580
ggtgaatgag ggtgttaatg cagatagcat caaacaagcc tcagaacaac tgaacagccg    2640
gtggatcgaa ttctgccagt tgctaagtga gagacttaac tggctggagt atcagaacaa    2700
catcatcgct ttctataatc agctacaaca attggagcag atgacaacta ctgctgaaaa    2760
ctggttgaaa atccaaccca ccaccccatc agagccaaca gcaattaaaa gtcagttaaa    2820
aatttgtaag gatgaagtca accggctatc aggtcttcaa cctcaaattg aacgattaaa    2880
aattcaaagc atagccctga agagaaagg acaaggaccc atgttcctgg atgcagactt     2940
tgtggccttt acaaatcatt ttaagcaagt cttttctgat gtgcaggcca gagagaaga    3000
gctacagaca attttttgaca ctttgccacc aatgcgctat caggagacca tgagtgccat   3060
caggacatgg gtccagcagt cagaaaccaa actctcccata cctcaactta gtgtcaccga  3120
ctatgaaatc atggagcaga gactcgggga attgcaggct ttacaaagtt ctctgcaaga   3180
gcaacaaagt ggcctatact atctcagcac cactgtgaaa gagatgtcga agaaagcgcc   3240
ctctgaaatt agccggaaat atcaatcaga atttgaagaa attgagggac gctggaagaa   3300
gctctcctcc cagctggttg agcattgtca aagctagag gagcaaatga ataaactccg    3360
aaaaattcag aatcacatac aaaccctgaa gaaatggatg gctgaagttg atgtttttct   3420
gaaggaggaa tggcctgccc ttggggattc agaaattcta aaaagcagc tgaaacagtg    3480
cagactttta gtcagtgata ttcagacaat tcagcccagt ctaaacagtg tcaatgaagg   3540
tgggcagaag ataaagaatg aagcagagcc agagtttgct tcgagacttg agacagaact   3600
caaagaactt aacactcagt gggatcacat gtgccaacag gtctatgcca gaaaggaggc   3660
cttgaaggga ggtttggaga aaactgtaag cctccagaaa gatctatcag agatgcacga   3720
atggatgaca caagctgaag aagtatctct tgagagagat tttgaatata aaactccaga   3780
tgaattacag aaaagcagttg aagagatgaa gagagctaaa aagaggccc aacaaaaaga    3840
agcgaaagtg aaactcctta ctgagtctgt aaatagtgtc atagctcaag ctccacctgt   3900
agcacaagag gccttaaaaa aggaacttga aactctaacc accaactacc agtggctctg   3960
cactaggctg aatgggaaat gcaagacttt ggaagaagtt tgggcatgtt ggcatgagtt   4020
attgtcatac ttggagaaag caaacaagtg gctaaatgaa gtagaatta aacttaaaac    4080
cactgaaaac attcctggcg gagctgagga aatctctgag gtgctagatt cacttgaaaa   4140
tttgatgcga cattcagagg ataacccaaa tcagattcgc atattggcac agaccctaac   4200
agatggcgga gtcatggatg agctaatcaa tgaggaactt gagacattta attctcgttg   4260
gagggaacta catgaagagg ctgtaaggag gcaaaagttg cttgaacaga gcatccagtc   4320
tgcccaggag actgaaaaat ccttacactt aatccaggag tccctcacat tcattgacaa   4380
gcagttggca gcttatattg cagacaaggt ggacgcagct caaatgcctc aggaagccca   4440
gaaaatccaa tctgatttga caagtcatga gatcagttta aagaaatga agaaacataa    4500
tcagggaag gaggctgccc aaagagtcct gtctcagatt gatgttgcac agaaaaatt     4560
acaagatgtc tccatgaagt ttcgattatt ccagaaacca gccaattttg agctgcgtct   4620
acaagaaagt aagatgattt tagatgaagt gaagatgcac ttgcctgcat tggaaacaaa   4680
gagtgtggaa caggaagtag tacagtcaca gctaaatcat tgtgtgaact tgtataaaag   4740
tctgagtgaa gtgaagtctg aagtggaaat ggtgataaag actggacgtc agattgtaca   4800
gaaaagcag acgaaaaatc ccaaagaact tgatgaaaga gtaacagctt tgaaattgca    4860
ttataatgag ctgggagcaa aggtaacaga aagaaagcaa cagttggaga aatgcttgaa   4920
```

```
attgtcccgt aagatgcgaa aggaaatgaa tgtcttgaca gaatggctgg cagctacaga    4980
tatggaattg acaaagagat cagcagttga aggaatgcct agtaatttgg attctgaagt    5040
tgcctgggga aaggctactc aaaaagagat tgagaaacag aaggtgcacc tgaagagtat    5100
cacagaggta ggagaggcct tgaaaacagt tttgggcaag aaggagacgt tggtggaaga    5160
taaactcagt cttctgaata gtaactggat agctgtcacc tcccgagcag aagagtggtt    5220
aaatcttttg ttggaatacc agaaacacat ggaaactttt gaccagaatg tggaccacat    5280
cacaaagtgg atcattcagg ctgacacact tttggatgaa tcagagaaaa agaaacccca    5340
gcaaaaagaa gacgtgctta agcgtttaaa ggcagaactg aatgacatac gcccaaaggt    5400
ggactctaca cgtgaccaag cagcaaactt gatggcaaac cgcggtgacc actgcaggaa    5460
attagtagag ccccaaatct cagagctcaa ccatcgattt gcagccattt cacacagaat    5520
taagactgga aaggcctcca ttcctttgaa ggaattggag cagtttaact cagatataca    5580
aaaattgctt gaaccactgg aggctgaaat tcagcagggg gtgaatctga agaggaaga    5640 cttcaataaa gatatgaatg aagacaatga gggtactgta aaagaattgt tgcaaagagg    5700
agacaactta caacaaagaa tcacagatga gagaaagaga gaggaaataa agataaaaca    5760
gcagctgtta cagacaaaac ataatgctct caaggatttg aggtctcaaa gaagaaaaaa    5820
ggctctagaa atttctcatc agtggtatca gtacaagagg caggctgatg atctcctgaa    5880
atgcttggat gacattgaaa aaaattagc cagcctacct gagcccagag atgaaaggaa    5940
aataaaggaa attgatcggg aattgcagaa gaagaaagag gagctgaatg cagtgcgtag    6000
gcaagctgag ggcttgtctg aggatggggc cgcaatggca gtggagccaa ctcagatcca    6060
gctcagcaag cgctggcggg aaattgagag caaatttgct cagtttcgaa gactcaactt    6120
tgcacaaatt cacactgtcc gtgaagaaac gatgatggtg atgactgaag acatgccttt    6180
ggaaatttct tatgtgcctt ctacttattt gactgaaatc actcatgtct cacaagccct    6240
attagaagtg gaacaacttc tcaatgctcc tgacctctgt gctaaggact ttgaagatct    6300
ctttaagcaa gaggagtctc tgaagaatat aaaagatagt ctacaacaaa gctcaggtcg    6360
gattgacatt attcatagca agaagacagc agcattgcaa agtgcaacgc ctgtggaaag    6420
ggtgaagcta caggaagctc tctcccagct tgatttccaa tgggaaaaag ttaacaaaat    6480
gtacaaggac cgacaagggc gatttgacag atctgttgag aaatggcggc gttttcatta    6540
tgatataaag atatttaatc agtggctaac agaagctgaa cagtttctca gaaagacaca    6600
aattcctgag aattgggaac atgctaaata caaatggtat cttaaggaac tccaggatgg    6660
cattgggcag cggcaaactg ttgtcagaac attgaatgca actggggaag aaataattca    6720
gcaatcctca aaaacagatg ccagtattct acaggaaaaa ttgggaagcc tgaatctgcg    6780
gtggcaggag gtctgcaaac agctgtcaga cagaaaaaag aggctagaag aacaaaagaa    6840
tatcttgtca gaatttcaaa gagatttaaa tgaatttgtt ttatggttgg aggaagcaga    6900
taacattgct agtatcccac ttgaacctgg aaaagagcag caactaaaag aaaagcttga    6960
gcaagtcaag ttactggtgg aagagttgcc cctgcgccag ggaattctca acaattaaa    7020 tgaaactgga ggacccgtgc ttgtaagtgc tcccataagc ccagaagagc aagataaact    7080
tgaaaataag ctcaagcaga caaatctcca gtggataaag gtttccagag ctttacctga    7140
gaaacaagga gaaattgaag ctcaaataaa agaccttggg cagcttgaaa aaaagcttga    7200
agaccttgaa gagcagttaa atcatctgct gctgtggtta tctcctatta ggaatcagtt    7260
```

-continued

```
ggaaatttat aaccaaccaa accaagaagg accatttgac gttcaggaaa ctgaaatagc   7320
agttcaagct aaacaaccgg atgtggaaga gattttgtct aaagggcagc atttgtacaa   7380
ggaaaaacca gccactcagc cagtgaagag gaagttagaa gatctgagct ctgagtggaa   7440
ggcggtaaac cgtttacttc aagagctgag ggcaaagcag cctgacctag ctcctggact   7500
gaccactatt ggagcctctc ctactcagac tgttactctg gtgacacaac ctgtggttac   7560
taaggaaact gccatctcca aactagaaat gccatcttcc ttgatgttgg aggtacctgc   7620
tctggcagat ttcaaccggg cttggacaga acttaccgac tggctttctc tgcttgatca   7680
agttataaaa tcacagaggg tgatggtggg tgaccttgag gatatcaacg agatgatcat   7740
caagcagaag gcaacaatgc aggatttgga acagaggcgt ccccagttgg aagaactcat   7800
taccgctgcc caaaatttga aaaacaagac cagcaatcaa gaggctagaa caatcattac   7860
ggatcgaatt gaaagaattc agaatcagtg ggatgaagta caagaacacc ttcagaaccg   7920
gaggcaacag ttgaatgaaa tgttaaagga ttcaacacaa tggctggaag ctaaggaaga   7980
agctgagcag gtcttaggac aggccagagc caagcttgag tcatggaagg agggtcccta   8040
tacagtagat gcaatccaaa agaaaatcac agaaaccaag cagttggcca aagacctccg   8100
ccagtggcag acaaatgtag atgtggcaaa tgacttggcc ctgaaacttc tccgggatta   8160
ttctgcagat gataccagaa aagtccacat gataacagag aatatcaatg cctcttggag   8220
aagcattcat aaaagggtga gtgagcgaga ggctgctttg gaagaaactc atagattact   8280
gcaacagttc cccctggacc tggaaaagtt tcttgcctgg cttacagaag ctgaaacaac   8340
tgccaatgtc ctacaggatg ctacccgtaa ggaaaggctc ctagaagact ccaagggagt   8400
aaaagagctg atgaaacaat ggcaagacct ccaaggtgaa attgaagctc acacagatgt   8460
ttatcacaac ctggatgaaa acagccaaaa aatcctgaga tccctggaag gttccgatga   8520
tgcagtcctg ttacaaagac gtttggataa catgaacttc aagtggagtg aacttcggaa   8580
aaagtctctc aacattaggt cccatttgga agccagttct gaccagtgga agcgtctgca   8640
cctttctctg caggaacttc tggtgtggct acagctgaaa gatgatgaat taagccggca   8700
ggcacctatt ggaggcgact ttccagcagt tcagaagcag aacgatgtac atagggcctt   8760
caagagggaa ttgaaaacta aagaacctgt aatcatgagt actcttgaga ctgtacgaat   8820
atttctgaca gagcagcctt tggaaggact agagaaactc taccaggagc ccagagagct   8880
gcctcctgag gagagagccc agaatgtcac tcggcttcta cgaaagcagg ctgaggaggt   8940
caatactgag tgggaaaaat tgaacctgca ctccgctgac tggcagagaa aaatagatga   9000
gacccttgaa agactccagg aacttcaaga ggccacggat gagctggacc tcaagctgcg   9060
ccaagctgag gtgatcaagg gatcctggca gcccgtgggc gatctcctca ttgactctct   9120
ccaagatcac ctcgagaaag tcaaggcact tcgaggagaa attgcgcctc tgaaagagaa   9180
cgtgagccac gtcaatgacc ttgctcgcca gcttaccact ttgggcattc agctctcacc   9240
gtataacctc agcactctgg aagacctgaa caccagatgg aagcttctgc aggtggccgt   9300
cgaggaccga gtcaggcagc tgcatgaagc ccacagggac tttggtccag catctcagca   9360
ctttctttcc acgtctgtcc agggtccctg ggagagagcc atctcgccaa acaaagtgcc   9420
ctactatatc aaccacgaga ctcaaacaac ttgctgggac catcccaaaa tgacagagct   9480
ctaccagtct ttagctgacc tgaataatgt cagattctca gcttatagga ctgccatgaa   9540
actccgaaga ctgcagaagg ccctttgctt ggatctcttg agcctgtcag ctgcatgtga   9600
tgccttggac cagcacaacc tcaagcaaaa tgaccagccc atggatatcc tgcagattat   9660
```

```
taattgtttg accactattt atgaccgcct ggagcaagag cacaacaatt tggtcaacgt    9720
ccctctctgc gtggatatgt gtctgaactg gctgctgaat gtttatgata cgggacgaac    9780
agggaggatc cgtgtcctgt cttttaaaac tggcatcatt tccctgtgta aagcacattt    9840
ggaagacaag tacagatacc ttttcaagca agtggcaagt tcaacaggat tttgtgacca    9900
gcgcaggctg ggcctccttc tgcatgattc tatccaaatt ccaagacagt tgggtgaagt    9960
tgcatccttt gggggcagta acattgagcc aagtgtccgg agctgcttcc aatttgctaa   10020
taataagcca gagatcgaag cggccctctt cctagactgg atgagactgg aaccccagtc   10080
catggtgtgg ctgcccgtcc tgcacagagt ggctgctgca gaaactgcca agcatcaggc   10140
caaatgtaac atctgcaaag agtgtccaat cattggattc aggtacagga gtctaaagca   10200 cttaattat gacatctgcc aaagctgctt tttttctggt cgagttgcaa aaggccataa    10260
aatgcactat cccatggtgg aatattgcac tccgactaca tcaggagaag atgttcgaga   10320
ctttgccaag gtactaaaaa acaaatttcg aaccaaaagg tattttgcga agcatccccg   10380
aatgggctac ctgccagtgc agactgtctt agaggggggac aacatggaaa ctcccgttac   10440
tctgatcaac ttctggccag tagattctgc gcctgcctcg tcccctcagc tttcacacga   10500
tgatactcat tcacgcattg aacattatgc tagcaggcta gcagaaatgg aaaacagcaa   10560
tggatcttat ctaaatgata gcatctctcc taatgagagc atagatgatg aacatttgtt   10620
aatccagcat tactgccaaa gtttgaacca ggactccccc ctgagccagc ctcgtagtcc   10680
tgcccagatc ttgatttcct tagagagtga ggaaagaggg gagctagaga gaatcctagc   10740
agatcttgag gaagaaaaca ggaatctgca agcagaatat gaccgtctaa agcagcagca   10800
cgaacataaa ggcctgtccc cactgccgtc ccctcctgaa atgatgccca cctctcccca   10860
gagtccccgg gatgctgagc tcattgctga ggccaagcta ctgcgtcaac acaaaggccg   10920
cctggaagcc aggatgcaaa tcctggaaga ccacaataaa cagctggagt cacagttaca   10980
caggctaagg cagctgctgg agcaaccccca ggcagaggcc aaagtgaatg cacaacggt    11040 gtcctctcct tctacctctc tacagaggtc cgacagcagt cagcctatgc tgctccgagt   11100
ggttggcagt caaacttcgg actccatggg tgaggaagat cttctcagtc ctccccagga   11160
cacaagcaca gggttagagg aggtgatgga gcaactcaac aactccttcc ctagttcaag   11220
aggaagaaat acccctggaa agccaatgag agaggacaca atgtaggaag tcttttccac   11280
atggcagatg atttgggcag agcgatggag tccttagtat cagtcatgac agatgaagaa   11340
ggagcagaat aaatgtttta caactcctga ttcccgcatg gttttttataa tattcataca   11400 acaaagagga ttagacagta agagtttaca agaaataaat ctatattttt gtgaagggta   11460
gtggtattat actgtagatt tcagtagttt ctaagtctgt tattgttttg ttaacaatgg   11520
caggttttac acgtctatgc aattgtacaa aaaagttata agaaaactac atgtaaaatc   11580
ttgatagcta ataacttgc catttcttta tatggaacgc attttgggtt gtttaaaaat    11640
ttataacagt tataagaaa gattgtaaac taaagtgtgc tttataaaaa aaagttgttt    11700 ataaaaccc ctaaaaacaa aacaaacaca cacacacaca catacacaca cacacaaa      11760 actttgaggc agcgcattgt tttgcatcct tttggcgtga tatccatatg aaattcatgg   11820 cttttttcttt ttttgcatat taaagataag acttcctcta ccaccacacc aaatgactac   11880
tacacactgc tcatttgaga actgtcagct gagtggggca ggcttgagtt ttcatttcat   11940
atatctatat gtctataagt atataaatac tatagttata tagataaaga gatacgaatt   12000
```

```
tctatagact gacttttttcc attttttaaa tgttcatgtc acatcctaat agaaagaaat    12060
tacttctagt cagtcatcca ggcttacctg cttggtctag aatggatttt tcccggagcc    12120
ggaagccagg aggaaactac accacactaa acattgtct acagctccag atgtttctca     12180
ttttaaacaa ctttccactg acaacgaaag taaagtaaag tattggatttt ttttaaaggg   12240 aacatgtgaa tgaatacaca ggacttatta tatcagagtg agtaatcggt tggttggttg    12300
attgattgat tgattgatac attcagcttc ctgctgctag caatgccacg atttagattt    12360
aatgatgctt cagtggaaat caatcagaag gtattctgac cttgtgaaca tcagaaggta    12420
ttttttaact cccaagcagt agcaggacga tgatagggct ggagggctat ggattcccag    12480
cccatccctg tgaaggagta ggccactctt taagtgaagg attggatgat tgttcataat    12540
acataaagtt ctctgtaatt acaactaaat tattatgccc tcttctcaca gtcaaaagga   12600
actgggtggt ttggtttttg ttgcttttttt agatttattg tcccatgtgg gatgagtttt   12660
taaatgccac aagacataat ttaaaataaa taaactttgg gaaaaggtgt aagacagtag    12720
ccccatcaca tttgtgatac tgacaggtat caacccagaa gcccatgaac tgtgtttcca    12780
tcctttgcat ttctctgcga gtagttccac acaggtttgt aagtaagtaa gaaagaaggc    12840
aaattgattc aaatgttaca aaaaacccct tcttggtgga ttagacaggt taaatatata   12900
aacaaacaaa caaaaattgc tcaaaaaaga ggagaaaagc tcaagaggaa aagctaagga    12960
ctggtaggaa aaagctttac tctttcatgc catttttattt cttttttgatt tttaaatcat  13020 tcattcaata gataccaccg tgtgacctat aattttgcaa atctgttacc tctgacatca    13080
agtgtaatta gcttttggag agtgggctga catcaagtgt aattagcttt tggagagtgg    13140
gttttgtcca ttattaataa ttaattaatt aacatcaaac acggcttctc atgctatttc    13200
tacctcactt tggttttggg gtgttcctga taattgtgca cacctgagtt cacagcttca    13260
ccacttgtcc attgcgttat tttctttttc ctttataatt cttttctttt ccttcataat    13320
tttcaaaaga aaacccaaag ctctaaggta acaaattacc aaattacatg aagatttggt    13380
ttttgtcttg cattttttttc ctttatgtga cgctggacct tttctttacc caaggatttt    13440
taaaactcag atttaaaaca aggggttact ttacatccta ctaagaagtt taagtaagta    13500
agtttcattc taaaatcaga ggtaaataga gtgcataaat aattttgttt taatcttttt    13560 gttttttcttt tagacacatt agctctggag tgagtctgtc ataatatttg aacaaaaatt   13620
gagagcttta ttgctgcatt ttaagcataa ttaatttgga cattatttcg tgttgtgttc    13680
tttataacca ccgagtatta aactgtaaat cataatgtaa ctgaagcata aacatcacat    13740 ggcatgttttt gtcattgttt tcaggtactg agttcttact tgagtatcat aatatattgt   13800
gttttaacac caacactgta acatttacga attattttt taaacttcag ttttactgca    13860
ttttcacaac atatcagact tcaccaaata tatgccttac tattgtatta tagtactgct   13920
ttactgtgta tctcaataaa gcacgcagtt atgttac                             13957
```

<210> SEQ ID NO 2
<211> LENGTH: 13815
<212> TYPE: DNA
<213> ORGANISM: Mus musculus

<400> SEQUENCE: 2

```
cctcactcac ttgcccctta caggactcag ctcttgaagg caatagcttt atagaaaaaa      60
cgaataggaa gacttgaagt gctatttttt tttttttttt tgtcaaggct gctgaagttt     120
attggcttct catcgtacct aagcctcctg gagcaataaa actgggagaa acttttacca    180
```

-continued

| | |
|---|---|
| agatttttat ccctgccttg atatatactt tttcttccaa atgctttggt gggaagaagt | 240 |
| agaggactgt tatgaaagag aagatgttca aaagaaaaca ttcacaaaat ggataaatgc | 300 |
| acaattttct aagtttggaa agcaacacat agacaacctc ttcagtgacc tgcaggatgg | 360 |
| aaaacgcctc ctagacctct tggaaggcct tacagggcaa aaactgccaa agaaaaggg | 420 |
| atctacaaga gttcatgccc tgaacaatgt caacaaggca ctgcgggtct tacagaaaaa | 480 |
| taatgttgat ttagtgaata taggaagcac tgacatagtg gatggaaatc ataaactcac | 540 |
| tcttggtttg atttggaata taatcctcca ctggcaggtc aaaaatgtga tgaaaactat | 600 |
| catggctgga ttgcagcaaa ccaacagtga aaagattctt ctgagctggg ttcgacagtc | 660 |
| aacacgtaat tatccacagg ttaacgtcat caacttcacc tctagctggt ccgacgggtt | 720 |
| ggctttgaat gctcttatcc atagtcacag gcccgacctg tttgattgga atagtgtggt | 780 |
| ttcacagcac tcagccaccc aaagactgga acatgccttc aacattgcaa aatgccagtt | 840 |
| aggcatagaa aaacttcttg atcctgaaga tgttgctacc acttatccag acaagaagtc | 900 |
| catcttaatg tacatcacat cactctttca gttttgcca caacaagtga gcattgaagc | 960 |
| cattcaagaa gtggaaatgt tgcccaggac atcttcaaaa gtaactagag aagaacattt | 1020 |
| tcaattacat caccagatgc attactctca acagatcaca gtcagtctag cacagggcta | 1080 |
| tgaacaaact tcttcatctc ctaagcctcg attcaagagt tatgccttca cacaggctgc | 1140 |
| ttatgttgcc acctctgatt ccacacagag cccctatcct tcacagcatt tggaagctcc | 1200 |
| cagagacaag tcacttgaca gttcattgat ggagacggaa gtaaatctgg atagttacca | 1260 |
| aactgcttta gaagaagtac tttcatggct tctttctgcc gaggatacat tgcgagcaca | 1320 |
| aggagagatt tcaaatgatg ttgaagaagt gaaagaacag tttcatgctc atgagggatt | 1380 |
| catgatggat ctgacatctc atcaaggact tgttggtaat gttctacagt taggaagtca | 1440 |
| actagttgga aaagggaaat tatcagaaga tgaagaagct gaagtgcaag aacaaatgaa | 1500 |
| tctcctaaat tcaagatggg aatgtctcag ggtagctagc atggaaaaac aaagcaaatt | 1560 |
| acacaaagtt ctaatggatc tccagaatca gaaattaaaa gaactagatg actggttaac | 1620 |
| aaaaactgaa gagagaacta agaaaatgga ggaagagccc tttggacctg atcttgaaga | 1680 |
| tctaaaatgc caagtacaac aacataaggt gcttcaagaa gatctagaac aggagcaggt | 1740 |
| cagggtcaac tcgctcactc acatggtagt agtggttgat gaatccagcg gtgatcatgc | 1800 |
| aacagctgct ttggaagaac aacttaaggt actgggagat cgatgggcaa atatctgcag | 1860 |
| atggactgaa gaccgctgga ttgttttaca agatattctt ctaaaatggc agcattttac | 1920 |
| tgaagaacag tgcctttta gtacatggct ttcagaaaaa aagatgcaa tgaagaacat | 1980 |
| tcagacaagt ggctttaaag atcaaaatga atgatgtca agtcttcaca aaatatctac | 2040 |
| tttaaaaata gatctagaaa agaaaaagcc aaccatggaa aaactaagtt cactcaatca | 2100 |
| agatctactt tcggcactga aaaataagtc agtgactcaa aagatggaaa tctggatgga | 2160 |
| aaactttgca caacgttggg acaatttaac ccaaaaactt gaaaagagtt cagcacaaat | 2220 |
| ttcacaggct gtcaccacca ctcaaccatc cctaacacag acaactgtaa tggaaacggt | 2280 |
| aactatggtg accacaaggg aacaaatcat ggtaaaacat gcccaagagg aacttccacc | 2340 |
| accacctcct caaaagaaga ggcagataac tgtggattct gaactcagga aaggttgga | 2400 |
| tgtcgatata actgaacttc acagttggat tactcgttca gaagctgtat tacagagttc | 2460 |
| tgaatttgca gtctatcgaa aagaaggcaa catctcagac ttgcaagaaa aagtcaatgc | 2520 |

```
catagcacga gaaaaagcag agaagttcag aaaactgcaa gatgccagca gatcagctca    2580
ggccctggtg gaacagatgg caaatgaggg tgttaatgct gaaagtatca gacaagcttc    2640
agaacaactg aacagccggt ggacagaatt ctgccaattg ctgagtgaga gagttaactg    2700
gctagagtat caaaccaaca tcattacctt ttataatcag ctacaacaat tggaacagat    2760
gacaactact gccgaaaact tgttgaaaac ccagtctacc accctatcag agccaacagc    2820
aattaaaagc cagttaaaaa tttgtaagga tgaagtcaac agattgtcag ctcttcagcc    2880
tcaaattgag caattaaaaa ttcagagtct acaactgaaa gaaaagggac aggggccaat    2940
gtttctggat gcagactttg tggcctttac taatcatttt aaccacatct ttgatggtgt    3000
gagggccaaa gagaaagagc tacagacaat ttttgacact ttaccaccaa tgcgctatca    3060
ggagacaatg agtagcatca ggacgtggat ccagcagtca gaaagcaaac tctctgtacc    3120
ttatcttagt gttactgaat atgaataat ggaggagaga ctcgggaaat tacaggctct    3180
gcaaagttct ttgaaagagc aacaaaatgg cttcaactat ctgagtgaca ctgtgaagga    3240
gatggccaag aaagcacctt cagaaatatg ccagaaatat ctgtcagaat tgaagagat    3300 tgaggggcac tggaagaaac tttcctccca gttggtggaa agctgccaaa agctagaaga    3360
acatatgaat aaacttcgaa aatttcagaa tcacataaaa accttacaga atggatggc    3420 tgaagttgat gttttcctga agaggaatg gcctgccctg ggggatgctg aaatcctgaa    3480
aaaacagctc aaacaatgca gacttttagt tggtgatatt caaacaattc agcccagttt    3540
aaatagtgtt aatgaaggtg ggcagaagat aaagagtgaa gctgaacttg agtttgcatc    3600
cagactggag acagaactta gagagcttaa cactcagtgg gatcacatat gccgccaggt    3660
ctacaccaga aaggaagcct taaggcaggt tttggataaa accgtaagcc tccaaaaaga    3720
tctatcagag atgcatgagt ggatgacaca agctgaagaa gaatatctag agagagattt    3780
tgaatataaa actccagatg aattacagac tgctgttgaa gaaatgaaga gagctaaaga    3840
agaggcacta caaaaagaaa ctaaagtgaa actccttact gagactgtaa atagtgtaat    3900
agctcacgct ccaccctcag cacaagaggc cttaaaaaag gaacttgaaa ctctgaccac    3960
caactaccaa tggctgtgca ccaggctgaa tggaaaatgc aaaactttgg aagaagtttg    4020
ggcatgttgg catgagttat tgtcatattt agagaaagca aacaagtggc tcaatgaagt    4080
agaattgaaa cttaaaacca tggaaaatgt tcctgcagga cctgaggaaa tcactgaagt    4140
gctagaatct cttgaaaatc tgatgcatca ttcagaggag aacccaaatc agattcgtct    4200
attggcacag actcttacag atggaggagt catggatgaa ctgatcaatg aggagcttga    4260
gacgtttaat tctcgttgga gggaactaca tgaagaggct gtgaggaaac aaaagttgct    4320
tgaacagagt atccagtctg cccaggaaat tgaaaagtcc ttgcacttaa ttcaggagtc    4380
gcttgaattc attgacaagc agttggcagc ttatatcact gacaaggtgg atgcagctca    4440
aatgcctcag gaagcccaga aaatccaatc agatttgaca agtcatgaga taagtttaga    4500
agaaatgaag aaacataacc aggggaagga tgccaaccaa agggttcttt cacaaattga    4560
tgttgcacag aaaaaattac aagatgtctc catgaaattt cgattattcc aaaaaccagc    4620
caattttgaa caacgtctag aggaaagtaa gatgatttta gatgaagtca agatgcattt    4680
gcctgcattg gaaccaagag gtgttgaaca ggaagtaatt cagtcacaac taagtcattg    4740
tgtgaacttg tataaaagcc tgagtgaagt caagtctgaa gtggaaatgg tgattaaaac    4800
cggacgtcaa attgtacaga aaagcagac agaaaatccc aaagagcttg atgaacgagt    4860
aacagctttg aaattgcatt acaatgagtt gggtgcgaag gtaacagaga gaaagcaaca    4920
```

```
gttggagaaa tgcttgaagt tgtcccgtaa gatgagaaag gaaatgaatg tcttaacaga    4980
atggctggca gcaacagata cagaattgac gaagagatca gcagttgaag gaatgccaag    5040
taatttggat tctgaagttg cctggggaaa ggctactcaa aaagagattg agaaacagaa    5100
ggctcacttg aagagtgtta cagaattagg agagtctttg aaaatggtgt tgggcaagaa    5160
agaaaccttg gtagaagata aactgagtct tctgaacagt aactggatag ctgtcacctc    5220
cagagtagaa gaatggctaa atcttttgtt ggaataccag aaacacatgg aaacctttga    5280
tcagaacata gaacaaatca caaagtggat cattcatgca gatgaacttt tagatgagtc    5340
tgaaaagaag aaaccacaac aaaaggaaga cattcttaag cgtttaaagg ctgaaatgaa    5400
tgacatgcgc ccaaaggtgg actccacacg tgaccaagca gcaaaattga tggcaaaccg    5460
cggtgaccac tgcaggaaag tagtagagcc ccaaatctct gagctcaacc gtcgatttgc    5520
agctatttct cacagaatta agactggaaa ggcctccatt cctttgaagg aattggagca    5580
gtttaactca gatatacaaa aattgcttga accactggag gctgaaattc agcaggggt    5640 gaatctgaaa gaggaagact tcaataaaga tatgagtgaa gacaatgagg gtactgtaaa    5700
tgaattgttg caaagaggag acaacttaca acaaagaatc acagatgaga gaaagcgaga    5760
ggaaataaag ataaaacagc agctgttaca gacaaaacat aatgctctca aggatttgag    5820
gtctcaaaga agaaaaaagg ccctagaaat ttctcaccag tggtatcagt acaagaggca    5880
ggctgatgat ctcctgaaat gcttggatga aattgaaaaa aaattagcca gcctacctga    5940
acccagagat gaaagaaaat taaggaaat tgatcgtgaa ttgcagaaga agaaagagga    6000
gctgaatgca gtgcgcaggc aagctgaggg cttgtctgag aatggggccg caatggcagt    6060
ggagccaact cagatccagc tcagcaagcg ctggcggcaa attgagagca atttgctca    6120 gtttcgaaga ctcaactttg cacaaattca cactctccat gaagaaacta tggtagtgac    6180
gactgaagat atgccttgg atgtttctta tgtgccttct acttatttga ccagagatcag    6240 tcatatctta caagctcttt cagaagttga tcatcttcta aatactcctg aactctgtgc    6300
taaagatttt gaagatcttt ttaagcaaga ggagtctctt aagaatataa agacaatttt    6360
gcaacaaatc tcaggtcgga ttgatattat tcacaagaag aagacagcag ccttgcaaag    6420
tgccacctcc atggaaaagg tgaaagtaca ggaagccgtg gcacagatgg atttccaggg    6480
ggaaaaactt catagaatgt acaaggaacg acaagggcga ttcgacagat cagttgaaaa    6540
atggcgacac tttcattatg atatgaaggt atttaatcaa tggctgaatg aagttgaaca    6600
gttttttcaa aagacacaaa atcctgaaaa ctgggaacat gctaaataca aatggtatct    6660
taaggaactc caggatggca ttgggcagcg tcaagctgtt gtcagaacac tgaatgcaac    6720
tggggaagaa ataattcaac agtcttcaaa aacagatgtc aatattctac aagaaaaatt    6780
aggaagcttg agtctgcggt ggcacgacat ctgcaaagag ctggcagaaa ggagaaagag    6840
gattgaagaa caaaagaatg tcttgtcaga atttcaaaga gatttaaatg aatttgtttt    6900
gtggctggaa gaagcagata acattgctat tactccactt ggagatgagc agcagctaaa    6960
agaacaactt gaacaagtca agttactggc agaagagttg ccctgcgcc agggaattct    7020 aaaacaatta aatgaaacag gaggagcagt acttgtaagt gctcccataa ggccagaaga    7080
gcaagataaa cttgaaaaga agctcaaaca gacaaatctc cagtggataa aggtctccag    7140
agctttacct gagaaacaag gagagcttga ggttcactta aaagatttta ggcagcttga    7200
agagcagctg gatcacctgc ttctgtggct ctctcctatt agaaaccagt tggaaattta    7260
```

```
taaccaacca agtcaggcag gaccgtttga cataaaggag attgaagtaa cagttcacgg    7320
taaacaagcg gatgtggaaa ggcttttgtc gaaagggcag catttgtata aggaaaaacc    7380
aagcactcag ccagtgaaga ggaagttaga agatctgagg tctgagtggg aggctgtaaa    7440
ccatttactt cgggagctga ggacaaagca gcctgaccgt gccctggac tgagcactac     7500 tggagcctct gccagtcaga ctgttactct agtgacacaa tctgtggtta ctaaggaaac    7560
tgtcatctcc aaactagaaa tgccatcttc tttgctgttg gaggtacctg cactggcaga    7620
cttcaaccga gcttggacag aacttacaga ctggctgtct ctgcttgatc gagttataaa    7680
atcacagaga gtgatggtgg gtgatctgga agacatcaat gaaatgatca tcaaacagaa    7740
ggcaacactg caagatttgg aacagagacg cccccaattg gaagaactca ttactgctgc    7800
ccagaatttg aaaacaaaa ccagcaatca gaagctaga acaatcatta ctgatcgaat      7860
tgaaagaatt cagattcagt gggatgaggt tcaagaacag ctgcagaaca ggagacaaca    7920
gttgaatgaa atgttaaagg attcaacaca atggctggaa gctaaggaag aagccgaaca    7980
ggtcatagga caggtcagag gcaagcttga ctcatggaaa gaaggtcctc acacagtaga    8040
tgcaatccaa aagaagatca cagaaaccaa gcagttggcc aaagacctcc gtcaacggca    8100
gataagtgta gacgtggcaa atgatttggc actgaaactt cttcgggact attctgctga    8160
tgataccaga aaagtacaca tgataacaga gaatatcaat acttcttggg gaaacattca    8220
taaaagagta agtgagcaag aggctgcttt ggaagaaact catagattac tgcagcagtt    8280
ccctctggac ctggagaagt ttctttcctg gattacggaa gcagaaacaa ctgccaatgt    8340
cctacaggac gcttcccgta aggagaagct cctagaagac tccaggggag tcagagagct    8400
gatgaaacca tggcaagatc tccaaggaga aattgaaact cacacagata tctatcacaa    8460
tcttgatgaa aatggccaaa aaatcctgag atccctggaa ggttcggatg aagcaccct    8520 gttacaaaga cgtttggata acatgaattt caagtggagt gaacttcaga aaagtctct    8580 caacattagg tcccatttgg aagcaagttc tgaccagtgg aagcgtttgc atcttctct   8640 tcaggaactt cttgttttgc tacagctgaa agatgatgaa ctgagccgtc aggcaccat   8700 cggtggtgat ttcccagcag ttcagaagca gaatgatata catagggcct tcaagaggga    8760
attgaaaact aaagaacctg taatcatgag tactctggag actgtgagaa tatttctgac    8820
agagcagcct ttggaaggac tagagaaact ctaccaggag cccagagaac tgcctcctga    8880
agaaagagct cagaatgtca ctcggctcct acgaaagcag gctgaagagg tcaacgctga    8940
atgggacaaa ttgaacctgc gctcagctga ttggcagaga aaaatagatg aagctcttga    9000
aagactccag gaacttcagg aagctgccga tgaactggac ctcaagttgc gccaagctga    9060
ggtgatcaag ggatcctggc agccagtggg ggatctcctc attgactctc tgcaagatca    9120
ccttgaaaaa gtcaaggcac ttcgggaga aattgcacct cttaaagaga atgtcaatcg      9180
tgtcaatgac cttgcacatc agctgaccac actgggcatt cagctctcac cttataacct    9240
cagcactttg gaagatctga ataccagatg gaggcttcta caggtggctg tggaggaccg    9300
tgtcagacag ctgcatgaag cccacaggga ctttggtcct gcatcccagc acttcctttc    9360
cacttcagtt cagggtccct gggagagagc catctcacca aacaaagtgc cctactatat    9420
caaccacaga acccaaaacca cttgttggga ccacccaaa atgacagagc tctaccagtc    9480
tttagctgac ctgaataatg tcaggttctc cgcgtatagg actgccatga agctcagaag    9540
gctccagaag gccctttgct tggatctctt gagcctgtca gctgcatgtg atgccctgga    9600
ccagcacaac ctcaagcaaa atgaccagcc catggatatc ctgcagataa ttaactgttt    9660
```

```
gactacaatt tatgatcgtc tggagcaaga gcacaacaat ctggtcaatg tccctctctg   9720
tgtggatatg tgtctcaact ggcttctcaa tgtttatgat acgggacgaa cagggaggat   9780
ccgtgtcctg tcttttaaaa ctggcatcat ttctctgtgt aaagcacact tggaagacaa   9840
gtacagatac cttttcaagc aagtggcaag ttcaactggc ttttgtgacc agcgtaggct   9900
gggtcttctt ctgcatgatt ctattcaaat cccaagacag ttgggtgaag ttgcttcctt   9960
tgggggcagt aacattgagc cgagtgtcag gagctgcttc caatttgcca ataataaacc  10020
tgagattgaa gctgctctct tccttgactg gatgcgcctg gaaccccagt ctatggtgtg  10080
gctgcccgtc ttgcacagag tggctgctgc tgaaactgcc aagcatcaag ccaagtgtaa  10140
catctgtaag gagtgtccaa tcattggatt caggtacaga agcctaaagc attttaatta  10200
tgacatctgc caaagttgct ttttttctgg ccgagttgca aagggccata aaatgcacta  10260
ccccatggta gagtattgca ctccgactac atccggagaa gatgttcgcg acttcgccaa  10320
ggtactaaaa aacaaatttc gaaccaaaag gtattttgcg aagcatcccc gaatgggcta  10380
cctgccagtg cagactgtgt tagaggggga caacatggaa actcccgtta ctctgatcaa  10440
cttctggcca gtagattctg cgcctgcctc gtcccccag ctttcacacg atgatactca  10500
ttcacgcatt gaacattatg ctagcaggct agcagaaatg gaaaacagca atggatctta  10560
tctaaatgat agcatctctc ctaatgagag catagatgat gaacatttgt taatccagca  10620
ttactgccaa agtttgaacc aggactcccc cctgagccag cctcgtagtc ctgcccagat  10680
cttgatttcc ttagagagtg aggaaagagg ggagctagag agaatcctag cagatcttga  10740
ggaagaaaac aggaatctgc aagcagaata tgatcgcctg aagcagcagc atgagcataa  10800
aggcctgtct ccactgccat ctcctcctga gatgatgccc acctctcctc agagtcccag  10860
ggatgctgag ctcattgctg aggctaagct actgcgccaa cacaaaggac gcctggaagc  10920
caggatgcaa atcctggaag accacaataa acagctggag tctcagttac atagactgag  10980
acagctcctg gagcagcccc aggctgaagc taaggtgaat ggcaccacgg tgtcctctcc  11040
ttccacctct ctgcagaggt cagatagcag tcagcctatg ctgctccgag tggttggcag  11100
tcaaacttca gaatctatgg gtgaggaaga tcttctgagt cctccccagg acacaagcac  11160
agggttagaa gaagtgatgg agcaactcaa caactccttc cctagttcaa gaggaagaaa  11220
tgcccccgga aagccaatga gagaggacac aatgtaggaa gccttttcca catggcagat  11280
gatttgggca gagcgatgga gtccttagtt tcagtcatga cagatgaaga aggagcagaa  11340
taaatgtttt acaactcctg attcccgcat ggttttttata atattcgtac aacaaagagg  11400
attagacagt aagagtttac aagaaataaa atctatattt ttgtgaaggg tagtggtact  11460
atactgtaga tttcagtagt ttctaagtct gttattgttt tgttaacaat ggcaggtttt  11520
acacgtctat gcaattgtac aaaaaagtta aagaaaaca tgtaaaatct tgatagctaa  11580
ataacttgcc atttctttat atggaacgca ttttgggttg tttaaaaatt tataacagtt  11640
ataaagagag attgtaaact aaagtgtgct ttataaaaaa agttgtttat aaaaacccct  11700
aaacaaacac acacgcacac acacacacac acacacacac acacacacac gcacacatac  11760
atgcacgaac ccaccacaca cacacacaca cacacacaca ctgaggcagc acattgtttt  11820
gcattacttt agcgtggtat tcatatggaa ttcatgacgt ttttttattt tcttgcatac  11880
gaacccacc aaatgactgc ttcatattgc tcttttgaga attgttgact gagtggggct  11940
ggctatgggc tttcatttta tacatctata tgtctacaag tatataaata ctataggtat  12000
```

-continued

```
atagataaat agatatgaag ttacttcttc aaatgttctt gccacttcct aatggaaatt      12060
gcttctagtc atctgggctt atctgcttgg gcaagagtga attttccctg gagcccaaag      12120
ccaggagact accgccacac taaaatattg tctagggctc cagatgtttc tagttttaaa      12180 cttttccactg agagctagag gattcatttt tttcaaggaa catgcgaatg aatacacagg     12240
acttactatc atagtaattt gttggctgat atattcaact tcctactgtt gggttatatt      12300
taatgatgtt tctgcaatag aacatcagat gacatttta actcccagac agtaggagga      12360
agatggtagg agctaaaggt tgcggctcct cagtcaattt atatgagggg agcaacaact      12420
ctgtaaaaga atggatgaat atttacaact atacatataa acatctctat aattacaact      12480
aaattgttct gccctcttca taaactcaac ctgaagtggg tggttttgtt gttgttgttg      12540
ttgttgttgt tgatgatgat gatgaatttt agatttaga ttttttgggt tttttttct       12600 tcattgtgat gatttttttt tttaatgctg caagacttag gattactgtt aagaaagtaa      12660
cccaatcaca ttgtgaccct ggtgaatatc agtccagaag cccatgaact gcatttgtct      12720
cctttgcatt ggtttccctg caagtaactc cacacaggat tgtgggtgag aaggcacagt      12780
ggttggaaag ttttgagagc aaaagcgtct ccaaactctc tggtctagtt gacgggctga      12840
aatgtctaaa caaatgcaag tcattgaacc aggagaaaaa gtgcaacaga aagctaagga      12900
ctgctaggaa gagctttact cctctcatgc cagtttcttc ttcttagcat ttaaagagca      12960
ttctctcaat agaaatcact gtcctatcat tttgcaaatc tgttacctct aacgtcaagt      13020
gtaattaact tctagcgagt gggttttgtc cattattaat tgtaattaac atcaaacaca      13080
gcttctcatg ctatttctac ctcactttgg ttttggggtg tttctagtaa ttgtgcacac      13140
ctaatttcac aacttcacca cttgtctgtt gtgtggacac cagtttcctt ttttcattta      13200
taatttccaa aagaaaaccc aaagctctaa gataacaaat tgaaatttgg ttctggtctt      13260
gcttttctct ctctctctcc tttatgtggc actgggcatt ttctttatcc aaggatttgt      13320
tttcaccaag atttaaaaca aggggttcct ttcctactaa gaagttttaa gtttcattct      13380
aaaatccaag gtagatagag tgcatagttt tgttttaatc tttttcgtttt atctttttaga   13440 tattagttct ggagtgaatc tatcaaaata tttgaataaa aactgagagc tttattgctg     13500
attttaagca taattggac atcatttcat gttctttata accatcaagt attaaagtgt      13560
aaatcataat cagtgtaact gaagcataat catcacatgg catgtatcat cattgtctcc     13620
aggtactgga ctcttacttg agtatcataa tagattgtgt tttaacacca acactgtaac     13680
atttactaat tatttttta aacttcagtt ttactgcatt ttcacaacat atcagatttc      13740
accaaatata tgccttacta ttgtattata ttactgcttt actgtgtatc tcaataaagc     13800
acgcagttat gttac                                                      13815

<210> SEQ ID NO 3
<211> LENGTH: 10302
<212> TYPE: DNA
<213> ORGANISM: Homo sapiens

<400> SEQUENCE: 3
atggccaagt atggagaaca tgaagccagt cctgacaatg gcagaacga attcagtgat         60 atcattaagt ccagatctga tgaacacaat gacgtacaga agaaaacctt taccaaatgg       120
ataaatgctc gattttcaaa gagtgggaaa ccacccatca tgatatgtt cacagacctc       180 aaagatggaa ggaagctatt ggatcttcta gaaggcctca caggaacatc actgccaaag       240
gaacgtggtt ccacaagggt acatgcctta ataacgtca acagagtgct gcaggtttta       300
```

-continued

```
catcagaaca atgtggaatt agtgaatata gggggaactg acattgtgga tggaaatcac      360
aaactgactt tggggttact ttggagcatc attttgcact ggcaggtgaa agatgtcatg      420
aaggatgtca tgtcggacct gcagcagacg aacagtgaga agatcctgct cagctgggtg      480
cgtcagacca ccaggcccta cagccaagtc aacgtcctca acttcaccac cagctggaca      540
gatggactcg cctttaatgc tgtcctccac cgacataaac ctgatctctt cagctgggat      600
aaagttgtca aaatgtcacc aattgagaga cttgaacatg ccttcagcaa ggctcaaact      660
tatttgggaa ttgaaaagct gttagatcct gaagatgttg ccgttcggct tcctgacaag      720
aaatccataa ttatgtattt aacatctttg tttgaggtgc tacctcagca agtcaccata      780
gacgccatcc gtgaggtaga cactccca aggaaatata aaaagaatg tgaagaagag         840 gcaattaata tacagagtac agcgcctgag gaggagcatg agagtcccg agctgaaact       900 cccagcactg tcactgaggt cgacatggat ctggacagct atcagattgc gttggaggaa      960
gtgctgacct ggttgctttc tgctgaggac actttccagg agcaggatga tatttctgat     1020
gatgttgaag aagtcaaaga ccagtttgca acccatgaag cttttatgat ggaactgact     1080
gcacaccaga gcagtgtggg cagcgtcctg caggcaggca accaactgat aacacaagga     1140
actctgtcag acgaagaaga atttgagatt caggaacaga tgaccctgct gaatgctaga     1200
tgggaggctc ttagggtgga gagtatggac agacagtccc ggctgcacga tgtgctgatg     1260
gaactgcaga agaagcaact gcagcagctc tccgcctggt taacactcac agaggagcgc     1320
attcagaaga tggaaacttg cccctggat gatgatgtaa atctctaca aaagctgcta       1380 gaagaacata aaagtttgca aagtgatctt gaggctgaac aggtgaaagt aaattcacta     1440
actcacatgg tggtcattgt tgatgaaaac agtggtgaga gcgctacagc tatcctagaa     1500
gaccagttac agaaacttgg tgagcgctgg acagcagtat gccgttggac tgaagaacgc     1560
tggaataggt tacaagaaat caatatattg tggcaggaat tattggaaga acagtgcttg     1620
ttgaaagctt ggttaaccga aaaagaagag gctttaaata aagtccagac aagcaacttc     1680
aaagaccaaa aggaactaag tgtcagtgtt cgacgtctgg ctattttgaa ggaagacatg     1740
gaaatgaagc gtcaaacatt ggatcagctg agtgagattg ccaggatgt gggacaatta     1800 cttgataatt ccaaggcatc taagaagatc aacagtgact cagaggaact gactcaaaga     1860
tgggattctt tggttcagag actagaagat tcctccaacc aggtgactca ggctgtagca     1920
aagctgggga tgtctcagat tcctcagaag gaccttttgg agactgttcg tgtaagagaa     1980
caagcaatta caaaaaatc taagcaggaa ctgcctcctc ctcctccccc aaagaagaga     2040
cagatccatg tggatattga agctaagaaa agtttgatg ctataagtgc agagctgttg       2100
aactggattt tgaaatggaa aactgccatt cagaccacag agataaaaga gtatatgaag     2160
atgcaagaca cttccgaaat gaaaagaag ttgaaggcat tagaaaaaga acagagagaa      2220
agaatcccca gagcagatga attaaaccaa actggacaaa tccttgtgga gcaaatggga     2280
aaagaaggcc ttcctactga agaaataaaa aatgttctgg agaaggtttc atcagaatgg     2340
aagaatgtat ctcaacattt ggaagatcta gaaagaaaga ttcagctaca ggaagatata     2400
aatgcttatt tcaagcagct tgatgagctt gaaaaggtca tcaagacaaa ggaggagtgg     2460
gtaaaacaca cttccatttc tgaatcttcc cggcagtcct tgccaagctt gaaggattcc     2520
tgtcagcggg aattgacaaa tcttcttggc cttcaccca aaattgaaat ggctcgtgca       2580
agctgctcgg ccctgatgtc tcagccttct gccccagatt ttgtccagcg gggcttcgat     2640
```

-continued

```
agctttctgg gccgctacca agctgtacaa gaggctgtag aggatcgtca acaacatcta   2700
gagaatgaac tgaagggcca acctggacat gcatatctgg aaacattgaa aacactgaaa   2760
gatgtgctaa atgattcaga aaataaggcc caggtgtctc tgaatgtcct taatgatctt   2820
gccaaggtgg agaaggccct gcaagaaaaa aagacccttg atgaaatcct tgagaatcag   2880
aaacctgcat tacataaact tgcagaagaa acaaaggctc tggagaaaaa tgttcatcct   2940
gatgtagaaa aattatataa gcaagaattt gatgatgtgc aaggaaagtg gaacaagcta   3000
aaggtcttgg tttccaaaga tctacatttg cttgaggaaa ttgctctcac actcagagct   3060
tttgaggccg attcaacagt cattgagaag tggatggatg gcgtgaaaga cttcttaatg   3120
aaacagcagg ctgcccaagg agacgacgca ggtctacaga ggcagttaga ccagtgctct   3180
gcatttgtta atgaaataga aacaattgaa tcatctctga aaacatgaa ggaaatagag   3240 actaatcttc gaagtggtcc agttgctgga ataaaaactt gggtgcagac aagactaggt   3300
gactaccaaa ctcaactgga gaaacttagc aaggagatcg ctactcaaaa aagtaggttg   3360
tctgaaagtc aagaaaaagc tgcgaacctg aagaaagact tggcagagat gcaggaatgg   3420
atgacccagg ccgaggaaga atatttggag cgggattttg agtacaagtc accagaagag   3480
cttgagagtg ctgtggaaga gatgaagagg gcaaagagg atgtgttgca gaaggaggtg   3540
agagtgaaga ttctcaagga caacatcaag ttattagctg ccaaggtgcc ctctggtggc   3600
caggagttga cgtctgagct gaatgttgtg ctggagaatt accaacttct ttgtaataga   3660
attcgaggaa gtgccacac gctagaggag gtctggtctt gttggattga actgcttcac   3720
tatttggatc ttgaaactac ctggttaaac actttggaag agcggatgaa gagcacagag   3780
gtcctgcctg agaagacgga tgctgtcaac gaagccctgg agtctctgga atctgttctg   3840
cgccacccgg cagataatcg cacccagatt cgagagcttg gccagactct gattgatggg   3900
gggatcctgg atgatataat cagtgagaaa ctggaggctt tcaacagccg atatgaagat   3960
ctaagtcacc tggcagagag caagcagatt tctttggaaa agcaactcca ggtgctgcgg   4020
gaaactgacc agatgcttca agtcttgcaa gagagcttgg gggagctgga caaacagctc   4080
accacatacc tgactgacag gatagatgct ttccaagttc cacaggaagc tcagaaaatc   4140
caagcagaga tctcagccca tgagctaacc ctagaggagt tgagaagaaa tatgcgttct   4200
cagcccctga cctccccaga gagtaggact gccagaggag gaagtcagat ggatgtgcta   4260
cagaggaaac tccgagaggt gtccacaaag ttccagcttt tccagaagcc agctaacttc   4320
gagcagcgca tgctggactg caagcgtgtg ctggatggcg tgaaagcaga acttcacgtt   4380
ctggatgtga aggacgtaga ccctgacgtc atacagacgc acctggacaa gtgtatgaaa   4440
ctgtataaaa ctttgagtga agtcaaactt gaagtggaaa ctgtgattaa acaggaaga   4500 catattgtcc agaaacagca aacggacaac ccaaaaggga tggatgagca gctgacttcc   4560
ctgaaggttc tttacaatga cctgggcgca caggtgacga aggaaaaca ggatctggaa   4620 agagcatcac agttggcccg gaaaatgaag aaagaggctg cttctctctc tgaatggctt   4680
tctgctactg aaactgaatt ggtacagaag tccacttcag aaggtctgct tggtgacttg   4740
gatacagaaa tttcctgggc taaaaatgtt ctgaaggatc tggaaaagag aaaagctgat   4800
ttaaatacca tcacagagag tagtgctgcc ctgcaaaact tgattgaggg cagtgagcct   4860
attttagaag agaggctctg cgtccttaac gctgggtgga gccgagttcg tacctggact   4920
gaagattggt gcaatacctt gatgaaccat cagaaccagc tagaaatatt tgatgggaac   4980
gtggctcaca taagtacctg gctttatcaa gctgaagctc tattggatga aattgaaaag   5040
```

-continued

```
aaaccaacaa gtaaacagga agaaattgtg aagcgtttag tatctgagct ggatgatgcc    5100
aacctccagg ttgaaaatgt ccgcgatcaa gcccttattt tgatgaatgc ccgtggaagc    5160
tcaagcaggg agcttgtaga accaaagtta gctgagctga ataggaactt tgaaaaggtg    5220
tctcaacata tcaaaagtgc caaattgcta attgctcagg aaccattata ccaatgtttg    5280
gtcaccactg aaacatttga aactggtgtg cctttctctg acttggaaaa attagaaaat    5340
gacatagaaa atatgttaaa atttgtggaa aaacacttgg aatccagtga tgaagatgaa    5400
aagatggatg aggagagtgc ccagattgag gaagttctac aaagaggaga gaaatgtta    5460 catcaaccta tggaagataa taaaaaagaa aagatccgtt tgcaattatt acttttgcat    5520
actagataca acaaaattaa ggcaatccct attcaacaga ggaaaatggg tcaacttgct    5580
tctggaatta gatcatcact tcttcctaca gattatctgg ttgaaattaa caaaatttta    5640 cttttgcatgg atgatgttga attatcgctt aatgttccag agctcaacac tgctatttac    5700
gaagacttct cttttcagga agactctctg aagaatatca aagaccaact ggacaaactt    5760
ggagagcaga ttgcagtcat tcatgaaaaa cagccagatg tcatccttga agcctctgga    5820
cctgaagcca ttcagatcag agatacactt actcagctga atgcaaaatg ggacagaatt    5880
aatagaatgt acagtgatcg gaaaggttgt tttgacaggg caatggaaga atggagacag    5940
ttccattgtg accttaatga cctcacacag tggataacag aggctgaaga attactggtt    6000
gatacctgtg ctccaggtgg cagcctggac ttagagaaag ccaggataca tcagcaggaa    6060
cttgaggtgg gcatcagcag ccaccagccc agttttgcag cactaaaccg aactggggat    6120
gggattgtgc agaaactctc ccaggcagat ggaagcttct tgaaagaaaa actggcaggt    6180
ttaaaccaac gctgggatgc aattgttgca gaagtgaagg ataggcagcc aaggctaaaa    6240
ggagaaagta agcaggtgat gaagtacagg catcagctag atgagattat ctgttggtta    6300
acaaaggctg agcatgctat gcaaaagaga tcaaccaccg aattgggaga aaacctgcaa    6360
gaattaagag acttaactca agaaatggaa gtacatgctg aaaaactcaa atggctgaat    6420
agaactgaat tggagatgct ttcagataaa agtctgagtt tacctgaaag ggataaaatt    6480
tcagaaagct taaggactgt aaatatgaca tggaataaga tttgcagaga ggtgcctacc    6540
accctgaagg aatgcatcca ggagcccagt tctgtttcac agacaaggat tgctgctcat    6600
cctaatgtcc aaaaggtggt gctagtatca tctgcgtcag atattcctgt tcagtctcat    6660
cgtacttcgg aaatttcaat tcctgctgat cttgataaaa ctataacaga actagccgac    6720
tggctggtat taatcgacca gatgctgaag tccaacattg tcactgttgg ggatgtagaa    6780
gagatcaata agaccgtttc ccgaatgaaa attacaaagg ctgacttaga acagcgccat    6840
cctcagctgg attatgtttt tacattggca cagaatttga aaaataaagc ttccagttca    6900
gatatgagaa cagcaattac agaaaaattg gaaagggtca agaaccagtg ggatggcacc    6960
cagcatggcg ttgagctaag acagcagcag cttgaggaca tgattattga cagtcttcag    7020
tgggatgacc ataggagga gactgaagaa ctgatgagaa aatatgaggc tcgactctat    7080
attcttcagc aagcccgacg ggatccactc accaaacaaa tttctgataa ccaaatactg    7140
cttcaagaac tgggtcctgg agatggtatc gtcatggcgt tcgataacgt cctgcagaaa    7200
ctcctggagg aatatgggag tgatgacaca aggaatgtga agaaaccac agagtactta    7260 aaaacatcat ggatcaatct caaacaaagt attgctgaca gacagaacgc cttggaggct    7320
gagtggagga cggtgcaggc ctctcgcaga gatctggaaa acttcctgaa gtggatccaa    7380
```

-continued

```
gaagcagaga ccacagtgaa tgtgcttgtg gatgcctctc atcgggagaa tgctcttcag    7440
gatagtatct tggccaggga actcaaacag cagatgcagg acatccaggc agaaattgat    7500
gcccacaatg acatatttaa aagcattgac ggaaacaggc agaagatggt aaaagctttg    7560
ggaaattctg aagaggctac tatgcttcaa catcgactgg atgatatgaa ccaaagatgg    7620
aatgacttaa aagcaaaatc tgctagcatc agggcccatt tggaggccag cgctgagaag    7680
tggaacaggt tgctgatgtc cttagaagaa ctgatcaaat ggctgaatat gaaagatgaa    7740
gagcttaaga aacaaatgcc tattggagga gatgttccag ccttacagct ccagtatgac    7800
cattgtaagg ccctgagacg ggagttaaag gagaaagaat attctgtcct gaatgctgtc    7860
gaccaggccc gagttttctt ggctgatcag ccaattgagg cccctgaaga gccaagaaga    7920
aacctacaat caaaaacaga attaactcct gaggagagag cccaaaagat tgccaaagcc    7980
atgcgcaaac agtcttctga agtcaaagaa aaatgggaaa gtctaaatgc tgtaactagc    8040
aattggcaaa agcaagtgga caaggcattg agaaaactca gagacctgca gggagctatg    8100
gatgacctgg acgctgacat gaaggaggca gagtccgtgc ggaatggctg aagcccgtg     8160 ggagacttac tcattgactc gctgcaggat cacattgaaa aaatcatggc atttagagaa    8220
gaaattgcac caatcaactt taaagttaaa acggtgaatg atttatccag tcagctgtct    8280
ccacttgacc tgcatccctc tctaaagatg tctcgccagc tagatgacct taatatgcga    8340
tggaaacttt tacaggtttc tgtggatgat cgccttaaac agcttcagga agcccacaga    8400
gattttggac catcctctca gcattttctc tctacgtcag tccagctgcc gtggcaaaga    8460
tccatttcac ataataaagt gccctattac atcaaccatc aaacacagac cacctgttgg    8520
gaccatccta aaatgaccga actctttcaa tcccttgctg acctgaataa tgtacgtttt    8580
tctgcctacc gtacagcaat caaaatccga agactacaaa aagcactatg tttggatctc    8640
ttagagttga gtacaacaaa tgaaattttc aaacagcaca agttaaacca aaatgaccag    8700
ctcctcagtg ttccagatgt catcaactgt ctgacaacaa cttatgatgg acttgagcaa    8760
atgcataagg acctggtcaa cgttccactc tgtgttgata tgtgtctcaa ttggttgctc    8820
aatgtctatg acacgggtcg aactggaaaa attagagtgc agagtctgaa gattggatta    8880
atgtctctct ccaaaggtct cttggaagaa aaatacagat atctctttaa ggaagttgcg    8940
gggccgacag aaatgtgtga ccagaggcag ctgggcctgt tacttcatga tgccatccag    9000
atcccccggc agctaggtga agtagcagct tttggaggca gtaatattga gcctagtgtt    9060
cgcagctgct tccaacagaa taacaataaa ccagaaataa gtgtgaaaga gtttatagat    9120
tggatgcatt tggaaccaca gtccatggtt tggctcccag ttttacatcg agtggcagca    9180
gcggagactg caaaacatca ggccaaatgc aacatctgta aagaatgtcc aattgtcggg    9240
ttcaggtata gaagccttaa gcattttaac tatgatgtct gccagagttg tttcttttcg    9300
ggtcgaacag caaaaggtca caaattacat tacccaatgg tggaatattg tatacctaca    9360
acatctgggg aagatgtacg agacttcaca aaggtactta agaacaagtt caggtcgaag    9420
aagtactttg ccaaacaccc tcgacttggt tacctgcctg tccagacagt tcttgaaggt    9480
gacaacttag agactcctat cacactcatc agtatgtggc cagagcacta tgacccctca    9540
caatctcctc aactgtttca tgatgacacc cattcaagaa tagaacaata tgccacacga    9600
ctggcccaga tggaaaggac taatgggtct tttctcactg atagcagctc caccacagga    9660
agtgtggaag acgagcacgc cctcatccag cagtattgcc aaacactcgg aggagagtcc    9720
ccagtgagcc agccgcagag cccagctcag atcctgaagt cagtagagag ggaagaacgt    9780
```

-continued

```
ggagaactgg agaggatcat tgctgacctg gaggaagaac aaagaaatct acaggtggag      9840
tatgagcagc tgaaggacca gcacctccga agggggctcc ctgtcggttc accgccagag      9900
tcgattatat ctccccatca cacgtctgag gattcagaac ttatagcaga agcaaaactc      9960
ctcaggcagc acaaaggtcg gctggaggct aggatgcaga ttttagaaga tcacaataaa     10020
cagctggagt ctcagctcca ccgcctccga cagctgctgg agcagcctga atctgattcc     10080
cgaatcaatg gtgtttcccc atgggcttct cctcagcatt ctgcactgag ctactcgctt     10140
gatccagatg cctccggccc acagttccac caggcagcgg gagaggacct gctggcccca     10200
ccgcacgaca ccagcacgga tctcacggag gtcatggagc agattcacag cacgtttcca     10260
tcttgctgcc caaatgttcc cagcaggcca caggcaatgt ga                        10302
```

<210> SEQ ID NO 4
<211> LENGTH: 11096
<212> TYPE: DNA
<213> ORGANISM: Mus musculus

<400> SEQUENCE: 4

```
atggccaagt atggggacct tgaagccagg cctgatgatg gcagaacgaa attcagtgac       60
atcattaagt ccagatctga tgaacacaat gatgtacaga agaaaacctt taccaaatgg      120
ataaacgctc gattttccaa gagtgggaaa ccacccatca gtgatatgtt ctcagacctc      180
aaagatggga aaagctctt ggatcttctc aaggcctca caggaacatc attgccaaag       240
gaacgtggtt ccacaagggt gcatgcctta acaatgtca ccgagtgct acaggtttta       300 catcagaaca atgtggactt ggtgaatatt ggaggcacgg acattgtggc tggaaatccc      360
aagctgactt tagggttact ctggagcatc attctgcact ggcaggtgaa ggatgtcatg      420
aaagatatca tgtcagacct gcagcagaca acagcgaga agatcctgct gagctgggtg       480
cggcagacca ccaggcccta cagtcaagtc aacgtcctca acttcaccac cagctggacc      540
gatggactcg cgttcaacgc cgtgctccac cggcacaaac cagatctctt cgactgggac      600
gagatggtca aaatgtcccc aattgagaga cttgaccatg cttttgacaa ggcccacact      660
tctttgggaa ttgaaaagct cctaagtcct gaaactgttg ctgtgcatct ccctgacaag      720 aaatcccataa ttatgtattt aacgtctctg tttgaggtgc ttcctcagca agtcacgata      780
gatgccatcc gagaggtgga gactctccca aggaagtata agaaagaatg tgaagaggaa      840
gaaattcata tccagagtgc agtgctggca gaggaaggcc agagtccccg agctgagacc      900
cctagcaccg tcactgaagt ggacatggat ttggacagct accagatagc gctagaggaa      960
gtgctgacgt ggctgctgtc cgcggaggac acgttccagg agcaacatga catttctgat     1020
gatgtcgaag aagtcaaaga gcagtttgct acccatgaaa cttttatgat ggagctgaca     1080
gcacaccaga gcagcgtggg gagcgtcctg caggctggca accagctgat gacacaaggg     1140
actctgtcca gagaggagga gtttgagatc caggaacaga tgaccttgct gaatgcaagg     1200
tgggaggcgc tccgggtgga gagcatggag aggcagtccc ggctgcacga cgctctgatg     1260
gagctgcaga gaaacagct gcagcagctc tcaagctggc tggccctcac agaagagcgc     1320
attcagaaga tggagagcct cccgctgggt gatgacctgc cctccctgca gaagctgctt     1380
caagaacata aagtttgca aaatgacctt gaagctgaac aggtgaaggt aaattcctta     1440
actcacatgg tggtgattgt ggatgaaaac agtggggaga gtgccacagc tcttctggaa     1500
gatcagttac agaaactggg tgagcgctgg acagctgtat gccgctggac tgaagaacgt     1560
```

```
tggaacaggt tgcaagaaat cagtattctg tggcaggaat tattggaaga gcagtgtctg   1620
ttggaggctt ggctcaccga aaaggaagag gctttggata aagttcaaac cagcaacttt   1680
aaagaccaga aggaactaag tgtcagtgtc cggcgtctgg ctatattgaa ggaagacatg   1740
gaaatgaaga ggcagactct ggatcaactg agtgagattg ccaggatgt gggccaatta    1800 ctcagtaatc ccaaggcatc taagaagatg aacagtgact ctgaggagct aacacagaga   1860
tgggattctc tggttcagag actcgaagac tcttctaacc aggtgactca ggcggtagcg   1920
aagctcggca tgtcccagat tccacagaag gacctattgg agaccgttca tgtgagagaa   1980
caagggatgg tgaagaagcc caagcaggaa ctgcctcctc ctcccccacc aaagaagaga   2040
cagattcacg tggacgtgga ggccaagaaa agtttgatg ctataagtac agagctgctg     2100
aactggattt tgaaatcaaa gactgccatt cagaacacag atgaaaga atataagaag     2160 tcgcaggaga cctcaggaat gaaaagaaa ttgaagggat tagagaaaga acagaaggaa    2220
aatctgcccc gactggacga actgaatcaa accggacaaa ccctccggga gcaaatggga   2280
aaagaaggcc ttccactgaa agaagtaaac gatgttctgg aaagggtttc gttggagtgg   2340
aagatgatat ctcagcagct agaagatctg ggaaggaaga tccagctgca ggaagatata   2400
aatgcttatt ttaagcagct tgatgccatt gaggagacca tcaaggagaa ggaagagtgg   2460
ctgaggggca cacccatttc tgaatcgccc cggcagccct tgccaggctt aaaggattct   2520
tgccagaggg aactgacaga tctccttggc cttcacccca gaattgagac gctgtgtgca   2580
agctgttcag ccctgaagtc tcagccctgt gtcccaggtt ttgtccagca gggttttgac   2640
gaccttcgac atcattacca ggctgttgcg aaggctttag aggaatacca acaacaacta   2700
gaaaatgagc tgaagagcca gcctggaccc gagtatttgg acacactgaa taccctgaaa   2760
aaaatgctaa gcgagtcaga aaaggcggcc caggcctctc tgaatgccct gaacgatccc   2820
atagcggtgg agcaggccct gcaggagaaa aaggcccttg atgaaaccct tgagaatcag   2880
aaacatacgt tacataagct ttcagaagaa acgaagactt tggagaaaaa tatgcttcct   2940
gatgtgggga aaatgtataa acaagaattt gatgatgtcc aaggcagatg gaataaagta   3000
aagaccaagg tttccagaga cttacacttg ctcgaggaaa tcaccccag actccgagat    3060 tttgaggctg attcagaagt cattgagaag tgggtgagtg gcatcaaaga cttcctcatg   3120
aaagaacagg ctgcccaagg agacgctgct gcgcagagcc agcttgacca atgtgctacg   3180
tttgctaatg aaatcgaaac catcgagtca tctctgaaga acatgaggga agtagagact   3240
agccttcaga ggtgtccagt cactggagtc aagacatggg tacaggcaag actagtggat   3300
taccaatccc aactggagaa attcagcaaa gagattgcta ttcaaaaaag caggctgtta   3360
gatagtcaag aaaaagccct gaacttgaaa aaggatttgg ctgagatgca ggagtggatg   3420
gcacaggctg aagaggacta cctggagagg gacttcgagt acaaatctcc agaagaactc   3480
gagagtgcgg tggaggaaat gaagagggca aagaggatg tgctgcagaa ggaggtgagg    3540
gtgaaaattc tgaaggacag catcaagctg gtggctgcca aggtgccctc tggtggccag   3600
gagttgacgt cggaattcaa cgaggtgctg gagagctacc agcttctgtg caatagaatt   3660
cgagggaagt gccacacact ggaggaggtc tggtcttgct gggtggagct gcttcactat   3720
ctggacctgg agaccacgtg gttgaacacc tggaggagc gcgtgaggag cacgaggcc     3780 ctgcctgaga gggcagaagc tgttcatgaa gctctggagt ctcttgagtc tgttttgcgc   3840
catccagcgg ataatcgcac ccagattcgg gaacttgggc agactctgat tgatggtgga   3900
atcctggatg acataatcag cgagaagctg gaggctttta acagccgcta cgaagagctg   3960
```

-continued

```
agtcacttgg cggagagcaa acagatttct ttggagaagc aactccaggt cctccgcgaa    4020
actgaccaca tgcttcaggt gctgaaggag agcctggggg agctggacaa acagcttacc    4080
acatacctga cggacaggat cgatgccttc caactgccac aggaagctca gaagatccaa    4140
gccgaaatct cagcccatga gctcaccctg gaggagctga ggaagaatgt gcgctcccag    4200
cccccgacgt cccctgaggg cagggccacc agaggaggaa gtcagatgga catgctacag    4260
aggaaacttc gagaggtctc caccaaattc cagcttttcc agaagcccgc aaatttcgag    4320
cagcggatgc tggactgcaa gcgtgtgttg gagggagtga aggccgagct tcatgtcctc    4380
gatgtgaggg atgtggaccc tgatgtcatt caggcccact tggacaagtg catgaaacta    4440
tataaaacgt tgagtgaagt caaacttgaa gttgagactg tcatcaaaac agggaggcac    4500
attgtccaga agcagcagac ggacaacccg aaaagcatgg acgaacagct tacatctctg    4560
aaagtcctct acaatgacct gggcgcacag gtgacagaag ggaagcaaga cctggaaaga    4620
gcctcacagc tgtccaggaa gatgaagaag gaggctgccg tcctctctga atggctctct    4680
gccacagagg cagaactagt gcagaaatcc acatcagaag gcgtgattgg tgacctggac    4740
acagaaatct cctgggctaa aagtattctc aaggatctgg aaaagaggaa agttgactta    4800
aatggcatta cagagagcag tgctgcccct cagcacttgg tcttgggcag tgagtctgtt    4860
ctggaagaga acctctgtgt gctcaatgct ggatggagcc gagtgcggac gtggaccgaa    4920
gactggtgca acaccttgct gaaccatcaa aaccagctgg agctatttga tggacacgtc    4980
gctcacatca gtacctggct ctatcaagca gaagctctgc tggatgagat cgaaaagaaa    5040
ccagcgagta acaggaaga aattgtgaag cgtttactgt ctgaattgga tgatgccagc    5100
ctccaggttg agaatgttcg ggaacaagcc atcatcttgg tgaatgctcg tggaagcgcc    5160
agcagggaac tcgtggaacc aaaattagcc gagctgagca ggaactttga aaaggtgtcc    5220
cagcacataa agagcgcccg aatgctgatt ggtcaggacc cttcatccta ccaaggcttg    5280
gaccctgctg gaactgttca agctgctgag tctttctctg acttggaaaa cttagaacaa    5340
gacatagaaa acatgttgaa agttgtggaa agcacttggg accccaataa cgatgagaag    5400
atggatgagg agcaagccca gattgaggaa gttctacaaa gagggagca tttgttacat    5460
gaacctatgg aggacagtaa gaaagaaaag atccgcttgc agttgttact tttgcatact    5520
cgttacaaca aaattaagac aatccctatc cagcagagaa aaacaattcc agtttcttct    5580
ggaattacat catcagccct ccctgcagat tatttggttg aaattaataa aatttactc    5640
actctggatg acattgaatt atcacttaat atgccggagc taaacaccac tgtctacaaa    5700
gacttctctt tccaggaaga ctctctgaag agtatcaaag gtcaactgga cagacttgga    5760
gagcagattg cagttgttca cgagaagcag ccggatgtca tcgtggaagc ctctggccct    5820
gaggccattc agatcaggga catgctcgct cagctgaacg caaaatggga ccgagtgaat    5880
agagtgtaca gtgatcggag agggtccttt gccagggctg tggaggaatg gaggcagttc    5940
caccatgacc ttgatgacct tacacagtgg ctatctgaag ctgaagacct gctggtagac    6000
acttgtgctc cagatggtag cctggacctg gagaaagcca gggcacagca gctggaactg    6060
gaagagggcc tcagcagcca ccagcccagc ctgatcaagg ttaaccgaaa ggggaggac    6120
cttgttcaga gactccgccc ctcggaggca agcttcctga aggagaagct ggcaggtttc    6180
aaccagcgct ggagcactct tgtagctgag gtggaggctt tgcagcccag gctaaaagga    6240
gaaagtcagc aggtgttggg gtataagaga cggctagatg aggtcacctg ctggttaacg    6300
```

```
aaagtggaga gtgctgtgca gaagagatca acccctgacc cggaagaaag cccacaggaa    6360
ttaacagatt tagcccaaga gacggaagtt caagctgaaa acattaagtg gctgaacaga    6420
gcagaactgg aaatgctttc agacaaaaat ctgagtttgc gtgaaagaga gaaactttcg    6480
gaaagtttaa agaatgtaaa cacaacatgg accaaggtat gcagagaagt gcctagcctc    6540
ctgaagacac gcacccaaga cccctgctct gccccacaga tgaggatggc tgctcatccc    6600
aacgtccaaa aggtggtgct agtatcatct gcatcagatg ctcctctgcg tggcggcctg    6660
gaaatctcgg ttcctgctga tttggataaa accatcacag aactggctga ctggctggta    6720
ttgatcgacc aaatgctgaa gtccaacatt gtcactgtgg gggacgtgaa agagatcaat    6780
aagacagttt cccggatgaa aatcacaaag gctgatttag aacaacgcca tcctcagctt    6840
gattgtgtat ttacgttggc ccaaaatttg aaaacaaag cttccagttc agatgtgaga    6900
acagcaatca cagaaaaatt ggaaaagctg aagacccagt gggagagtac tcagcatggt    6960
gtggagctgc ggcggcagca gctggaggac atggttgtgg acagcctgca gtgggacgac    7020
cacagggaag agactgaaga gctcatgaga aaatacgagg ctcgcttcta catgctgcag    7080
caggcccgcc gggacccact tagcaaacaa gtttctgata tcaactatt gcttcaagag    7140
ctggggtctg gcgatggtgt catcatggcg tttgataatg tcctgcagaa acttctggaa    7200
gaatacagtg gcgatgacac aaggaatgtg aagaaaacca ggagtacttt gaaaacatca    7260
tgggtcaatc tcaaacaaag catcgctgat agacagagtg ccttggaggc tgagctacag    7320
acagtgcaga cttctcgtag agacctggag aactttgtca gtggcttca ggaagcagaa    7380
accacagcaa atgtgctggc cgatgcctct cagcgggaga atgctcttca ggacagtgtc    7440
ctggcccggc agctccgaca gcagatgctg acatccagg cagaaattga tgcccacaat    7500
gacatattta aaagcatcga tggaaaccgg cagaagatgg tgaaagctct ggggaattct    7560
gaggaagcaa caatgcttca acatcgactg gatgacatga accaaagatg gaatgatttg    7620
aaggcaaaat ctgctagcat cagggcccat ttggaggcca gtgctgagaa atggaaccgg    7680
ttgctggcat cgctggaaga gctgatcaaa tggctcaata tgaaagatga ggagcttaag    7740
aagcagatgc ccattggagg ggacgtccct gccttacagc tccagtatga ccactgcaag    7800
gtgctgagac gtgagctaaa ggagaaagag tattctgtgc tgaacgccgt agatcaagct    7860
cgagttttc tggctgatca gccaatagag gcccccgaag aaccaagaag aaacccacaa    7920
tcaaagacag agttgactcc tgaggagaga gcccagaaga tcgccaaagc catgcgcaag    7980
cagtcttctg aagtccgaga gaagtgggaa atctaaatg ctgtcactag caactggcaa    8040
aagcaagtag ggaaggcgtt agagaaactc cgagacctgc agggagctat ggacgacctg    8100
gacgcagaca tgaaggaggt ggaggctgtg cggaatggct ggaagcccgt gggagacctg    8160
cttatagact ccctgcagga tcacatcgag aaaaccctgg cgtttagaga agaaattgca    8220
ccaatcaact taaaagtaaa aacaatgaat gacctgtcca gtcagctgtc tccacttgac    8280
ttgcatccat ctctaaagat gtctcgccag ctggatgacc ttaatatgcg atggaaactt    8340
ctacaggttt ccgtggacga tcgccttaag cagctccagg aagcccacag agattttggg    8400
ccatcttctc aacactttct gtccacttca gtccagctgc cgtggcagag atccatttca    8460
cataataaag tgccctatta catcaaccat caaacacaga caacctgttg ggatcatcct    8520
aaaatgactg agctcttcca atcccttgct gatctgaata atgtacgttt tctctgcctac    8580
cgcacagcaa tcaaaattcg aaggctgcaa aaagcattat gtctggatct cttagagctg    8640
aatacgacga atgaagtttt caagcagcac aaaactgaacc aaaatgatca gctcctgagt    8700
```

```
gtcccagacg tcatcaactg tctgaccacc acttacgatg ggcttgagca gctgcacaag    8760
gacttggtca atgttccact ctgcgtcgat atgtgtctca actggctgct caacgtatac    8820
gacacgggcc ggactggaaa aattcgggta cagagtctga agattggatt gatgtctctc    8880
tccaaaggcc tcttagaaga gaaatacaga tgtctcttta aggaggtggc agggccaact    8940
gagatgtgtg accagcggca gcttggcctg ctacttcacg atgccatcca gatccctagg    9000
cagctggggg aagtagcagc ctttgggggc agtaacattg agcccagtgt ccgcagctgc    9060
ttccagcaga ataacaacaa gccagaaatc agtgtgaagg agtttataga ctggatgcat    9120
ttggaacccc agtccatggt gtggttgccg gttctgcatc gggtcgcagc tgctgagact    9180
gcaaaacatc aggccaaatg caacatctgc aaagaatgcc cgattgttgg gttcagatac    9240
aggagcctaa agcattttaa ttatgatgtc tgccagagtt gcttctttc tggaagaaca    9300
gcaaggggcc acaagttaca ttacccgatg gtagaatact gcataccgac aacatctggg    9360
gaagatgtga gagatttcac taaggtgctg aagaacaagt tcaggtccaa gaaatatttt    9420
gccaaacatc ctcggcttgg ctacctgcct gtccagaccg tgctggaagg ggacaactta    9480
gaaactccta tcacgctcat cagtatgtgg ccagagcact atgacccctc ccagtcccct    9540
cagctgtttc atgatgacac ccactcaaga atagagcaat acgctacacg actggcccag    9600
atggaaagga caaacgggtc cttcctaact gatagcagct ctacaacagg aagcgtggag    9660
gatgagcatg ccctcatcca gcagtactgc cagaccctgg gcggggagtc acctgtgagt    9720
cagccgcaga gtccagctca gatcctgaag tccgtggaga gggaagagcg tggggaactg    9780
gagcggatca ttgctgactt ggaggaagag caaagaaatc tgcaggtgga gtatgagcag    9840
ctgaaggagc agcacctaag aagggggtctc cctgtgggct ccctccagga ctccatcgta    9900
tctcctcacc acacatctga ggactcagaa cttatagcag aagctaaact cctgcggcag    9960
cacaaagggc ggctggaggc gaggatgcaa attttggaag atcacaataa acagctggag   10020
tctcagctgc accgcctcag acagctcctg gagcagcctg actctgactc ccgcatcaat   10080
ggtgtctccc cctgggcttc cccacagcat tctgcattga gctactcact tgacactgac   10140
ccaggcccac agttccacca ggcagcatct gaggacctgc tggccccacc tcacgacact   10200
agcacggacc tcacggacgt gatggagcag atcaacagca cgtttccctc ttgcagctca   10260
aatgtcccca gcaggccaca ggcaatgtga gcatctatcc agccagccaa catttcccga   10320
ccttcagtat tgccctcttc tgcaaatgcc aatcccaaga cccattcaac cccaaagctc   10380
cgtggctcca cgacacaagc tgttgagtgc ttactgggtg ttctactgag ggaaccaaac   10440
actgactatc caaagatatt ttggtttct aataacgtat attattgttt tctttctccc   10500
cttcctatgc aactgtaaat taatgaacag agaagtattt ggaggtggta aagcatttgt   10560
cactgatttg tataatatat acagccatgg gaaagtgggt ggggcttc taatatgaaa   10620
ctgtcttttt aataaccaag agaaaaaatt gcataagaat tagaccactt tacattatta   10680
cattccttct gctgttcaca ttaaccttgt acaataactt cacttattat ttgactgttt   10740
taccattatg ttttggttat ttataaattt atcagccata ccaaacgaat agattctatg   10800
tatttggttt ctataatctg gccaaattcc taagttcata tatttgaatc aaatatttta   10860
catatgtgga gtaggcaggc attctgaaga tactatttaa ctttagttga cgtcacacac   10920
accatccttt agtaaccact ggatgactac actaaaaatc ctgtggactt taacggcaag   10980
ctgctggggt attttttcctc ctgttttat tccttttttg taagtagatc ttgacgtctt   11040
```

```
tatttatttc atcttgcaat ctctataata aagaagactg tattgtaata gtcccc      11096
```

<210> SEQ ID NO 5
<211> LENGTH: 208
<212> TYPE: DNA
<213> ORGANISM: Homo sapiens

<400> SEQUENCE: 5

```
gggattccct cactttcccc ctacaggact cagatctggg aggcaattac cttcggagaa    60
aaacgaatag gaaaaactga agtgttactt tttttaaagc tgctgaagtt tgttggtttc   120
tcattgtttt taagcctact ggagcaataa agtttgaaga acttttacca ggttttttt    180
atcgctgcct tgatatacac ttttcaaa                                      208
```

<210> SEQ ID NO 6
<211> LENGTH: 756
<212> TYPE: DNA
<213> ORGANISM: Homo sapiens

<400> SEQUENCE: 6

```
atgctttggt gggaagaagt agaggactgt tatgaaagag aagatgttca aaagaaaaca    60
ttcacaaaat gggtaaatgc acaattttct aagtttggga agcagcatat tgagaacctc   120
ttcagtgacc tacaggatgg gaggcgcctc ctagacctcc tcgaaggcct gacagggcaa   180
aaactgccaa agaaaaagg atccacaaga gttcatgccc tgaacaatgt caacaaggca    240
ctgcggtttt tgcagaacaa taatgttgat ttagtgaata ttggaagtac tgacatcgta   300
gatggaaatc ataaactgac tcttggtttg atttggaata taatcctcca ctggcaggtc   360
aaaaatgtaa tgaaaaatat catggctgga ttgcaacaaa ccaacagtga aaagattctc   420
ctgagctggg tccgacaatc aactcgtaat tatccacagg ttaatgtaat caacttcacc   480
accagctggt ctgatggcct ggctttgaat gctctcatcc atagtcatag gccagaccta   540
tttgactgga atagtgtggt tgccagcag tcagccacac aacgactgga acatgcattc    600
aacatcgcca gatatcaatt aggcatagag aaactactcg atcctgaaga tgttgatacc   660
acctatccag ataagaagtc catcttaatg tacatcacat cactcttcca agttttgcct   720
caacaagtga gcattgaagc catccaggaa gtggaa                             756
```

<210> SEQ ID NO 7
<211> LENGTH: 255
<212> TYPE: DNA
<213> ORGANISM: Homo sapiens

<400> SEQUENCE: 7

```
atgttgccaa ggccacctaa agtgactaaa gaagaacatt ttcagttaca tcatcaaatg    60
cactattctc aacagatcac ggtcagtcta gcacagggat atgagagaac ttcttcccct   120
aagcctcgat tcaagagcta tgcctacaca caggctgctt atgtcaccac ctctgaccct   180
acacggagcc catttccttc acagcatttg gaagctcctg aagacaagtc atttggcagt   240
tcattgatgg agagt                                                    255
```

<210> SEQ ID NO 8
<211> LENGTH: 327
<212> TYPE: DNA
<213> ORGANISM: Homo sapiens

<400> SEQUENCE: 8

```
gaagtaaacc tggaccgtta tcaaacagct ttagaagaag tattatcgtg gcttctttct    60
```

```
gctgaggaca cattgcaagc acaaggagag atttctaatg atgtggaagt ggtgaaagac      120
cagtttcata ctcatgaggg gtacatgatg gatttgacag cccatcaggg ccgggttggt      180
aatattctac aattgggaag taagctgatt ggaacaggaa aattatcaga agatgaagaa      240
actgaagtac aagagcagat gaatctccta aattcaagat gggaatgcct cagggtagct      300
agcatggaaa acaaagcaa tttacat                                           327

<210> SEQ ID NO 9
<211> LENGTH: 333
<212> TYPE: DNA
<213> ORGANISM: Homo sapiens

<400> SEQUENCE: 9
agagttttaa tggatctcca gaatcagaaa ctgaaagagt tgaatgactg gctaacaaaa       60
acagaagaaa gaacaaggaa aatggaggaa gagcctcttg gacctgatct tgaagaccta      120
aaacgccaag tacaacaaca taaggtgctt caagaagatc tagaacaaga acaagtcagg      180
gtcaattctc tcactcacat ggtggtggta gttgatgaat ctagtggaga tcacgcaact      240
gctgctttgg aagaacaact taaggtattg ggagatcgat gggcaaacat ctgtagatgg      300
acagaagacc gctgggttct tttacaagac atc                                   333

<210> SEQ ID NO 10
<211> LENGTH: 333
<212> TYPE: DNA
<213> ORGANISM: Homo sapiens

<400> SEQUENCE: 10
cttctcaaat ggcaacgtct tactgaagaa cagtgccttt ttagtgcatg gctttcagaa       60
aaagaagatg cagtgaacaa gattcacaca actggcttta agatcaaaa tgaaatgtta      120 tcaagtcttc aaaaactggc cgttttaaaa gcggatctag aaaagaaaaa gcaatccatg      180
ggcaaactgt attcactcaa acaagatctt cttcaacac tgaagaataa gtcagtgacc      240
cagaagacgg aagcatggct ggataacttt gcccggtgtt gggataattt agtccaaaaa      300
cttgaaaaga gtacagcaca gatttcacag gct                                   333

<210> SEQ ID NO 11
<211> LENGTH: 147
<212> TYPE: DNA
<213> ORGANISM: Homo sapiens

<400> SEQUENCE: 11
gtcaccacca ctcagccatc actaacacag acaactgtaa tggaaacagt aactacggtg       60
accacaaggg aacagatcct ggtaaagcat gctcaagagg aacttccacc accacctccc      120
caaaagaaga ggcagattac tgtggat                                          147

<210> SEQ ID NO 12
<211> LENGTH: 333
<212> TYPE: DNA
<213> ORGANISM: Homo sapiens

<400> SEQUENCE: 12
tctgaaatta ggaaaaggtt ggatgttgat ataactgaac ttcacagctg gattactcgc       60
tcagaagctg tgttgcagag tcctgaattt gcaatctttc ggaaggaagg caacttctca      120
gacttaaaag aaaagtcaa tgccatagag cgagaaaaag ctgagaagtt cagaaaactg      180
```

-continued

| caagatgcca gcagatcagc tcaggccctg gtggaacaga tggtgaatga gggtgttaat | 240 |
| gcagatagca tcaaacaagc ctcagaacaa ctgaacagcc ggtggatcga attctgccag | 300 |
| ttgctaagtg agagacttaa ctggctggag tat | 333 |

<210> SEQ ID NO 13
<211> LENGTH: 327
<212> TYPE: DNA
<213> ORGANISM: Homo sapiens

<400> SEQUENCE: 13

| cagaacaaca tcatcgcttt ctataatcag ctacaacaat tggagcagat gacaactact | 60 |
| gctgaaaact ggttgaaaat ccaacccacc accccatcag agccaacagc aattaaaagt | 120 |
| cagttaaaaa tttgtaagga tgaagtcaac cggctatcag gtcttcaacc tcaaattgaa | 180 |
| cgattaaaaa ttcaaagcat agccctgaaa gagaaggac aaggacccat gttcctggat | 240 |
| gcagactttg tggcctttac aaatcatttt aagcaagtct tttctgatgt gcaggccaga | 300 |
| gagaaagagc tacagacaat ttttgac | 327 |

<210> SEQ ID NO 14
<211> LENGTH: 327
<212> TYPE: DNA
<213> ORGANISM: Homo sapiens

<400> SEQUENCE: 14

| actttgccac caatgcgcta tcaggagacc atgagtgcca tcaggacatg ggtccagcag | 60 |
| tcagaaacca aactctccat acctcaactt agtgtcaccg actatgaaat catggagcag | 120 |
| agactcgggg aattgcaggc tttacaaagt tctctgcaag agcaacaaag tggcctatac | 180 |
| tatctcagca ccactgtgaa agagatgtcg aagaaagcgc cctctgaaat tagccggaaa | 240 |
| tatcaatcag aatttgaaga aattgaggga cgctggaaga agctctcctc ccagctggtt | 300 |
| gagcattgtc aaaagctaga ggagcaa | 327 |

<210> SEQ ID NO 15
<211> LENGTH: 327
<212> TYPE: DNA
<213> ORGANISM: Homo sapiens

<400> SEQUENCE: 15

| atgaataaac tccgaaaaat tcagaatcac atacaaaccc tgaagaaatg gatggctgaa | 60 |
| gttgatgttt ttctgaagga ggaatggcct gcccttgggg attcagaaat tctaaaaaag | 120 |
| cagctgaaac agtgcagact tttagtcagt gatattcaga caattcagcc cagtctaaac | 180 |
| agtgtcaatg aaggtgggca gaagataaag aatgaagcag agccagagtt tgcttcgaga | 240 |
| cttgagacag aactcaaaga acttaacact cagtgggatc acatgtgcca acaggtctat | 300 |
| gccagaaagg aggccttgaa gggaggt | 327 |

<210> SEQ ID NO 16
<211> LENGTH: 327
<212> TYPE: DNA
<213> ORGANISM: Homo sapiens

<400> SEQUENCE: 16

| ttggagaaaa ctgtaagcct ccagaaagat ctatcagaga tgcacgaatg gatgacacaa | 60 |
| gctgaagaag agtatcttga gagagatttt gaatataaaa ctccagatga attacagaaa | 120 |
| gcagttgaag agatgaagag agctaaagaa gaggcccaac aaaaagaagc gaaagtgaaa | 180 |

```
ctccttactg agtctgtaaa tagtgtcata gctcaagctc cacctgtagc acaagaggcc        240
ttaaaaaagg aacttgaaac tctaaccacc aactaccagt ggctctgcac taggctgaat        300
gggaaatgca agactttgga agaagtt                                            327

<210> SEQ ID NO 17
<211> LENGTH: 312
<212> TYPE: DNA
<213> ORGANISM: Homo sapiens

<400> SEQUENCE: 17
tgggcatgtt ggcatgagtt attgtcatac ttggagaaag caaacaagtg gctaaatgaa         60
gtagaattta aacttaaaac cactgaaaac attcctggcg gagctgagga aatctctgag        120
gtgctagatt cacttgaaaa tttgatgcga cattcagagg ataacccaaa tcagattcgc        180
atattggcac agaccctaac agatggcgga gtcatggatg agctaatcaa tgaggaactt        240
gagacattta attctcgttg gagggaacta catgaagagg ctgtaaggag gcaaaagttg        300
cttgaacaga gc                                                            312

<210> SEQ ID NO 18
<211> LENGTH: 276
<212> TYPE: DNA
<213> ORGANISM: Homo sapiens

<400> SEQUENCE: 18
atccagtctg cccaggagac tgaaaaatcc ttacacttaa tccaggagtc cctcacattc         60
attgacaagc agttggcagc ttatattgca gacaaggtgg acgcagctca aatgcctcag        120
gaagcccaga aaatccaatc tgatttgaca agtcatgaga tcagtttaga agaaatgaag        180
aaacataatc aggggaagga ggctgcccaa agagtcctgt ctcagattga tgttgcacag        240
aaaaaattac aagatgtctc catgaagttt cgatta                                  276

<210> SEQ ID NO 19
<211> LENGTH: 327
<212> TYPE: DNA
<213> ORGANISM: Homo sapiens

<400> SEQUENCE: 19
ttccagaaac cagccaattt tgagctgcgt ctacaagaaa gtaagatgat tttagatgaa         60
gtgaagatgc acttgcctgc attggaaaca aagagtgtgg aacaggaagt agtacagtca        120
cagctaaatc attgtgtgaa cttgtataaa agtctgagtg aagtgaagtc tgaagtggaa        180
atggtgataa agactggacg tcagattgta cagaaaaagc agacgaaaaa tcccaaagaa        240
cttgatgaaa gagtaacagc tttgaaattg cattataatg agctgggagc aaaggtaaca        300
gaaagaaagc aacagttgga gaaatgc                                            327

<210> SEQ ID NO 20
<211> LENGTH: 324
<212> TYPE: DNA
<213> ORGANISM: Homo sapiens

<400> SEQUENCE: 20
ttgaaattgt cccgtaagat gcgaaaggaa atgaatgtct tgacagaatg gctggcagct         60
acagatatgg aattgacaaa gagatcagca gttgaaggaa tgcctagtaa tttggattct        120
gaagttgcct gggaaaaggc tactcaaaaa gagattgaga aacagaaggt gcacctgaag        180
```

```
agtatcacag aggtaggaga ggccttgaaa acagttttgg gcaagaagga gacgttggtg      240
gaagataaac tcagtcttct gaatagtaac tggatagctg tcacctcccg agcagaagag      300
tggttaaatc ttttgttgga atac                                             324
```

```
<210> SEQ ID NO 21
<211> LENGTH: 312
<212> TYPE: DNA
<213> ORGANISM: Homo sapiens

<400> SEQUENCE: 21
cagaaacaca tggaaacttt tgaccagaat gtggaccaca tcacaaagtg gatcattcag       60
gctgacacac ttttggatga atcagagaaa aagaaacccc agcaaaaaga agacgtgctt      120
aagcgtttaa aggcagaact gaatgacata cgcccaaagg tggactctac acgtgaccaa      180 gcagcaaaact tgatggcaaa ccgcggtgac cactgcagga aattagtaga gccccaaatc    240
tcagagctca accatcgatt tgcagccatt tcacacagaa ttaagactgg aaaggcctcc     300
attcctttga ag                                                         312
```

```
<210> SEQ ID NO 22
<211> LENGTH: 282
<212> TYPE: DNA
<213> ORGANISM: Homo sapiens

<400> SEQUENCE: 22
gaattggagc agtttaactc agatatacaa aaattgcttg aaccactgga ggctgaaatt       60 cagcagggg tgaatctgaa agaggaagac ttcaataaag atatgaatga agacaatgag      120
ggtactgtaa agaattgtt gcaaagagga gacaacttac aacaaagaat cacagatgag      180
agaaagagag aggaaataaa gataaaacag cagctgttac agacaaaaca taatgctctc     240
aaggatttga ggtctcaaag aagaaaaaag gctctagaaa tt                        282
```

```
<210> SEQ ID NO 23
<211> LENGTH: 294
<212> TYPE: DNA
<213> ORGANISM: Homo sapiens

<400> SEQUENCE: 23
tctcatcagt ggtatcagta caagaggcag gctgatgatc tcctgaaatg cttggatgac       60
attgaaaaaa aattagccag cctacctgag cccagagatg aaaggaaaat aaaggaaatt     120
gatcgggaat tgcagaagaa gaaagaggag ctgaatgcag tgcgtaggca agctgagggc     180
ttgtctgagg atggggccgc aatggcagtg gagccaactc agatccagct cagcaagcgc     240
tggcgggaaa ttgagagcaa atttgctcag tttcgaagac tcaactttgc acaa           294
```

```
<210> SEQ ID NO 24
<211> LENGTH: 327
<212> TYPE: DNA
<213> ORGANISM: Homo sapiens

<400> SEQUENCE: 24
tcttatgtgc cttctactta tttgactgaa atcactcatg tctcacaagc cctattagaa       60
gtggaacaac ttctcaatgc tcctgacctc tgtgctaagg actttgaaga tctctttaag     120
caagaggagt ctctgaagaa tataaaagat agtctacaac aaagctcagg tcggattgac     180
attattcata gcaagaagac agcagcattg caaagtgcaa cgcctgtgga aagggtgaag     240
ctacaggaag ctctctccca gcttgatttc caatgggaaa agttaacaa aatgtacaag     300
```

```
gaccgacaag ggcgatttga cagatct                                          327

<210> SEQ ID NO 25
<211> LENGTH: 321
<212> TYPE: DNA
<213> ORGANISM: Homo sapiens

<400> SEQUENCE: 25
gttgagaaat ggcggcgttt tcattatgat ataaagatat ttaatcagtg gctaacagaa       60
gctgaacagt ttctcagaaa gacacaaatt cctgagaatt gggaacatgc taaatacaaa      120
tggtatctta aggaactcca ggatggcatt gggcagcggc aaactgttgt cagaacattg      180
aatgcaactg gggaagaaat aattcagcaa tcctcaaaaa cagatgccag tattctacag      240
gaaaaattgg gaagcctgaa tctgcggtgg caggaggtct gcaaacagct gtcagacaga      300
aaaaagaggc tagaagaaca a                                                321

<210> SEQ ID NO 26
<211> LENGTH: 351
<212> TYPE: DNA
<213> ORGANISM: Homo sapiens

<400> SEQUENCE: 26
aagaatatct tgtcagaatt tcaaagagat ttaaatgaat ttgttttatg gttggaggaa       60
gcagataaca ttgctagtat cccacttgaa cctggaaaag agcagcaact aaaagaaaag      120
cttgagcaag tcaagttact ggtggaagag ttgcccctgc gccagggaat tctcaaacaa      180
ttaaatgaaa ctggaggacc cgtgcttgta agtgctccca taagcccaga agagcaagat      240
aaacttgaaa ataagctcaa gcagacaaat ctccagtgga taaggtttc cagagcttta      300 cctgagaaac aaggagaaat tgaagctcaa ataaagacc ttgggcagct t                351

<210> SEQ ID NO 27
<211> LENGTH: 303
<212> TYPE: DNA
<213> ORGANISM: Homo sapiens

<400> SEQUENCE: 27
gaaaaaaagc ttgaagacct tgaagagcag ttaaatcatc tgctgctgtg gttatctcct       60
attaggaatc agttggaaat ttataaccaa ccaaaccaag aaggaccatt tgacgttcag      120
gaaactgaaa tagcagttca agctaaacaa ccggatgtgg aagagatttt gtctaaaggg      180
cagcatttgt acaaggaaaa accagccact cagccagtga agaggaagtt agaagatctg      240
agctctgagt ggaaggcggt aaaccgttta cttcaagagc tgagggcaaa gcagcctgac      300
cta                                                                    303

<210> SEQ ID NO 28
<211> LENGTH: 123
<212> TYPE: DNA
<213> ORGANISM: Homo sapiens

<400> SEQUENCE: 28
gctcctggac tgaccactat tggagcctct cctactcaga ctgttactct ggtgacacaa       60
cctgtggtta ctaaggaaac tgccatctcc aaactagaaa tgccatcttc cttgatgttg      120
gag                                                                    123

<210> SEQ ID NO 29
```

<210> SEQ ID NO 29
<211> LENGTH: 330
<212> TYPE: DNA
<213> ORGANISM: Homo sapiens

<400> SEQUENCE: 29

| | | | | | |
|---|---|---|---|---|---|
| gtacctgctc | tggcagattt | caaccgggct | tggacagaac | ttaccgactg | gctttctctg | 60 |
| cttgatcaag | ttataaaatc | acagagggtg | atggtgggtg | accttgagga | tatcaacgag | 120 |
| atgatcatca | agcagaaggc | aacaatgcag | gatttgaac | agaggcgtcc | ccagttggaa | 180 |
| gaactcatta | ccgctgccca | aaatttgaaa | aacaagacca | gcaatcaaga | ggctagaaca | 240 |
| atcattacgg | atcgaattga | aagaattcag | aatcagtggg | atgaagtaca | agaacaccttt | 300 |
| cagaaccgga | ggcaacagtt | gaatgaaatg | | | | 330 |

<210> SEQ ID NO 30
<211> LENGTH: 327
<212> TYPE: DNA
<213> ORGANISM: Homo sapiens

<400> SEQUENCE: 30
ttaaaggatt caacacaatg gctggaagct aaggaagaag ctgagcaggt cttaggacag     60
gccagagcca agcttgagtc atggaaggag ggtccctata cagtagatgc aatccaaaag    120
aaaatcacag aaaccaagca gttggccaaa gacctccgcc agtggcagac aaatgtagat    180
gtggcaaatg acttggccct gaaacttctc cgggattatt ctgcagatga taccagaaaa    240
gtccacatga taacagagaa tatcaatgcc tcttggagaa gcattcataa aagggtgagt    300
gagcgagagg ctgctttgga agaaact                                       327

<210> SEQ ID NO 31
<211> LENGTH: 348
<212> TYPE: DNA
<213> ORGANISM: Homo sapiens

<400> SEQUENCE: 31
catagattac tgcaacagtt cccctggac ctggaaaagt ttcttgcctg gcttacagaa       60
gctgaaacaa ctgccaatgt cctacaggat gctacccgta aggaaaggct cctagaagac    120
tccaagggag taaagagct gatgaaacaa tggcaagacc tccaaggtga aattgaagct    180
cacacagatg tttatcacaa cctggatgaa acagccaaa aaatcctgag atccctggaa    240
ggttccgatg atgcagtcct gttacaaaga cgtttggata acatgaactt caagtggagt    300
gaacttcgga aaagtctct caacattagg tcccatttgg aagccagt                 348

<210> SEQ ID NO 32
<211> LENGTH: 387
<212> TYPE: DNA
<213> ORGANISM: Homo sapiens

<400> SEQUENCE: 32
tctgaccagt ggaagcgtct gcacctttct ctgcaggaac ttctggtgtg gctacagctg      60
aaagatgatg aattaagccg gcaggcacct attggaggcg actttccagc agttcagaag    120
cagaacgatg tacatagggc cttcaagagg gaattgaaaa ctaaagaacc tgtaatcatg    180
agtactcttg agactgtacg aatatttctg acagagcagc ctttggaagg actagagaaa    240
ctctaccagg agcccagaga gctgcctcct gaggagagag cccagaatgt cactcggctt    300
ctacgaaagc aggctgagga ggtcaatact gagtgggaaa aattgaacct gcactccgct    360
gactggcaga gaaaaataga tgagacc                                       387

<210> SEQ ID NO 33
<211> LENGTH: 324
<212> TYPE: DNA
<213> ORGANISM: Homo sapiens

<400> SEQUENCE: 33

| | | |
|---|---|---|
| cttgaaagac tccaggaact tcaagaggcc acggatgagc tggacctcaa gctgcgccaa | 60 |
| gctgaggtga tcaagggatc ctggcagccc gtgggcgatc tcctcattga ctctctccaa | 120 |
| gatcacctcg agaaagtcaa ggcacttcga ggagaaattg cgcctctgaa agagaacgtg | 180 |
| agccacgtca atgaccttgc tcgccagctt accactttgg gcattcagct ctcaccgtat | 240 |
| aacctcagca ctctggaaga cctgaacacc agatggaagc ttctgcaggt ggccgtcgag | 300 |
| gaccgagtca ggcagctgca tgaa | 324 |

<210> SEQ ID NO 34
<211> LENGTH: 216
<212> TYPE: DNA
<213> ORGANISM: Homo sapiens

<400> SEQUENCE: 34

| | | |
|---|---|---|
| gcccacaggg actttggtcc agcatctcag cactttcttt ccacgtctgt ccagggtccc | 60 |
| tgggagagag ccatctcgcc aaacaaagtg ccctactata tcaaccacga gactcaaaca | 120 |
| acttgctggg accatcccaa aatgacagag ctctaccagt ctttagctga cctgaataat | 180 |
| gtcagattct cagcttatag gactgccatg aaactc | 216 |

<210> SEQ ID NO 35
<211> LENGTH: 887
<212> TYPE: DNA
<213> ORGANISM: Homo sapiens

<400> SEQUENCE: 35

| | | |
|---|---|---|
| cgaagactgc agaaggccct ttgcttggat ctcttgagcc tgtcagctgc atgtgatgcc | 60 |
| ttggaccagc acaacctcaa gcaaaatgac cagcccatgg atatcctgca gattattaat | 120 |
| tgtttgacca ctatttatga ccgcctggag caagagcaca caatttggt caacgtccct | 180 |
| ctctgcgtgg atatgtgtct gaactggctg ctgaatgttt atgatacggg acgaacaggg | 240 |
| aggatccgtg tcctgtcttt taaaactggc atcatttccc tgtgtaaagc acatttggaa | 300 |
| gacaagtaca gtaccttttt caagcaagtg gcaagttcaa caggattttg tgaccagcgc | 360 |
| aggctgggcc tccttctgca tgattctatc caaattccaa gacagttggg tgaagttgca | 420 |
| tcctttgggg gcagtaacat tgagccaagt gtccggagct gcttccaatt tgctaataat | 480 |
| aagccagaga tcgaagcggc cctcttccta gactggatga actggaaacc ccagtccatg | 540 |
| gtgtggctgc ccgtcctgca cagagtggct gctgcagaaa ctgccaagca tcaggccaaa | 600 |
| tgtaacatct gcaaagagtg tccaatcatt ggattcaggt acaggagtct aaagcacttt | 660 |
| aattatgaca tctgccaaag ctgctttttt tctggtcgag ttgcaaaagg ccataaaatg | 720 |
| cactatccca tggtggaata ttgcactccg actacatcag gagaagatgt tcgagacttt | 780 |
| gccaaggtac taaaaaacaa atttcgaacc aaaaaggtatt ttgcgaagca tccccgaatg | 840 |
| ggctacctgc cagtgcagac tgtcttagag ggggacaaca tggaaac | 887 |

<210> SEQ ID NO 36
<211> LENGTH: 823
<212> TYPE: DNA

<213> ORGANISM: Homo sapiens

<400> SEQUENCE: 36

```
tcccgttact ctgatcaact tctggccagt agattctgcg cctgcctcgt cccctcagct    60
ttcacacgat gatactcatt cacgcattga acattatgct agcaggctag cagaaatgga   120
aaacagcaat ggatcttatc taaatgatag catctctcct aatgagagca tagatgatga   180
acatttgtta atccagcatt actgccaaag tttgaaccag gactccccc tgagccagcc    240
tcgtagtcct gcccagatct tgatttcctt agagagtgag gaaagagggg agctagagag   300
aatcctagca gatcttgagg aagaaaacag gaatctgcaa gcagaatatg accgtctaaa   360
gcagcagcac gaacataaag gcctgtcccc actgccgtcc cctcctgaaa tgatgcccac   420
ctctccccag agtccccggg atgctgagct cattgctgag gccaagctac tgcgtcaaca   480
caaaggccgc ctggaagcca ggatgcaaat cctggaagac acaataaac agctggagtc    540
acagttacac aggctaaggc agctgctgga gcaaccccag gcagaggcca aagtgaatgg   600
cacaacggtg tcctctcctt ctacctctct acagaggtcc gacagcagtc agcctatgct   660
gctccgagtg gttggcagtc aaacttcgga ctccatgggt gaggaagatc ttctcagtcc   720
tccccaggac acaagcacag ggttagagga ggtgatggag caactcaaca actccttccc   780
tagttcaaga ggaagaaata cccctggaaa gccaatgaga gag                     823
```

<210> SEQ ID NO 37
<211> LENGTH: 12
<212> TYPE: DNA
<213> ORGANISM: Homo sapiens

<400> SEQUENCE: 37

```
gacacaatgt ag                                                        12
```

<210> SEQ ID NO 38
<211> LENGTH: 2691
<212> TYPE: DNA
<213> ORGANISM: Homo sapiens

<400> SEQUENCE: 38

```
gaagtcttt ccacatggca gatgatttgg gcagagcgat ggagtcctta gtatcagtca    60
tgacagatga agaaggagca gaataaatgt tttacaactc ctgattcccg catggttttt   120
ataatattca tacaacaaag aggattagac agtaagagtt tacaagaaat aaatctatat   180
ttttgtgaag ggtagtggta ttatactgta gatttcagta gtttctaagt ctgttattgt   240
tttgttaaca atggcaggtt ttacacgtct atgcaattgt acaaaaaagt tataagaaaa   300
ctacatgtaa aatcttgata gctaaataac ttgccatttc tttatatgga acgcattttg   360
ggttgtttaa aaatttataa cagttataaa gaaagattgt aaactaaagt gtgctttata   420
aaaaaagtt gtttataaaa acccctaaaa acaaacaaa cacacacaca cacacataca     480
cacacacaca caaaactttg aggcagcgca ttgttttgca tccttttggc gtgatatcca   540
tatgaaattc atggctttt cttttttgc atattaaaga taagacttcc tctaccacca    600
caccaaatga ctactacaca ctgctcattt gagaactgtc agctgagtgg ggcaggcttg   660
agttttcatt tcatatatct atatgtctat aagtatataa atactatagt tatatagata   720
aagagatacg aatttctata gactgacttt ttccattttt taaatgttca tgtcacatcc   780
taatagaaag aaattacttc tagtcagtca tccaggctta cctgcttggt ctagaatgga   840
tttttcccgg agccggaagc caggaggaaa ctacaccaca ctaaaacatt gtctacagct   900
```

-continued

```
ccagatgttt ctcattttaa acaactttcc actgacaacg aaagtaaagt aaagtattgg      960
atttttttaa agggaacatg tgaatgaata cacaggactt attatatcag agtgagtaat     1020
cggttggttg gttgattgat tgattgattg atacattcag cttcctgctg ctagcaatgc     1080
cacgatttag atttaatgat gcttcagtgg aaatcaatca gaaggtattc tgaccttgtg     1140
aacatcagaa ggtattttt aactcccaag cagtagcagg acgatgatag ggctggaggg     1200
ctatggattc ccagcccatc cctgtgaagg agtaggccac tctttaagtg aaggattgga     1260
tgattgttca taatacataa agttctctgt aattacaact aaattattat gccctcttct     1320
cacagtcaaa aggaactggg tggtttggtt tttgttgctt ttttagattt attgtcccat     1380
gtgggatgag ttttttaaatg ccacaagaca taatttaaaa taaataaaact ttgggaaaag     1440
gtgtaagaca gtagccccat cacatttgtg atactgacag gtatcaaccc agaagcccat     1500
gaactgtgtt tccatccttt gcatttctct gcgagtagtt ccacacaggt ttgtaagtaa     1560
gtaagaaaga aggcaaattg attcaaatgt tacaaaaaaa cccttcttgg tggattagac     1620
aggttaaata tataaacaaa caaacaaaaa ttgctcaaaa aagaggagaa aagctcaaga     1680
ggaaaagcta aggactggta ggaaaaagct ttactctttc atgccatttt atttctttt     1740
gatttttaaa tcattcattc aatagatacc accgtgtgac ctataattt gcaaatctgt     1800
tacctctgac atcaagtgta attagctttt ggagagtggg ctgacatcaa gtgtaattag     1860
cttttggaga gtgggttttg tccattatta ataattaatt aattaacatc aaacacggct     1920
tctcatgcta tttctacctc actttggttt tggggtgttc ctgataattg tgcacacctg     1980
agttcacagc ttcaccactt gtccattgcg ttattttctt tttcctttat aattcttct     2040
ttttccttca taattttcaa aagaaaaccc aaagctctaa ggtaacaaat taccaaatta     2100
catgaagatt tggttttgt cttgcatttt tttccttat gtgacgctgg accttttctt     2160
tacccaagga tttttaaaac tcagatttaa acaagggt tactttacat cctactaaga     2220
agtttaagta agtaagtttc attctaaaat cagaggtaaa tagagtgcat aaataatttt     2280
gttttaatct ttttgtttt cttttagaca cattagctct ggagtgagtc tgtcataata     2340
tttgaacaaa aattgagagc tttattgctg cattttaagc ataattaatt tggacattat     2400
ttcgtgttgt gttctttata accaccgagt attaaactgt aaatcataat gtaactgaag     2460
cataaacatc acatggcatg ttttgtcatt gttttcaggt actgagttct tacttgagta     2520
tcataatata ttgtgtttta acaccaacac tgtaacattt acgaattatt ttttaaact     2580
tcagttttac tgcattttca caacatatca gacttcacca aatatatgcc ttactattgt     2640
attatagtac tgcttactg tgtatctcaa taaagcacgc agttatgtta c              2691
```

<210> SEQ ID NO 39
<211> LENGTH: 5417
<212> TYPE: DNA
<213> ORGANISM: Artificial Sequence
<220> FEATURE:
<223> OTHER INFORMATION: Synthetic

<400> SEQUENCE: 39

```
gggattccct cactttcccc ctacaggact cagatctggg aggcaattac cttcggagaa       60
aaacgaatag gaaaaactga agtgttactt ttttttaaagc tgctgaagtt tgttggtttc      120
tcattgtttt taagcctact ggagcaataa agtttgaaga acttttacca ggttttttt      180
atcgctgcct tgatatacac ttttcaaaat gctttggtgg gaagaagtag aggactgtta      240
```

```
tgaaagagaa gatgttcaaa agaaaacatt cacaaaatgg gtaaatgcac aattttctaa      300
gtttgggaag cagcatattg agaacctctt cagtgaccta caggatggga ggcgcctcct      360
agacctcctc gaaggcctga cagggcaaaa actgccaaaa gaaaaaggat ccacaagagt      420
tcatgccctg aacaatgtca acaaggcact gcgggttttg cagaacaata atgttgattt      480
agtgaatatt ggaagtactg acatcgtaga tggaaatcat aaactgactc ttggtttgat      540
ttggaatata atcctccact ggcaggtcaa aaatgtaatg aaaaatatca tggctggatt      600
gcaacaaacc aacagtgaaa agattctcct gagctgggtc cgacaatcaa ctcgtaatta      660
tccacaggtt aatgtaatca acttcaccac cagctggtct gatggcctgg ctttgaatgc      720
tctcatccat agtcataggc cagaccattt tgactggaat agtgtggttt gccagcagtc      780
agccacacaa cgactggaac atgcattcaa catcgccaga tatcaattag gcatagagaa      840
actactcgat cctgaagatg ttgataccac ctatccagat aagaagtcca tcttaatgta      900
catcacatca ctcttccaag ttttgcctca acaagtgagc attgaagcca tccaggaagt      960
ggaaatgttg ccaaggccac ctaaagtgac taaagaagaa cattttcagt tacatcatca     1020
aatgcactat tctcaacaga tcacggtcag tctagcacag ggatatgaga gaacttcttc     1080
ccctaagcct cgattcaaga gctatgccta cacacaggct gcttatgtca ccacctctga     1140
ccctacacgg agcccatttc cttcacagca tttggaagct cctgaagaca agtcatttgg     1200
cagttcattg atggagagtg aagtaaacct ggaccgttat caaacagctt tagaagaagt     1260
attatcgtgg cttctttctg ctgaggcaca attgcaagca caggagaga tttctaatga      1320
tgtggaagtg gtgaaagacc agtttcatac tcatgagggg tacatgatgg atttgacagc     1380
ccatcagggc cggggttggta atattctaca attgggaagt aagctgattg gaacaggaaa     1440
attatcagaa gatgaagaaa ctgaagtaca agagcagatg aatctcctaa attcaagatg     1500
ggaatgcctc agggtagcta gcatggaaaa acaaagcaat ttacatagag ttttaatgga     1560
tctccagaat cagaaactga aagagttgaa tgactggcta acaaaaacag aagaaagaac     1620
aaggaaaatg gaggaagagc ctcttggacc tgatcttgaa gacctaaaac gccaagtaca     1680
acaacataag gtgcttcaag aagatctaga acaagaacaa gtcagggtca attctctcac     1740
tcacatggtg gtggtagttg atgaatctag tggagatcac gcaactgctg ctttggaaga     1800
acaacttaag gtattgggag atcgatgggc aaacatctgt agatggacag aagaccgctg     1860
ggttcttta caagacatcc ttctcaaatg gcaacgtctt actgaagaac agtgcctttt      1920
tagtgcatgg ctttcagaaa aagaagatgc agtgaacaag attcacacaa ctggctttaa     1980
agatcaaaat gaaatgttat caagtcttca aaaactggcc gttttaaaag cggatctaga     2040
aaagaaaaag caatccatgg gcaaactgta ttcactcaaa caagatcttc tttcaacact     2100
gaagaataag tcagtgaccc agaagacgga agcatggctg ataactttg cccggtgttg      2160
ggataattta gtccaaaaac ttgaaaagag tacagcacag atttcacagg ctgtcaccac     2220
cactcagcca tcactaacac agacaactgt aatggaaaca gtaactacgg tgaccacaag     2280
ggaacagatc ctggtaaagc atgctcaaga ggaacttcca ccaccactc cccaaaagaa      2340
gaggcagatt actgtggatc ttgaaagact ccaggaactt caagaggcca cggatgagct     2400
ggacctcaag ctgcgccaag ctgaggtgat caagggatcc tggcagcccg tgggcgatct     2460
cctcattgac tctctccaag atcaccctcga gaaagtcaag gcacttcgag agaaattgc      2520
gcctctgaaa gagaacgtga gccacgtcaa tgaccttgct cgccagctta ccactttggg     2580
cattcagctc tcaccgtata acctcagcac tctggaagac ctgaacacca gatggaagct     2640
```

-continued

```
tctgcaggtg gccgtcgagg accgagtcag gcagctgcat gaagcccaca gggactttgg    2700
tccagcatct cagcactttc tttccacgtc tgtccaggt ccctgggaga gagccatctc     2760
gccaaacaaa gtgccctact atatcaacca cgagactcaa acaacttgct ggaccatcc     2820
caaaatgaca gagctctacc agtctttagc tgacctgaat aatgtcagat tctcagctta   2880
taggactgcc atgaaactcc gaagactgca gaaggccctt tgcttggatc tcttgagcct   2940
gtcagctgca tgtgatgcct tggaccagca aacctcaag caaaatgacc agcccatgga    3000
tatcctgcag attattaatt gtttgaccac tatttatgac cgcctggagc aagagcacaa   3060
caatttggtc aacgtccctc tctgcgtgga tatgtgtctg aactggctgc tgaatgttta  3120
tgatacggga cgaacaggga ggatccgtgt cctgtctttt aaaactggca tcatttccct   3180
gtgtaaagca catttggaag acaagtacag atacctttc aagcaagtgg caagttcaac    3240
aggattttgt gaccacgcca ggctgggcct ccttctgcat gattctatcc aaattccaag   3300
acagttgggt gaagttgcat cctttggggg cagtaacatt gagccaagtg tccggagctg  3360
cttccaattt gctaataata agccagagat cgaagcggcc ctcttcctag actggatgag   3420
actggaaccc cagtccatgg tgtggctgcc cgtcctgcac agagtggctg ctgcagaaac   3480
tgccaagcat caggccaaat gtaacatctg caaagagtgt ccaatcattg gattcaggta  3540
caggagtcta aagcacttta attatgacat ctgccaaagc tgcttttttt ctggtcgagt   3600
tgcaaaaggc cataaaatgc actatcccat ggtggaatat tgcactccga ctacatcagg   3660
agaagatgtt cgagactttg ccaaggtact aaaaaacaaa tttcgaacca aaaggtattt   3720
tgcgaagcat ccccgaatgg gctacctgcc agtgcagact gtcttagagg gggacaacat   3780
ggaaacgcct gcctcgtccc ctcagctttc acacgatgat actcattcac gcattgaaca   3840
ttatgctagc aggctagcag aaatggaaaa cagcaatgga tcttatctaa atgatagcat   3900
ctctcctaat gagagcatag atgatgaaca tttgttaatc cagcattact gccaaagttt   3960
gaaccaggac tcccccctga gccagcctcg tagtcctgcc cagatcttga tttccttaga  4020
gagtgaggaa agaggggagc tagagagaat cctagcagat cttgaggaag aaaacaggaa   4080
tctgcaagca gaatatgacc gtctaaagca gcagcacgaa cataaaggcc tgtccccact   4140
gccgtccect cctgaaatga tgcccacctc tccccagagt cccgggatg ctgagctcat   4200
tgctgaggcc aagctactgc gtcaacacaa aggccgcctg gaagccagga tgcaaatcct   4260
ggaagaccac aataaacagc tggagtcaca gttacacagg ctaaggcagc tgctggagca   4320
accccaggca gaggccaaag tgaatggcac aacggtgtcc tctccttcta cctctctaca   4380
gaggtccgac agcagtcagc ctatgctgct ccgagtggtt ggcagtcaaa cttcggactc   4440
catggggtgag gaagatcttc tcagtcctcc ccaggacaca agcacagggt tagaggaggt   4500
gatgagcaa ctcaacaact ccttccctag ttcaagagga agaaatcccc ctggaaagcc    4560
aatgagagag gacacaatgt aggaagtctt ttccacatgg cagatgattt gggcagagcg   4620
atggagtcct tagtatcagt catgacagat gaagaaggag cagaataaat gttttacaac   4680
tcctgattcc cgcatggttt ttataatatt catacaacaa agaggattag acagtaagag   4740
tttacaagaa ataaatctat attttgtga agggtagtgg tattatactg tagatttcag   4800
tagtttctaa gtctgttatt gttttgttaa caatggcagg ttttacacgt ctatgcaatt   4860
gtacaaaaaa gttataagaa aactacatgt aaaatcttga tagctaaata acttgccatt   4920
tcttatatg gaacgcattt tgggttgttt aaaaatttat aacagttata aagaaagatt    4980
```

-continued

| | |
|---|---|
| gtaaactaaa gtgtgcttta taaaaaaaag ttgtttataa aaaccsctaa aacaaaaca | 5040 |
| aacacacaca cacacacata cacacacaca cacaaaactt tgaggcagcg cattgttttg | 5100 |
| catccttttg gcgtgatatc catatgaaat tcatggcttt ttcttttttt gcatattaaa | 5160 |
| gataagactt cctctaccac cacaccaaat gactactaca cactgctcat ttgagaactg | 5220 |
| tcagctgagt ggggcaggct tgagttttca tttcatatat ctatatgtct ataagtatat | 5280 |
| aaatactata gttatataga taaagagata cgaatttcta tagactgact ttttccattt | 5340 |
| tttaaatgtt catgtcacat cctaatagaa agaaattact tctagtcagt catccaggct | 5400 |
| tacctgcttg gtctaga | 5417 |

<210> SEQ ID NO 40
<211> LENGTH: 5339
<212> TYPE: DNA
<213> ORGANISM: Artificial Sequence
<220> FEATURE:
<223> OTHER INFORMATION: Synthetic

<400> SEQUENCE: 40

| | |
|---|---|
| gggattccct cactttcccc ctacaggact cagatctggg aggcaattac cttcggagaa | 60 |
| aaacgaatag gaaaaactga agtgttactt ttttttaaagc tgctgaagtt tgttggtttc | 120 |
| tcattgtttt taagcctact ggagcaataa agtttgaaga actttaccaa ggttttttt | 180 |
| atcgctgcct tgatatacac ttttcaaaat gctttggtgg aagaagtag aggactgtta | 240 |
| tgaaagagaa gatgttcaaa agaaacatt cacaaaatgg gtaaatgcac aattttctaa | 300 |
| gtttgggaag cagcatattg agaacctctt cagtgaccta caggatggga ggcgcctcct | 360 |
| agacctcctc gaaggcctga cagggcaaaa actgccaaaa gaaaaggat ccacaagagt | 420 |
| tcatgccctg aacaatgtca acaaggcact gcgggttttg cagaacaata atgttgattt | 480 |
| agtgaatatt ggaagtactg acatcgtaga tggaaatcat aaactgactc ttggtttgat | 540 |
| ttggaatata atcctccact ggcaggtcaa aaatgtaatg aaaaatatca tggctggatt | 600 |
| gcaacaaacc aacagtgaaa agattctcct gagctgggtc cgacaatcaa ctcgtaatta | 660 |
| tccacaggtt aatgtaatca acttcaccac cagctggtct gatggcctgg ctttgaatgc | 720 |
| tctcatccat agtcataggc cagaccatt tgactggaat agtgtggttt gccagcagtc | 780 |
| agccacacaa cgactggaac atgcattcaa catcgccaga tatcaattag gcatagagaa | 840 |
| actactcgat cctgaagatg ttgataccac ctatccagat aagaagtcca tcttaatgta | 900 |
| catcacatca ctcttccaag ttttgcctca acaagtgagc attgaagcca tccaggaagt | 960 |
| ggaaatgttg ccaaggccac ctaaagtgac taaagaagaa cattttcagt tacatcatca | 1020 |
| aatgcactat tctcaacaga tcacggtcag tctagcacag gatatgagaa gaacttcttc | 1080 |
| ccctaagcct cgattcaaga gctatgccta cacacaggct gcttatgtca ccacctctga | 1140 |
| ccctacacgg agcccatttc cttcacagca tttggaagct cctgaagaca gtcatttgg | 1200 |
| cagttcattg atggagagtg aagtaaacct ggaccgttat caaacagctt tagaagaagt | 1260 |
| attatcgtgg cttctttctg ctgaggacac attgcaagca caggagaga tttctaatga | 1320 |
| tgtggaagtg gtgaaagacc agtttcatac tcatgagggg tacatgatgg atttgacagc | 1380 |
| ccatcagggc cggttggta atattctaca attgggaagt aagctgattg gaacaggaaa | 1440 |
| attatcagaa gatgaagaaa ctgaagtaca agagcagatg aatctcctaa attcaagatg | 1500 |
| ggaatgcctc agggtagcta gcatggaaaa acaaagcaat ttacatcata gattactgca | 1560 |
| acagttcccc ctggacctgg aaaagttct tgcctggctt acagaagctg aaacaactgc | 1620 |

-continued

| | |
|---|---|
| caatgtccta caggatgcta cccgtaagga aaggctccta gaagactcca agggagtaaa | 1680 |
| agagctgatg aaacaatggc aagacctcca aggtgaaatt gaagctcaca cagatgttta | 1740 |
| tcacaacctg gatgaaaaca gccaaaaaat cctgagatcc ctggaaggtt ccgatgatgc | 1800 |
| agtcctgtta caaagacgtt tggataacat gaacttcaag tggagtgaac ttcggaaaaa | 1860 |
| gtctctcaac attaggtccc atttggaagc cagttctgac cagtggaagc gtctgcacct | 1920 |
| ttctctgcag gaacttctgg tgtggctaca gctgaaagat gatgaattaa gccggcaggc | 1980 |
| acctattgga ggcgactttc cagcagttca gaagcagaac gatgtacata ggccttcaa | 2040 |
| gagggaattg aaaactaaag aacctgtaat catgagtact cttgagactg tacgaatatt | 2100 |
| tctgacagag cagcctttgg aaggactaga gaaactctac caggagccca gagagctgcc | 2160 |
| tcctgaggag agagcccaga atgtcactcg gcttctacga aagcaggctg aggaggtcaa | 2220 |
| tactgagtgg gaaaaattga acctgcactc cgctgactgg cagagaaaaa tagatgagac | 2280 |
| ccttgaaaga ctccaggaac ttcaagaggc cacggatgag ctggacctca gctgcgcca | 2340 |
| agctgaggtg atcaagggat cctggcagcc cgtgggcgat ctcctcattg actctctcca | 2400 |
| agatcacctc gagaaagtca aggcacttcg aggagaaatt gcgcctctga aagagaacgt | 2460 |
| gagccacgtc aatgaccttg ctcgccagct taccactttg ggcattcagc tctcaccgta | 2520 |
| taacctcagc actctggaag acctgaacac cagatggaag cttctgcagg tggccgtcga | 2580 |
| ggaccgagtc aggcagctgc atgaagccca cagggacttt ggtccagcat ctcagcactt | 2640 |
| tctttccacg tctgtccagg gtccctggga gagagccatc tcgccaaaca aagtgcccta | 2700 |
| ctatatcaac cacgagactc aaacaacttg ctgggaccat cccaaaatga cagagctcta | 2760 |
| ccagtctttta gctgacctga ataatgtcag attctcagct tataggactg ccatgaaact | 2820 |
| ccgaagactg cagaaggccc tttgcttgga tctcttgagc ctgtcagctg catgtgatgc | 2880 |
| cttggaccag cacaacctca gcaaaatga ccagcccatg gatatcctgc agattattaa | 2940 |
| ttgtttgacc actatttatg accgcctgga gcaagagcac aacaatttgg tcaacgtccc | 3000 |
| tctctgcgtg gatatgtgtc tgaactggct gctgaatgtt tatgatacgg gacgaacagg | 3060 |
| gaggatccgt gtcctgtctt ttaaaactgg catcatttcc ctgtgtaaag cacatttgga | 3120 |
| agacaagtac agatacctttt tcaagcaagt ggcaagttca acaggattttt gtgaccagcg | 3180 |
| caggctgggc ctccttctgc atgattctat ccaaattcca agacagttgg gtgaagttgc | 3240 |
| atcctttggg ggcagtaaca ttgagccaag tgtccggagc tgcttccaat ttgctaataa | 3300 |
| taagccagag atcgaagcgg ccctcttcct agactggatg agactggaac cccagtccat | 3360 |
| ggtgtggctg cccgtcctgc acagagtggc tgctgcagaa actgccaagc atcaggccaa | 3420 |
| atgtaacatc tgcaaagagt gtccaatcat tggattcagg tacaggagtc taaagcactt | 3480 |
| taattatgac atctgccaaa gctgcttttt ttctggtcga gttgcaaaag gccataaaat | 3540 |
| gcactatccc atggtggaat attgcactcc gactacatca ggagaagatg ttcgagactt | 3600 |
| tgccaaggta ctaaaaaaca aatttcgaac caaaaggtat tttgcgaagc atccccgaat | 3660 |
| gggctacctg ccagtgcaga ctgtcttaga gggggacaac atggaaacgc ctgcctcgtc | 3720 |
| ccctcagctt tcacacgatg atactcattc acgcattgaa cattatgcta gcaggctagc | 3780 |
| agaaatggaa aacagcaatg gatcttatct aaatgatagc atctctccta atgagagcat | 3840 |
| agatgatgaa catttgttaa tccagcatta ctgccaaagt ttgaaccagg actccccct | 3900 |
| gagccagcct cgtagtcctg cccagatctt gatttcctta gagagtgagg aaagagggga | 3960 |

-continued

```
gctagagaga atcctagcag atcttgagga agaaaacagg aatctgcaag cagaatatga      4020
ccgtctaaag cagcagcacg aacataaagg cctgtcccca ctgccgtccc ctcctgaaat      4080
gatgcccacc tctccccaga gtccccggga tgctgagctc attgctgagg ccaagctact      4140
gcgtcaacac aaaggccgcc tggaagccag gatgcaaatc ctggaagacc acaataaaca      4200
gctggagtca cagttacaca ggctaaggca gctgctggag caaccccagg cagaggccaa      4260
agtgaatggc acaacggtgt cctctccttc tacctctcta cagaggtccg acagcagtca      4320
gcctatgctg ctccgagtgg ttggcagtca aacttcggac tccatgggtg aggaagatct      4380
tctcagtcct ccccaggaca caagcacagg gttagaggag gtgatggagc aactcaacaa      4440
ctccttccct agttcaagag gaagaaatac ccctggaaag ccaatgagag aggacacaat      4500
gtaggaagtc ttttccacat ggcagatgat ttgggcagag cgatggagtc cttagtatca      4560
gtcatgacag atgaagaagg agcagaataa atgttttaca actcctgatt cccgcatggt      4620
ttttataata ttcatacaac aaagaggatt agacagtaag agtttacaag aaataaatct      4680 atattttgt gaagggtagt ggtattatac tgtagatttc agtagtttct aagtctgtta       4740
ttgttttgtt aacaatggca ggttttacac gtctatgcaa ttgtacaaaa aagttataag      4800
aaaactacat gtaaatcttt gatagctaaa taacttgcca tttctttata tggaacgcat      4860
tttgggttgt ttaaaaattt ataacagtta taagaaaga ttgtaaacta aagtgtgctt       4920 tataaaaaa agttgtttat aaaaccccct aaaaacaaaa caaacacaca cacacacaca      4980
tacacacaca cacacaaaac tttgaggcag cgcattgttt tgcatccttt tggcgtgata      5040
tccatatgaa attcatggct ttttctttt ttgcatatta aagataagac ttcctctacc       5100
accacaccaa atgactacta cacactgctc atttgagaac tgtcagctga gtggggcagg      5160
cttgagtttt catttcatat atctatatgt ctataagtat ataaatacta tagttatata      5220
gataaagaga tacgaatttc tatagactga ctttttccat ttttaaatg ttcatgtcac       5280 atcctaatag aaagaaatta cttctagtca gtcatccagg cttacctgct tggtctaga      5339
```

<210> SEQ ID NO 41
<211> LENGTH: 5462
<212> TYPE: DNA
<213> ORGANISM: Artificial Sequence
<220> FEATURE:
<223> OTHER INFORMATION: Synthetic

<400> SEQUENCE: 41

```
gggattccct cactttcccc ctacaggact cagatctggg aggcaattac cttcggagaa       60
aaacgaatag gaaaaactga agtgttactt tttttaaagc tgctgaagtt tgttggtttc      120
tcattgtttt taagcctact ggagcaataa agtttgaaga acttttacca ggttttttt       180 atcgctgcct tgatatacac ttttcaaaat gctttggtgg aagaagtag aggactgtta        240 tgaaagagaa gatgttcaaa agaaacatt cacaaaatgg gtaaatgcac aattttctaa       300
gtttgggaag cagcatattg agaacctctt cagtgaccta caggatggga ggcgcctcct      360
agacctcctc gaaggcctga cagggcaaaa actgccaaaa gaaaaggat ccacaagagt       420 tcatgccctg aacaatgtca acaaggcact gcgggttttg cagaacaata atgttgattt      480
agtgaatatt ggaagtactg acatcgtaga tggaaatcat aaactgactc ttggtttgat      540
ttggaatata atcctccact ggcaggtcaa aaatgtaatg aaaaatatca tggctggatt      600
gcaacaaacc aacagtgaaa agattctcct gagctgggtc cgacaatcaa ctcgtaatta      660
tccacaggtt aatgtaatca acttcaccac cagctggtct gatggcctgg ctttgaatgc      720
```

-continued

```
tctcatccat agtcataggc cagacctatt tgactggaat agtgtggttt gccagcagtc    780
agccacacaa cgactggaac atgcattcaa catcgccaga tatcaattag gcatagagaa    840
actactcgat cctgaagatg ttgataccac ctatccagat aagaagtcca tcttaatgta    900
catcacatca ctcttccaag ttttgcctca acaagtgagc attgaagcca tccaggaagt    960
ggaaatgttg ccaaggccac ctaaagtgac taaagaagaa cattttcagt tacatcatca   1020
aatgcactat tctcaacaga tcacggtcag tctagcacag ggatatgaga gaacttcttc   1080
ccctaagcct cgattcaaga gctatgccta cacacaggct gcttatgtca ccacctctga   1140
ccctacacgg agcccatttc cttcacagca tttggaagct cctgaagaca agtcatttgg   1200
cagttcattg atggagagtg aagtaaacct ggaccgttat caaacagctt tagaagaagt   1260
attatcgtgg cttctttctg ctgaggacac attgcaagca caaggagaga tttctaatga   1320
tgtggaagtg gtgaaagacc agtttcatac tcatgagggg tacatgatgg atttgacagc   1380
ccatcagggc cggggttggta atattctaca attgggaagt aagctgattg gaacaggaaa   1440
attatcagaa gatgaagaaa ctgaagtaca agagcagatg aatctcctaa attcaagatg   1500
ggaatgcctc agggtagcta gcatggaaaa acaaagcaat ttacatgctc ctggactgac   1560
cactattgga gcctctccta ctcagactgt tactctggtg acacaacctg tggttactaa   1620
ggaaactgcc atctccaaac tagaaatgcc atcttccttg atgttggagc atagattact   1680
gcaacagttc cccctggacc tggaaaagtt tcttgcctgg cttacagaag ctgaaacaac   1740
tgccaatgtc ctacaggatg ctacccgtaa ggaaaggctc ctagaagact ccaagggagt   1800
aaaagagctg atgaaacaat ggcaagacct ccaaggtgaa attgaagctc acacagatgt   1860
ttatcacaac ctggatgaaa acagccaaaa atcctgaga tccctggaag gttccgatga   1920
tgcagtcctg ttacaaagac gtttggataa catgaacttc aagtggagtg aacttcggaa   1980
aaagtctctc aacattaggt cccatttgga agccagttct gaccagtgga agcgtctgca   2040
cctttctctg caggaacttc tggtgtggct acagctgaaa gatgatgaat taagccggca   2100
ggcacctatt ggaggcgact ttccagcagt tcagaagcag aacgatgtac ataggccttt   2160
caagagggaa ttgaaaacta agaaccctgt aatcatgagt actcttgaga ctgtacgaat   2220
atttctgaca gagcagcctt tggaaggact agagaaactc taccaggagc ccagagagct   2280
gcctcctgag gagagagccc agaatgtcac tcggcttcta cgaaagcagg ctgaggaggt   2340
caatactgag tgggaaaaat tgaacctgca ctccgctgac tggcagagaa aaatagatga   2400
gacccttgaa agactccagg aacttcaaga ggccacggat gagctggacc tcaagctgcg   2460
ccaagctgag gtgatcaagg gatcctggca gcccgtgggc gatctcctca ttgactctct   2520
ccaagatcac ctcgagaaag tcaaggcact tcgaggagaa attgcgcctc tgaaagagaa   2580
cgtgagccac gtcaatgacc ttgctcgcca gcttaccact ttgggcattc agctctcacc   2640
gtataacctc agcactctgg aagacctgaa caccagatgg aagcttctgc aggtggccgt   2700
cgaggaccga gtcaggcagc tgcatgaagc ccacagggac tttggtccag catctcagca   2760 cttttctttcc acgtctgtcc agggtccctg ggagagagcc atctcgccaa acaaagtgcc   2820
ctactatatc aaccacgaga ctcaaacaac ttgctgggac catcccaaaa tgacagagct   2880
ctaccagtct ttagctgacc tgaataatgt cagattctca gcttatagga ctgccatgaa   2940
actccgaaga ctgcagaagg cccttttgctt ggatctcttg agcctgtcag ctgcatgtga   3000
tgccttggac cagcacaacc tcaagcaaaa tgaccagccc atggatatcc tgcagattat   3060
```

-continued

| | | | | |
|---|---|---|---|---|
| taattgtttg | accactattt | atgaccgcct | ggagcaagag | cacaacaatt | tggtcaacgt | 3120 |
| ccctctctgc | gtggatatgt | gtctgaactg | gctgctgaat | gtttatgata | cgggacgaac | 3180 |
| agggaggatc | cgtgtcctgt | cttttaaaac | tggcatcatt | tccctgtgta | aagcacattt | 3240 |
| ggaagacaag | tacagatacc | ttttcaagca | agtggcaagt | tcaacaggat | tttgtgacca | 3300 |
| gcgcaggctg | ggcctccttc | tgcatgattc | tatccaaatt | ccaagacagt | tgggtgaagt | 3360 |
| tgcatccttt | gggggcagta | acattgagcc | aagtgtccgg | agctgcttcc | aatttgctaa | 3420 |
| taataagcca | gagatcgaag | cggccctctt | cctagactgg | atgagactgg | aaccccagtc | 3480 |
| catggtgtgg | ctgcccgtcc | tgcacagagt | ggctgctgca | gaaactgcca | agcatcaggc | 3540 |
| caaatgtaac | atctgcaaag | agtgtccaat | cattggattc | aggtacagga | gtctaaagca | 3600 |
| ctttaattat | gacatctgcc | aaagctgctt | tttttctggt | cgagttgcaa | aaggccataa | 3660 |
| aatgcactat | cccatggtgg | aatattgcac | tccgactaca | tcaggagaag | atgttcgaga | 3720 |
| cttgtccaag | gtactaaaaa | acaaatttcg | aaccaaaagg | tattttgcga | agcatccccg | 3780 |
| aatgggctac | ctgccagtgc | agactgtctt | agaggggac | aacatggaaa | cgcctgcctc | 3840 |
| gtccctcag | ctttcacacg | atgatactca | ttcacgcatt | gaacattatg | ctagcaggct | 3900 |
| agcagaaatg | gaaaacagca | atggatctta | tctaaatgat | agcatctctc | ctaatgagag | 3960 |
| catagatgat | gaacatttgt | taatccagca | ttactgccaa | agtttgaacc | aggactcccc | 4020 |
| cctgagccag | cctcgtagtc | ctgcccagat | cttgatttcc | ttagagagtg | aggaagagg | 4080 |
| ggagctagag | agaatcctag | cagatcttga | ggaagaaaac | aggaatctgc | aagcagaata | 4140 |
| tgaccgtcta | aagcagcagc | acgaacataa | aggcctgtcc | ccactgccgt | cccctcctga | 4200 |
| aatgatgccc | acctctcccc | agagtccccg | ggatgctgag | ctcattgctg | aggccaagct | 4260 |
| actgcgtcaa | cacaaaggcc | gcctggaagc | caggatgcaa | atcctggaag | accacaataa | 4320 |
| acagctggag | tcacagttac | acaggctaag | gcagctgctg | gagcaacccc | aggcagaggc | 4380 |
| caaagtgaat | ggcacaacgg | tgtcctctcc | ttctacctct | ctacagaggt | ccgacagcag | 4440 |
| tcagcctatg | ctgctccgag | tggttggcag | tcaaacttcg | gactccatgg | gtgaggaaga | 4500 |
| tcttctcagt | cctccccagg | acacaagcac | agggttagag | gaggtgatgg | agcaactcaa | 4560 |
| caactccttc | cctagttcaa | gaggaagaaa | taccccctgga | aagccaatga | gagaggacac | 4620 |
| aatgtaggaa | gtcttttcca | catggcagat | gatttgggca | gagcgatgga | gtccttagta | 4680 |
| tcagtcatga | cagatgaaga | aggagcagaa | taaatgtttt | acaactcctg | attcccgcat | 4740 |
| ggttttata | atattcatac | aacaaagagg | attagacagt | aagagtttac | aagaaataaa | 4800 |
| tctatatttt | tgtgaagggt | agtggtatta | tactgtagat | ttcagtagtt | tctaagtctg | 4860 |
| ttattgtttt | gttaacaatg | gcaggtttta | cacgtctatg | caattgtaca | aaaagttat | 4920 |
| aagaaaacta | catgtaaaat | cttgatagct | aaataacttg | ccatttcttt | atatggaacg | 4980 |
| cattttgggt | tgtttaaaaa | tttataacag | ttataaagaa | agattgtaaa | ctaaagtgtg | 5040 |
| ctttataaaa | aaaagttgtt | tataaaaacc | cctaaaaaca | aaacaaacac | acacacacac | 5100 |
| acatacacac | acacacacaa | aactttgagg | cagcgcattg | ttttgcatcc | ttttggcgtg | 5160 |
| atatccatat | gaaattcatg | gctttttctt | tttttgcata | ttaaagataa | gacttcctct | 5220 |
| accaccacac | caaatgacta | ctacacactg | ctcatttgag | aactgtcagc | tgagtggggc | 5280 |
| aggcttgagt | tttcatttca | tatatctata | tgtctataag | tatataaata | ctatagttat | 5340 |
| atagataaag | agatacgaat | ttctatagac | tgacttttc | cattttttaa | atgttcatgt | 5400 |
| cacatcctaa | tagaaagaaa | ttacttctag | tcagtcatcc | aggcttacct | gcttggtcta | 5460 | ga                                                                      5462

<210> SEQ ID NO 42
<211> LENGTH: 8689
<212> TYPE: DNA
<213> ORGANISM: Artificial Sequence
<220> FEATURE:
<223> OTHER INFORMATION: Synthetic

<400> SEQUENCE: 42

| | | | | | |
|---|---|---|---|---|---|
| gggattccct | cactttcccc | ctacaggact | cagatctggg | aggcaattac | cttcggagaa |   60 |
| aaacgaatag | gaaaaactga | agtgttactt | tttttaaagc | tgctgaagtt | tgttggtttc |  120 |
| tcattgtttt | taagcctact | ggagcaataa | agtttgaaga | acttttacca | ggttttttt |  180 |
| atcgctgcct | tgatatacac | ttttcaaaat | gctttggtgg | aagaagtag | aggactgtta |  240 |
| tgaaagagaa | gatgttcaaa | agaaacatt | cacaaaatgg | gtaaatgcac | aattttctaa |  300 |
| gtttgggaag | cagcatattg | agaacctctt | cagtgaccta | caggatggga | ggcgcctcct |  360 |
| agacctcctc | gaaggcctga | cagggcaaaa | actgccaaaa | gaaaaggat | ccacaagagt |  420 |
| tcatgccctg | aacaatgtca | acaaggcact | gcgggtttg | cagaacaata | atgttgattt |  480 |
| agtgaatatt | ggaagtactg | acatcgtaga | tggaaatcat | aaactgactc | ttggtttgat |  540 |
| ttggaatata | atcctccact | ggcaggtcaa | aaatgtaatg | aaaatatca | tggctggatt |  600 |
| gcaacaaacc | aacagtgaaa | agattctcct | gagctgggtc | cgacaatcaa | ctcgtaatta |  660 |
| tccacaggtt | aatgtaatca | acttcaccac | cagctggtct | gatggcctgg | ctttgaatgc |  720 |
| tctcatccat | agtcataggc | cagacctatt | tgactggaat | agtgtggttt | gccagcagtc |  780 |
| agccacacaa | cgactggaac | atgcattcaa | catcgccaga | tatcaattag | gcatagagaa |  840 |
| actactcgat | cctgaagatg | ttgataccac | ctatccagat | aagaagtcca | tcttaatgta |  900 |
| catcacatca | ctcttccaag | tttgcctca | acaagtgagc | attgaagcca | tccaggaagt |  960 |
| ggaaatgttg | ccaaggccac | ctaaagtgac | taaagaagaa | catttcagt | tacatcatca | 1020 |
| aatgcactat | tctcaacaga | tcacggtcag | tctagcacag | ggatatgaga | gaacttcttc | 1080 |
| ccctaagcct | cgattcaaga | gctatgccta | cacacaggct | gcttatgtca | ccacctctga | 1140 |
| ccctacacgg | agcccatttc | cttcacagca | tttggaagct | cctgaagaca | agtcatttgg | 1200 |
| cagttcattg | atggagagtg | aagtaaacct | ggaccgttat | caaacagctt | tagaagaagt | 1260 |
| attatcgtgg | cttctttctg | ctgaggacac | attgcaagca | caggagaga | tttctaatga | 1320 |
| tgtggaagtg | gtgaaagacc | agtttcatac | tcatgagggg | tacatgatgg | atttgacagc | 1380 |
| ccatcagggc | cgggttggta | atattctaca | attgggaagt | aagctgattg | gaacaggaaa | 1440 |
| attatcagaa | gatgaagaaa | ctgaagtaca | agagcagatg | aatctcctaa | attcaagatg | 1500 |
| ggaatgcctc | agggtagcta | gcatggaaaa | acaaagcaat | ttacatagag | ttttaatgga | 1560 |
| tctccagaat | cagaaactga | aagagttgaa | tgactggcta | acaaaaacag | aagaaagaac | 1620 |
| aaggaaaatg | gaggaagagc | ctcttggacc | tgatcttgaa | gacctaaaac | gccaagtaca | 1680 |
| acaacataag | gtgcttcaag | aagatctaga | acaagaacaa | gtcagggtca | attctctcac | 1740 |
| tcacatggtg | gtggtagttg | atgaatctag | tggagatcac | gcaactgctg | ctttggaaga | 1800 |
| acaacttaag | gtattgggag | atcgatgggc | aaacatctgt | agatggacag | aagaccgctg | 1860 |
| ggttcttta | caagacatcc | ttctcaaatg | gcaacgtctt | actgaagaac | agtgccttt | 1920 |
| tagtgcatgg | ctttcagaaa | aagaagatgc | agtgaacaag | attcacacaa | ctggctttaa | 1980 |

-continued

```
agatcaaaat gaaatgttat caagtcttca aaaactggcc gttttaaaag cggatctaga    2040
aaagaaaaag caatccatgg gcaaactgta ttcactcaaa caagatcttc tttcaacact    2100
gaagaataag tcagtgaccc agaagacgga agcatggctg ataactttg  cccggtgttg    2160 ggataattta gtccaaaaac ttgaaaagag tacagcacag atttcacagc agcctgacct    2220
agctcctgga ctgaccacta ttggagcctc tcctactcag actgttactc tggtgacaca    2280
acctgtggtt actaaggaaa ctgccatctc caaactagaa atgccatctt ccttgatgtt    2340
ggaggtacct gctctggcag atttcaaccg ggcttggaca gaacttaccg actggctttc    2400
tctgcttgat caagttataa aatcacagag ggtgatggtg ggtgaccttg aggatatcaa    2460
cgagatgatc atcaagcaga aggcaacaat gcaggatttg aacagaggc  gtccccagtt    2520 ggaagaactc attaccgctg cccaaaattt gaaaacaag  accagcaatc aagaggctag    2580
aacaatcatt acggatcgaa ttgaaagaat tcagaatcag tgggatgaag tacaagaaca    2640
ccttcagaac cggaggcaac agttgaatga aatgttaaag gattcaacac aatggctgga    2700
agctaaggaa gaagctgagc aggtcttagg acaggccaga gccaagcttg agtcatggaa    2760
ggagggtccc tatacagtag atgcaatcca aagaaaatc  acagaaacca agcagttggc    2820
caaagacctc cgccagtggc agacaaatgt agatgtggca aatgacttgg ccctgaaact    2880
tctccgggat tattctgcag atgataccag aaaagtccac atgataacag agaatatcaa    2940
tgcctcttgg agaagcattc ataaaagggt gagtgagcga gaggctgctt tggaagaaac    3000
tcatagatta ctgcaacagt tccccctgga cctggaaaag tttcttgcct ggcttacaga    3060
agctgaaaca actgccaatg tcctacagga tgctacccgt aaggaaaggc tcctagaaga    3120
ctccaaggga gtaaaagagc tgatgaaaca atggcaagac ctccaaggtg aaattgaagc    3180
tcacacagat gtttatcaca acctggatga aaacagccaa aaaatcctga gatccctgga    3240
aggttccgat gatgcagtcc tgttacaaag acgtttggat aacatgaact tcaagtggag    3300
tgaacttcgg aaaaagtctc tcaacattag gtcccatttg gaagccagtt ctgaccagtg    3360
gaagcgtctg cacctttctc tgcaggaact tctggtgtgg ctacagctga agatgatga    3420 attaagccgg caggcaccta ttggaggcga ctttccagca gttcagaagc agaacgatgt    3480
acatagggcc ttcaagaggg aattgaaaac taaagaacct gtaatcatga gtactcttga    3540
gactgtacga atatttctga cagagcagcc tttggaagga ctagagaaac tctaccagga    3600
gcccagagag ctgcctcctg aggagagagc ccagaatgtc actcggcttc tacgaaagca    3660
ggctgaggag gtcaatactg agtgggaaaa attgaacctg cactccgctg actggcagag    3720
aaaaatagat gagaccccttg aaagactcca ggaacttcaa gaggccacgg atgagctgga    3780
cctcaagctg cgccaagctg aggtgatcaa gggatcctgg cagcccgtgg gcgatctcct    3840
cattgactct ctccaagatc acctcgagaa agtcaaggca cttcgaggag aaattgcgcc    3900
tctgaaagag aacgtgagcc acgtcaatga ccttgctcgc cagcttacca ctttgggcat    3960
tcagctctca ccgtataacc tcagcactct ggaagacctg aacaccagat ggaagcttct    4020
gcaggtggcc gtcgaggacc gagtcaggca gctgcatgaa gcccacaggg actttggtcc    4080
agcatctcag cactttcttt ccacgtctgt ccagggtccc tgggagagag ccatctcgcc    4140
aaacaaagtg ccctactata tcaaccacga gactcaaaca acttgctggg accatcccaa    4200
aatgacagag ctctaccagt cttagctga  cctgaataat gtcagattct cagcttatag    4260
gactgccatg aaactccgaa gactgcagaa ggccctttgc ttggatctct tgagcctgtc    4320
agctgcatgt gatgccttgg accagcacaa cctcaagcaa aatgaccagc ccatggatat    4380
```

-continued

```
cctgcagatt attaattgtt tgaccactat ttatgaccgc ctggagcaag agcacaacaa    4440
tttggtcaac gtccctctct gcgtggatat gtgtctgaac tggctgctga atgtttatga    4500
tacgggacga acagggagga tccgtgtcct gtcttttaaa actggcatca tttccctgtg    4560
taaagcacat ttggaagaca agtacagata ccttttcaag caagtggcaa gttcaacagg    4620
attttgtgac cagcgcaggc tgggcctcct tctgcatgat tctatccaaa ttccaagaca    4680
gttgggtgaa gttgcatcct ttgggggcag taacattgag ccaagtgtcc ggagctgctt    4740
ccaatttgct aataataagc cagagatcga agcggccctc ttcctagact ggatgagact    4800
ggaaccccag tccatggtgt ggctgcccgt cctgcacaga gtggctgctg cagaaactgc    4860
caagcatcag gccaaatgta acatctgcaa agagtgtcca atcattggat tcaggtacag    4920
gagtctaaag cactttaatt atgacatctg ccaaagctgc tttttttctg gtcgagttgc    4980
aaaaggccat aaaatgcact atcccatggt ggaatattgc actccgacta catcaggaga    5040
agatgttcga gactttgcca aggtactaaa aaacaaattt cgaaccaaaa ggtattttgc    5100
gaagcatccc cgaatgggct acctgccagt gcagactgtc ttagaggggg acaacatgga    5160
aactcccgtt actctgatca acttctggcc agtagattct gcgcctgcct cgtcccctca    5220
gctttcacac gatgatactc attcacgcat tgaacattat gctagcaggc tagcagaaat    5280
ggaaaacagc aatggatctt atctaaatga tagcatctct cctaatgaga gcatagatga    5340
tgaacatttg ttaatccagc attactgcca aagtttgaac caggactccc ccctgagcca    5400
gcctcgtagt cctgcccaga tcttgatttc cttagagagt gaggaaagag gggagctaga    5460
gagaatccta gcagatcttg aggaagaaaa caggaatctg caagcagaat atgaccgtct    5520
aaagcagcag cacgaacata aaggcctgtc cccactgccg tcccctcctg aaatgatgcc    5580
cacctctccc cagagtcccc gggatgctga gctcattgct gaggccaagc tactgcgtca    5640
acacaaaggc cgcctggaag ccaggatgca aatcctggaa gaccacaata acagctgga    5700
gtcacagtta cacaggctaa ggcagctgct ggagcaaccc caggcagagg ccaaagtgaa    5760
tggcacaacg gtgtcctctc cttctacctc tctacagagg tccgcagca gtcagcctat    5820
gctgctccga gtggttggca gtcaaacttc ggactccatg ggtgaggaag atcttctcag    5880
tcctccccag gacacaagca cagggttaga ggaggtgatg gagcaactca acaactcctt    5940
ccctagttca agaggaagaa ataccccctgg aaagccaatg agagaggaca caatgtagga    6000
agtcttttcc acatggcaga tgatttgggc agagcgatgg agtccttagt atcagtcatg    6060
acagatgaag aaggagcaga ataaatgttt tacaactcct gattcccgca tggttttat    6120
aatattcata caacaaagag gattagacag taagagttta caagaaataa atctatattt    6180
ttgtgaaggg tagtggtatt atactgtaga tttcagtagt ttctaagtct gttattgttt    6240
tgttaacaat ggcaggtttt acacgtctat gcaattgtac aaaaaagtta taagaaaact    6300
acatgtaaaa tcttgatagc taaataactt gccatttctt tatatggaac gcattttggg    6360
ttgtttaaaa atttataaca gttataaaga aagattgtaa actaaagtgt gctttataaa    6420
aaaagttgt ttataaaaac ccctaaaaac aaaacaaaca cacacacaca cacatacaca    6480
cacacacaca aaactttgag gcagcgcatt gttttgcatc cttttggcgt gatatccata    6540
tgaaattcat ggctttttct tttttgcat attaaagata agacttcctc taccaccaca    6600
ccaaatgact actacacact gctcatttga gaactgtcag ctgagtgggg caggcttgag    6660
ttttcatttc atatatctat atgtctataa gtatataaat actatagtta tatagataaa    6720
```

-continued

| | |
|---|---|
| gagatacgaa tttctataga ctgactttt ccattttta aatgttcatg tcacatccta | 6780 |
| atagaaagaa attacttcta gtcagtcatc caggcttacc tgcttggtct agaatggatt | 6840 |
| tttcccggag ccggaagcca ggaggaaact acaccacact aaaacattgt ctacagctcc | 6900 |
| agatgtttct cattttaaac aactttccac tgacaacgaa agtaaagtaa agtattggat | 6960 |
| tttttttaaag gaacatgtg aatgaataca caggacttat tatatcagag tgagtaatcg | 7020 |
| gttggttggt tgattgattg attgattgat acattcagct tcctgctgct agcaatgcca | 7080 |
| cgatttagat ttaatgatgc ttcagtggaa atcaatcaga aggtattctg accttgtgaa | 7140 |
| catcagaagg tattttttaa ctcccaagca gtagcaggac gatgataggg ctggagggct | 7200 |
| atggattccc agcccatccc tgtgaaggag taggccactc tttaagtgaa ggattggatg | 7260 |
| attgttcata atacataaag ttctctgtaa ttacaactaa attattatgc cctcttctca | 7320 |
| cagtcaaaag gaactgggtg gtttggtttt tgttgctttt ttagatttat tgtcccatgt | 7380 |
| gggatgagtt tttaaatgcc acaagacata atttaaaata aataaacttt gggaaaaggt | 7440 |
| gtaagacagt agccccatca catttgtgat actgacaggt atcaacccag aagcccatga | 7500 |
| actgtgtttc catcctttgc atttctctgc gagtagttcc acacaggttt gtaagtaagt | 7560 |
| aagaaagaag gcaaattgat tcaaatgtta caaaaaaacc cttcttggtg gattagacag | 7620 |
| gttaaatata taaacaaaca aacaaaaatt gctcaaaaaa gaggagaaaa gctcaagagg | 7680 |
| aaaagctaag gactggtagg aaaaagcttt actctttcat gccatttat ttcttttga | 7740 |
| tttttaaatc attcattcaa tagataccac cgtgtgacct ataattttgc aaatctgtta | 7800 |
| cctctgacat caagtgtaat tagcttttgg agagtgggct gacatcaagt gtaattagct | 7860 |
| tttggagagt gggttttgtc cattattaat aattaattaa ttaacatcaa acacggcttc | 7920 |
| tcatgctatt tctacctcac tttggttttg gggtgttcct gataattgtg cacacctgag | 7980 |
| ttcacagctt caccacttgt ccattgcgtt attttctttt ccttttataa ttctttctt | 8040 |
| ttccttcata attttcaaaa gaaaacccaa agctctaagg taacaaatta ccaaattaca | 8100 |
| tgaagatttg gttttttgtct tgcatttttt tccttatgt gacgctggac cttttcttta | 8160 |
| cccaaggatt tttaaaactc agatttaaaa caaggggtta ctttacatcc tactaagaag | 8220 |
| tttaagtaag taagtttcat tctaaaatca gaggtaaata gagtgcataa ataattttgt | 8280 |
| tttaatctt ttgttttct tttagacaca ttagctctgg agtgagtctg tcataatatt | 8340 |
| tgaacaaaaa ttgagagctt tattgctgca tttaagcat aattaatttg gacattattt | 8400 |
| cgtgttgtgt tctttataac caccgagtat taaactgtaa atcataatgt aactgaagca | 8460 |
| taaacatcac atggcatgtt ttgtcattgt tttcaggtac tgagttctta cttgagtatc | 8520 |
| ataatatatt gtgtttaac accaacactg taacatttac gaattatttt tttaaacttc | 8580 |
| agttttactg cattttcaca acatatcaga cttcaccaaa tatatgcctt actattgtat | 8640 |
| tatagtactg ctttactgtg tatctcaata aagcacgcag ttatgttac | 8689 |

<210> SEQ ID NO 43
<211> LENGTH: 4181
<212> TYPE: DNA
<213> ORGANISM: Homo sapiens

<400> SEQUENCE: 43

| | |
|---|---|
| ggaactccgc ttcgcccgag acccagcgcc caggcgtgtc gcccgagagg agccgcgcga | 60 |
| aggtcacccc gcgcccgccg cccgccgccc gccgcctccg tgggtccgtt tgccagtcag | 120 |
| cccgtgcgtc cgagcccctc gcgccccgcc gcagccccgg ccaaccgagc gccatgaacc | 180 |

-continued

```
agatagagcc cggcgtgcag tacaactacg tgtacgacga ggatgagtac atgatccagg      240
aggaggagtg ggaccgcgac ctgctcctgg acccagcctg ggagaagcag cagaggaaga      300
ccttcactgc ctggtgtaac tcccacctaa ggaaagccgg cacccagatt gagaacatcg      360
aggaagactt caggaatggc cttaagctca tgctgctttt ggaagtcatc tcaggggaaa      420
ggctgcccaa acctgaccgg ggaaaaatgc ggttccacaa aattgctaat gtcaacaaag      480
ctttggatta catagccagc aaaggggtga aactggtgtc catcggcgct gaagaaattg      540
ttgatggcaa tgtgaaaatg accctgggta tgatctggac catcatcctt cgctttgcta      600
ttcaggatat ttcggttgaa gaaacatctg ccaaagaagg tctgctgctt tggtgtcaga      660
ggaaaactgc tccttataga aatgtgaaca ttcagaactt ccatactagc tggaaagatg      720
gccttggact ctgtgccctc atccaccgac accggcctga cctcattgac tactcaaagc      780
ttaacaagga tgaccccata ggaaatatta acctggccat ggaaatcgct gagaagcacc      840
tggatattcc taaaatgttg gatgctgaag acatcgtgaa caccctaaa cccgatgaaa       900 gagccatcat gacgtacgtc tcttgcttct accacgcttt tgcgggcgcg gagcaggccg      960
agacagcggc taacaggata tgtaaggttc ttgctgtgaa tcaagagaat gagaggctga     1020
tggaagaata tgagaggcta gcgagtgagc ttttggaatg gattcgtcgc acgatcccct     1080
ggctggagaa ccggactccc gagaagacca tgcaagccat gcaagaagaag ctggaggact    1140 tccgggatta ccgccggaag cacaagccac ccaaggtgca ggagaaatgc cagctggaga     1200
tcaacttcaa cacgctgcag accaagctgc ggatcagcaa ccgtcctgcc ttcatgccct     1260
ccgagggcaa gatggtgtcg gatattgctg gtgcctggca gaggctggag caggctgaga     1320
agggttacga ggagtggttg ctcaatgaga ttcggagact ggagcgcttg gaacacctgg     1380
ctgagaagtt caggcagaag gcctcaacgc acgagacttg ggcttatggc aaagagcaga     1440
tcttgctgca gaaggattac gagtcggcgt cgctgacaga ggtgcgggct ctgctgcgga     1500
agcacgaggc gttcgagagc gacctggcag cgcaccagga ccgcgtggag cagatcgcag     1560
ccatcgcgca ggagctcaat gaactggact atcacgacgc tgtgaatgtc aatgatcggt     1620
gccagaaaat ttgtgaccag tgggaccgac tgggaacgct tactcagaag aggagagaag     1680
ccctagagag aatggagaaa ttgctagaaa ccattgatca gcttcacctg gagtttgcca     1740
agagggctgc tcctttcaac aattggatgg agggcgctat ggaggatctg caagatatgt     1800
tcattgtcca cagcattgag gagatccaga gtctgatcac tgcgcatgag cagttcaagg     1860
ccacgctgcc cgaggcggac ggagagcggc agtccatcat ggccatccag aacgaggtgg     1920
agaaggtgat tcagagctac aacatcgaaa tcagctcaag caacccgtac agcactgtca     1980
ccatggatga gctccggacc aagtgggaca aggtgaagca actcgtgccc atccgcgatc     2040
aatccctgca ggaggagctg gctcgccagc atgctaacga gcgtctgagg cgccagtttg     2100
ctgcccaagc caatgccatt gggccctgga tccagaacaa gatggaggag attgcccgga     2160
gctccatcca gatcacagga gccctggaag accagatgaa ccagctgaag cagtatgagc     2220
acaacatcat caactataag aacaacatcg acaagctgga gggagaccat cagctcatcc     2280
aggaggccct tgtctttgac aacaagcaca cgaactacac gatggagcac attcgtgttg     2340
gatgggagct gctgctgaca accatcgcca gaaccatcaa tgaggtggag actcagatcc     2400
tgacagagag tgcgaagggc atcacccagg agcagatgaa tgagttcaga gcctccttca     2460
accactttga caggaggaag aatggcctga tggatcatga ggatttcaga gcctgcctga     2520
```

-continued

```
tttccatggg ttatgacctg ggtgaagccg aatttgcccg cattatgacc ctggtagatc    2580
ccaacgggca aggcaccgtc accttccaat ccttcatcga cttcatgact agagagacgg    2640
ctgacaccga cactgccgag caggtcatcg cctccttccg gatcctggct tctgataagc    2700
catacatcct ggcggaggag ctgcgtcggg agctgccccc ggatcaggcc cagtactgca    2760
tcaagaggat gcccgcctac tcgggcccag gcagtgtgcc tggtgcactg gattacgctg    2820
cgttctcttc cgcactctac ggggagagcg atctgtgatg ctgagcttct gtaatcactc    2880
atcccatcag aatgcaataa aagcggaagt cacagtttgt ttcctggaaa ctttgacaag    2940
ctttattaag ttgagagaga gagaggggga aaaaaaaaa gcctttcgta gttcagtaat    3000
tgccagcaat ataacacggc taaaatgaag tttttacagt atatgacata gtgcgcttca    3060
taaataggtt tatttctgag ttttttagcaa aatgtaatga aatatcaggt tgatttcttt    3120
gattaaacag aacaaattac ttgagtaata ggaaattagg aggatctagg gacagaagga    3180
aagtgaaaaa tgtgaaaata caaatacccc aagatttaag accggggggga aaaaccaca    3240 aattggtaaa taaaggtttg ctatttgtaa aaaatttcat ttatctctaa tatgcttatg    3300
tgattggccc taggggagta tatttgggat tctaatgttt tattttcatg cttatccaaa    3360
gattactatt gtatcttcaa atgaacttaa tattgtgaga tggaactgcc ggggattaaa    3420
aagactaccc aaaagatttt tggcacttac aattttttaaa atagtttatg tcatctcttc    3480
attatttagg gctggatggt caactcagtc agtgattttt tgatgcttct cttatcctcc    3540
agaatagaga cctaaggaca cgtggaagtc agtttaattg ccagagagaa ggatgcaatc    3600
actaggtgaa atgaggtttt taggattatt tattgattcc aggttcccat gcttttttgtt    3660 agagcttatt agtacaggtt ctcaagagat gaccacataa aagtgctctg tttataaata    3720
agcaggtttc tgtagtactg actggttcat cacaaggcaa gtcagaaacc agtatccttc    3780
tagctctcca gtcaggactt ccttatgcct ctagtttttat gaccggttaa ggagaagcca    3840
gagttagagt aggagaggac taattctcag cagcagtgga ggtgagttct ttcttttgcg    3900
gaagctttac atatgttttg tgtagtagga ataactagat attttagcta gtgtgcggtg    3960
tgtgttcacc cctgggattg gacagtgtat cctaacaagt cccatgtctg gttctgtgtc    4020
taaaggcctg ctccatgaca caggatgcta catgcactcc tgctagcaca tcttgatctg    4080
ttgaatgttc attctttctt tttgctcata ctgctgtagg ctataattcc ccctgttttt    4140
tccatcttgt tgacagcttg tagagaataa agcaggaatt c                        4181
```

<210> SEQ ID NO 44
<211> LENGTH: 11443
<212> TYPE: DNA
<213> ORGANISM: Artificial Sequence
<220> FEATURE:
<223> OTHER INFORMATION: Synthetic

<400> SEQUENCE: 44

```
gggattccct cactttcccc ctacaggact cagatctggg aggcaattac cttcggagaa      60
aaacgaatag gaaaaactga agtgttactt tttttaaagc tgctgaagtt tgttggtttc     120
tcattgtttt taagcctact ggagcaataa agtttgaaga acttttacca ggttttttttt     180 atcgctgcct tgatatacac ttttcaaaat gctttggtgg gaagaagtag aggactgtta     240
tgaaagagaa gatgttcaaa agaaaacatt cacaaaatgg gtaaatgcac aattttctaa     300
gtttgggaag cagcatattg agaacctctt cagtgaccta caggatggga ggcgcctcct     360
agacctcctc gaaggcctga cagggcaaaa actgccaaaa gaaaaaggat ccacaagagt     420
```

-continued

```
tcatgccctg aacaatgtca acaaggcact gcgggttttg cagaacaata atgttgattt    480
agtgaatatt ggaagtactg acatcgtaga tggaaatcat aaactgactc ttggtttgat    540
ttggaatata atcctccact ggcaggtcaa aaatgtaatg aaaaatatca tggctggatt    600
gcaacaaacc aacagtgaaa agattctcct gagctgggtc cgacaatcaa ctcgtaatta    660
tccacaggtt aatgtaatca acttccaccac cagctggtct gatggcctgg ctttgaatgc    720
tctcatccat agtcataggc cagacctatt tgactggaat agtgtggttt gccagcagtc    780
agccacacaa cgactggaac atgcattcaa catcgccaga tatcaattag gcatagagaa    840
actactcgat cctgaagatg ttgataccac ctatccagat aagaagtcca tcttaatgta    900
catcacatca ctcttccaag ttttgcctca acaagtgagc attgaagcca tccaggaagt    960
ggaaatgttg ccaaggccac ctaaagtgac taaagaagaa cattttcagt tacatcatca   1020
aatgcactat tctcaacaga tcacggtcag tctagcacag ggatatgaga gaacttcttc   1080
ccctaagcct cgattcaaga gctatgccta cacacaggct gcttatgtca ccacctctga   1140
ccctacacgg agcccatttc cttcacagca tttggaagct cctgaagaca agtcatttgg   1200
cagttcattg atggagagtg aagtaaaacct ggaccgttat caaacagctt tagaagaagt   1260
attatcgtgg cttcttttctg ctgaggacac attgcaagca caggagaga tttctaatga   1320
tgtggaagtg gtgaaagacc agtttcatac tcatgagggg tacatgatgg atttgacagc   1380
ccatcagggc cgggttggta atattctaca attgggaagt aagctgattg gaacaggaaa   1440
attatcagaa gatgaagaaa ctgaagtaca agagcagatg aatctcctaa attcaagatg   1500
ggaatgcctc agggtagcta gcatggaaaa acaaagcaat ttacatagag ttttaatgga   1560
tctccagaat cagaaactga aagagttgaa tgactggcta acaaaaacag aagaaagaac   1620
aaggaaaatg gaggaagagc ctcttggacc tgatcttgaa gacctaaaac gccaagtaca   1680
acaacataag gtgcttcaag aagatctaga acaagaacaa gtcagggtca attctctcac   1740
tcacatggtg gtggtagttg atgaatctag tggagatcac gcaactgctg ctttggaaga   1800
acaacttaag gtattgggag atcgatgggc aaacatctgt agatggacag aagaccgctg   1860
ggttctttta caagacatcc ttctcaaatg gcaacgtctt actgaagaac agtgccttt   1920
tagtgcatgc ctttcagaaa aagaagatgc agtgaacaag attcacacaa ctggctttaa   1980
agatcaaaat gaaatgttat caagtcttca aaaactggcc gttttaaaag cggatctaga   2040
aaagaaaaag caatccatgg gcaaactgta ttcactcaaa caagatcttc tttcaacact   2100
gaagaataag tcagtgaccc agaagacgga agcatggctg ataactttg cccggtgttg   2160
ggataattta gtccaaaaac ttgaaaagag tacagcacag atttcacagg ctgtcaccac   2220
cactcagcca tcactaacac agacaactgt aatggaaaca gtaactacgg tgaccacaag   2280
ggaacagatc ctggtaaagc atgctcaaga ggaacttcca ccaccacctc cccaaaagaa   2340
gaggcagatt actgtggatt ctgaaattag gaaaggttg gatgttgata taactgaact   2400
tcacagctgg attactcgct cagaagctgt gttgcagagt cctgaatttg caatctttcg   2460
gaaggaaggc aacttctcag acttaaaaga aaaagtcaat gccatagagc gagaaaaagc   2520
tgagaagttc agaaaactgc aagatgccag cagatcagct caggccctgg tgaacagat   2580
ggtgaatgag ggtgttaatg cagatagcat caaacaagcc tcagaacaac tgaacagccg   2640
gtggatcgaa ttctgccagt tgctaagtga gagacttaac tggctggagt atcagaacaa   2700
catcatcgct ttctataatc agctacaaca attggagcag atgacaacta ctgctgaaaa   2760
```

```
ctggttgaaa atccaaccca ccaccccatc agagccaaca gcaattaaaa gtcagttaaa    2820
aatttgtaag gatgaagtca accggctatc aggtcttcaa cctcaaattg aacgattaaa    2880
aattcaaagc atagccctga agagaaagg caaggaccc atgttcctgg atgcagactt     2940
tgtggccttt acaaatcatt ttaagcaagt ctttctgat gtgcaggcca gagagaaaga    3000
gctacagaca attttgaca ctttgccacc aatgcgctat caggagacca tgagtgccat    3060
caggacatgg gtccagcagt cagaaaccaa actctccata cctcaactta gtgtcaccga   3120
ctatgaaatc atggagcaga gactcgggga attgcaggct ttacaaagtt ctctgcaaga   3180
gcaacaaagt ggcctatact atctcagcac cactgtgaaa gagatgtcga agaaagcgcc   3240
ctctgaaatt agccggaaat atcaatcaga atttgaagaa attgagggac gctggaagaa   3300
gctctcctcc cagctggttg agcattgtca aaagctagag gagcaaatga ataaactccg   3360
aaaaattcag aatcacatac aaaccctgaa gaaatggatg gctgaagttg atgttttct   3420 gaaggaggaa tggcctgccc ttggggattc agaaattcta aaaaagcagc tgaaacagtg   3480 cagacttta gtcagtgata ttcagacaat tcagcccagt ctaaacagtg tcaatgaagg    3540
tgggcagaag ataaagaatg aagcagagcc agagtttgct tcgagacttg agacagaact   3600
caaagaactt aacactcagt gggatcacat gtgccaacag gtctatgcca gaaaggaggc   3660
cttgaaggga ggtttggaga aactgtaag cctccagaaa gatctatcag agatgcacga   3720
atggatgaca caagctgaag aagagtatct tgagagagat tttgaatata aaactccaga   3780
tgaattacag aaagcagttg aagagatgaa gagagctaaa aagaggccc aacaaaaaga    3840 agcgaaagtg aaactcctta ctgagtctgt aaatagtgtc atagctcaag ctccacctgt   3900
agcacaagag gccttaaaaa aggaacttga aactctaacc accaactacc agtggctctg   3960
cactaggctg aatgggaaat gcaagacttt ggaagaatct gttgagaaat ggcggcgttt   4020
tcattatgat ataaagatat ttaatcagtg gctaacagaa gctgaacagt ttctcagaaa   4080
gacacaaatt cctgagaatt gggaacatgc taaatacaaa tggtatctta aggaactcca   4140
ggatggcatt gggcagcggc aaactgttgt cagaacattg aatgcaactg ggaagaaat    4200 aattcagcaa tcctcaaaaa cagatgccag tattctacag gaaaaattgg gaagcctgaa   4260
tctgcggtgg caggaggtct gcaaacagct gtcagacaga aaaaagaggc tagaagaaca   4320
aaagaatatc ttgtcagaat ttcaaagaga tttaaatgaa tttgttttat ggttggagga   4380
agcagataac attgctagta tcccacttga acctggaaaa gagcagcaac taaaagaaaa   4440
gcttgagcaa gtcaagttac tggtggaaga gttgccctg cgccagggaa ttctcaaaca    4500
attaaatgaa actggaggac ccgtgcttgt aagtgctccc ataagcccag aagagcaaga   4560
taaacttgaa aataagctca agcagacaaa tctccagtgg ataaaggttt ccagagcttt   4620
acctgagaaa caaggagaaa ttgaagctca aataaaagac cttgggcagc ttgaaaaaaa   4680
gcttgaagac cttgaagagc agttaaatca tctgctgctg tggttatctc ctattaggaa   4740
tcagttggaa atttataacc aaccaaacca agaaggacca tttgacgttc aggaaactga   4800
aatagcagtt caagctaaac aaccggatgt ggaaagagatt ttgtctaaag gcagcattt   4860 gtacaaggaa aaaccagcca ctcagccagt gaagaggaag ttagaagatc tgagctctga   4920
gtggaaggcg gtaaaccgtt tacttcaaga gctgagggca aagcagcctg acctagctcc   4980
tggactgacc actattggag cctctcctac tcagactgtt actctggtga cacaacctgt   5040
ggttactaag gaaactgcca tctccaaact agaaatgcca tcttccttga tgttggaggt   5100
acctgctctg gcagatttca accgggcttg gacagaactt accgactggc tttctctgct   5160
```

-continued

```
tgatcaagtt ataaaatcac agagggtgat ggtgggtgac cttgaggata tcaacgagat    5220
gatcatcaag cagaaggcaa caatgcagga tttggaacag aggcgtcccc agttggaaga    5280
actcattacc gctgcccaaa atttgaaaaa caagaccagc aatcaagagg ctagaacaat    5340
cattacggat cgaattgaaa gaattcagaa tcagtgggat gaagtacaag aacaccttca    5400
gaaccggagg caacagttga atgaaatgtt aaaggattca acacaatggc tggaagctaa    5460
ggaagaagct gagcaggtct taggacaggc cagagccaag cttgagtcat ggaaggaggg    5520
tccctataca gtagatgcaa tccaaaagaa aatcacagaa accaagcagt ggccaaaga    5580
cctccgccag tggcagacaa atgtagatgt ggcaaatgac ttggccctga aacttctccg    5640
ggattattct gcagatgata ccagaaaagt ccacatgata acagaaata tcaatgcctc    5700
ttggagaagc attcataaaa gggtgagtga gcgagaggct gctttggaag aaactcatag    5760
attactgcaa cagttccccc tggacctgga aaagtttctt gcctggctta cagaagctga    5820
aacaactgcc aatgtcctac aggatgctac ccgtaaggaa aggctcctag aagactccaa    5880
gggagtaaaa gagctgatga acaatggca agacctccaa ggtgaaattg aagctcacac    5940
agatgtttat cacaacctgg atgaaaacag ccaaaaaatc ctgagatccc tggaaggttc    6000
cgatgatgca gtcctgttac aaagacgttt ggataacatg aacttcaagt ggagtgaact    6060
tcggaaaaag tctctcaaca ttaggtccca tttggaagcc agttctgacc agtggaagcg    6120
tctgcacctt tctctgcagg aacttctggt gtggctacag ctgaaagatg atgaattaag    6180
ccggcaggca cctattggag cgactttcc agcagttcag aagcagaacg atgtacatag    6240
ggccttcaag agggaattga aaactaaaga acctgtaatc atgagtactc ttgagactgt    6300
acgaatattt ctgacagagc agcctttgga aggactagaa aaactctacc aggagcccag    6360
agagctgcct cctgaggaga gagcccagaa tgtcactcgg cttctacgaa gcaggctga    6420
ggaggtcaat actgagtggg aaaaattgaa cctgcactcc gctgactggc agagaaaaat    6480
agatgagacc cttgaaagac tccaggaact tcaagaggcc acggatgagc tggacctcaa    6540
gctgcgccaa gctgaggtga tcaagggatc ctggcagccc gtgggcgatc tcctcattga    6600
ctctctccaa gatcacctcg agaaagtcaa ggcacttcga ggagaaattg cgcctctgaa    6660
agagaacgtg agccacgtca atgaccttgc tcgccagctt accactttgg gcattcagct    6720
ctcaccgtat aacctcagca ctctggaaga cctgaacacc agatggaagc ttctgcaggt    6780
ggccgtcgag gaccgagtca ggcagctgca tgaagcccac agggactttg gtccagcatc    6840
tcagcacttt cttttccacgt ctgtccaggg tccctgggag agagccatct cgccaaacaa    6900
agtgccctac tatatcaacc acgagactca aacaacttgc tgggaccatc ccaaaatgac    6960
agagctctac cagtctttag ctgacctgaa taatgtcaga ttctcagctt ataggactgc    7020
catgaaactc cgaagactgc agaaggccct ttgcttggat ctcttgagcc tgtcagctgc    7080
atgtgatgcc ttggaccagc acaacctcaa gcaaaatgac cagcccatgg atatcctgca    7140
gattattaat tgtttgacca ctatttatga ccgcctggag caagagcaca caatttggt    7200
caacgtccct ctctgcgtgg atatgtgtct gaactggctg ctgaatgttt atgatacggg    7260
acgaacaggg aggatccgtg tcctgtcttt taaaactggc atcatttccc tgtgtaaagc    7320
acatttggaa gacaagtaca gatacctttt caagcaagtg gcagttcaa caggattttg    7380
tgaccagcgc aggctgggcc tccttctgca tgattctatc caaattccaa gacagttggg    7440
tgaagttgca tccctttgggg gcagtaacat tgagccaagt gtccggagct gcttccaatt    7500
```

```
tgctaataat aagccagaga tcgaagcggc cctcttccta gactggatga gactggaacc   7560
ccagtccatg gtgtggctgc ccgtcctgca cagagtggct gctgcagaaa ctgccaagca   7620
tcaggccaaa tgtaacatct gcaaagagtg tccaatcatt ggattcaggt acaggagtct   7680
aaagcacttt aattatgaca tctgccaaag ctgctttttt tctggtcgag ttgcaaaagg   7740
ccataaaatg cactatccca tggtggaata ttgcactccg actacatcag gagaagatgt   7800
tcgagacttt gccaaggtac taaaaaacaa atttcgaacc aaaaggtatt ttgcgaagca   7860
tccccgaatg ggctacctgc cagtgcagac tgtcttagag ggggacaaca tggaaactcc   7920
cgttactctg atcaacttct ggccagtaga ttctgcgcct gcctcgtccc ctcagctttc   7980
acacgatgat actcattcac gcattgaaca ttatgctagc aggctagcag aaatggaaaa   8040
cagcaatgga tcttatctaa atgatagcat ctctcctaat gagagcatag atgatgaaca   8100
tttgttaatc cagcattact gccaaagttt gaaccaggac tccccctga gccagcctcg   8160
tagtcctgcc cagatcttga tttccttaga gagtgaggaa agaggggagc tagagagaat   8220
cctagcagat cttgaggaag aaaacaggaa tctgcaagca gaatatgacc gtctaaagca   8280
gcagcacgaa cataaaggcc tgtccccact gccgtcccct cctgaaatga tgcccacctc   8340
tccccagagt ccccgggatg ctgagctcat tgctgaggcc aagctactgc gtcaacacaa   8400
aggccgcctg gaagccagga tgcaaatcct ggaagaccac aataaacagc tggagtcaca   8460
gttacacagg ctaaggcagc tgctggagca acccaggca gaggccaaag tgaatggcac   8520
aacggtgtcc tctccttcta cctctctaca gaggtccgac agcagtcagc ctatgctgct   8580
ccgagtggtt ggcagtcaaa cttcggactc catgggtgag gaagatcttc tcagtcctcc   8640
ccaggacaca agcacagggt tagaggaggt gatggagcaa ctcaacaact ccttccctag   8700
ttcaagagga agaaataccc ctggaaagcc aatgagagag gacacaatgt aggaagtctt   8760
ttccacatgg cagatgattt gggcagagcg atggagtcct tagtatcagt catgacagat   8820
gaagaaggag cagaataaat gttttacaac tcctgattcc cgcatggttt ttataatatt   8880
catacaacaa agaggattag acagtaagag tttacaagaa ataaatctat attttttgtga   8940
agggtagtgg tattatactg tagatttcag tagtttctaa gtctgttatt gttttgttaa   9000
caatggcagg ttttcacgt ctatgcaatt gtacaaaaaa gttataagaa aactacatgt   9060
aaaatcttga tagctaaata acttgccatt tctttatatg gaacgcattt tgggttgttt   9120
aaaaatttat aacagttata agaaagatt gtaaactaaa gtgtgcttta taaaaaaaag   9180
ttgtttataa aaaccctaa aaacaaaaca aacacacaca cacacacata cacacacaca   9240
cacaaaactt tgaggcagcg cattgttttg catcctttg gcgtgatatc catatgaaat   9300
tcatggctt tctttttttt gcatattaaa gataagactt cctctaccac cacaccaaat   9360
gactactaca cactgctcat ttgagaactg tcagctgagt ggggcaggct tgagttttca   9420
tttcatatat ctatatgtct ataagtatat aaatactata gttatataga taagagata   9480
cgaatttcta tagactgact ttttccattt tttaaatgtt catgtcacat cctaatagaa   9540
agaaattact tctagtcagt catccaggct tacctgcttg gtctagaatg gattttccc   9600
ggagccggaa gccaggagga aactacacca cactaaaaca ttgtctacag ctccagatgt   9660
ttctcatttt aaacaacttt ccactgacaa cgaaagtaaa gtaaagtatt ggattttttt   9720
aaagggaaca tgtgaatgaa tacacaggac ttattatatc agagtgagta atcggttggt   9780
tggttgattg attgattgat tgatacattc agcttcctgc tgctagcaat gccacgattt   9840
agatttaatg atgcttcagt ggaaatcaat cagaaggtat tctgaccttg tgaacatcag   9900
```

-continued

```
aaggtatttt ttaactccca agcagtagca ggacgatgat agggctggag ggctatggat      9960
tcccagccca tccctgtgaa ggagtaggcc actctttaag tgaaggattg gatgattgtt     10020
cataatacat aaagttctct gtaattacaa ctaaattatt atgccctctt ctcacagtca     10080
aaaggaactg ggtggtttgg tttttgttgc tttttagat ttattgtccc atgtgggatg      10140 agttttaaa tgccacaaga cataatttaa aataaataaa ctttgggaaa aggtgtaaga      10200
cagtagcccc atcacatttg tgatactgac aggtatcaac ccagaagccc atgaactgtg     10260
tttccatcct ttgcatttct ctgcgagtag ttccacacag gtttgtaagt aagtaagaaa     10320
gaaggcaaat tgattcaaat gttacaaaaa aaccttctt ggtggattag acaggttaaa      10380
tatataaaca aacaaacaaa aattgctcaa aaagaggag aaaagctcaa gaggaaaagc      10440
taaggactgg taggaaaaag ctttactctt tcatgccatt ttatttcttt ttgattttta     10500
aatcattcat tcaatagata ccaccgtgtg acctataatt ttgcaaatct gttacctctg     10560
acatcaagtg taattagctt ttggagagtg ggctgacatc aagtgtaatt agcttttgga     10620
gagtgggttt tgtccattat taataattaa ttaattaaca tcaaacacgg cttctcatgc     10680
tatttctacc tcactttggt tttggggtgt tcctgataat tgtgcacacc tgagttcaca     10740
gcttcaccac ttgtccattg cgttattttc ttttcctttt ataattcttt ctttttcctt    10800 cataatttc aaagaaaac ccaaagctct aaggtaacaa attaccaaat tacatgaaga      10860
tttggttttt gtcttgcatt ttttccttt atgtgacgct ggaccttttc tttacccaag     10920
gatttttaaa actcagattt aaaacaaggg gttactttac atcctactaa gaagtttaag    10980
taagtaagtt tcattctaaa atcagaggta aatagagtgc ataaataatt ttgttttaat    11040
ctttttgttt ttcttttaga cacattagct ctggagtgag tctgtcataa tatttgaaca    11100
aaaattgaga gctttattgc tgcattttaa gcataattaa tttggacatt atttcgtgtt    11160
gtgttcttta taaccaccga gtattaaact gtaaatcata atgtaactga agcataaaca    11220
tcacatggca tgttttgtca ttgttttcag gtactgagtt cttacttgag tatcataata    11280
tattgtgttt taacaccaac actgtaacat ttacgaatta ttttttttaaa cttcagtttt   11340 actgcatttt cacaacatat cagacttcac caaatatatg ccttactatt gtattatagt    11400
actgctttac tgtgtatctc aataaagcac gcagttatgt tac                      11443
```

<210> SEQ ID NO 45
<211> LENGTH: 114
<212> TYPE: DNA
<213> ORGANISM: Artificial Sequence
<220> FEATURE:
<223> OTHER INFORMATION: Synthetic

<400> SEQUENCE: 45

```
acgtctgtcc agggtccctg ggagagagcc atctcgccaa acaaagtgcc ctactatatc       60
aaccacgaga ctcaaacaac ttgctgggac catcccaaaa tgacagagct ctac             114
```

<210> SEQ ID NO 46
<211> LENGTH: 2989
<212> TYPE: DNA
<213> ORGANISM: Artificial Sequence
<220> FEATURE:
<223> OTHER INFORMATION: Synthetic

<400> SEQUENCE: 46

```
ctaaattgta agcgttaata ttttgttaaa attcgcgtta aatttttgtt aaatcagctc       60
```

-continued

| | |
|---|---|
| atttttttaac caataggccg aaatcggcaa aatcccttat aaatcaaaag aatagaccga | 120 |
| gataggggttg agtgttgttc cagtttggaa caagagtcca ctattaaaga acgtggactc | 180 |
| caacgtcaaa gggcgaaaaa ccgtctatca gggcgatggc ccactacgtg aaccatcacc | 240 |
| ctaatcaagt tttttgggggt cgaggtgccg taaagcacta aatcggaacc ctaaagggag | 300 |
| cccccgattt agagcttgac ggggaaagcc ggcgaacgtg gcgagaaagg aagggaagaa | 360 |
| agcgaaagga gcgggcgcta gggcgctggc aagtgtagcg gtcacgctgc gcgtaaccac | 420 |
| cacacccgcc gcgcttaatg cgccgctaca gggcgcgtcc cattcgccat tcaggctgcg | 480 |
| caactgttgg gaagggcgat cggtgcgggc ctcttcgcta ttacgccagc tggcgaaagg | 540 |
| gggatgtgct gcaaggcgat taagttgggt aacgccaggg ttttcccagt cacgacgttg | 600 |
| taaaacgacg gccagtgagc gcgcgtaata cgactcacta tagggcgaat tggagcttac | 660 |
| gtattaatta aggcgccgcg gtggcggccg ctctagaact agtggatccc ccgggctgca | 720 |
| ggaattcggc cgcctaggcc acgcgtaagc ttatcgatac cgtcgacctc gagggggggc | 780 |
| ccggtaccca gcttttgttc cctttagtga gggttaattg cgcgcttggc gtaatcatgg | 840 |
| tcatagctgt ttcctgtgtg aaattgttat ccgctcacaa ttccacacaa catacgagcc | 900 |
| ggaagcataa agtgtaaagc ctggggtgcc taatgagtga gctaactcac attaattgcg | 960 |
| ttgcgctcac tgcccgcttt ccagtcggga aacctgtcgt gccagctgca ttaatgaatc | 1020 |
| ggccaacgcg cggggagagg cggtttgcgt attgggcgct cttccgcttc ctcgctcact | 1080 |
| gactcgctgc gctcggtcgt tcggctgcgg cgagcggtat cagctcactc aaaggcggta | 1140 |
| atacggttat ccacagaatc aggggataac gcaggaaaga acatgtgagc aaaaggccag | 1200 |
| caaaaggcca ggaaccgtaa aaaggccgcg ttgctggcgt ttttccatag gctccgcccc | 1260 |
| cctgacgagc atcacaaaaa tcgacgctca agtcagaggt ggcgaaaccc gacaggacta | 1320 |
| taaagatacc aggcgtttcc ccctggaagc tccctcgtgc gctctcctgt tccgaccctg | 1380 |
| ccgcttaccg gatacctgtc cgcctttctc ccttcgggaa gcgtggcgct ttctcatagc | 1440 |
| tcacgctgta ggtatctcag ttcggtgtag gtcgttcgct ccaagctggg ctgtgtgcac | 1500 |
| gaaccccccg ttcagcccga ccgctgcgcc ttatccggta actatcgtct tgagtccaac | 1560 |
| ccggtaagac acgacttatc gccactggca gcagccactg gtaacaggat tagcagagcg | 1620 |
| aggtatgtag gcggtgctac agagttcttg aagtggtggc ctaactacgg ctacactaga | 1680 |
| aggacagtat ttggtatctg cgctctgctg aagccagtta ccttcggaaa aagagttggt | 1740 |
| agctcttgat ccggcaaaca aaccaccgct ggtagcggtg ttttttttgt ttgcaagcag | 1800 |
| cagattacgc gcagaaaaaa aggatctcaa gaagatcctt tgatcttttc tacgggtct | 1860 |
| gacgctcagt ggaacgaaaa ctcacgttaa gggattttgg tcatgagatt atcaaaaagg | 1920 |
| atcttcacct agatcctttt aaattaaaaa tgaagtttta aatcaatcta agtatatat | 1980 |
| gagtaaactt ggtctgacag ttaccaatgc ttaatcagtg aggcacctat ctcagcgatc | 2040 |
| tgtctatttc gttcatccat agttgcctga ctccccgtcg tgtagataac tacgatacgg | 2100 |
| gagggcttac catctggccc cagtgctgca atgataccgc gagacccacg ctcaccggct | 2160 |
| ccagatttat cagcaataaa ccagccagcc ggaagggccg agcgcagaag tggtcctgca | 2220 |
| actttatccg cctccatcca gtctattaat tgttgccggg aagctagagt aagtagttcg | 2280 |
| ccagttaata gtttgcgcaa cgttgttgcc attgctacag gcatcgtggt gtcacgctcg | 2340 |
| tcgtttggta tggcttcatt cagctccggt tcccaacgat caaggcgagt tacatgatcc | 2400 |
| cccatgttgt gcaaaaaagc ggttagctcc ttcggtcctc cgatcgttgt cagaagtaag | 2460 |

-continued

| | |
|---|---|
| ttggccgcag tgttatcact catggttatg gcagcactgc ataattctct tactgtcatg | 2520 |
| ccatccgtaa gatgcttttc tgtgactggt gagtactcaa ccaagtcatt ctgagaatag | 2580 |
| tgtatgcggc gaccgagttg ctcttgcccg cgtcaatac gggataatac cgcgccacat | 2640 |
| agcagaactt taaaagtgct catcattgga aaacgttctt cggggcgaaa actctcaagg | 2700 |
| atcttaccgc tgttgagatc cagttcgatg taacccactc gtgcacccaa ctgatcttca | 2760 |
| gcatcttta ctttcaccag cgtttctggg tgagcaaaaa caggaaggca aaatgccgca | 2820 |
| aaaaagggaa taagggcgac acggaaatgt tgaatactca tactcttcct ttttcaatat | 2880 |
| tattgaagca tttatcaggg ttattgtctc atgagcggat acatatttga atgtatttag | 2940 |
| aaaaataaac aaatagggt tccgcgcaca tttccccgaa aagtgccac | 2989 |

<210> SEQ ID NO 47
<211> LENGTH: 12057
<212> TYPE: DNA
<213> ORGANISM: Artificial Sequence
<220> FEATURE:
<223> OTHER INFORMATION: Synthetic

<400> SEQUENCE: 47

| | |
|---|---|
| gggattccct cactttcccc ctacaggact cagatctggg aggcaattac cttcggagaa | 60 |
| aaacgaatag gaaaaactga agtgttactt tttttaaagc tgctgaagtt tgttggtttc | 120 |
| tcattgtttt taagcctact ggagcaataa agtttgaaga acttttacca ggttttttt | 180 |
| atcgctgcct tgatatacac ttttcaaaat gctttggtgg gaagaagtag aggactgtta | 240 |
| tgaaagagaa gatgttcaaa agaaaacatt cacaaaatgg gtaaatgcac aattttctaa | 300 |
| gtttgggaag cagcatattg agaacctctt cagtgaccta caggatggga ggcgcctcct | 360 |
| agacctcctc gaaggcctga cagggcaaaa actgccaaaa gaaaaaggat ccacaagagt | 420 |
| tcatgccctg aacaatgtca acaaggcact gcgggttttg cagaacaata atgttgattt | 480 |
| agtgaatatt ggaagtactg acatcgtaga tggaaatcat aaactgactc ttggtttgat | 540 |
| ttggaatata atcctccact ggcaggtcaa aaatgtaatg aaaatatca tggctggatt | 600 |
| gcaacaaacc aacagtgaaa agattctcct gagctgggtc cgacaatcaa ctcgtaatta | 660 |
| tccacaggtt aatgtaatca acttcaccac cagctggtct gatggcctgg ctttgaatgc | 720 |
| tctcatccat agtcataggc cagacctatt tgactggaat agtgtggttt gccagcagtc | 780 |
| agccacacaa cgactggaac atgcattcaa catcgccaga tatcaattag gcatagagaa | 840 |
| actactcgat cctgaagatg ttgataccac ctatccagat aagaagtcca tcttaatgta | 900 |
| catcacatca ctccttccaag tttttgcctca acaagtgagc attgaagcca tccaggaagt | 960 |
| ggaaatgttg ccaaggccac ctaaagtgac taaagaagaa cattttcagt tacatcatca | 1020 |
| aatgcactat tctcaacaga tcacggtcag tctagcacag ggatatgaga gaacttcttc | 1080 |
| ccctaagcct cgattcaaga gctatgccta cacacaggct gcttatgtca ccacctctga | 1140 |
| ccctacacgg agcccatttc cttcacagca tttggaagct cctgaagaca agtcatttgg | 1200 |
| cagttcattg atggagagtg aagtaaacct ggaccgttat caaacagctt tagaagaagt | 1260 |
| attatcgtgg cttctttctg ctgaggacac attgcaagca caaggagaga tttctaatga | 1320 |
| tgtggaagtg gtgaaagacc agtttcatac tcatgagggg tacatgatgg atttgacagc | 1380 |
| ccatcagggc cggttggta atattctaca attgggaagt aagctgattg gaacaggaaa | 1440 |
| attatcagaa gatgaagaaa ctgaagtaca agagcagatg aatctcctaa attcaagatg | 1500 |

-continued

| | | | | |
|---|---|---|---|---|
| ggaatgcctc | agggtagcta | gcatggaaaa | acaaagcaat | ttacatagag ttttaatgga | 1560 |
| tctccagaat | cagaaactga | aagagttgaa | tgactggcta | acaaaaacag aagaaagaac | 1620 |
| aaggaaaatg | gaggaagagc | ctcttggacc | tgatcttgaa | gacctaaaac gccaagtaca | 1680 |
| acaacataag | gtgcttcaag | aagatctaga | acaagaacaa | gtcagggtca attctctcac | 1740 |
| tcacatggtg | gtggtagttg | atgaatctag | tggagatcac | gcaactgctg ctttggaaga | 1800 |
| acaacttaag | gtattgggag | atcgatgggc | aaacatctgt | agatggacag aagaccgctg | 1860 |
| ggttcttttta | caagacatcc | ttctcaaatg | gcaacgtctt | actgaagaac agtgccttt | 1920 |
| tagtgcatgg | ctttcagaaa | aagaagatgc | agtgaacaag | attcacacaa ctggctttaa | 1980 |
| agatcaaaat | gaaatgttat | caagtcttca | aaaactggcc | gttttaaaag cggatctaga | 2040 |
| aaagaaaaag | caatccatgg | gcaaactgta | ttcactcaaa | caagatcttc tttcaacact | 2100 |
| gaagaataag | tcagtgaccc | agaagacgga | agcatggctg | ataactttg cccggtgttg | 2160 |
| ggataattta | gtccaaaaac | ttgaaaagag | tacagcacag | atttcacagg ctgtcaccac | 2220 |
| cactcagcca | tcactaacac | agacaactgt | aatggaaaca | gtaactacgg tgaccacaag | 2280 |
| ggaacagatc | ctggtaaagc | atgctcaaga | ggaacttcca | ccaccacctc cccaaaagaa | 2340 |
| gaggcagatt | actgtggatt | ctgaaattag | gaaaaggttg | gatgttgata taactgaact | 2400 |
| tcacagctgg | attactcgct | cagaagctgt | gttgcagagt | cctgaatttg caatcttttcg | 2460 |
| gaaggaaggc | aacttctcag | acttaaaaga | aaagtcaat | gccatagagc gagaaaaagc | 2520 |
| tgagaagttc | agaaaactgc | aagatgccag | cagatcagct | caggccctgg tgaacagat | 2580 |
| ggtgaatgag | ggtgttaatg | cagatagcat | caaacaagcc | tcagaacaac tgaacagccg | 2640 |
| gtggatcgaa | ttctgccagt | tgctaagtga | gagacttaac | tggctggagt atcagaacaa | 2700 |
| catcatcgct | ttctataatc | agctacaaca | attggagcag | atgacaacta ctgctgaaaa | 2760 |
| ctggttgaaaa | atccaaccca | ccaccccatc | agagccaaca | gcaattaaaa gtcagttaaa | 2820 |
| aatttgtaag | gatgaagtca | accggctatc | aggtcttcaa | cctcaaattg aacgattaaa | 2880 |
| aattcaaagc | atagccctga | agagaaagg | acaaggaccc | atgttcctgg atgcagactt | 2940 |
| tgtggccttt | acaaatcatt | ttaagcaagt | cttttctgat | gtgcaggcca gagagaaaga | 3000 |
| gctacagaca | attttttgaca | ctttgccacc | aatgcgctat | caggagacca tgagtgccat | 3060 |
| caggacatgg | gtccagcagt | cagaaaccaa | actctccata | cctcaactta gtgtcaccga | 3120 |
| ctatgaaatc | atggagcaga | gactcgggga | attgcaggct | ttacaaagtt ctctgcaaga | 3180 |
| gcaacaaagt | ggcctatact | atctcagcac | cactgtgaaa | gagatgtcga agaaagcgcc | 3240 |
| ctctgaaatt | agccggaaat | atcaatcaga | atttgaagaa | attgagggac gctggaagaa | 3300 |
| gctctcctcc | cagctggttg | agcattgtca | aaagctagag | gagcaaatga ataaactccg | 3360 |
| aaaaattcag | aatcacatac | aaaccctgaa | gaaatggatg | gctgaagttg atgttttttct | 3420 |
| gaaggaggaa | tggcctgccc | ttgggggattc | agaaattcta | aaaagcagc tgaaacagtg | 3480 |
| cagacttttta | gtcagtgata | ttcagacaat | tcagcccagt | ctaaacagtg tcaatgaagg | 3540 |
| tgggcagaag | ataagaatg | aagcagagcc | agagtttgct | tcgagacttg agacagaact | 3600 |
| caaagaactt | aacactcagt | gggatcacat | gtgccaacag | gtctatgcca gaaggaggc | 3660 |
| cttgaaggga | ggtttggaga | aaactgtaag | cctccagaaa | gatctatcag agatgcacga | 3720 |
| atggatgaca | caagctgaag | aagagtatct | tgagagagat | tttgaatata aaactccaga | 3780 |
| tgaattacag | aaagcagttg | aagagatgaa | gagagctaaa | gaagaggccc aacaaaaga | 3840 |
| agcgaaagtg | aaactcctta | ctgagtctgt | aaatagtgtc | atagctcaag ctccacctgt | 3900 |

```
agcacaagag gccttaaaaa aggaacttga aactctaacc accaactacc agtggctctg    3960
cactaggctg aatgggaaat gcaagacttt ggaagaagtt tgggcatgtt ggcatgagtt    4020
attgtcatac ttggagaaag caaacaagtg gctaaatgaa gtagaattta aacttaaaac    4080
cactgaaaac attcctggcg gagctgagga atctctgag gtgctagatt cacttgaaaa    4140
tttgatgcga cattcagagg ataacccaaa tcagattcgc atattggcac agaccctaac    4200
agatggcgga gtcatggatg agctaatcaa tgaggaactt gagacattta attctcgttg    4260
gagggaacta catgaagagg ctgtaaggag gcaaaagttg cttgaacaga gcatccagtc    4320
tgcccaggag actgaaaaat ccttacactt aatccaggag tccctcacat tcattgacaa    4380
gcagttggca gcttatattg cagacaaggt ggacgcagct caaatgcctc aggaagccca    4440
gaaaatccaa tctgatttga caagtcatga gatcagttta aagaaatga agaaacataa    4500
tcaggggaag gaggctgccc aaagagtcct gtctcagatt gatgttgcac agaaaaaatt    4560
acaagatgtc tccatgaagt ttcgattatt ccagaaacca gccaattttg agctgcgtct    4620
acaagaaagt aagatgattt tagatgaagt gaagatgcac ttgcctgcat ggaaacaaa    4680
gagtgtggaa caggaagtag tacagtcaca gctaaatcat tgtgtgaact tgtataaag    4740
tctgagtgaa gtgaagtctg aagtggaaat ggtgataaag actggacgtc agattgtaca    4800
gaaaaagcag acgaaaatc ccaaagaact tgatgaaaga gtaacagctt tgaaattgca    4860
ttataatgag ctgggagcaa aggtaacaga aagaaagcaa cagttggaga atgcttgaa    4920
attgtcccgt aagatgcgaa aggaaatgaa tgtcttgaca gaatggctgg cagctacaga    4980
tatggaattg acaaagagat cagcagttga aggaatgcct agtaatttgg attctgaagt    5040
tgcctgggga aaggctactc aaaaagagat tgagaaacag aaggtgcacc tgaagagtat    5100
cacagaggta ggagaggcct tgaaaacagt tttgggcaag aaggagacgt tggtggaaga    5160
taaactcagt cttctgaata gtaactggat agctgtcacc tcccgagcag aagagtggtt    5220
aaatctttg ttggaatacc agaaacacat ggaaactttt gaccagaatg tggaccacat    5280
cacaaagtgg atcattcagg ctgacacact tttggatgaa tcagagaaaa agaaacccca    5340
gcaaaaagaa gacgtgctta agcgtttaaa ggcagaactg aatgacatac gcccaaaggt    5400
ggactctaca cgtgaccaag cagcaaaact gatggcaaac cgcggtgacc actgcaggaa    5460
attagtagag ccccaaatct cagagctcaa ccatcgattt gcagccattt cacacagaat    5520
taagactgga aaggcctcca ttcctttgaa ggaattggag cagtttaact cagatataca    5580
aaaattgctt gaaccactgg aggctgaaat tcagcagggg gtgaatctga agaggaaga    5640
cttcaataaa gatatgaatg aagacaatga gggtactgta aaagaattgt tgcaaagagg    5700
agacaactta caacaaagaa tcacagatga gagaaagaga gaggaaataa agataaaaca    5760
gcagctgtta cagacaaaac ataatgctct caaggatttg aggtctcaaa gaagaaaaaa    5820
ggctctagaa atttctcatc agtggtatca gtacaagagg caggctgatg atctcctgaa    5880
atgcttggat gacattgaaa aaaattagc cagcctacct gagcccagag atgaaaggaa    5940
aataaggaa attgatcggg aattgcagaa gaagaaagag gagctgaatg cagtgcgtag    6000
gcaagctgag ggcttgtctg aggatggggc cgcaatggca gtggagccaa ctcagatcca    6060
gctcagcaag cgctggcggg aaattgagag caaatttgct cagtttcgaa gactcaactt    6120
tgcacaaatt cacactgtcc gtgaagaaac gatgatggtg atgactgaag acatgccttt    6180
ggaaatttct tatgtgcctt ctacttattt gactgaaatc actcatgtct cacaagccct    6240
```

```
attagaagtg gaacaacttc tcaatgctcc tgacctctgt gctaaggact ttgaagatct   6300
ctttaagcaa gaggagtctc tgaagaatat aaaagatagt ctacaacaaa gctcaggtcg   6360
gattgacatt attcatagca agaagacagc agcattgcaa agtgcaacgc ctgtggaaag   6420
ggtgaagcta caggaagctc tctcccagct tgatttccaa tgggaaaaag ttaacaaaat   6480
gtacaaggac cgacaagggc gatttgacag atctgttgag aaatggcggc gttttcatta   6540
tgatataaag atatttaatc agtggctaac agaagctgaa cagtttctca gaaagacaca   6600
aattcctgag aattgggaac atgctaaata caaatggtat cttaaggaac tccaggatgg   6660
cattgggcag cggcaaactg ttgtcagaac attgaatgca actggggaag aaataattca   6720
gcaatcctca aaaacagatg ccagtattct acaggaaaaa ttgggaagcc tgaatctgcg   6780
gtggcaggag gtctgcaaac agctgtcaga cagaaaaaag aggctagaag aacaaaagaa   6840
tatcttgtca gaatttcaaa gagatttaaa tgaatttgtt ttatggttgg aggaagcaga   6900
taacattgct agtatcccac ttgaacctgg aaaagagcag caactaaaag aaaagcttga   6960
gcaagtcaag ttactggtgg aagagttgcc cctgcgccag ggaattctca acaattaaa    7020 tgaaactgga ggacccgtgc ttgtaagtgc tcccataagc ccagaagagc aagataaact   7080
tgaaaataag ctcaagcaga caaatctcca gtggataaag gtttccagag ctttacctga   7140
gaaacaagga gaaattgaag ctcaaataaa agaccttggg cagcttgaaa aaagcttga    7200 agaccttgaa gagcagttaa atcatctgct gctgtggtta tctcctatta ggaatcagtt   7260
ggaaatttat aaccaaccaa accaagaagg accatttgac gttcaggaaa ctgaaatagc   7320
agttcaagct aaacaaccgg atgtggaaga gattttgtct aaagggcagc atttgtacaa   7380
ggaaaaacca gccactcagc cagtgaagag gaagttagaa gatctgagct ctgagtggaa   7440
ggcggtaaac cgtttacttc aagagctgag ggcaaagcag cctgacctag ctcctggact   7500
gaccactatt ggagcctctc ctactcgagc tgttactctg gtgacacaac ctgtggttac   7560
taaggaaact gccatctcca aactagaaat gccatcttcc ttgatgttgg aggtacctgc   7620
tctggcagat ttcaaccggg cttggacaga acttaccgac tggctttctc tgcttgatca   7680
agttataaaa tcacagaggg tgatggtggg tgaccttgag gatatcaacg atgatgatcat  7740 caagcagaag gcaacaatgc aggatttgga acagaggcgt ccccagttgg aagaactcat   7800
taccgctgcc caaaatttga aaaacaagac cagcaatcaa gaggctagaa caatcattac   7860
ggatcgaatt gaaagaattc agaatcagtg ggatgaagta caagaacacc ttcagaaccg   7920
gaggcaacag ttgaatgaaa tgttaaagga ttcaacacaa tggctggaag ctaaggaaga   7980
agctgagcag gtcttaggac aggccagagc caagcttgag tcatggaagg agggtcccta   8040
tacagtagat gcaatccaaa agaaaatcac agaaaccaag cagttggcca aagacctccg   8100
ccagtggcag acaaatgtag atgtggcaaa tgacttggcc ctgaaacttc tccgggatta   8160
ttctgcagat gataccagaa aagtccacat gataacagaa aatatcaatg cctcttggag   8220
aagcattcat aaaagggtga gtgagcgaga ggctgctttg aagaaactc atagattact    8280 gcaacagttc ccctggacc tggaaaagtt tcttgcctgg cttacagaag ctgaaacaac    8340
tgccaatgtc ctacaggatg ctacccgtaa ggaaaggctc ctagaagact ccaagggagt   8400
aaaagagctg atgaaacaat ggcaagacct ccaaggtgaa attgaagctc acacagatgt   8460
ttatcacaac ctggatgaaa acagccaaaa aatcctgaga tccctggaag gttccgatga   8520
tgcagtcctg ttacaaagac gttttggataa catgaacttc aagtggagtg aacttcggaa   8580
aaagtctctc aacattaggt cccatttgga agccagttct gaccagtgga gcgtctgca   8640
```

-continued

| | | | | | |
|---|---|---|---|---|---|
| cctttctctg | caggaacttc | tggtgtggct | acagctgaaa | gatgatgaat | taagccggca | 8700 |
| ggcacctatt | ggaggcgact | ttccagcagt | tcagaagcag | aacgatgtac | ataggccttt | 8760 |
| caagagggaa | ttgaaaacta | agaacctgt | aatcatgagt | actcttgaga | ctgtacgaat | 8820 |
| atttctgaca | gagcagcctt | tggaaggact | agagaaactc | taccaggagc | ccagagagct | 8880 |
| gcctcctgag | gagagagccc | agaatgtcac | tcggcttcta | cgaaagcagg | ctgaggaggt | 8940 |
| caatactgag | tgggaaaaat | tgaacctgca | ctccgctgac | tggcagagaa | aaatagatga | 9000 |
| gacccttgaa | agactccagg | aacttcaaga | ggccacggat | gagctggacc | tcaagctgcg | 9060 |
| ccaagctgag | gtgatcaagg | gatcctggca | gcccgtgggc | gatctcctca | ttgactctct | 9120 |
| ccaagatcac | ctcgagaaag | tcaaggcact | tcgaggagaa | attgcgcctc | tgaaagagaa | 9180 |
| cgtgagccac | gtcaatgacc | ttgctcgcca | gcttaccact | ttgggcattc | agctctcacc | 9240 |
| gtataacctc | agcactctgg | aagacctgaa | caccagatgg | aagcttctgc | aggtggccgt | 9300 |
| cgaggaccga | gtcaggcagc | tgcatgaagc | ccacagggac | tttggtccag | catctcagca | 9360 |
| cttttcttcc | acgtctgtcc | agggtccctg | ggagagagcc | atctcgccaa | acaaagtgcc | 9420 |
| ctactatatc | aaccacgaga | ctcaaacaac | ttgctgggac | catcccaaaa | tgacagagct | 9480 |
| ctaccagtct | ttagctgacc | tgaataatgt | cagattctca | gcttatagga | ctgccatgaa | 9540 |
| actccgaaga | ctgcagaagg | ccctttgctt | ggatctcttg | agcctgtcag | ctgcatgtga | 9600 |
| tgccttggac | cagcacaacc | tcaagcaaaa | tgaccagccc | atggatatcc | tgcagattat | 9660 |
| taattgtttg | accactattt | atgaccgcct | ggagcaagag | cacaacaatt | tggtcaacgt | 9720 |
| ccctctctgc | gtggatatgt | gtctgaactg | gctgctgaat | gtttatgata | cgggacgaac | 9780 |
| agggaggatc | cgtgtcctgt | cttttaaaac | tggcatcatt | tccctgtgta | aagcacattt | 9840 |
| ggaagacaag | tacagatacc | ttttcaagca | agtggcaagt | tcaacaggat | tttgtgacca | 9900 |
| gcgcaggctg | ggcctccttc | tgcatgattc | tatccaaatt | ccaagacagt | tgggtgaagt | 9960 |
| tgcatccttt | ggggggcagta | acattgagcc | aagtgtccgg | agctgcttcc | aatttgctaa | 10020 |
| taataagcca | gagatcgaag | cggccctctt | cctagactgg | atgagactgg | aaccccagtc | 10080 |
| catggtgtgg | ctgcccgtcc | tgcacagagt | ggctgctgca | gaaactgcca | agcatcaggc | 10140 |
| caaatgtaac | atctgcaaag | agtgtccaat | cattggattc | aggtacagga | gtctaaagca | 10200 |
| ctttaattat | gacatctgcc | aaagctgctt | tttttctggt | cgagttgcaa | aaggccataa | 10260 |
| aatgcactat | cccatggtgg | aatattgcac | tccgactaca | tcaggagaag | atgttcgaga | 10320 |
| cttttgccaag | gtactaaaaa | acaaatttcg | aaccaaaagg | tattttgcga | agcatccccg | 10380 |
| aatgggctac | ctgccagtgc | agactgtctt | agaggggggac | aacatggaaa | cgcctgcctc | 10440 |
| gtcccctcag | ctttcacacg | atgatactca | ttcacgcatt | gaacattatg | ctagcaggct | 10500 |
| agcagaaatg | gaaaacagca | atggatctta | tctaaatgat | agcatctctc | ctaatgagag | 10560 |
| catagatgat | gaacatttgt | taatccagca | ttactgccaa | agtttgaacc | aggactcccc | 10620 |
| cctgagccag | cctcgtagtc | ctgcccagat | cttgatttcc | ttagagagtg | aggaaagagg | 10680 |
| ggagctagag | agaatcctag | cagatcttga | ggaagaaaac | aggaatctgc | aagcagaata | 10740 |
| tgaccgtcta | aagcagcagc | acgaacataa | aggcctgtcc | ccactgccgt | cccctcctga | 10800 |
| aatgatgccc | acctctcccc | agagtccccg | ggatgctgag | ctcattgctg | aggccaagct | 10860 |
| actgcgtcaa | cacaaaggcc | gcctggaagc | caggatgcaa | atcctggaag | accacaataa | 10920 |
| acagctggag | tcacagttac | acaggctaag | gcagctgctg | gagcaacccc | aggcagaggc | 10980 |

```
                                    -continued caaagtgaat ggcacaacgg tgtcctctcc ttctacctct ctacagaggt ccgacagcag   11040
tcagcctatg ctgctccgag tggttggcag tcaaacttcg gactccatgg gtgaggaaga   11100
tcttctcagt cctccccagg acacaagcac agggttagag gaggtgatgg agcaactcaa   11160
caactccttc cctagttcaa gaggaagaaa taccctgga  aagccaatga gagaggacac   11220
aatgtaggaa gtcttttcca catggcagat gatttgggca gagcgatgga gtccttagta   11280
tcagtcatga cagatgaaga aggagcagaa taaatgtttt acaactcctg attcccgcat   11340 ggttttttata atattcatac aacaaagagg attagacagt aagagtttac aagaaataaa   11400
tctatatttt tgtgaagggt agtggtatta tactgtagat ttcagtagtt tctaagtctg   11460
ttattgtttt gttaacaatg gcaggtttta cacgtctatg caattgtaca aaaaagttat   11520
aagaaaacta catgtaaaat cttgatagct aaataacttg ccatttcttt atatggaacg   11580
cattttgggt tgtttaaaaa tttataacag ttataaagaa agattgtaaa ctaaagtgtg   11640
ctttataaaa aaaagttgtt tataaaaacc cctaaaaaca aaacaaacac acacacacac   11700
acatacacac acacacacaa aactttgagg cagcgcattg ttttgcatcc ttttggcgtg   11760
atatccatat gaaattcatg gcttttctt  tttttgcata ttaaagataa gacttcctct   11820
accaccacac caaatgacta ctacacactg ctcatttgag aactgtcagc tgagtggggc   11880
aggcttgagt tttcatttca tatatctata tgtctataag tatataaata ctatagttat   11940
atagataaag agatacgaat ttctatagac tgactttttc catttttttaa atgttcatgt   12000 cacatcctaa tagaaagaaa ttacttctag tcagtcatcc aggcttacct gcttggt      12057

<210> SEQ ID NO 48
<211> LENGTH: 22
<212> TYPE: DNA
<213> ORGANISM: Artificial Sequence
<220> FEATURE:
<223> OTHER INFORMATION: Synthetic

<400> SEQUENCE: 48
gaacaagatt cacacaactg gc                                              22

<210> SEQ ID NO 49
<211> LENGTH: 38
<212> TYPE: DNA
<213> ORGANISM: Artificial Sequence
<220> FEATURE:
<223> OTHER INFORMATION: Synthetic

<400> SEQUENCE: 49
gttcctggag tctttcaaga tccacagtaa tctgcctc                             38

<210> SEQ ID NO 50
<211> LENGTH: 38
<212> TYPE: DNA
<213> ORGANISM: Artificial Sequence
<220> FEATURE:
<223> OTHER INFORMATION: Synthetic

<400> SEQUENCE: 50
gaggcagatt actgtggatc ttgaaagact ccaggaac                             38

<210> SEQ ID NO 51
<211> LENGTH: 18
<212> TYPE: DNA
<213> ORGANISM: Artificial Sequence
<220> FEATURE:
<223> OTHER INFORMATION: Synthetic
```

<400> SEQUENCE: 51
tgtttggcga gatggctc                                            18

<210> SEQ ID NO 52
<211> LENGTH: 21
<212> TYPE: DNA
<213> ORGANISM: Artificial Sequence
<220> FEATURE:
<223> OTHER INFORMATION: Synthetic

<400> SEQUENCE: 52
gatgtggaag tggtgaaaga c                                        21

<210> SEQ ID NO 53
<211> LENGTH: 38
<212> TYPE: DNA
<213> ORGANISM: Artificial Sequence
<220> FEATURE:
<223> OTHER INFORMATION: Synthetic

<400> SEQUENCE: 53
ccaatagtgg tcagtccagg agcatgtaaa ttgctttg                      38

<210> SEQ ID NO 54
<211> LENGTH: 38
<212> TYPE: DNA
<213> ORGANISM: Artificial Sequence
<220> FEATURE:
<223> OTHER INFORMATION: Synthetic

<400> SEQUENCE: 54
caaagcaatt tacatgctcc tggactgacc actattgg                      38

<210> SEQ ID NO 55
<211> LENGTH: 38
<212> TYPE: DNA
<213> ORGANISM: Artificial Sequence
<220> FEATURE:
<223> OTHER INFORMATION: Synthetic

<400> SEQUENCE: 55
ctgttgcagt aatctatgct ccaacatcaa ggaagatg                      38

<210> SEQ ID NO 56
<211> LENGTH: 38
<212> TYPE: DNA
<213> ORGANISM: Artificial Sequence
<220> FEATURE:
<223> OTHER INFORMATION: Synthetic

<400> SEQUENCE: 56
catcttcctt gatgttggag catagattac tgcaacag                      38

<210> SEQ ID NO 57
<211> LENGTH: 33
<212> TYPE: DNA
<213> ORGANISM: Artificial Sequence
<220> FEATURE:
<223> OTHER INFORMATION: Synthetic

<400> SEQUENCE: 57
ctgttgcagt aatctatgat gtaaattgct ttg                           33

<210> SEQ ID NO 58

```
<211> LENGTH: 33
<212> TYPE: DNA
<213> ORGANISM: Artificial Sequence
<220> FEATURE:
<223> OTHER INFORMATION: Synthetic

<400> SEQUENCE: 58
caaagcaatt tacatcatag attactgcaa cag                                    33

<210> SEQ ID NO 59
<211> LENGTH: 70
<212> TYPE: DNA
<213> ORGANISM: Artificial Sequence
<220> FEATURE:
<223> OTHER INFORMATION: Synthetic

<400> SEQUENCE: 59
tagcggccgc ggttttttttt atcgctgcct tgatatacac tttccaccat gctttggtgg      60
gaagaagtag                                                              70

<210> SEQ ID NO 60
<211> LENGTH: 19
<212> TYPE: DNA
<213> ORGANISM: Artificial Sequence
<220> FEATURE:
<223> OTHER INFORMATION: Synthetic

<400> SEQUENCE: 60
ttttcctgtt ccaatcagc                                                    19

<210> SEQ ID NO 61
<211> LENGTH: 591
<212> TYPE: DNA
<213> ORGANISM: Artificial Sequence
<220> FEATURE:
<223> OTHER INFORMATION: Synthetic

<400> SEQUENCE: 61
actacgggtc taggctgccc atgtaaggag gcaaggcctg gggacacccg agatgcctgg       60
ttataattaa ccccaacacc tgctgccccc cccccccaa cacctgctgc ctgagcctga       120
gcggttaccc cacccggtg cctgggtctt aggctctgta caccatggag gagaagctcg       180
ctctaaaaat aaccctgtcc ctggtgggcc caatcaaggc tgtgggggac tgagggcagg      240
ctgtaacagg cttgggggcc agggcttata cgtgcctggg actcccaaag tattactgtt      300
ccatgttccc ggcgaagggc cagctgtccc ccgccagcta gactcagcac ttagtttagg      360
aaccagtgag caagtcagcc cttggggcag cccatacaag gccatgggc tgggcaagct      420 gcacgcctgg gtccggggtg ggcacggtgc ccggcaacg agctgaaagc tcatctgctc      480
tcagggcccc tccctgggga cagcccctcc tggctagtca caccctgtag gctcctctat      540
ataacccagg ggcacagggg ctgccccgg gtcacgggga tcctctagac c                591

<210> SEQ ID NO 62
<211> LENGTH: 26
<212> TYPE: DNA
<213> ORGANISM: Artificial Sequence
<220> FEATURE:
<223> OTHER INFORMATION: Synthetic

<400> SEQUENCE: 62
agcggccgcg gtactacggg tctagg                                            26
```

```
<210> SEQ ID NO 63
<211> LENGTH: 28
<212> TYPE: DNA
<213> ORGANISM: Artificial Sequence
<220> FEATURE:
<223> OTHER INFORMATION: Synthetic

<400> SEQUENCE: 63
atcggccgtc tagaggatcc ccgtgacc                                28

<210> SEQ ID NO 64
<211> LENGTH: 19
<212> TYPE: DNA
<213> ORGANISM: Artificial Sequence
<220> FEATURE:
<223> OTHER INFORMATION: Synthetic

<400> SEQUENCE: 64
tctctccaag atcacctcg                                          19

<210> SEQ ID NO 65
<211> LENGTH: 36
<212> TYPE: DNA
<213> ORGANISM: Artificial Sequence
<220> FEATURE:
<223> OTHER INFORMATION: Synthetic

<400> SEQUENCE: 65
atgaagcttg cggccgcatg cgggaatcag gagttg                       36

<210> SEQ ID NO 66
<211> LENGTH: 36
<212> TYPE: DNA
<213> ORGANISM: Artificial Sequence
<220> FEATURE:
<223> OTHER INFORMATION: Synthetic

<400> SEQUENCE: 66
ggcttcctac attgtgtcag tttccatgtt gtcccc                       36

<210> SEQ ID NO 67
<211> LENGTH: 18
<212> TYPE: DNA
<213> ORGANISM: Artificial Sequence
<220> FEATURE:
<223> OTHER INFORMATION: Synthetic

<400> SEQUENCE: 67
tctctccaag atcacctc                                           18

<210> SEQ ID NO 68
<211> LENGTH: 36
<212> TYPE: DNA
<213> ORGANISM: Artificial Sequence
<220> FEATURE:
<223> OTHER INFORMATION: Synthetic

<400> SEQUENCE: 68
ggggacaaca tggaaactga cacaatgtag gaagcc                       36

<210> SEQ ID NO 69
<211> LENGTH: 29
<212> TYPE: DNA
<213> ORGANISM: Artificial Sequence
<220> FEATURE:
<223> OTHER INFORMATION: Synthetic
```

```
<400> SEQUENCE: 69
agcggccgca aaaaacctcc cacacctcc                                           29

<210> SEQ ID NO 70
<211> LENGTH: 28
<212> TYPE: DNA
<213> ORGANISM: Artificial Sequence
<220> FEATURE:
<223> OTHER INFORMATION: Synthetic

<400> SEQUENCE: 70
tacggccgat ccagacatga taagatac                                            28

<210> SEQ ID NO 71
<211> LENGTH: 202
<212> TYPE: DNA
<213> ORGANISM: Artificial Sequence
<220> FEATURE:
<223> OTHER INFORMATION: Synthetic

<400> SEQUENCE: 71
gatccagaca tgataagata cattgatgag tttggacaaa ccacaactag aatgcagtga         60
aaaaaatgct ttatttgtga aatttgtgat gctattgctt tatttgtaac cattataagc        120
tgcaataaac aagttaacaa caacaattgc attcatttta tgtttcaggt tcaggggag         180 gtgtgggagg tttttcgga tc                                                  202

<210> SEQ ID NO 72
<211> LENGTH: 24
<212> TYPE: DNA
<213> ORGANISM: Artificial Sequence
<220> FEATURE:
<223> OTHER INFORMATION: Synthetic

<400> SEQUENCE: 72
tgtgctgcaa ggcgattaag ttgg                                                24

<210> SEQ ID NO 73
<211> LENGTH: 24
<212> TYPE: DNA
<213> ORGANISM: Artificial Sequence
<220> FEATURE:
<223> OTHER INFORMATION: Synthetic

<400> SEQUENCE: 73
ccaggcttta cactttatgc ttcc                                                24

<210> SEQ ID NO 74
<211> LENGTH: 31
<212> TYPE: DNA
<213> ORGANISM: Artificial Sequence
<220> FEATURE:
<223> OTHER INFORMATION: Synthetic

<400> SEQUENCE: 74
gcacagattt cacagcagcc tgacctagct c                                        31

<210> SEQ ID NO 75
<211> LENGTH: 31
<212> TYPE: DNA
<213> ORGANISM: Artificial Sequence
<220> FEATURE:
<223> OTHER INFORMATION: Synthetic

<400> SEQUENCE: 75
```

```
gagctaggtc aggctgctgt gaaatctgtg c                               31

<210> SEQ ID NO 76
<211> LENGTH: 30
<212> TYPE: DNA
<213> ORGANISM: Artificial Sequence
<220> FEATURE:
<223> OTHER INFORMATION: Synthetic

<400> SEQUENCE: 76
caagactttg gaagatctgt tgagaaatgg                                 30

<210> SEQ ID NO 77
<211> LENGTH: 30
<212> TYPE: DNA
<213> ORGANISM: Artificial Sequence
<220> FEATURE:
<223> OTHER INFORMATION: Synthetic

<400> SEQUENCE: 77
ccatttctca acagatcttc caaagtcttg                                 30

<210> SEQ ID NO 78
<211> LENGTH: 32
<212> TYPE: DNA
<213> ORGANISM: Artificial Sequence
<220> FEATURE:
<223> OTHER INFORMATION: Synthetic

<400> SEQUENCE: 78
ggaagctcct gaagacgccc acagggactt tg                              32

<210> SEQ ID NO 79
<211> LENGTH: 32
<212> TYPE: DNA
<213> ORGANISM: Artificial Sequence
<220> FEATURE:
<223> OTHER INFORMATION: Synthetic

<400> SEQUENCE: 79
caaagtccct gtgggcgtct tcaggagctt cc                              32

<210> SEQ ID NO 80
<211> LENGTH: 20
<212> TYPE: DNA
<213> ORGANISM: Artificial Sequence
<220> FEATURE:
<223> OTHER INFORMATION: Synthetic

<400> SEQUENCE: 80
agtgtggttt gccagcagtc                                            20

<210> SEQ ID NO 81
<211> LENGTH: 20
<212> TYPE: DNA
<213> ORGANISM: Artificial Sequence
<220> FEATURE:
<223> OTHER INFORMATION: Synthetic

<400> SEQUENCE: 81
tggttgatat agtagggcac                                            20

<210> SEQ ID NO 82
<211> LENGTH: 30
<212> TYPE: DNA
```

<213> ORGANISM: Artificial Sequence
<220> FEATURE:
<223> OTHER INFORMATION: Synthetic

<400> SEQUENCE: 82
cagatttcac aggctgctct ggcagatttc                              30

<210> SEQ ID NO 83
<211> LENGTH: 12
<212> TYPE: DNA
<213> ORGANISM: Artificial Sequence
<220> FEATURE:
<223> OTHER INFORMATION: Synthetic

<400> SEQUENCE: 83
aattcgtcga cg                                                 12

<210> SEQ ID NO 84
<211> LENGTH: 30
<212> TYPE: DNA
<213> ORGANISM: Artificial Sequence
<220> FEATURE:
<223> OTHER INFORMATION: Synthetic

<400> SEQUENCE: 84
gaaatctgcc agagcagcct gtgaaatctg                              30

<210> SEQ ID NO 85
<211> LENGTH: 30
<212> TYPE: DNA
<213> ORGANISM: Artificial Sequence
<220> FEATURE:
<223> OTHER INFORMATION: Synthetic

<400> SEQUENCE: 85
tgaatccttt aacataggta cctccaacat                              30

<210> SEQ ID NO 86
<211> LENGTH: 30
<212> TYPE: DNA
<213> ORGANISM: Artificial Sequence
<220> FEATURE:
<223> OTHER INFORMATION: Synthetic

<400> SEQUENCE: 86
atgttggagg tacctatgtt aaaggattca                              30

<210> SEQ ID NO 87
<211> LENGTH: 206
<212> TYPE: DNA
<213> ORGANISM: Mus musculus

<400> SEQUENCE: 87
ccactacggg tctaggctgc ccatgtaagg aggcaaggcc tggggacacc cgagatgcct      60
ggttataatt aacccagaca tgtggctgcc ccccccccc caacacctgc tgcctgagcc     120 tcaccccac cccggtgcct gggtcttagg ctctgtacac catggaggag aagctcgctc     180
taaaaataac cctgtccctg gtggat                                        206

<210> SEQ ID NO 88
<211> LENGTH: 205
<212> TYPE: DNA
<213> ORGANISM: Artificial Sequence
<220> FEATURE:
<223> OTHER INFORMATION: Synthetic -continued

```
<400> SEQUENCE: 88
ccactacggg tctaggctgc ccatgtaagg aggcaaggcc tggggacacc cgagatgcct    60
ggttataatt aaccccaaca cctgctgccc cccccccc aacacctgct gcctgagcct    120
cacccccacc ccggtgcctg ggtcttaggc tctgtacacc atggaggaga agctcgctct    180
aaaaataacc ctgtccctgg tggat                                         205

<210> SEQ ID NO 89
<211> LENGTH: 212
<212> TYPE: DNA
<213> ORGANISM: Artificial Sequence
<220> FEATURE:
<223> OTHER INFORMATION: Synthetic

<400> SEQUENCE: 89
ccactacggg tctaggctgc ccatgtaagg aggcaaggcc tggggacacc cgagatgcct    60
ggttataatt aacccagaca tgtggctgcc cccccccc caacacctgc tgcctgagcc    120
tgagcggtta ccccacccg gtgcctgggt cttaggctct gtacaccatg gaggagaagc    180
tcgctctaaa ataaccctg tccctggtgg at                                  212

<210> SEQ ID NO 90
<211> LENGTH: 211
<212> TYPE: DNA
<213> ORGANISM: Artificial Sequence
<220> FEATURE:
<223> OTHER INFORMATION: Synthetic

<400> SEQUENCE: 90
ccactacggg tctaggctgc ccatgtaagg aggcaaggcc tggggacacc cgagatgcct    60
ggttataatt aaccccaaca cctgctgccc cccccccc aacacctgct gcctgagcct    120
gagcggttac cccaccccgg tgcctgggtc ttaggctctg tacaccatgg aggagaagct    180
cgctctaaaa ataaccctgt ccctggtgga t                                  211

<210> SEQ ID NO 91
<211> LENGTH: 170
<212> TYPE: DNA
<213> ORGANISM: Artificial Sequence
<220> FEATURE:
<223> OTHER INFORMATION: Synthetic

<400> SEQUENCE: 91
ccactacggg tctaggctgc ccatgtaagg aggcaaggcc tggggacacc cgagatgcct    60
ggttataatt aaccccaaca cctgctgccc cccccccc aacacctgct gcctgagcct    120
gagcggttac cccaccccgg tgcctgggtc ttaggctctg tacaccatgg               170

<210> SEQ ID NO 92
<211> LENGTH: 951
<212> TYPE: DNA
<213> ORGANISM: Mus musculus

<400> SEQUENCE: 92
gtggagcagc ctgcactggg cttctgggag aaaccaaacc gggttctaac ctttcagcta    60
cagttattgc cttttcctgta gatgggcgac tacagcccca ccccacccc cgtctcctgt    120 atccttcctg ggcctgggga tcctaggctt tcactggaaa tttcccccca ggtgctgtag    180
gctagagtca cggctcccaa gaacagtgct tgcctggcat gcatggttct gaacctccaa    240
```

```
ctgcaaaaaa tgacacatac cttgacccct ggaaggctga ggcaggggga ttgccatgag      300
tgcaaagcca gactgggtgg catagttaga ccctgtctca aaaaaccaaa acaattaaa       360 taactaaagt caggcaagta atcctactcg ggagactgag gcagagggat tgttacatgt      420
ctgaggccag cctggactac atagggtttc aggctagccc tgtctacaga gtaaggccct     480
atttcaaaaa cacaaacaaa atggttctcc cagctgctaa tgctcaccag gcaatgaagc      540
ctggtgagca ttagcaatga aggcaatgaa ggagggtgct ggctacaatc aaggctgtgg     600
gggactgagg gcaggctgta acaggcttgg gggccagggc ttatacgtgc ctgggactcc     660
caaagtatta ctgttccatg ttcccggcga agggccagct gtcccccgcc agctagactc     720
agcacttagt ttaggaacca gtgagcaagt cagcccttgg ggcagcccat acaaggccat      780
ggggctgggc aagctgcacg cctgggtccg ggtgggcac ggtgcccggg caacgagctg        840
aaagctcatc tgctctcagg ggcccctccc tggggacagc ccctcctggc tagtcacacc      900
ctgtaggctc ctctatataa cccaggggca caggggctgc cccgggtca c                951
```

<210> SEQ ID NO 93
<211> LENGTH: 365
<212> TYPE: DNA
<213> ORGANISM: Mus musculus

<400> SEQUENCE: 93

```
aatcaaggct gtgggggact gagggcaggc tgtaacaggc ttggggggcca gggcttatac    60 gtgcctggga ctcccaaagt attactgttc catgttcccg gcgaagggcc agctgtcccc    120
cgccagctag actcagcact tagtttagga accagtgagc aagtcagccc ttggggcagc    180
ccatacaagg ccatggggct gggcaagctg cacgcctggg tccggggtgg gcacggtgcc    240
cgggcaacga gctgaaagct catctgctct caggggcccc tccctgggga cagcccctcc    300
tggctagtca caccctgtag gctcctctat ataacccagg ggcacagggg ctgcccccgg    360
gtcac                                                                  365
```

<210> SEQ ID NO 94
<211> LENGTH: 87
<212> TYPE: DNA
<213> ORGANISM: Mus musculus

<400> SEQUENCE: 94

```
cctccctggg gacagcccct cctggctagt cacaccctgt aggctcctct ataacccca     60 ggggcacagg ggctgccccc gggtcac                                         87
```

<210> SEQ ID NO 95
<211> LENGTH: 130
<212> TYPE: DNA
<213> ORGANISM: Artificial Sequence
<220> FEATURE:
<223> OTHER INFORMATION: Synthetic

<400> SEQUENCE: 95

```
gtaaaacgac ggccagtgaa ttcgagctcg gtacccgggg atcctctaga gtcgacctgc    60
aggcatgcaa gctttcccta tagtgagtcg tattagagct tggcgtaatc atggtcatag    120
ctgtttcctg                                                            130
```

<210> SEQ ID NO 96
<211> LENGTH: 38
<212> TYPE: PRT
<213> ORGANISM: Artificial Sequence -continued

```
<220> FEATURE:
<223> OTHER INFORMATION: Synthetic

<400> SEQUENCE: 96

Val Val Ala Leu Ser Asn Ser Ser Pro Val Arg Pro Asp Glu Leu Thr
 1               5                  10                  15

Ser Arg Cys Ala His Leu Ser Glu Arg Tyr His Thr Thr Asn Ser Ser
            20                  25                  30

Pro Thr Ile Met Thr Met
            35
```